(12) United States Patent
Patterson et al.

(10) Patent No.: US 8,614,253 B2
(45) Date of Patent: Dec. 24, 2013

(54) IRE-1α INHIBITORS

(75) Inventors: John Bruce Patterson, Ventura, CA (US); David Gregory Lonergan, Ventura, CA (US); Gary A. Flynn, Tucson, AZ (US); Qingping Zeng, Thousand Oaks, CA (US); Peter V. Pallai, Carlsbad, CA (US)

(73) Assignee: MannKind Corporation, Valencia, CA (US)

( * ) Notice: Subject to any disclaimer, the term of this patent is extended or adjusted under 35 U.S.C. 154(b) by 215 days.

(21) Appl. No.: 12/941,530

(22) Filed: Nov. 8, 2010

(65) Prior Publication Data

US 2011/0065162 A1    Mar. 17, 2011

Related U.S. Application Data

(63) Continuation of application No. 12/135,571, filed on Jun. 9, 2008, now Pat. No. 7,858,666.

(60) Provisional application No. 60/942,743, filed on Jun. 8, 2007.

(51) Int. Cl.
*A61K 31/11* (2006.01)

(52) U.S. Cl.
USPC ............ 514/700; 514/702; 514/703; 514/704

(58) Field of Classification Search
USPC ................................. 514/700, 702, 703, 704
See application file for complete search history.

(56) References Cited

U.S. PATENT DOCUMENTS

| | | | |
|---|---|---|---|
| 675,543 A | 6/1901 | Eichengrün |
| 2,282,907 A | 5/1942 | ter Horst |
| 2,346,662 A | 4/1944 | Chenicek |
| 2,649,444 A | 8/1953 | Barrett |
| 2,771,391 A | 11/1956 | Bockstahler |
| 2,778,853 A | 1/1957 | Schultz |
| 3,080,372 A | 3/1963 | Janssen |
| 3,148,997 A | 9/1964 | Hemwall |
| 3,151,124 A | 9/1964 | Huebner |
| 3,203,962 A | 8/1965 | Huebner |
| 3,211,613 A | 10/1965 | Clark |
| 3,249,606 A | 5/1966 | Pellegrini |
| 3,252,996 A | 5/1966 | Huebner |
| 3,305,562 A | 2/1967 | Heffe |

(Continued)

FOREIGN PATENT DOCUMENTS

| | | |
|---|---|---|
| DE | 209 910 C | 5/1909 |
| DE | 1679900 A1 | 4/1971 |

(Continued)

OTHER PUBLICATIONS

Cory AH, Cory JG. Phenolic compounds, sodium salicylate and related compounds, as inhibitors of tumor cell growth and inducers of apoptosis in mouse leukemia L1210 cells. In Vivo. Jan.-Feb. 2005;19(1):31-5.*

(Continued)

*Primary Examiner* — Paul Zarek
(74) *Attorney, Agent, or Firm* — Banner & Witcoff, Ltd.

(57) ABSTRACT

Compounds which directly inhibit IRE-1α activity in vitro, prodrugs, and pharmaceutically acceptable salts thereof. Such compounds and prodrugs are useful for treating diseases associated with the unfolded protein response and can be used as single agents or in combination therapies.

56 Claims, 10 Drawing Sheets

(56) References Cited

U.S. PATENT DOCUMENTS

| | | |
|---|---|---|
| 3,325,521 A | 6/1967 | Elslager |
| 3,357,883 A | 12/1967 | Pilln |
| 3,364,210 A | 1/1968 | Safir |
| 3,417,087 A | 12/1968 | Campaigne |
| 3,507,963 A | 4/1970 | Menasse |
| 3,574,837 A | 4/1971 | Pacheco |
| 3,651,085 A | 3/1972 | Lunsford |
| 3,652,770 A | 3/1972 | Rohr |
| 3,681,445 A | 8/1972 | Ruyle |
| 3,703,527 A | 11/1972 | Saucy |
| 3,714,226 A | 1/1973 | Ruyle |
| 3,721,741 A | 3/1973 | Rohr |
| 3,753,983 A | 8/1973 | Raabe |
| 3,806,526 A | 4/1974 | Carr |
| 3,816,433 A | 6/1974 | Hernestam |
| 3,873,539 A | 3/1975 | Houlihan |
| 3,895,030 A | 7/1975 | Lafon |
| 3,912,755 A | 10/1975 | Booher |
| 3,931,197 A | 1/1976 | Carr |
| 3,962,459 A | 6/1976 | Kathawala |
| 3,969,356 A | 7/1976 | Milkowski |
| 3,992,546 A | 11/1976 | Huebner |
| 3,995,047 A | 11/1976 | Morita |
| 4,015,014 A | 3/1977 | Vatne |
| 4,028,366 A | 6/1977 | Zenitz |
| 4,054,570 A | 10/1977 | Huebner |
| 4,066,788 A | 1/1978 | Blohm |
| 4,072,852 A | 2/1978 | Hogan et al. |
| 4,145,427 A | 3/1979 | Langbein |
| 4,148,895 A | 4/1979 | Lattrell |
| 4,151,201 A | 4/1979 | Casnati |
| 4,169,892 A | 10/1979 | Robba |
| 4,176,198 A | 11/1979 | Nuss, Jr. |
| 4,219,570 A | 8/1980 | Inazuka |
| 4,230,727 A | 10/1980 | Nuss, Jr. |
| 4,231,967 A | 11/1980 | Matsuda |
| 4,239,759 A | 12/1980 | Gante |
| 4,277,474 A | 7/1981 | Kohda |
| 4,333,941 A | 6/1982 | Baratz |
| 4,341,794 A | 7/1982 | Royer |
| 4,435,601 A | 3/1984 | Formanek |
| 4,465,678 A | 8/1984 | Knops |
| 4,495,184 A | 1/1985 | Knops |
| 4,524,032 A | 6/1985 | Misaki |
| 4,528,299 A | 7/1985 | Uno |
| 4,544,663 A | 10/1985 | Manning |
| 4,638,009 A | 1/1987 | Itho |
| 4,661,636 A | 4/1987 | Englert |
| 4,686,235 A | 8/1987 | Chang |
| 4,695,652 A | 9/1987 | Seng |
| 4,705,795 A | 11/1987 | Lafon |
| 4,755,522 A | 7/1988 | Lafon |
| 4,758,560 A | 7/1988 | Lafon |
| 4,847,429 A | 7/1989 | Lentz |
| 4,912,116 A | 3/1990 | Itoh |
| 4,927,956 A | 5/1990 | Vicari |
| 4,997,850 A | 3/1991 | Kimura |
| 5,025,006 A | 6/1991 | Dininno |
| 5,025,036 A | 6/1991 | Carson |
| 5,057,535 A | 10/1991 | Shiozawa |
| 5,130,493 A | 7/1992 | Schnatterer |
| 5,149,858 A | 9/1992 | Desmurs |
| 5,198,422 A | 3/1993 | Clark |
| 5,202,355 A | 4/1993 | Nakatsu |
| 5,354,920 A | 10/1994 | Cox |
| 5,413,892 A | 5/1995 | Matsuura |
| 5,420,362 A | 5/1995 | Lim |
| 5,565,416 A | 10/1996 | Wu |
| 5,571,886 A | 11/1996 | Zampini |
| 5,593,994 A | 1/1997 | Batt |
| 5,599,974 A | 2/1997 | Abraham |
| 5,654,260 A | 8/1997 | Wu |
| 5,668,182 A | 9/1997 | Abraham |
| 5,705,501 A | 1/1998 | DeBernardis |
| 5,763,496 A | 6/1998 | Holland |
| 5,861,435 A | 1/1999 | Yokoi |
| 6,005,009 A | 12/1999 | Murad |
| 6,013,841 A | 1/2000 | Pansegrau |
| 6,040,484 A | 3/2000 | Costantini |
| 6,124,507 A | 9/2000 | Wilson |
| 6,136,826 A | 10/2000 | Fujioka |
| 6,184,421 B1 | 2/2001 | Metivier |
| 6,214,994 B1 | 4/2001 | DeBernardis |
| 6,245,936 B1 | 6/2001 | Metivier |
| 6,251,927 B1 | 6/2001 | Lai |
| 6,288,276 B1 | 9/2001 | Dimmit |
| 6,307,087 B1 | 10/2001 | Buchwald |
| 6,329,129 B1 | 12/2001 | Yamazaki |
| 6,340,685 B1 | 1/2002 | Mavunkel |
| 6,355,661 B1 | 3/2002 | Lai |
| 6,380,229 B1 | 4/2002 | Yoneda |
| 6,420,610 B1 | 7/2002 | Nakamura |
| 6,462,064 B1 | 10/2002 | Pfahl |
| 6,486,342 B1 | 11/2002 | Abraham |
| 6,521,641 B1 | 2/2003 | Klein |
| 6,521,643 B1 | 2/2003 | Tomishima |
| 6,528,529 B1 | 3/2003 | Brann |
| 6,605,620 B1 | 8/2003 | Kodama |
| 6,613,803 B1 | 9/2003 | Wang |
| 6,638,947 B2 | 10/2003 | Wang |
| 6,656,967 B2 | 12/2003 | Gerusz |
| RE38,425 E | 2/2004 | Dimmock |
| 6,764,993 B2 | 7/2004 | Shalaev |
| 6,903,239 B2 | 6/2005 | Peilstöcker |
| 7,009,079 B2 | 3/2006 | Kamitamari |
| 7,105,577 B2 | 9/2006 | Hölzl |
| 7,250,521 B2 | 7/2007 | Kraatz |
| 7,858,666 B2 | 12/2010 | Patterson |
| 2001/0020100 A1 | 9/2001 | Manning |
| 2001/0049354 A1 | 12/2001 | Shalaev |
| 2002/0004618 A1 | 1/2002 | Kamitamari |
| 2002/0052003 A1 | 5/2002 | Alberte et al. |
| 2003/0022923 A1 | 1/2003 | Lai |
| 2003/0100774 A1 | 5/2003 | Gross |
| 2003/0114390 A1 | 6/2003 | Washburn |
| 2003/0124157 A1 | 7/2003 | Engles |
| 2003/0125528 A1 | 7/2003 | Hay |
| 2003/0157154 A1 | 8/2003 | Fuller |
| 2003/0162836 A1 | 8/2003 | Hölzl |
| 2003/0199570 A1 | 10/2003 | Coghlan |
| 2003/0229149 A1 | 12/2003 | Baschong |
| 2004/0010147 A1 | 1/2004 | Kodama |
| 2004/0034064 A1 | 2/2004 | Kuduk |
| 2004/0044041 A1 | 3/2004 | Kuduk |
| 2004/0063761 A1 | 4/2004 | Kuduk |
| 2004/0092754 A1 | 5/2004 | Schafer |
| 2004/0157801 A1 | 8/2004 | Safo |
| 2004/0186174 A1 | 9/2004 | Hölzl |
| 2004/0223909 A1 | 11/2004 | Montalto |
| 2004/0235877 A1 | 11/2004 | Ishizuka |
| 2005/0049306 A1 | 3/2005 | Harper |
| 2005/0113567 A1 | 5/2005 | Onishi |
| 2005/0165025 A1 | 7/2005 | Leonardi et al. |
| 2005/0203179 A1 | 9/2005 | Banowski |
| 2005/0209199 A1 | 9/2005 | Safo |
| 2005/0215783 A1 | 9/2005 | Yang et al. |
| 2006/0094747 A1 | 5/2006 | Van Zandt |
| 2006/0194805 A1 | 8/2006 | Bakthavatchalam |
| 2006/0199806 A1 | 9/2006 | Failli |
| 2006/0246177 A1 | 11/2006 | Kimura et al. |
| 2006/0258644 A1 | 11/2006 | Failli |
| 2006/0258645 A1 | 11/2006 | Failli |
| 2006/0258672 A1 | 11/2006 | Barbosa |
| 2006/0287337 A1 | 12/2006 | Reiss |
| 2007/0140960 A1 | 6/2007 | Siclovan |
| 2007/0189967 A1 | 8/2007 | Siclovan |
| 2008/0051445 A1 | 2/2008 | Surolia |

FOREIGN PATENT DOCUMENTS

| | | |
|---|---|---|
| DE | 2142245 A1 | 3/1973 |
| DE | 44 44 244 A1 | 6/1996 |
| DE | 19631131 | 2/1998 |
| DE | 1989548 | 11/1999 |

(56) References Cited

FOREIGN PATENT DOCUMENTS

| | | |
|---|---|---|
| DE | 102005009705 | 9/2006 |
| EP | 0 033 702 A | 8/1981 |
| EP | 435827 | 7/1991 |
| EP | 464900 | 1/1992 |
| EP | 467434 | 1/1992 |
| EP | 533266 | 3/1993 |
| EP | 548798 | 6/1993 |
| EP | 564333 | 10/1993 |
| EP | 599688 | 6/1994 |
| EP | 620216 | 10/1994 |
| EP | 658807 | 6/1995 |
| EP | 690046 | 1/1996 |
| EP | 702012 | 3/1996 |
| EP | 749964 | 12/1996 |
| EP | 938025 | 8/1999 |
| EP | 1085013 | 3/2001 |
| EP | 1195166 | 4/2002 |
| EP | 1233016 | 8/2002 |
| EP | 1834642 | 9/2007 |
| FR | 2745285 | 8/1997 |
| FR | 2745287 | 8/1997 |
| FR | 2756279 | 5/1998 |
| FR | 2768728 | 3/1999 |
| FR | 2768729 | 3/1999 |
| FR | 2857010 | 1/2005 |
| FR | 2868417 | 10/2005 |
| FR | 2874611 | 3/2006 |
| GB | 2276162 | 9/1994 |
| JP | 63243085 | 10/1988 |
| JP | 02264946 | 10/1990 |
| JP | 04331954 | 11/1992 |
| JP | 05127330 | 5/1993 |
| JP | 5127335 | 5/1993 |
| JP | 06135153 | 5/1994 |
| JP | 07084415 | 3/1995 |
| JP | 09149797 | 6/1997 |
| JP | 2000026438 | 6/1997 |
| JP | 2001215669 | 8/2001 |
| JP | 2001335476 | 12/2001 |
| JP | 2002275165 | 9/2002 |
| JP | 2004189599 | 7/2004 |
| JP | 2006151946 | 6/2006 |
| JP | 2007084454 | 4/2007 |
| WO | WO9313096 | 7/1993 |
| WO | WO9321184 | 10/1993 |
| WO | WO9420473 | 9/1994 |
| WO | WO9425430 | 11/1994 |
| WO | WO9501326 | 1/1995 |
| WO | WO9501426 | 1/1995 |
| WO | WO9504049 | 2/1995 |
| WO | WO9506044 | 3/1995 |
| WO | WO9515954 | 6/1995 |
| WO | WO9517398 | 6/1995 |
| WO | WO9517401 | 6/1995 |
| WO | WO9522992 | 8/1995 |
| WO | WO9526328 | 10/1995 |
| WO | WO9529907 | 11/1995 |
| WO | WO9539675 | 11/1995 |
| WO | WO9532967 | 12/1995 |
| WO | WO9607079 | 2/1996 |
| WO | WO9611934 | 4/1996 |
| WO | WO9619477 | 6/1996 |
| WO | WO9623783 | 8/1996 |
| WO | WO9630333 | 10/1996 |
| WO | WO9631492 | 10/1996 |
| WO | WO9631508 | 10/1996 |
| WO | WO9633723 | 10/1996 |
| WO | WO9705131 | 2/1997 |
| WO | WO9710824 | 3/1997 |
| WO | WO9711930 | 4/1997 |
| WO | WO9717350 | 5/1997 |
| WO | WO9719070 | 5/1997 |
| WO | WO9720815 | 6/1997 |
| WO | WO9734900 | 9/1997 |
| WO | WO9735861 | 10/1997 |
| WO | WO9735862 | 10/1997 |
| WO | WO9737989 | 10/1997 |
| WO | WO9748786 | 12/1997 |
| WO | WO9801132 | 1/1998 |
| WO | WO9804508 | 2/1998 |
| WO | WO9816504 | 4/1998 |
| WO | WO 98/45269 | 10/1998 |
| WO | WO9932465 | 7/1999 |
| WO | WO9966927 | 12/1999 |
| WO | WO0002887 | 1/2000 |
| WO | WO0015603 | 3/2000 |
| WO | WO0019990 | 4/2000 |
| WO | WO0021954 | 4/2000 |
| WO | WO0042026 | 7/2000 |
| WO | WO0059506 | 10/2000 |
| WO | WO0105774 | 1/2001 |
| WO | WO0107031 | 2/2001 |
| WO | WO0114314 | 3/2001 |
| WO | WO0116122 | 3/2001 |
| WO | WO0116123 | 3/2001 |
| WO | WO0127068 | 4/2001 |
| WO | WO0156563 | 8/2001 |
| WO | WO0160821 | 8/2001 |
| WO | WO02057044 | 8/2001 |
| WO | WO0183451 | 11/2001 |
| WO | WO0198296 | 12/2001 |
| WO | WO0204433 | 1/2002 |
| WO | WO0210143 | 2/2002 |
| WO | WO0212178 | 2/2002 |
| WO | WO0224654 | 3/2002 |
| WO | WO0241882 | 5/2002 |
| WO | WO02055497 | 7/2002 |
| WO | WO02072543 | 9/2002 |
| WO | WO02083134 | 10/2002 |
| WO | WO02083678 | 10/2002 |
| WO | WO02083680 | 10/2002 |
| WO | WO02083682 | 10/2002 |
| WO | WO02089781 | 11/2002 |
| WO | WO 02/096867 | 12/2002 |
| WO | WO03002533 | 1/2003 |
| WO | WO03013509 | 2/2003 |
| WO | WO0224645 | 3/2003 |
| WO | WO03020703 | 3/2003 |
| WO | WO03026587 | 4/2003 |
| WO | WO03033510 | 4/2003 |
| WO | WO03065789 | 8/2003 |
| WO | WO03066577 | 8/2003 |
| WO | WO03080545 | 10/2003 |
| WO | WO03086394 | 10/2003 |
| WO | WO03086397 | 10/2003 |
| WO | WO03086403 | 10/2003 |
| WO | WO2004006922 | 1/2004 |
| WO | WO2004006923 | 1/2004 |
| WO | WO2004006924 | 1/2004 |
| WO | WO2004110974 | 1/2004 |
| WO | WO0224642 | 3/2004 |
| WO | WO2004024060 | 3/2004 |
| WO | WO 2004/037816 | 5/2004 |
| WO | WO2004050631 | 6/2004 |
| WO | WO2004052488 | 6/2004 |
| WO | WO2004052859 | 6/2004 |
| WO | WO2004056727 | 7/2004 |
| WO | WO2004077885 | 9/2004 |
| WO | WO2004083189 | 9/2004 |
| WO | WO2004083190 | 9/2004 |
| WO | WO2004084824 | 10/2004 |
| WO | WO2004084890 | 10/2004 |
| WO | WO2004092140 | 10/2004 |
| WO | WO2004094379 | 11/2004 |
| WO | WO2004094395 | 11/2004 |
| WO | WO2004098582 | 11/2004 |
| WO | WO2005009539 | 2/2005 |
| WO | WO2005009954 | 2/2005 |
| WO | WO2005009993 | 2/2005 |
| WO | WO2005016862 | 2/2005 |
| WO | WO2005023960 | 3/2005 |
| WO | WO2005026120 | 3/2005 |
| WO | WO2005034953 | 4/2005 |
| WO | WO2005042498 | 5/2005 |

(56) References Cited

FOREIGN PATENT DOCUMENTS

| | | |
|---|---|---|
| WO | WO2005044007 | 5/2005 |
| WO | WO2005053048 | 6/2005 |
| WO | WO2005063222 | 7/2005 |
| WO | WO2005121152 | 12/2005 |
| WO | WO2006002099 | 1/2006 |
| WO | WO2006008316 | 1/2006 |
| WO | WO2006014413 | 2/2006 |
| WO | WO2006071538 | 7/2006 |
| WO | WO2006074919 | 7/2006 |
| WO | WO2006084773 | 8/2006 |
| WO | WO2006092430 | 9/2006 |
| WO | WO2006093353 | 9/2006 |
| WO | WO2006107115 | 10/2006 |
| WO | WO2006122186 | 11/2006 |
| WO | WO2006124780 | 11/2006 |
| WO | WO2006124865 | 11/2006 |
| WO | WO2006124897 | 11/2006 |
| WO | WO2006135687 | 12/2006 |
| WO | WO2007017143 | 2/2007 |
| WO | WO2007020888 | 2/2007 |
| WO | WO2007023430 | 3/2007 |
| WO | WO2007027878 | 3/2007 |
| WO | WO2007031507 | 3/2007 |
| WO | WO2007031529 | 3/2007 |
| WO | WO2007033781 | 3/2007 |
| WO | WO2007034277 | 3/2007 |
| WO | WO2007036701 | 4/2007 |
| WO | WO 2007/056155 | 5/2007 |
| WO | WO2007051408 | 5/2007 |
| WO | WO2007062028 | 5/2007 |
| WO | WO2007063522 | 6/2007 |
| WO | WO2007063523 | 6/2007 |
| WO | WO2007064773 | 6/2007 |
| WO | WO2007067593 | 6/2007 |
| WO | WO2007075387 | 7/2007 |
| WO | WO2007077457 | 7/2007 |
| WO | WO2007078523 | 7/2007 |
| WO | WO2007079186 | 7/2007 |
| WO | WO2007081091 | 7/2007 |
| WO | WO2007082713 | 7/2007 |
| WO | WO2007087066 | 8/2007 |
| WO | WO2007092930 | 8/2007 |
| WO | WO 2007/101224 | 9/2007 |
| WO | WO2007115408 | 10/2007 |
| WO | WO2007121389 | 10/2007 |
| WO | WO2007137107 | 11/2007 |
| WO | WO2008002246 | 1/2008 |
| WO | WO2008007900 | 1/2008 |
| WO | WO2008021927 | 2/2008 |
| WO | WO2008021928 | 2/2008 |
| WO | WO2008021936 | 2/2008 |
| WO | WO2008022286 | 2/2008 |
| WO | WO2008024963 | 2/2008 |
| WO | WO2008030752 | 3/2008 |
| WO | WO2008037266 | 4/2008 |
| WO | WO2008042892 | 4/2008 |

OTHER PUBLICATIONS

Satou Y, Nosaka K, Koya Y, Yasunaga JI, Toyokuni S, Matsuoka M. Proteasome inhibitor, bortezomib, potently inhibits the growth of adult T-cell leukemia cells both in vivo and in vitro. Leukemia. Aug. 2004;18(8):1357-63.*

Yoo ID, Yun BS, Lee IK, Ryoo IJ, Choung DH, Han KH. Three naphthalenes from root bark of *Hibiscus syriacus*. Phytochemistry. Mar. 1998;47(5):799-802.*

Testa B. Prodrug research: futile or fertile? Biochem Pharmacol. Dec. 1, 2004;68(11):2097-106.*

Cross et al., "The molecular basis for selective inhibition of unconventional mRNA splicing by an IRE1-binding small molecule," *Proc. Natl. Acad. Sci. USA*, Apr. 10, 2012; 109(15): E869-E878, published online Feb. 6, 2012.

Papandreou et al., "Identification of an Ire1 alpha endonuclease specific inhibitor with cytotoxic activity against human multiple myeloma," Blood 117, 1311-14, 2011.

Volkmann et al., "Potent and selective inhibitors of the inositol-requiring enzyme 1 endoribonuclease," J. Biol. Chem. 286, 12743-55, 2011.

Birch et al., "N-Substituted (2,3-dihydro-1,4-benzodioxin-2-yl)methylamine Derivatives as D2 Antagonists/5-HY1A Partial Agonists with Potential as Atypical Antipsychotic Agents," *J. Med. Chem.* 42, 3342-55, Jan. 1, 1999.

Crich & Grant, "Synthesis of a 4,6-Disubstituted Dibenzofuran β-Sheet Initiator by Reductive Radical Arylation of Benzene," *J. Org. Chem.* 70, 2384-86, 2005.

Ginsburg, "The Action of t-Butyl Hypochloride on Organic Compounds. II. Aromatic Aldehydes," *J. Am. Chem. Soc.* 73, 702-04, 1951.

Kulkarni et al., "Synthesis and antiradiation activity of thiazolidines," *Current Science, Indian Academy of Sciences* 41, 637, Sep. 5, 1972.

Marvel & Tarkoy, "Heat Stability Studies on Chelates from Schiff Bases of Salicylaldehyde Derivatives," *J. Am. Chem. Soc.* 79, 6000-02, 1957.

Acosta-Alvear et al., "XBP1 Controls Diverse Cell Type- and Condition-Specific Transcriptional Regulatory Networks," Mol. Cell. 6, 53-66, 2007.

Back et al., "Cytlplasmic IRE1alpha-mediatee XBP1 mRA Splicing in the Absence of Nuclear Processing and Endoplasmic Reticulum Stress," J. Biol. Chem. 281, 18691-706, 2006.

Baiocchi & Bonanomi, "Aromatization of aliphatic compounds. IX. Benzofuranones from (4-substituted 2-oxo-3-cyclohexen-1-yl)acetic acids," Gazzetta Chimica Italiana 199, 441-43, 1989.

Balch et al., "Adapting Proteostasis for Disease Intervention," Science 319, 916-18, 2008.

Bazarbachi et al., "New therapeutic approaches for adult T-cell leukaemia," Lancet Oncol. 5, 664-72, 2004.

Brown et al., "Crystal Structures of Interleukin-2 Tyrosine Kinase and Their Implications for the Design of Selective Inhibitors," J. Biol. Chem. 279, 18727-32, 2004.

Brown et al., "Naphthyl Ketones: A New Class of Janus Kinase 3 Inhibitors," Bioorganic & Medicinal Chemistry Letters 10, 575-79, 2000.

Carrasco et al., "The Differentiation and Stress Response Factor XBP-1 Drives Multiple Myeloma Pathogenesis," Cancer Cell 11, 349-60, Apr. 2007.

Chauhan et al., "A novel orally active proteasome inhibitor induces apoptosis in multiple myeloma cells with mechanisms distinct from Bortezomib," Cancer Cell 8, 407-19, 2005.

Chawla et al, "Agents Activing on the Central Nervous System. XII. 3-t-Aminopropiophenones as Central Muscle Relaxants and Diuretics," J. Med. Chem. 13, 480-88, 1970.

Fitzharris et al., "The effects in volunteers of BW12C, a compound designed to left-shift the blood-oxygen saturation curve," Br. J. Clin. Pharmac. 19, 471-81, 1985.

Graux et al., "Cytogenetics and molecular genetics of T-cell acute lymphoblastic leukemia: from thymocytes to lymphoblast," *Leukemia 20*, 1496-1510, 2006.

Hayden et al., "Type 2 Diabetes Mellitus as a Conformational Disease," J. Pancrease (Online) 6, 287-302, 2005.

Iwawaki et al., "A transgenic mouse model for monitoring endoplasmic reticulum stress," Nat. Med. 10, 98-102, 2004 (e-pub Dec. 14, 2003) (abstract).

Iwakoshi et al., "Plasma cell differentiation and the unfolded protein response intersect at the transcription factor XBP-1," *Nature Immunology 4*, 321-29, 2003.

Klemke et al., "New insights into the molecular biology and targeted therapy of cutaneous T-cell lymphomas," JJDG 4, 395-406, 2006.

Lawless et al., "Activation of Endoplasmic Reticulum-Specific Stress Responses Associated with the Conformational Disease Z alpha1-Antitrypsin Deficiency," J. Immunol. 172, 5722-26, 2004.

Liu et al., "The Protein Kinase/Endoribonuclease IRE1alpha That Signals the Unfolded Protein Response Has a Luminal N-terminal Ligand-independent Dimerization Domain," J. Biol. Chem. 277, 18346-56, 2002.

(56) References Cited

OTHER PUBLICATIONS

Mao et al., "Crystal Structure of Bruton's Tyrosine Kinase Domain Suggests a Novel Pathway for Activation and Provides Insights into the Molecular Basis of X-linked Agammaglobulinemia," J. Biol. Chem. 276, 41435-43, 2001.
Merrett et al., "Characterization of the binding of the anti-sickling compound, BW12C, to haemoglobin," Biochem. J. 239, 387-92, 1986.
Nakamura et al., "Activation of the endoplasmic reticulum stress pathway is associated with survival of myeloma cells," *Leukemia & Lymphoma 47*, 531-39, 2006.
Pathak & Singh, "Studies in Fluorinated Mannich Bases," Pharmazie 35, H. 7, 1980.
Propper et al., "Phase II study of the oxygen saturation curve left shifting agent BW12C in combination with the hypoxia activated drug mitomycin C in advanced colorectal cancer," Br. J. ancer 82, 1776-82, 2000.
Taylor & Nobles, "Some Ketonic Mannich Bases," J. Am. Pharmaceutical Assoc. 49, 317-19, 1960.
Weigel et al., "Stereoselective Photocyclization to 2-Aminocyclopropanols by Photolysis of beta-Aminoketones and Oxidative Ring Opening to Enaminones," Tetrahedron 53, 7855-66, 1997.
Van De Waterbeemd H. et al., "Property-based design; optimization of drug absorption and pharmacokinetics," Journal of Medicinal Chemistry, Apr. 2001, 44(9), 1313-133.
Weigel et al., "The Influence of Substitutents on the Photochemical Generation and Stability of 2-Morpholinocyclopropanols," Tetrahedron Letters 34, 6737-40, 1993.
Wireko & Abraham, "X-ray diffraction study of the binding of the antisickling agent 12C79 to human hemoglobin," Proc. Natl. Acad. Sci. USA 88, 2209-11, 1991.
Wissner et al., "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," J. Med. Chem. 46, 49-63, 2003.
Zhang et al., "Anti-sickling effect of MX-1520, a prodrug of vanillin: an in vivo study using rodents," Br. J. Haematol. 125, 788-95, 2004.
Davenport et al., "Heat shock protein inhibition is associated with activation of the unfolded protein response pathway in myeloma plasma cells," *Blood 110*, 2641-49, 2007.
Ding et al., "Linking of autophagy to ubiquitin-proteasome system is important for the regulation of endoplasmic reticulum stress and cell viability," *Am. J. pathol.* 171, 413-24, 2007.
Gomez et al., "Human X-box binding protein-1 confers both estrogen independence and antiestrogen resistance in breast cancer cell lines," *FASEB J. 21*, 4013-27, 2007.
Jiang & Wek, "Phosphorylation of the alpha-subunit of the eukaryotic initiation factor-2 (elF2alpha) reduces protein synthesis and enhances apoptosis in response to proeasome inhibition," *J. Biol. Chem.* 280, 14189-202, 2005.
Lee et al., "Proteasome inhibitors disrupt the unfolded protein response in myeloma cells," *Proc. Natl. Acad. Sci. USA 100*, 9946-51, 2003.
Pittelkow et al., "Carbocations in Action. Design, Synthesis, and Evaluation of a Highly Acid-Sensitive Naphthalene-Based Backbone Amide Linker for Solid-Phase Synthesis," *Org. Lett. 8*, 5817-20, 2006.
Rahmani et al., "The kinase inhibitor sorafenib induces cell death through a process involving induction of endoplasmic reticulum stress," *Mol. Cell. Biol.* 27, 5499-513, 2007.

Weng et al., "Chiral N-salicylidene vanadyl carboxylate-catalyzed enantioselective aerobic oxidation of α-hydroxy esters and amides," *Proc. Natl. Acad. Sci. USA 103*, 3522-27, 2006.
Baluja, "Acoustical studies of some Schiff bases in 1,4-dioxane and dimethylformamide at 318.15 K'," Russian Journal of Physical Chemistry, vol. 80, No. 7, Jul. 1, 2006, pp. 1056-1060.
Calinescu et al., "Spectral and magnetic studies on mixed-ligand complexes of Co(II) and Cu(II) with 2-hydroxy-1-naphthaldehyde dimethylhydrazone," Database CA (Online) Chemical Abstracts Service, 2004, XP-002684376, Database Accession No. 140:263004.
Cupertino et al., "Synthesis of cobalt(II) complexes of derivatised salicylaldoxime ligands; X-ray crystal structures of DMSO adducts of bis(3-nitro-5-methylsalicylaldoximato)cobalt(II) and bis(3-nitro-5-phenylsalicylaldoximato)cobalt(II)," Polyhedron, vol. 20, No. 26-27, Dec. 1, 2001, pp. 3239-3247.
El-Sonbati, "Stereochemistry of Uranyl Complexes of New Heterocyclic Nitrogen Containing Aldehydes.l. Novel Relationship for 0-U-0 Frequencies Center," Spectroscopy Letters, vol. 30, No. 3, Jan. 1, 1997, pp. 459-472.
Fiedler, "Synthesis of 8-hydroxyquinoline-7-aldehydes," Database Ca (Online) Chemical Abstracts Service, 2001, XP-002684377, Database Accession No. 60:60787, pp. 1-2.
Kehoe et al., "Tyrosylprotein Sulfotransferase Inhibitors Generated by Combinatorial Target-Guided Ligand Assembly." Bioorganic & Medicinal Chemistry Letters, vol. 12, No. 3, Feb.1, pp. 329-332, 2002.
Lo et al., "Heterobimetallic Zn(II)-Ln(III) Phenylene-Bridged Schiff Base Complexes, Computational Studies, and Evidence for Singlet Energy Transfer as the Main Pathway in the Sensitization of Near-Infrared Nd3+ Luminescence," Inorganic Chemistry, vol. 45, No. 23, Nov. 13, 2006, pp. 9315-9325.
Supsana et al., "DMF-Catalysed Thermal Dehydration of Aldoximes: A Convenient Access to Functionalized Aliphatic and Aromatic Nitriles," Synlett, 2007, No. 17, Oct. 1, 2007, pp. 2671-2674.
Tsumaki et al., "Coordinate valency rings. XXI. Some derivatives of salicylaldimine and hydrosalicylamide," Database CA (Online) Chemical Abstracts Service, 2001, XP-002684372, Database Accession No. 28:32534, pp. 1-2.
European Search Report for Application No. 12 17 1202, dated Oct. 1, 2012.
Choubal et al., "The action of hexamethylenetetramine on phenols and the methyl esters of phenolcarboxylic acids. VI. The synthesis and study of the arylamides of 1-formyl-2-hydroxy-3-naphthoic acid," Journal of the Indian Chemical Society, 35, pp. 860-864, 1958 (abstract).
Rodriguez et al., "Equilibrium constants and thermodynamic parameters in coordination compounds," Boletin del Instituto de Quimica de la Universidad Nacional Autonoma de Mexico, 20, pp. 56-67, 1968 (abstract).
Choubal et al., "The action of hexamethylenetetramine on phenols and the methyl esters of phenolcarboxylic acids. VI. The synthesis and study of the arylamides of 1-formyl-2-hydroxy-3-napthoic acid," Chemical Abstracts 53, Dec. 31, 1958.
Hoyer et al., "Formation of intramolecular hydrogen bonds by hindrance of the rotation of the proton," Chem. Abstracts 64, Dec. 31, 1966.
Ashram et al., "Synthesis of Hexahomotrioxacalix[3]naphthalenes and a Study of Their Alkali-Metal Cation Binding Properties," J. Org. Chem. 66, 1473-79, Oct. 23, 2001.
Grozinger et al., "Identification of a Class of Small Molecule Inhibitors of the Sirtuin Family of NAD-dependent Deacetylases by Phenotypic Screening," J. Biol. Chem. 276, 38837-43, Aug. 1, 2001.

* cited by examiner

FIG. 4
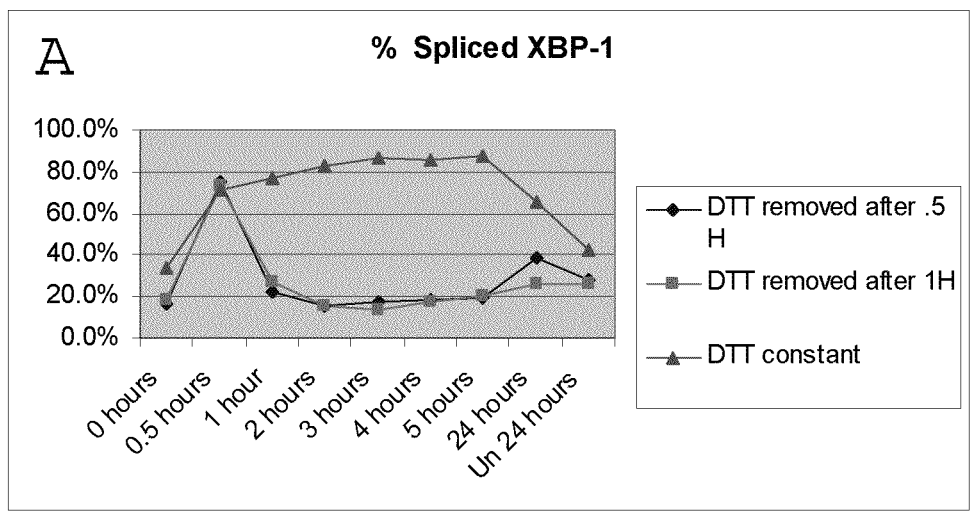
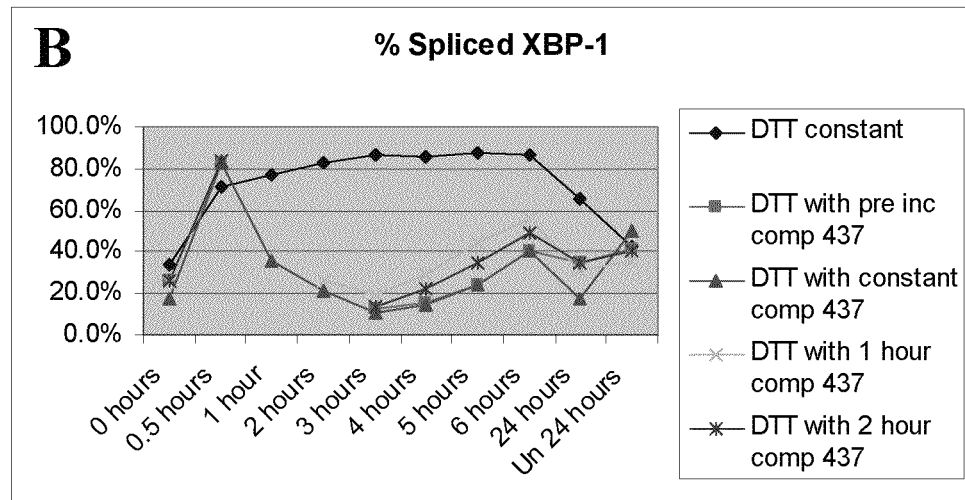

FIGS. 6A-B

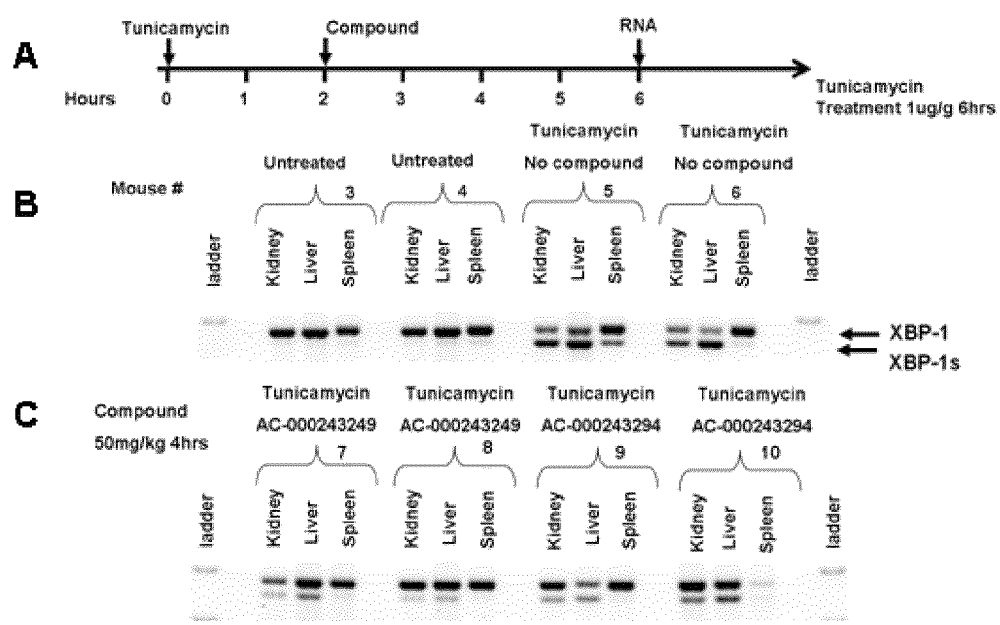
FIGS. 8A-C

IRE-1α INHIBITORS

This application is a continuation of Ser. No. 12/135,571 filed on Jun. 9, 2008, which claims the benefit of Ser. No. 60/942,743 filed Jun. 8, 2007. Each of these applications is incorporated herein by reference in its entirety.

FIELD OF THE INVENTION

The invention relates to IRE-1α inhibitors and their therapeutic uses.

BACKGROUND OF THE INVENTION

Protein folding stress in the endoplasmic reticulum of a cell initiates a signal transduction cascade termed the unfolded protein response or UPR. A key enzyme, inositol requiring enzyme 1 (IRE-1α), relieves protein folding stress by enhancing molecular chaperone activity and therefore protects cells from stress induced apoptosis. Inhibitors of IRE-1α are useful for treating at least B cell autoimmune diseases, certain cancers, and some viral infections.

BRIEF DESCRIPTION OF THE DRAWINGS

FIG. 4. Graphs showing that an IRE-1α inhibitor reversibly inhibits the activated form of the IRE-1α in cells. Cellular inhibition of XBP-1 splicing was measured using 10 μM compound 2 in HEK 293 cells. FIG. 4A shows relative amounts of spliced XBP-1 using standard RT-PCR when 2 mM DTT is added and left in culture (▲) or after washing DTT out 30 minutes (♦) or 1 hour after induction (■). The XBP-1 messenger RNA is rapidly converted to the spliced form when cells are stressed with DTT. Conversely, when the stress is removed, spliced XBP-1 is rapidly degraded by the cell and replaced by the unspliced form. FIG. 4B demonstrates that when compound 2 is added to DTT stressed cells 2 hours before (■), or 1 hour after DDT induction (▲), the unspliced form rapidly accumulates similar to the removal of the DTT stress, suggesting the compound inhibits the activated form of the enzyme. When the compound is washed out while leaving the DDT stress on, spliced XBP-1 increases over several hours after complete inhibition suggesting the inhibition is reversible (■, X, *). Percent splicing was determined by scanning gel for unspliced and spliced XBP-1 bands (as in FIG. 3). Enzyme activity is represented on the Y axis by the percent of spliced XBP-1 (calculated as the amount of spliced divided by the total amount of spliced and unspliced XBP-1).

FIG. 7A, 100 nM MG-132; FIG. 7B, 200 nM MG-132.

FIG. 8. Results of in vivo assays of IRE-1α inhibitors in mouse tissues. FIG. 8A, protocol for tunicamycin and IRE-1α inhibitor treatment. FIG. 8B, agarose gel of RT-PCR products demonstrating that IRE-1α specific XBP-1 splicing is largely inactive in the kidney, liver, and spleen of adult NOD-SCID mice. FIG. 8C, treatment with tunicamycin for 6 hours resulted in significant levels of spliced XBP-1 (Wu et al., 2007) FIG. 8C, agarose gel of RT-PCR products demonstrating diminished levels of spliced XBP-1 in mice treated with IRE-1α inhibitors four hours after IP treatment with tunicamycin. FIG. 8D, graphical representation of the average relative percentage of spliced XBP-1 over total XBP-1 from the two mice per group in FIGS. 8B and 8C.

DETAILED DESCRIPTION OF THE INVENTION

Figure 1:
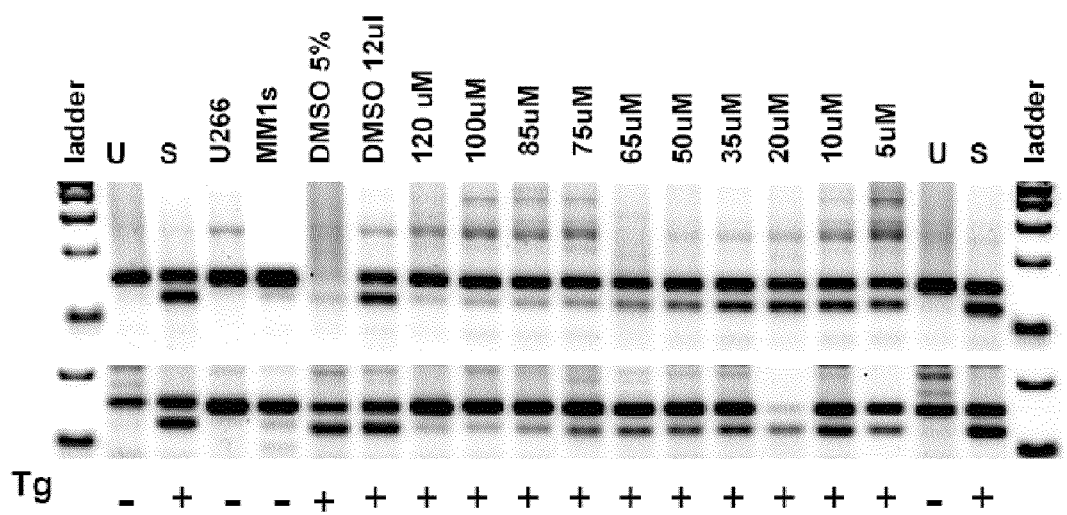
FIG. 1. Results of cell-based IRE-1α XBP-1-specific endoribonuclease inhibition by 6-bromo o-vanillin. 12 μL DMSO is 1.2%.

The invention provides IRE-1α inhibitor compounds and prodrugs and pharmaceutically acceptable salts thereof. The invention also provides pharmaceutical compositions and methods of using the IRE-1α inhibitor compounds, prodrugs, and pharmaceutically acceptable salts thereof therapeutically to treat disorders associated with the unfolded protein response. Patients who can be treated include those with B cell autoimmune diseases, certain cancers, and some viral infections.

The present invention comprises numerous chemical compounds related by structure and by function, as well as methods for their use. Various groupings of these compounds comprising from one to any number of them, and their uses, can be defined and constitute individual embodiments of the invention. Some embodiments will specifically include certain compounds whereas others will specifically exclude certain compounds. Criteria for inclusion or exclusion include specific structures or structural features, levels or ranges of activity (for example, $IC_{50}s$ or $EC_{50}s$), suitability for administration by a particular route of administration, disease treated, and the like.

IRE-1α Inhibitor Compounds

IRE-1α inhibitor compounds of the invention are aromatic and heteroaromatic hydroxyaldehydes which directly inhibit the enzyme. The compounds are understood to act through inhibition of the RNAse activity of enzyme. In particular embodiments of the invention this activity is detected as cleavage of a human mini-XBP-1 mRNA stem-loop substrate 5'-CAGUCCGCAGGACUG-3' (SEQ ID NO:1) by IRE-1α in vitro by at least 10, 15, 20, 25, 30, 40, 50, 60, or 75%. Other substrates also can be used to detect cleavage. See US 20070105123.

In some embodiments, compounds inhibit IRE-1α in the in vitro assay with an average $IC_{50}$ of approximately 20 μM (20,000 nM) or less (e.g., 20000, 15000, 10000, 7500, 7250, 7000, 6750, 6500, 6250, 6000, 5750, 5500, 5250, 5000, 4750, 4500, 4250, 4000, 3750, 3500, 3250, 3000, 2750, 2500, 2250, 2000, 1750, 1500, 1250, 1000, 950, 900, 850, 800, 750, 700, 650, 600, 550, 500, 450, 400, 350, 300, 250, 200, 150, 100, 90, 80, 70, 60, 50, 40, 30, 20, 15, 10, 5, 2, or 1 nM or less). In some embodiments, compounds inhibit IRE-1α in an in vivo XBP-1 splicing assay (e.g., in myeloma cells) with an average $EC_{50}$ of 80 μM (80,000 nM) or less (e.g., 80000, 75000, 70000, 65000, 60000, 55000, 50000, 45000, 40000, 35000, 30000, 25000, 20000, 15000, 10000, 7500, 7250, 7000, 6750, 6500, 6250, 6000, 5750, 5500, 5250, 5000, 4750, 4500, 4250, 4000, 3750, 3500, 3250, 3000, 2750, 2500, 2250, 2000, 1750, 1500, 1250, 1000, 950, 900, 850, 800, 750, 700, 650, 600, 550, 500, 450, 400, 350, 300, 250, 200, 150, 100, 90, 80, 70, 60, 50, 40, 30, 20, 15, 10, 5, 2, or 1 nM or less). IRE-1α inhibitor compounds can meet either of both of these criteria.

As is well known in the art, the aldehyde group in these compounds can be represented by any of the three equivalent forms shown below:

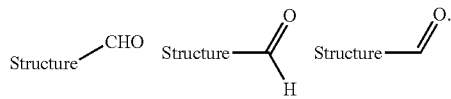

Compounds useful according to the invention are encompassed within structural formula (I):

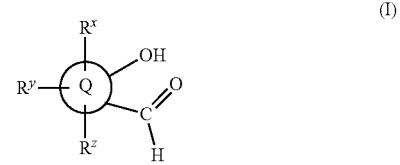

wherein:
the OH substituent is located ortho to the aldehyde substituent;
Q is an aromatic isocyclic or heterocyclic ring system selected from benzene, naphthalene, pyridine, pyridine N-oxide, thiophene, benzo[b]thiophene, benzo[c]thiophene, furan, pyrrole, pyridazine, pyrmidine, pyrazine, triazine, isoxazoline, oxazoline, thiazoline, pyrazoline, imidazoline, fluorine, biphenyl, quinoline, isoquinoline, cinnoline, phthalazine, quinazoline, quinoxaline, benzofuran, indole, isoindole, isobenzofuran, benzimidazole, 1,2-benzisoxazole, and carbazole;

$R^x$, $R^y$, and $R^z$ can be present or absent and are independently selected from hydrogen, aryl, heterocyclic, -A"$R^a$, —OH, —OA"$R^a$, —NO$_2$, —NH$_2$, —NHA"$R^a$, —N(A"$R^a$)(A'''$R^b$), —NHCOA"$R^a$, —NHCOOA"$R^a$, —NHCONH$_2$, —NHCONHA"$R^a$, —NHCON(A"$R^a$)(A'''$R^b$), halogen, —COOH, —COOA"$R^a$, —CONH$_2$, —CONHA"$R^a$, —CON(A"$R^a$)(A'''$R^b$), and

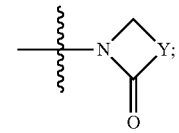

$R^a$ and $R^b$ are independently hydrogen, —COOH, —COOA, —CONH$_2$, —CONHA, —CONAA', —NH$_2$, —NHA, —NAA', —NCOA, —NCOOA, —OH, or —OA;

Y is $C_1$-$C_{10}$ alkylene or $C_2$-$C_8$ alkenylene, in which (a) one, two or three CH$_2$ groups may be replaced by O, S, SO, SO$_2$, NH, or NR$^c$ and/or (b) 1-7 H atoms may be independently replaced by F or Cl;

A and A' are:
(a) independently $C_1$-$C_{10}$ alkyl or $C_2$-$C_8$ alkenyl, in which (i) one, two or three CH$_2$ groups may be replaced by O, S, SO, SO$_2$, NH, or NR$^c$ and/or (ii) 1-7 H atoms may be independently replaced by F or Cl, aryl or heterocyclic; or
(b) A and A' together are alternatively $C_2$-$C_7$ alkylene, in which one, two or three CH$_2$ groups may be replaced by O, S, SO, SO$_2$, NH, NR$^c$, NCOR$^c$ or NCOOR$^c$, to form, for example, an alkylenedioxy group;

A", A'" are independently (a) absent, (b) $C_1$-$C_{10}$ alkylene, $C_2$-$C_8$ alkenylene, or $C_3$-$C_7$ cycloalkyl in which one, two or three CH$_2$ groups may be replaced by O, S, SO, SO$_2$, NH or NR$^c$ and/or 1-7 H atoms may be replaced by F and/or Cl; or (c) together are $C_2$-$C_7$ alkyl in which one, two or three CH$_2$ groups may be replaced by O, S, SO, SO$_2$, NH, NR$^c$, NCOR$^c$ or NCOOR$^c$, $R^c$ is $C_1$-$C_{10}$ alkyl, $C_3$-$C_7$ cycloalkyl, $C_4$-$C_8$ alkylenecycloalkyl, or $C_2$-$C_8$ alkenyl; in which one, two or three CH₂ groups may be replaced by O, S, SO, SO₂, NH, NMe, NEt and/or by —CH=CH— groups, 1-7 H atoms may be replaced by F and/or Cl, and/or 1 H atom may be replaced by $R^a$;

aryl is phenyl, benzyl, naphthyl, fluorenyl or biphenyl, each of which is unsubstituted or monosubstituted, disubstituted or trisubstituted by halogen, —CF₃, —$R^f$, —$OR^d$, —N($R^d$)₂), —NO₂, —CN, —$COOR^d$, CON($R^d$)₂, —$NR^d COR^e$, —$NR^d CON(R^e)_2$, —$NR^d SO_2 A$, —$COR^d$, —$SO_2 N(R^d)_2$, —$S(O)_m R^f$, AA' together, or —O(aryl), $R^d$ and $R^e$ are independently H or C₁-C₆ alkyl;

$R^f$ is C₁-C₆ alkyl;

heterocyclic is a monocyclic or bicyclic saturated, unsaturated or aromatic heterocyclic ring having 1 to 2 N, O and/or S atoms, which may be unsubstituted or monosubstituted or disubstituted by carbonyl oxygen, halogen, $R^f$, —$OR^d$, —N($R^d$)₂, —NO₂, —CN, —$COOR^d$, —CON($R^d$)₂, —$NR^d COR^e$, —$NR^d CON(R^e)_2$, —$NR^f SO_2 R^e$, —$COR^d$, —$SO_2 NR^d$ and/or —$S(O)_m R^f$; and m is 0, 1 or 2.

Groups of IRE-1α inhibitor compounds within formula (I) include the following, in which $R^x$, $R^y$, and $R^z$ are as defined above:

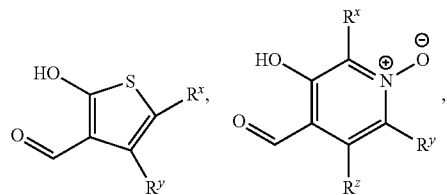
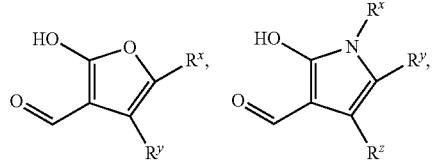
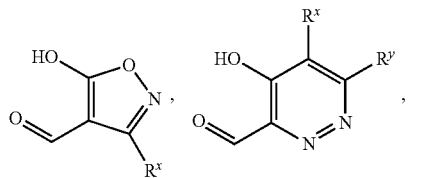
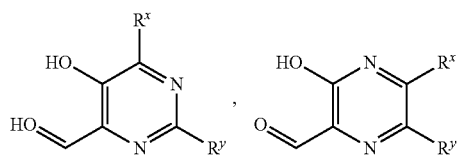

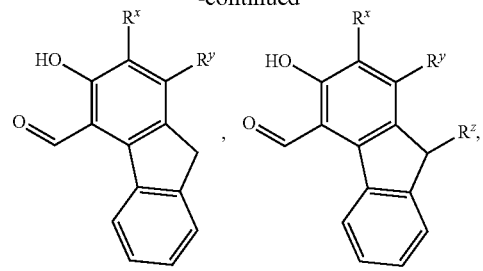
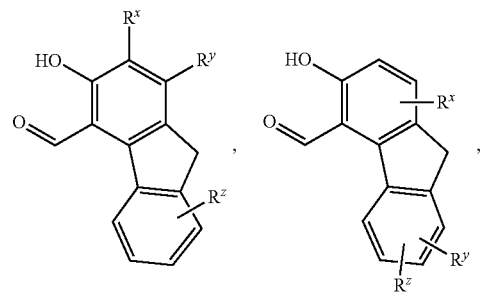
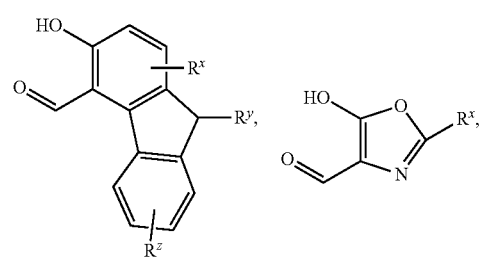
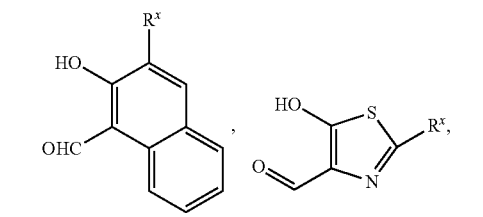
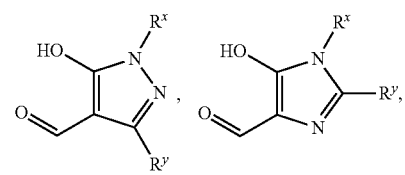
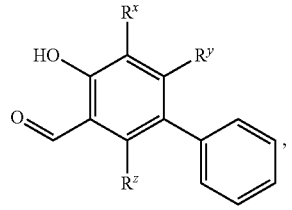
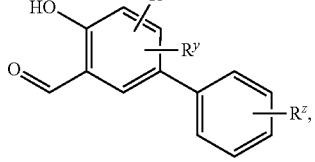

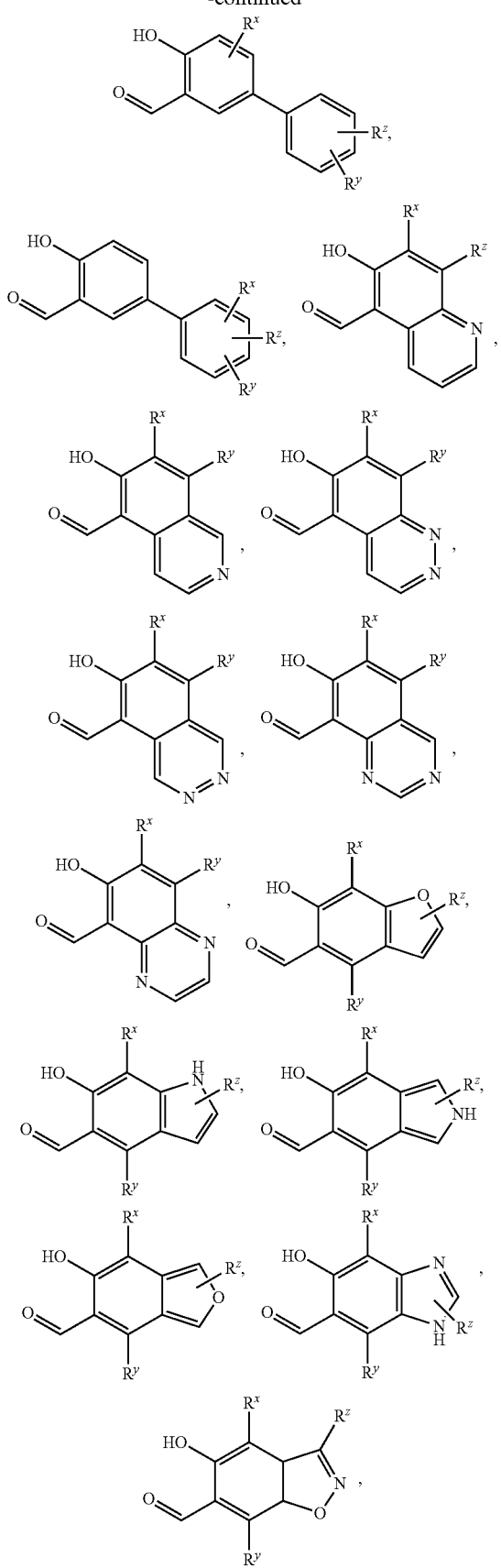

C$_1$-C$_{10}$ alkyl (i.e., alkyl having 1, 2, 3, 4, 5, 6, 7, 8, 9, or 10 carbon atoms) and C$_1$-C$_6$ alkyl (i.e., alkyl having 1, 2, 3, 4, 5, or 6 carbon atoms) can be branched or unbranched and can be substituted or unsubstituted. Optional substituents include halogens (e.g., F, Cl, I, Br). Examples include methyl, ethyl, trifluoromethyl, pentafluoroethyl, propyl, isopropyl, butyl, isobutyl, sec-butyl, tert-butyl, n-pentyl, neopentyl, isopentyl, n-hexyl, and n-decyl. In some embodiments C$_1$-C$_{10}$ is methyl, ethyl, trifluoromethyl, propyl, isopropyl, butyl, n-pentyl, n-hexyl, or n-decyl.

C$_3$-C$_7$ cycloalkyl includes cyclopropyl, cyclobutyl, cyclopentyl, cyclohexyl, and cycloheptyl. In some embodiments, C$_3$-C$_7$ cycloalkyl is cyclopentyl.

In some embodiments C$_2$-C$_8$ alkenyl is vinyl, allyl, 2-butenyl, 3-butenyl, isobutenyl, sec-butenyl, 4-pentenyl, isopentenyl or 5-hexenyl. In some embodiments C$_2$-C$_8$ alkenyl is 4-pentenyl, isopentenyl, or 5-hexenyl.

C$_1$-C$_{10}$ alkylene is preferably unbranched and in some embodiments is methylene or ethylene, propylene, or butylene.

In some embodiments C$_2$-C$_8$ alkenylene is ethenylene, or propenylene.

C$_2$-C$_7$ alkylene is preferably unbranched. In some embodiments, C$_2$-C$_7$ alkylene is ethylene, propylene, or butylene.

In some embodiments C$_4$-C$_8$ alkylenecycloalkyl is cyclohexylmethyl or cyclopentylethyl.

In some embodiments R$^x$, R$^y$, and R$^z$ are independently —OH, —OA, —NO$_2$, or —NAA'.

In some embodiments, Q is benzene, naphthalene, thiophene, benzo[b]thiophene, or benzo[c]thiophene, R$^x$ and R$^y$ are hydrogen, and R$^z$ is hydrogen or —OR$^d$, —NO$_2$, pyridyl, or pyridyl N-oxide.

In some embodiments, R$^x$ is hydrogen, OR$^d$, NO$_2$, —NH$_2$, or —NHCOOA"R$^a$.

In some embodiments R$^a$ is hydrogen, —COOH, —NHA, or —NAA'.

In some embodiments R$^c$ is C$_1$-C$_{10}$ alkyl or C$_1$-C$_6$ alkyl.

In some embodiments Y is methylene, ethylene, propylene, or butylene.

In some embodiments A and A' are independently C$_1$-C$_{10}$ alkyl; C$_1$-C$_{10}$ alkyl in which 1-7 hydrogen atoms are replaced by F and/or Cl; aryl; or heterocyclic.

In some embodiments A" and A'" are independently absent or are C$_1$-C$_{10}$ alkylene in which one CH$_2$ group may be replaced by NH or NR$^c$.

In some embodiments A" and A'" are together C$_2$-C$_7$ alkylene chain in which one CH$_2$ group may be replaced by NH or NR$^c$.

In some embodiments, aryl is monosubstituted, disubstituted or trisubstituted with methyl, ethyl, propyl, butyl, fluorine, chlorine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, sulfonamido, methylsulfonamido, ethylsulfonamido, propylsulfonamido, butylsulfonamido, dimethylsulfonamido, carboxyl, methoxycarbonyl, ethoxycarbonyl, or aminocarbonyl.

In some embodiments, heterocyclic is selected from 2-furyl, 3-furyl, 2-thienyl, 3-thienyl, 1-pyrrolyl, 2-pyrrolyl, 3-pyrrolyl, 1-imidazolyl, 2-imidazolyl, 4-imidazolyl, 5-imidazolyl, 1-pyrrolyl, 3-pyrazolyl, 4-pyrazolyl, 5-pyrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidyl, 4-pyrimidyl, 5-pyrimidinyl, 6-pyrimidinyl, 1,2,3-triazol-1-yl, 1,2,3-triazol-4-yl, or 1,2,3-triazol-5-yl, 1,2,4-triazol-1-yl, 1,2,4-triazol-3-yl, 1,2,4-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl or 1,3,4-thiadiazol-5-yl, 1,2,4-thiadiazol-3-yl, or 1,2,4-thiadiazol-3-5-yl, 1,2,3-thiadiazol-4-yl, 1,2,3-thiadiazol-5-yl, 3-pyridazinyl, 4-pyridazinyl, pyrazinyl, 1-indolyl, 2-indolyl, 3-indolyl, 4-indolyl, 5-indolyl, 6-indolyl, 7-indolyl, 4-isoindolyl, 5-isoindolyl, 1-benzimidazolyl, 2-benzimidazolyl, 4-benzimidazolyl, 5-benzimidazolyl, 1-benzopyrazolyl, 3-benzopyrazolyl, 4-benzopyrazolyl, 5-benzopyrazolyl, 6-benzopyrazolyl, 7-benzopyrazolyl, 2-benzoxazolyl, 4-benzoxazolyl, 5-benzoxazolyl, 6-benzoxazolyl, 7-benzoxazolyl, 3-benzisoxazolyl, 4-benzisoxazolyl, 5-benzisoxazolyl, 6-benzisoxazolyl, 7-benzisoxazolyl, 2-benzothiazolyl, 4-benzothiazolyl, 5-benzothiazolyl, 6-benzothiazolyl, 7-benzothiazolyl, 2-benzisothiazolyl, 4-benzisothiazolyl, 5-benzisothiazolyl, 6-benzisothiazolyl, 7-benzisothiazolyl, 4-benz-2,1,3-oxadiazolyl, 5-benz-2,1,3-oxadiazolyl, 6-benz-2,1,3-oxadiazolyl, 7-benz-2,1,3-oxadiazolyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 5-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 5-quinoxalinyl, 6-quinoxalinyl, 2-2H-benz-1,4-oxazinyl, 3-2H-benz-1,4-oxazinyl, 5-2H-benz-1,4-oxazinyl, 6-2H-benz-1,4-oxazinyl, 7-2H-benz-1,4-oxazinyl, 8-2H-benz-1,4-oxazinyl, 1,3-benzodioxol-5-yl, 1,4-benzodioxan-6-yl, 2,1,3-benzothiadiazol-4-yl, 2,1,3-benzothiadiazol-5-yl, and 2,1,3-benzoxadiazol-5-yl.

The heterocyclic radicals may also be partially or completely hydrogenated. For example, in some embodiments heterocyclic is 2,3-dihydro-2-furyl, 2,3-dihydro-3-furyl, 2,3-dihydro-4-furyl, 2,3-dihydro-5-furyl, 2,5-dihydro-2-furyl, 2,5-dihydro-3-furyl, 2,5-dihydro-4-furyl, 2,5-dihydro-5-furyl, tetrahydro-2-furyl, tetrahydro-3-furyl, 1,3-dioxolan-4-yl, tetrahydro-2-thienyl, tetrahydro-3-thienyl, 2,3-dihydro-1-pyrrolyl, 2,3-dihydro-2-pyrrolyl, 2,3-dihydro-3-pyrrolyl, 2,3-dihydro-4-pyrrolyl, 2,3-dihydro-5-pyrrolyl, 2,5-dihydro-1-pyrrolyl, 2,5-dihydro-2-pyrrolyl, 2,5-dihydro-3-pyrrolyl, 2,5-dihydro-4-pyrrolyl, 2,5-dihydro-5-pyrrolyl, 1-pyrrolidinyl, 2-pyrrolidinyl, 3-pyrrolidinyl, tetrahydro-1-imidazolyl, tetrahydro-2-imidazolyl, tetrahydro-4-imidazolyl, 2,3-dihydro-1-pyrazolyl, 2,3-dihydro-2-pyrazolyl, 2,3-dihydro-3-pyrazolyl, 2,3-dihydro-4-pyrazolyl, 2,3-dihydro-5-pyrazolyl, tetrahydro-1-pyrazolyl, tetrahydro-3-pyrazolyl, tetrahydro-4-pyrazolyl, 1,4-dihydro-1-pyridyl, 1,4-dihydro-2-pyridyl, 1,4-dihydro-3-pyridyl, 1,4-dihydro-4-pyridyl, 1,2,3,4-tetrahydro-1-, 1,2,3,4-tetrahydro-2-, 1,2,3,4-tetrahydro-3-pyridyl, 1,2,3,4-tetrahydro-4-pyridyl, 1,2,3,4-tetrahydro-5-pyridyl, 1,2,3,4-tetrahydro-6-pyridyl, 1-piperidinyl, 2-piperidinyl, 3-piperidinyl, 4-piperidinyl, 2-morpholinyl, 3-morpholinyl, 4-morpholinyl, tetrahydro-2-pyranyl, tetrahydro-3-pyranyl, tetrahydro-4-pyranyl, 1,4-dioxanyl, 1,3-dioxan-2-yl, 1,3-dioxan-4-yl, 1,3-dioxan-5-yl, hexahydro-1-pyridazinyl, hexahydro-3-pyridazinyl, hexahydro-4-pyridazinyl, hexahydro-1-pyrimidinyl, hexahydro-2-pyrimidinyl, hexahydro-4-pyrimidinyl, hexahydro-5-pyrimidinyl, 1-piperazinyl, 2-piperazinyl, 3-piperazinyl, 1,2,3,4-tetrahydro-1-, 1,2,3,4-tetrahydro-2-quinolyl, 1,2,3,4-tetrahydro-3-quinolyl, 1,2,3,4-tetrahydro-4-quinolyl, 1,2,3,4-tetrahydro-5-quinolyl, 1,2,3,4-tetrahydro-6-quinolyl, 1,2,3,4-tetrahydro-7-quinolyl, 1,2,3,4-tetrahydro-8-quinolyl, 1,2,3,4-tetrahydro-1-isoquinolyl, 1,2,3,4-tetrahydro-2-isoquinolyl, 1,2,3,4-tetrahydro-3-isoquinolyl, 1,2,3,4-tetrahydro-4-isoquinolyl, 1,2,3,4-tetrahydro-5-isoquinolyl, 1,2,3,4-tetrahydro-6-isoquinolyl, 1,2,3,4-tetrahydro-7-isoquinolyl, 1,2,3,4-tetrahydro-8-isoquinolyl, 2-3,4-dihydro-2H-benzo-1,4-oxazinyl, 3-3,4-dihydro-2H-benzo-1,4-oxazinyl, 5-3,4-dihydro-2H-benzo-1,4-oxazinyl, 6-3,4-dihydro-2H-benzo-1,4-oxazinyl, 7-3,4-dihydro-2H-benzo-1,4-oxazinyl, 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5-yl, 2,3-dihydrobenzofuran-6-yl, 2,3-(2-oxomethylenedioxy)phenyl, 3,4-dihydro-2H-1,5-benzodioxepin-6-yl, 3,4-dihydro-2H-1,5-benzodioxepin-7-yl, 2,3-dihydrobenzofuranyl, or 2,3-dihydro-2-oxofuranyl.

In some other embodiments, heterocyclic is unsubstituted pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl, or quinoxalinyl. In other embodiments, heterocyclic is pyridyl.

In some embodiments, heterocyclic is a monocyclic saturated or unsaturated heterocyclic ring having 1 to 2 N and/or O atoms, which may be monosubstituted or disubstituted by carbonyl oxygen, OH or OA, such as 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]-octan-3-on-2-yl, or 2-oxopiperidin-1-yl. In some embodiments heterocyclic is 2-oxopiperidin-1-yl.

In other embodiments, heterocyclic is a monocyclic saturated heterocyclic radical having 1 to 2 N atoms, which may be mono-substituted or disubstituted by $C_1$-$C_6$ alkyl.

Groups of IRE-1α inhibitor compounds within formula (I) also include those having the structural formula (II)

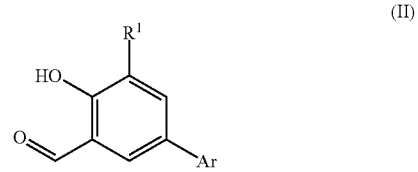

(II)

wherein:
R$^1$ is hydrogen, halogen, —NO$_2$, —OCH$_3$, or —OCH$_2$CH$_3$; and

Ar is

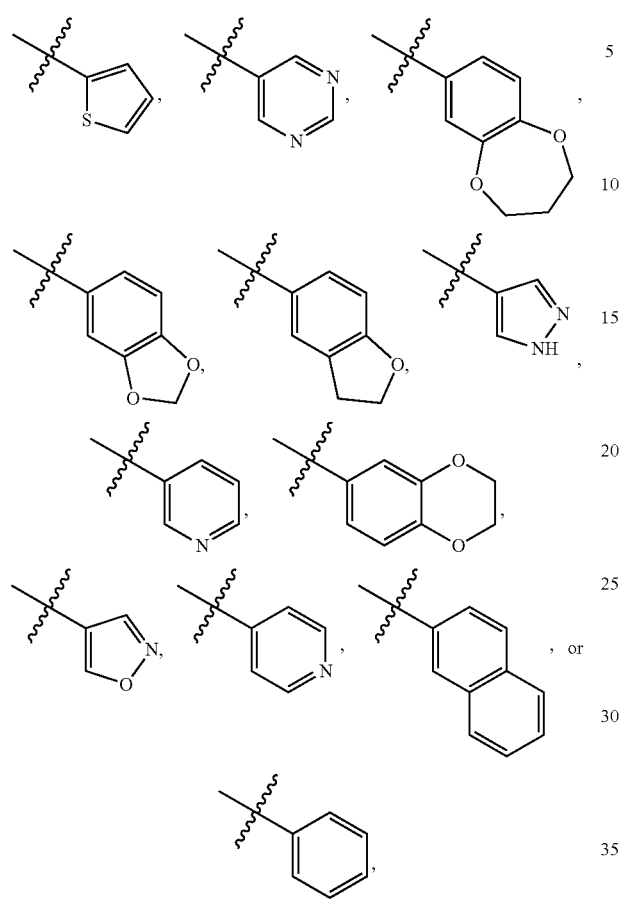

each of which may be unsubstituted or substituted with 1, 2, or 3 substitutents independently selected from halogen, —OH, —COOH, —CH$_2$OCH$_3$, C$_1$-C$_3$ alkyl, C$_1$-C$_3$ alkoxy, —CH$_2$OH, phenyloxy, and phenyl-C$_1$-C$_3$ alkoxy. Alkoxys may be linear or branched.

In some embodiments R$^1$ is —OCH$_3$.

Representative IRE-1α inhibitor compounds of formula (II) include those listed in Tables 1 and 2.

TABLE 1

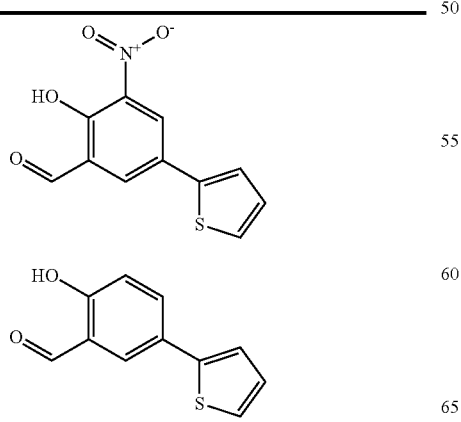

TABLE 1-continued

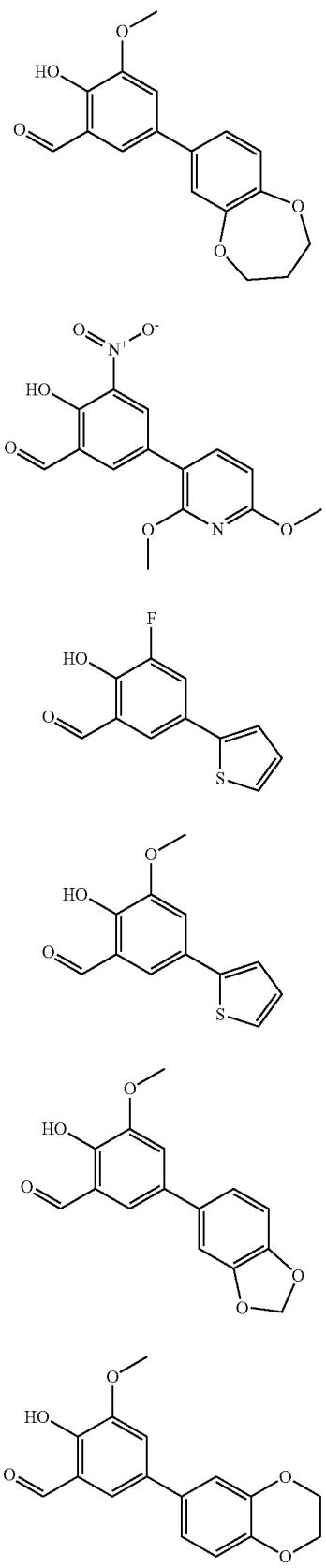

TABLE 1-continued

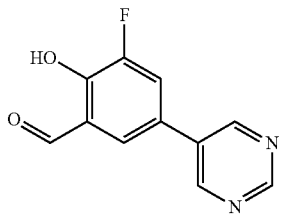 [SMILES: O=Cc1cc(-c2cncnc2)cc(F)c1O]

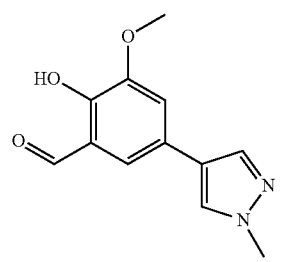 [SMILES: COc1cc(-c2cnn(C)c2)cc(C=O)c1O]

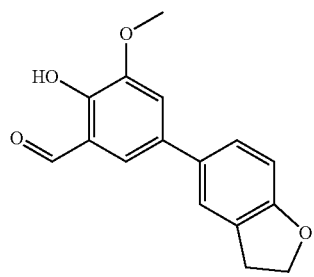 [SMILES: COc1cc(-c2ccc3c(c2)CCO3)cc(C=O)c1O]

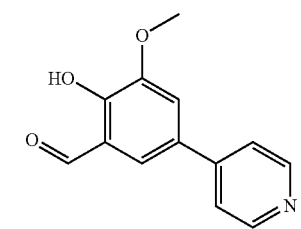 [SMILES: COc1cc(-c2ccncc2)cc(C=O)c1O]

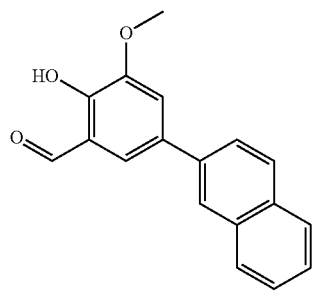 [SMILES: COc1cc(-c2ccc3ccccc3c2)cc(C=O)c1O]

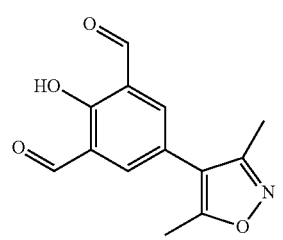 [SMILES: Cc1noc(C)c1-c1cc(C=O)c(O)c(C=O)c1]

Groups of IRE-1α inhibitor compounds within formula (I) also include those having the structural formula (III):

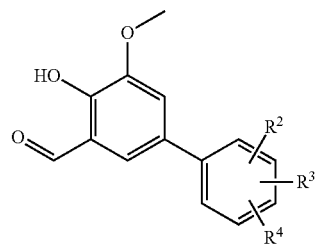

wherein $R^2$, $R^3$, and $R^4$ are independently selected from hydrogen, halogen, —OH, —COOH, —CH$_2$OCH$_3$, C$_1$-C$_3$ alkyl, C$_1$-C$_3$ alkoxy, —CH$_2$OH, phenyloxy, and phenyl-C$_1$-C$_3$ alkoxy.

Representative IRE-1α inhibitor compounds of formula (III) include those listed in Table 2.

TABLE 2

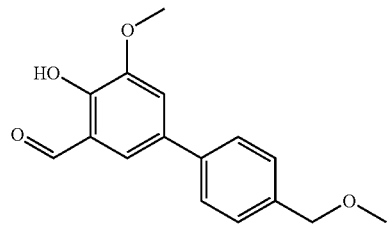 [SMILES: COCc1ccc(-c2cc(C=O)c(O)c(OC)c2)cc1]

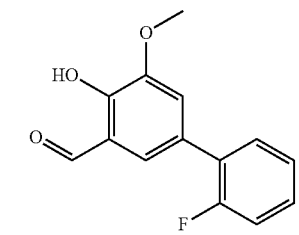 [SMILES: COc1cc(-c2ccccc2F)cc(C=O)c1O]

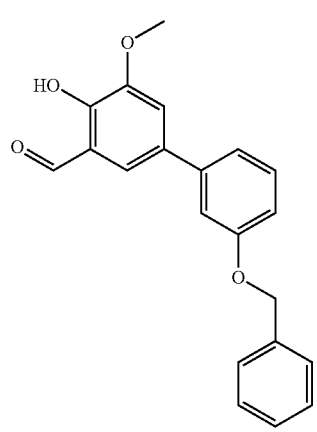 [SMILES: COc1cc(-c2cccc(OCc3ccccc3)c2)cc(C=O)c1O]

TABLE 2-continued
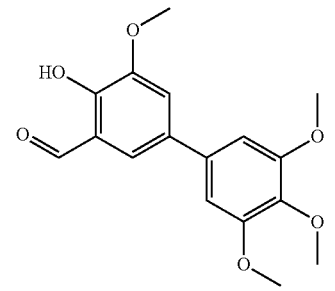 [SMILES: COc1cc(-c2cc(OC)c(OC)c(OC)c2)cc(C=O)c1O]
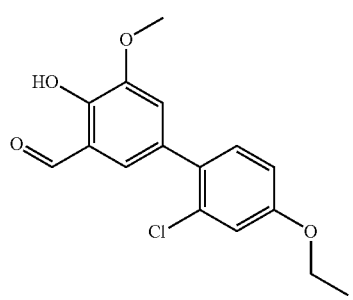 [SMILES: CCOc1ccc(-c2cc(C=O)c(O)c(OC)c2)c(Cl)c1]
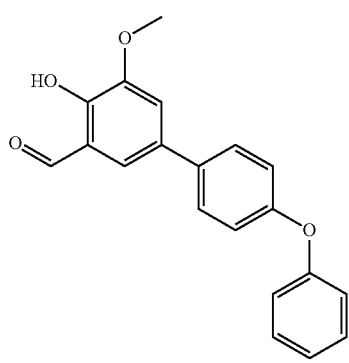 [SMILES: COc1cc(-c2ccc(Oc3ccccc3)cc2)cc(C=O)c1O]
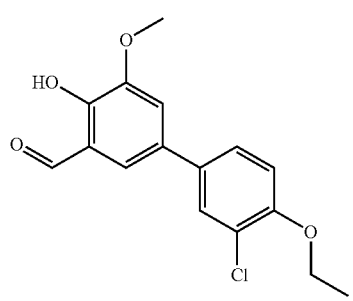 [SMILES: CCOc1ccc(-c2cc(C=O)c(O)c(OC)c2)cc1Cl]
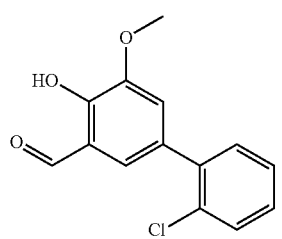 [SMILES: COc1cc(-c2ccccc2Cl)cc(C=O)c1O]
TABLE 2-continued
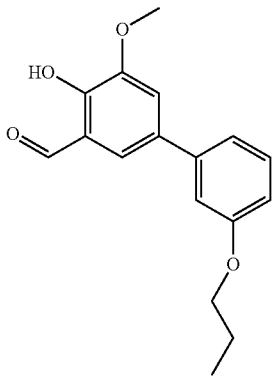 [SMILES: CCCOc1cccc(-c2cc(C=O)c(O)c(OC)c2)c1]
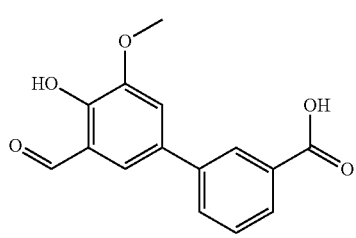 [SMILES: COc1cc(-c2cccc(C(=O)O)c2)cc(C=O)c1O]
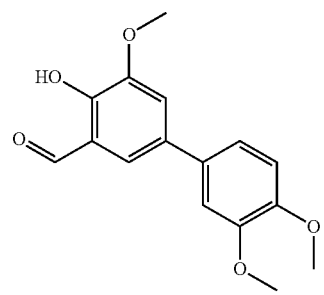 [SMILES: COc1ccc(-c2cc(C=O)c(O)c(OC)c2)cc1OC]
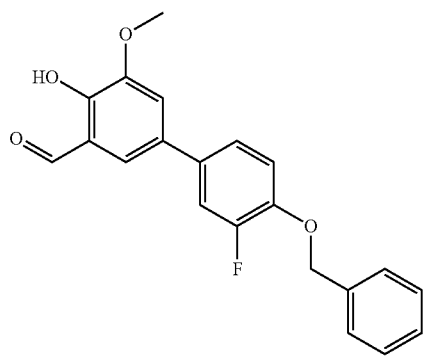 [SMILES: COc1cc(-c2ccc(OCc3ccccc3)c(F)c2)cc(C=O)c1O]
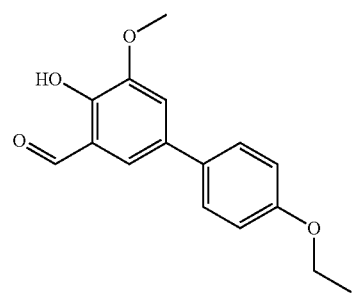 [SMILES: CCOc1ccc(-c2cc(C=O)c(O)c(OC)c2)cc1]

TABLE 2-continued
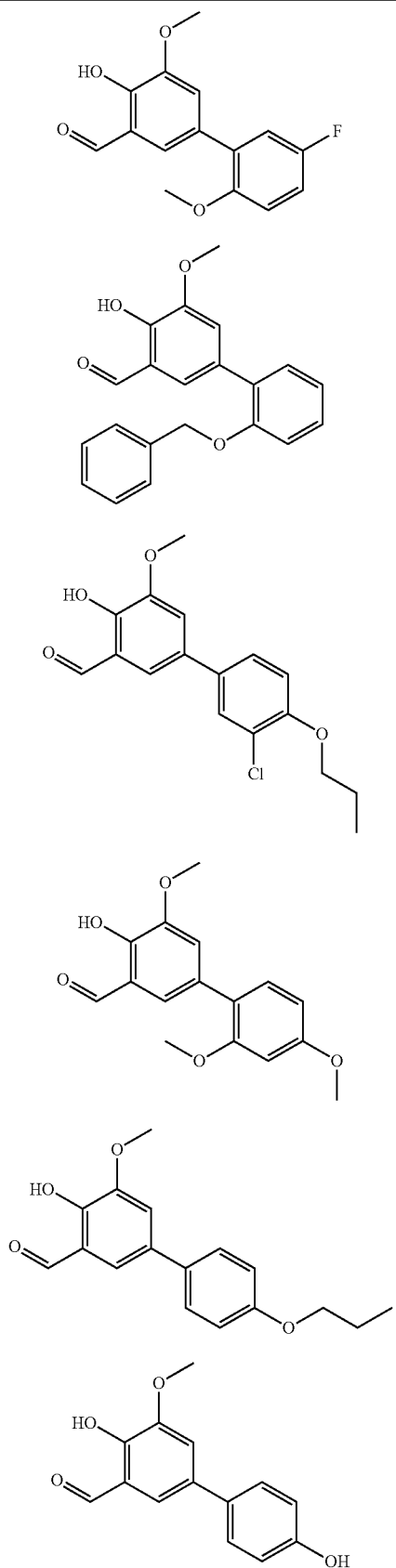
TABLE 2-continued
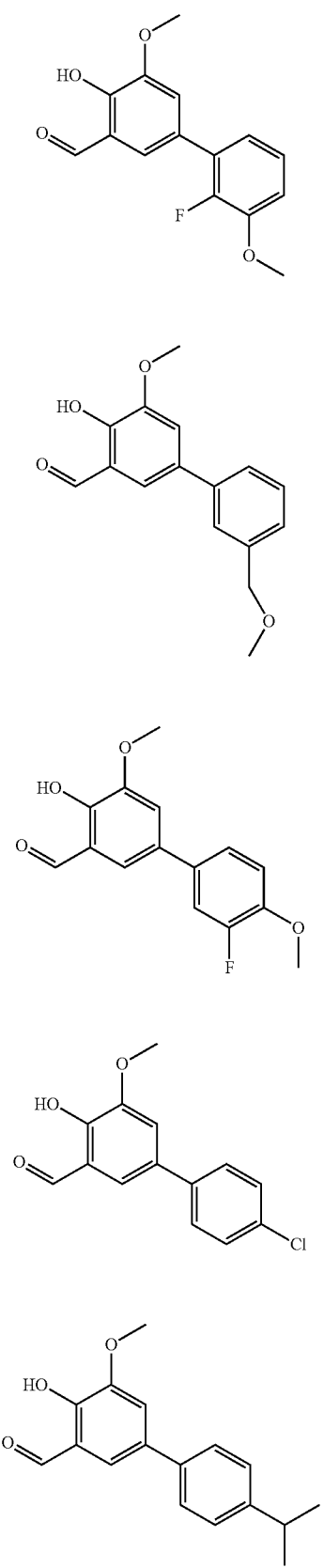

TABLE 2-continued
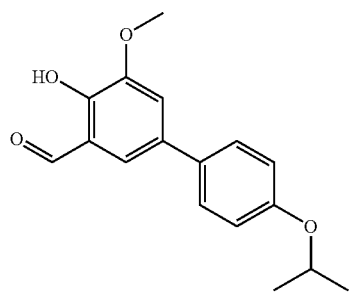 [SMILES: COc1cc(-c2ccc(OC(C)C)cc2)cc(C=O)c1O]
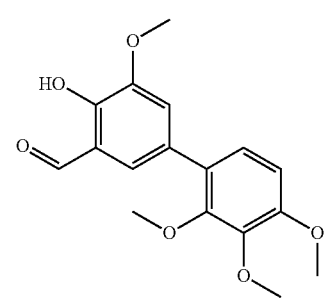 [SMILES: COc1cc(-c2ccc(OC)c(OC)c2OC)cc(C=O)c1O]
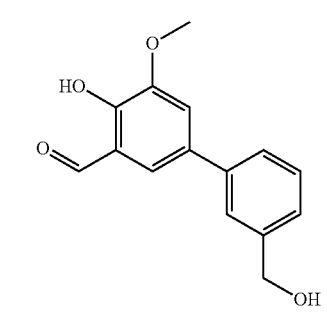 [SMILES: COc1cc(-c2cccc(CO)c2)cc(C=O)c1O]
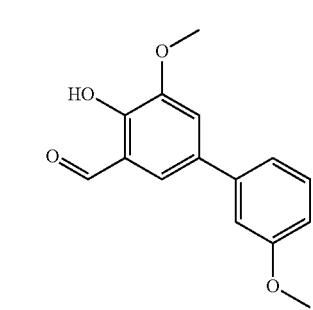 [SMILES: COc1cccc(-c2cc(C=O)c(O)c(OC)c2)c1]
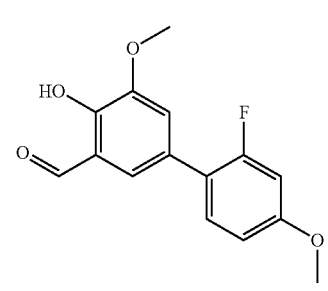 [SMILES: COc1ccc(-c2cc(C=O)c(O)c(OC)c2)c(F)c1]
TABLE 2-continued
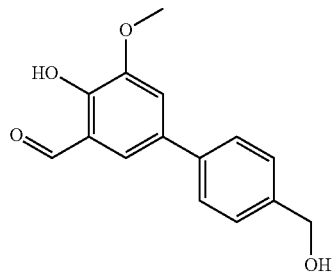 [SMILES: COc1cc(-c2ccc(CO)cc2)cc(C=O)c1O]
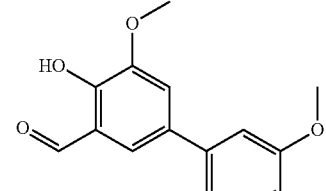
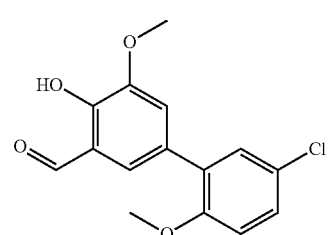
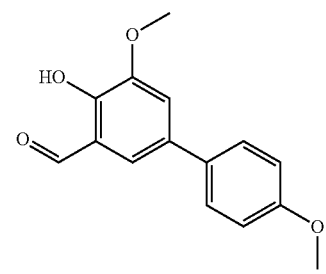 [SMILES: COc1ccc(-c2cc(C=O)c(O)c(OC)c2)cc1]
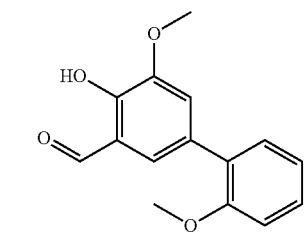 [SMILES: COc1ccccc1-c1cc(C=O)c(O)c(OC)c1]
Groups of IRE-1α inhibitor compounds within formula (I) also include those having the structural formula (IV):
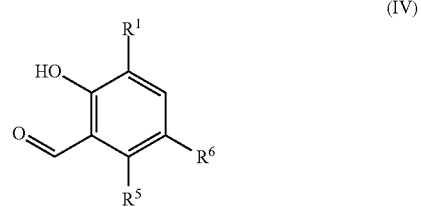
(IV)

wherein:
R¹ is selected from hydrogen, —OH, —OCH₃, —OCH₂CH₃, —C=O, or —NO₂; and
R⁵ and R⁶ independently are hydrogen, halogen, $C_1$-$C_3$ alkyl, or —NO₂.

In some embodiments, the IRE-1α inhibitor compounds have the structural formula (IV) with the exception of compounds in which:
R¹, R⁵, and R⁶ are each hydrogen;
R¹ is —OCH₃, and R⁵ and R⁶ are both hydrogen;
R¹ and R⁵ are both hydrogen and R⁶ is fluorine;
R¹ and R⁶ are both —NO₂ and R⁵ is hydrogen;
R¹ and R⁵ are both hydrogen and R⁶ is —CH₃;
R¹ is —CH₃ and R⁵ and R⁶ are both hydrogen;
R¹ is —OCH₃, R⁵ is

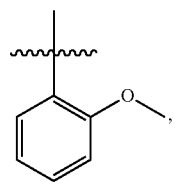 [SMILES: *c1ccccc1OC]

and R⁶ is hydrogen;
R¹ and R⁶ are both Cl, I, or F;
R¹ is Br, and R⁶ is Cl;
R¹ is —NO₂, and R⁶ is Br;
R¹ is carbonyl, and R⁶ is Cl or methyl;
R¹ is methoxy, and R⁶ is —NO₂, Br, methoxy, or Cl; and
R¹ is methoxy, and R⁵ is Br.

Other IRE-1α inhibitor compounds have the following structural formula:

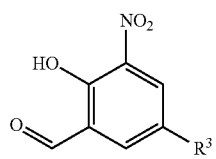

(V)

wherein R³ is as defined above. Representative IRE-1α inhibitor compounds of Formula (V) include:

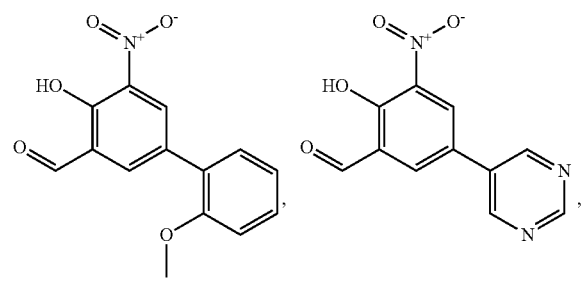

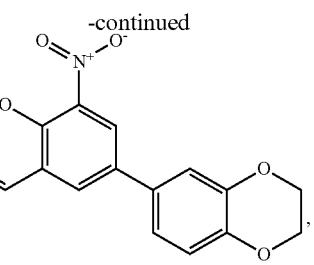

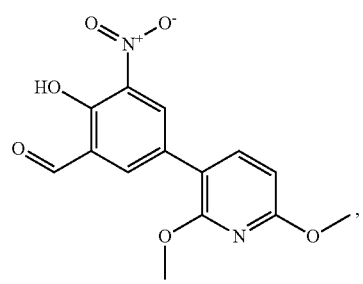

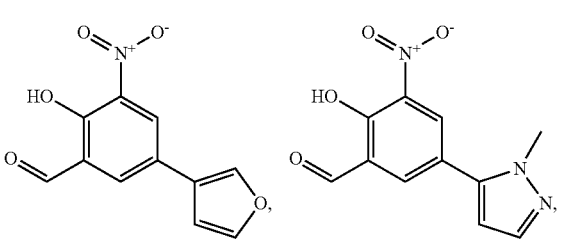

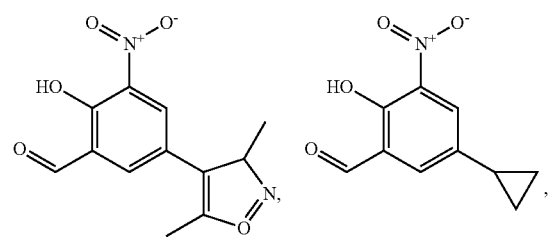

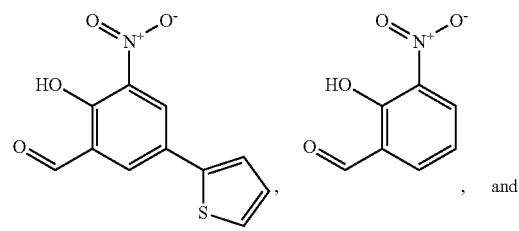

, and

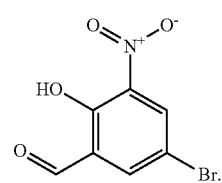

Other IRE-1α inhibitor compounds have structural formula (VI):

(VI)

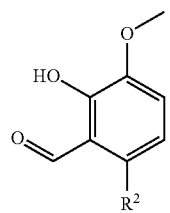

wherein R² is as defined above. For example, IRE-1α inhibitor compounds in which R² is phenyl can have the following structure:

(VII)

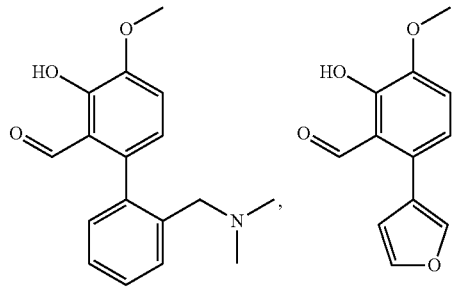

wherein R⁴ and R⁵ independently are selected from the substituents for R² and R³ defined above.

Representative IRE-1α inhibitor compounds of Formula (VI) include:

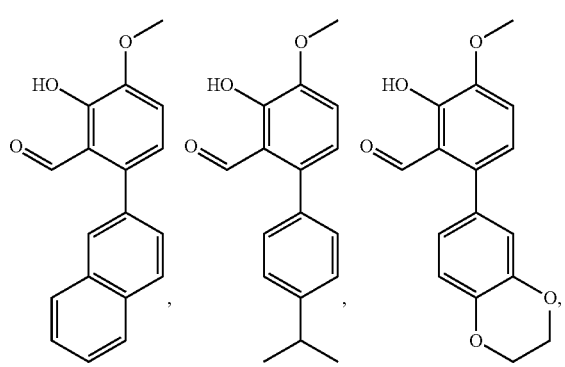

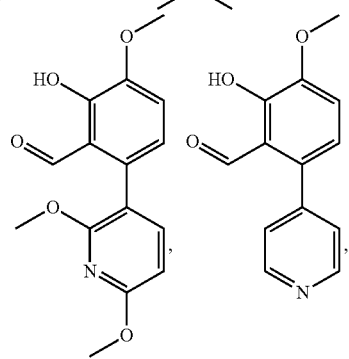

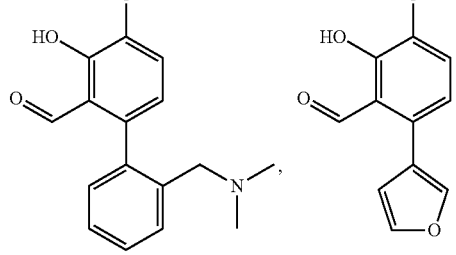

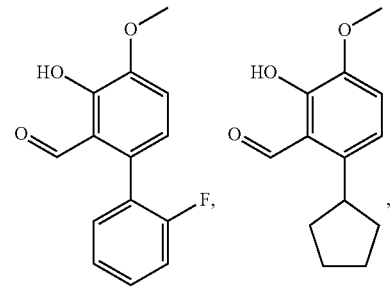

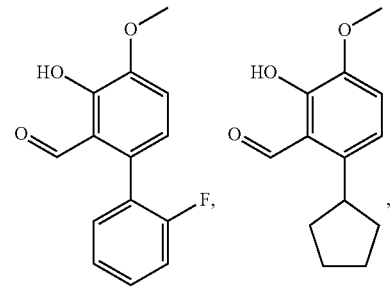

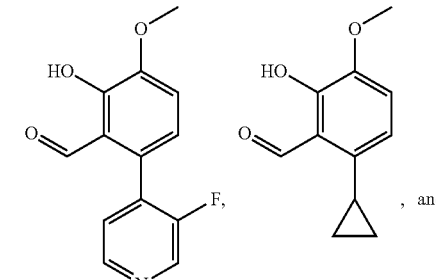

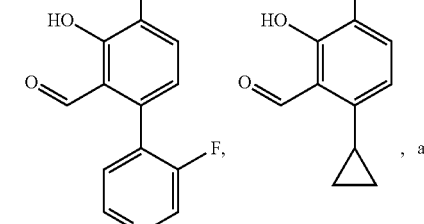

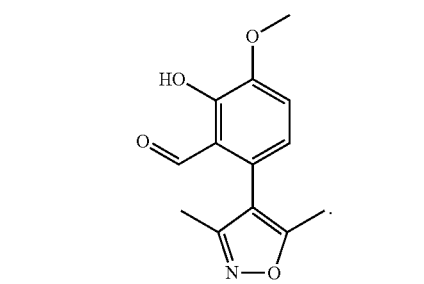 [SMILES: COc1ccc(-c2c(C)noc2C)c(C=O)c1O], and

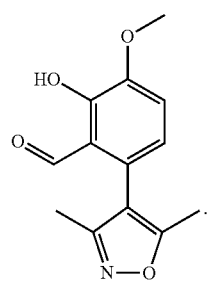

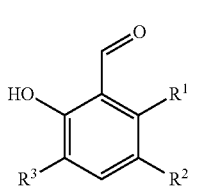

Other useful IRE-1α inhibitor compounds are provided in Table 3, below.

In some embodiments, IRE-1α inhibitor compounds have structural formula (A), which falls within the scope of formula (I):

(A)

wherein:

R¹ is hydrogen, halogen, or a 5- or 6-membered heterocyclic containing one or two heteroatoms independently selected from nitrogen, oxygen, and sulfur;

$R^2$ is hydrogen,

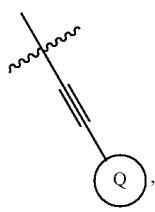

phenyl, or a 5- or 6-membered heterocyclic containing 1 or 2 heteroatoms independently selected from nitrogen, oxygen, and sulfur, wherein the heterocyclic is optionally benzofused and wherein the heterocyclic is optionally substituted by 1, 2, or 3 substituents independently selected from

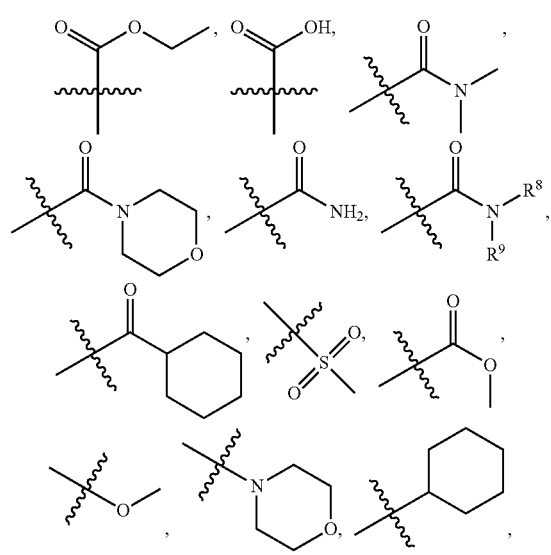

$C_1$-$C_3$ linear or branched alkyl,

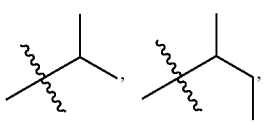

$C_1$-$C_3$ phenylalkyl, $C_1$-$C_3$ alkoxyphenylalkyl,

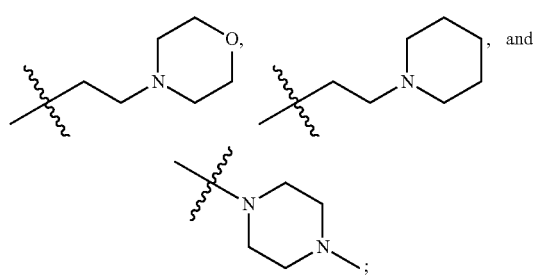

$R^3$ is hydrogen, halogen, —$NO_2$, $C_1$-$C_3$ linear or branched alkoxy, $C_1$-$C_3$ linear or branched hydroxyl alkyl,

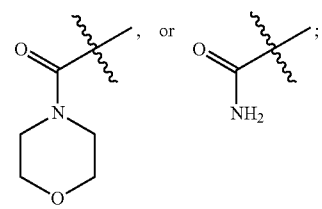

and

Q is a five- or six-membered heterocycle.

In some compounds of structural formula (A), $R^1$ is selected from the group consisting of hydrogen,

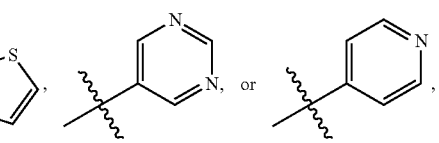

and Br.

In some compounds of structural formula (A) $R^2$ is selected from the group consisting of hydrogen,

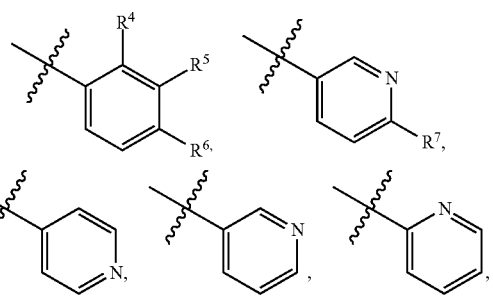

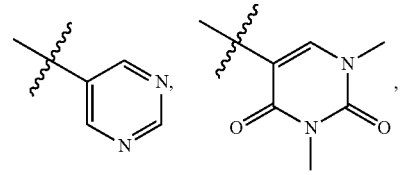

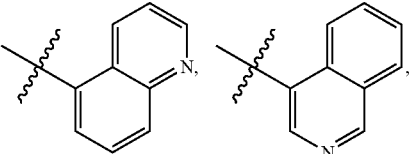

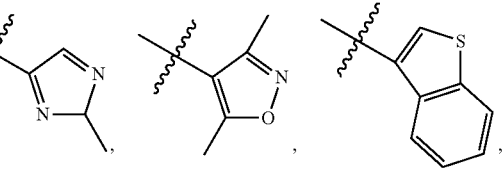

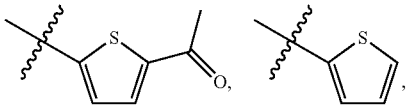

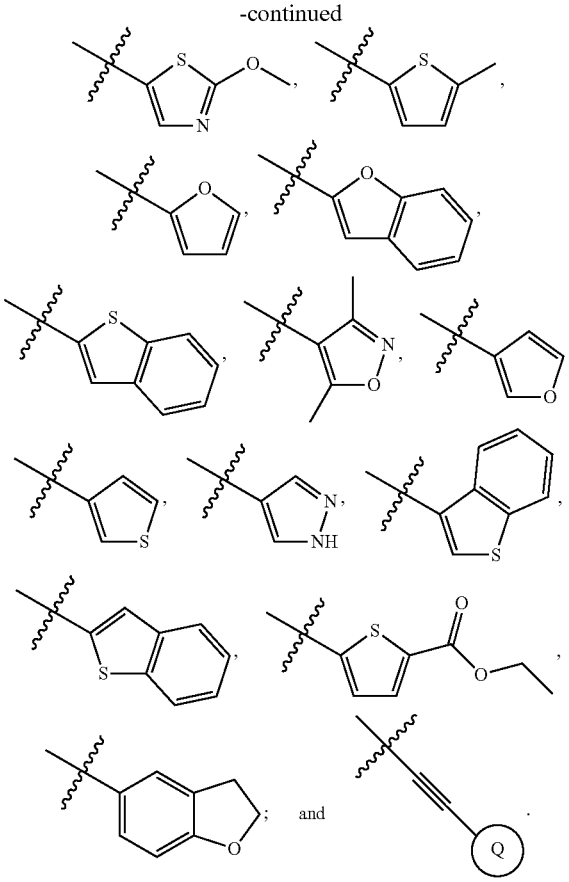

In some compounds of structural formula (A) R⁴ is selected from the group consisting of hydrogen,

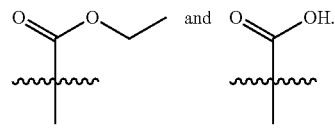

In some compounds of structural formula (A) R⁵ is selected from the group consisting of hydrogen,

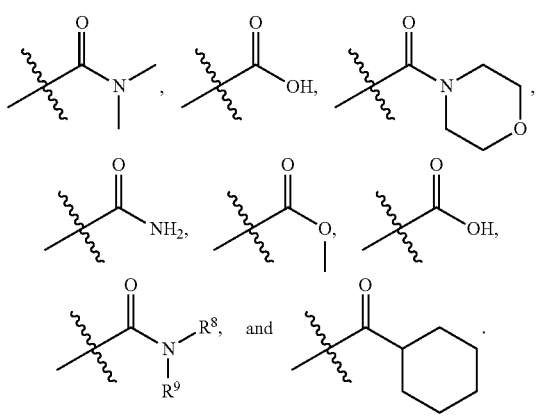

In some compounds of structural formula (A) R⁶ is selected from the group consisting of hydrogen,

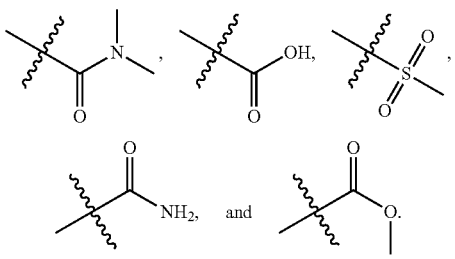

In some compounds of structural formula (A) R⁷ is selected from the group consisting of hydrogen,

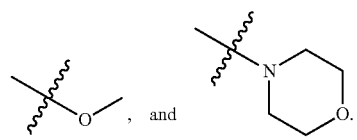

In some compounds of structural formula (A) R⁸ is selected from the group consisting of hydrogen,

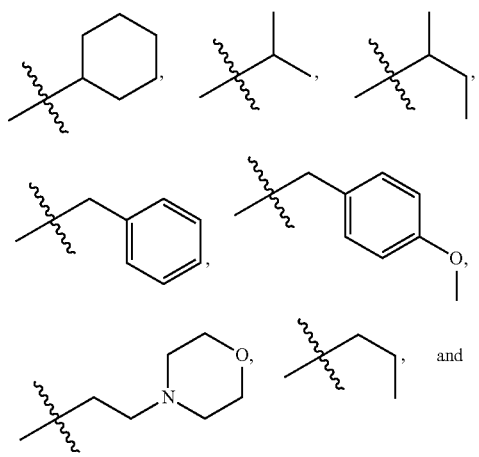

or, together with R⁹ and the nitrogen atom to which they are attached, is

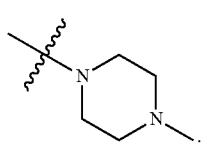 [SMILES: *N1CCN(C)CC1]

In some compounds of structural formula (A) R⁹ is hydrogen or, together with R⁸ and the nitrogen atom to which they are attached, is

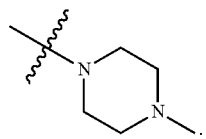 [SMILES: *N1CCN(C)CC1]

In some compounds of structural formula (A) R³ is selected from the group consisting of hydrogen, —F, —CF₃, —NO₂, —O, —OCH₃, —CH₂OH,

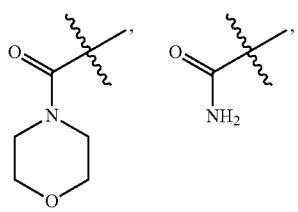

and

—OR¹⁰, wherein R¹⁰ is hydrogen, C₁-C₆ linear or branched alkyl, or

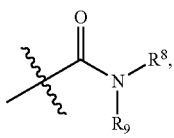

wherein

R⁸ and R⁹ are as defined above for structural formula (A).

In some embodiments compounds are represented by structural formula (A1), which falls within the scope of formula (A):

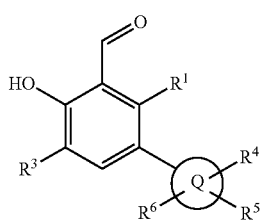

(A1)

wherein:
R¹ is hydrogen or a six-membered heterocyclic containing 1 or 2 heteroatoms independently selected from nitrogen, oxygen, or sulfur;
Q is an optionally benzofused five or six-membered heterocyclic ring;
R³ is hydrogen, halogen, —NO₂, C₁-C₃ linear or branched alkoxy, C₁-C₃ linear or branched hydroxyl alkyl,

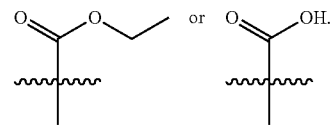

and
R⁴, R⁵, and R⁶ are independently hydrogen, =O, —CH₃,

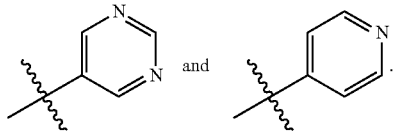 [SMILES: *c1cncnc1 ; *c1ccncc1]

In some compounds of structural formula (A1) R¹ is selected from the group consisting of hydrogen,

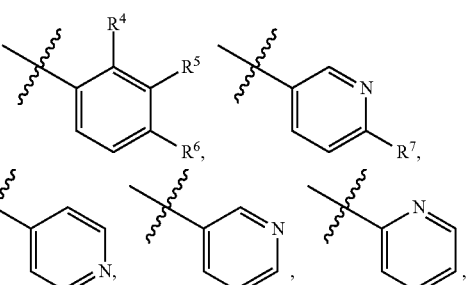

In some compounds of structural formula (I) Q is selected from the group consisting of

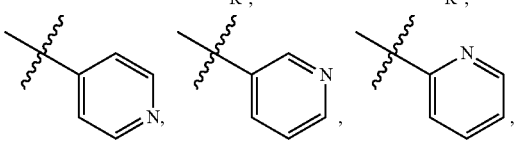

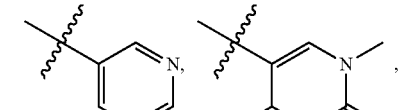

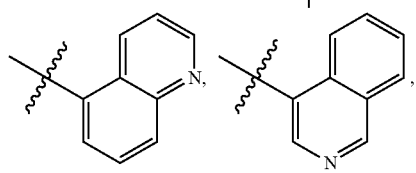

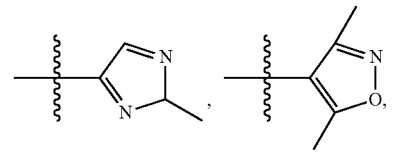

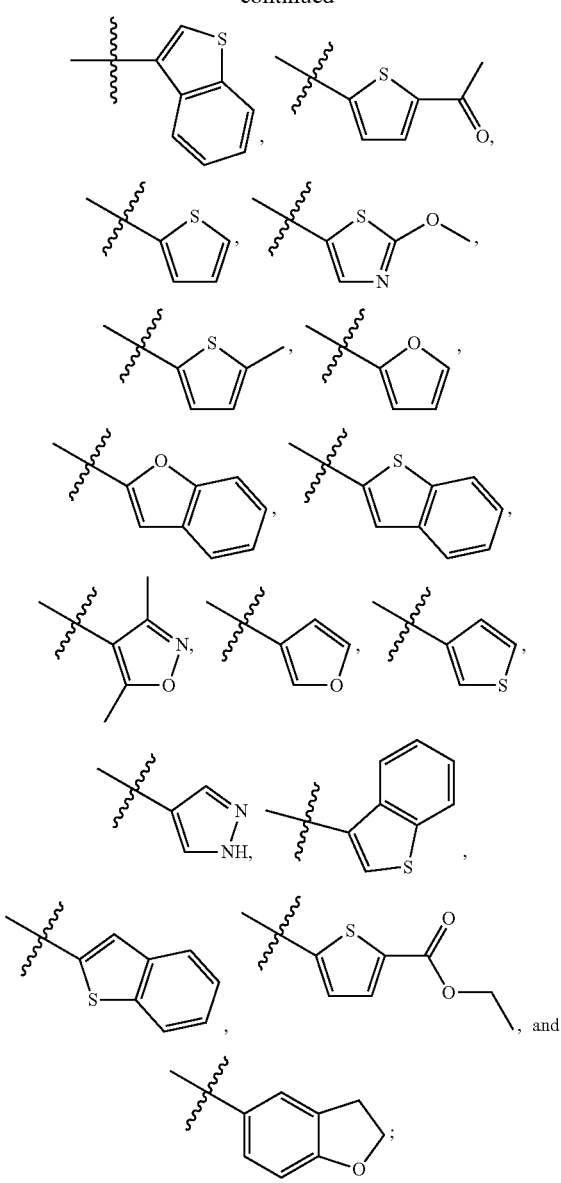

and R⁴, R⁵, and R⁶ are independently selected from

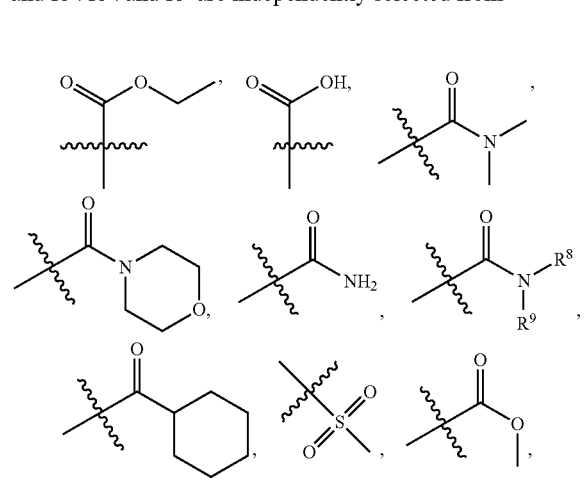

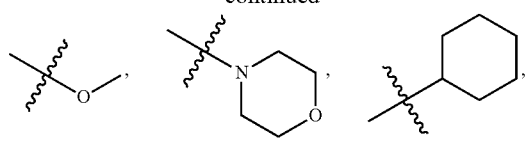

$C_1$-$C_3$ linear or branched alkyl,

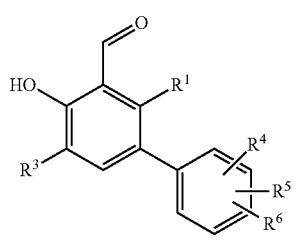

$C_1$-$C_3$ phenylalkyl, $C_1$-$C_3$ alkoxyphenylalkyl,

In some compounds of structural formula (A1) $R^3$ is selected from the group consisting of hydrogen, —F, —CF₃, —NO₂, and —OCH₃.

In some embodiments compounds represented by structural formula (A2), which falls within the scope of formula (A):

(A2)

wherein:

$R^1$ is hydrogen, halogen, or a 5- or 6-membered heterocyclic containing one or two heteroatoms independently selected from nitrogen, oxygen, and sulfur;

$R^3$ is hydrogen, halogen, —NO₂, $C_1$-$C_3$ linear or branched alkyl, $C_1$-$C_3$ linear or branched alkoxy, $C_1$-$C_3$ linear or branched hydroxyl alkyl,

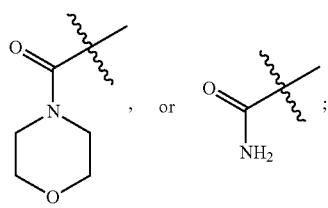, or 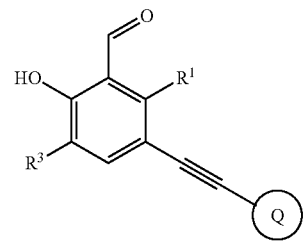

(A3)

and
R⁴, R⁵, and R⁶ are independently selected from

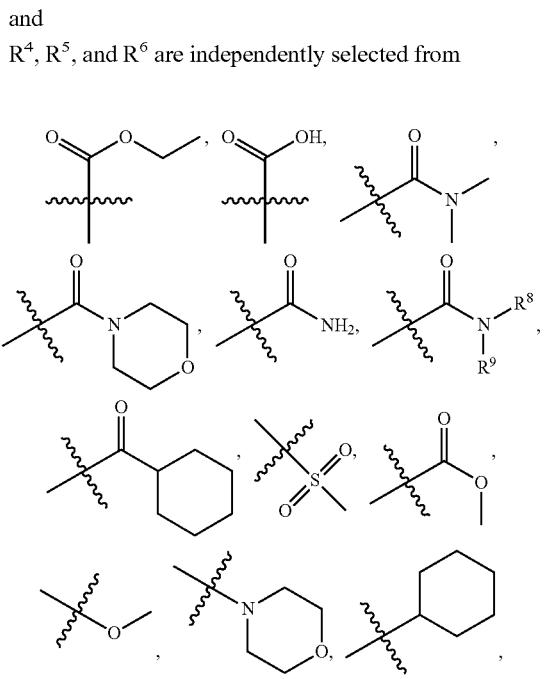

$C_1$-$C_3$ linear or branched alkyl,

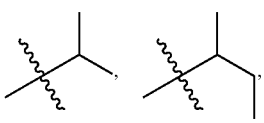

$C_1$-$C_3$ phenylalkyl, $C_1$-$C_3$ alkoxyphenylalkyl,

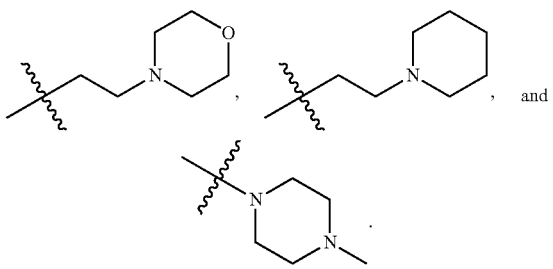

In some embodiments compounds are represented by the structural formula (A3), which falls within the scope of formula (A):

wherein:
Q is a five- or six-membered heterocyclic containing 1 or 2 heteroatoms independently selected from nitrogen, oxygen, and sulfur;
$R^1$ is hydrogen; and
$R^3$ is hydrogen or $C_1$-$C_3$ alkyoxy.

In some compounds of structural formula (A3) Q is selected from the group consisting of

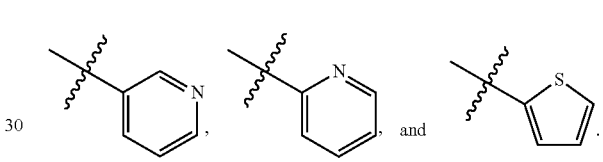

In some compounds of structural formula (A3) $R_3$ is

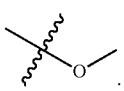

In some embodiments compounds are represented by the structural formula (A4), which falls within the scope of formula (A):

(A4)

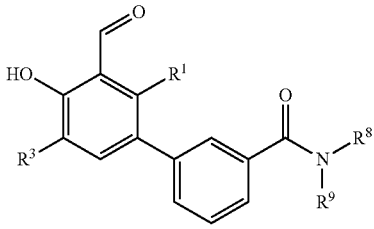

wherein:
$R^1$ is hydrogen;
$R^3$ is hydrogen, —F, —NO₂, or

R⁸ is
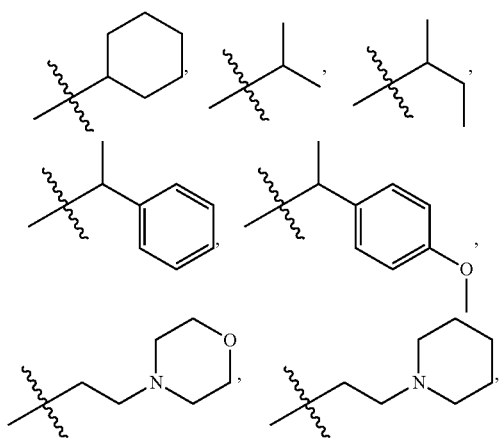
or, together with R⁹ and the nitrogen atom to which they are attached, is
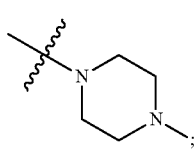
and
R⁹ is hydrogen or, together with R⁸ and the nitrogen atom to which they are attached, is
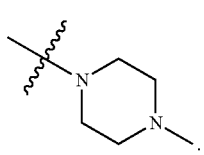 [SMILES: *N1CCN(C)CC1]
In some embodiments, compounds have one of the following structural formulae:
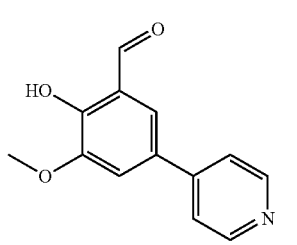 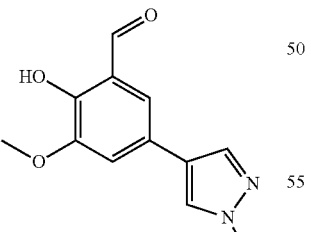
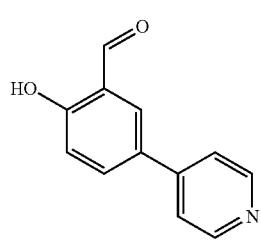 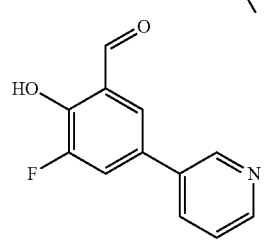
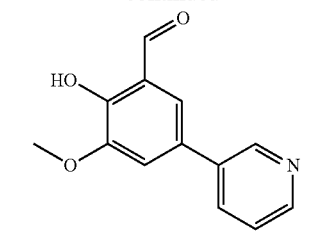
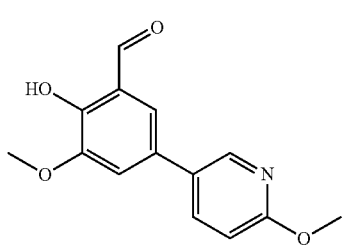
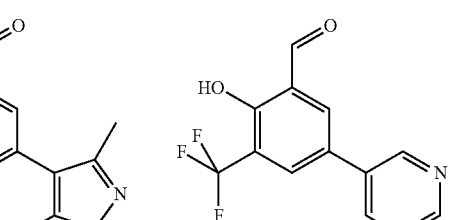
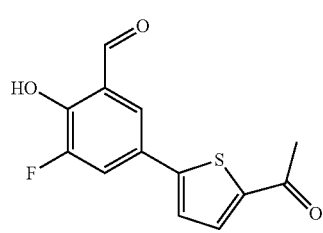
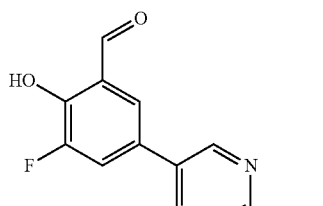
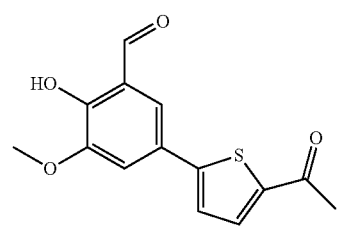
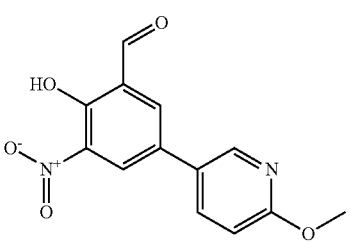

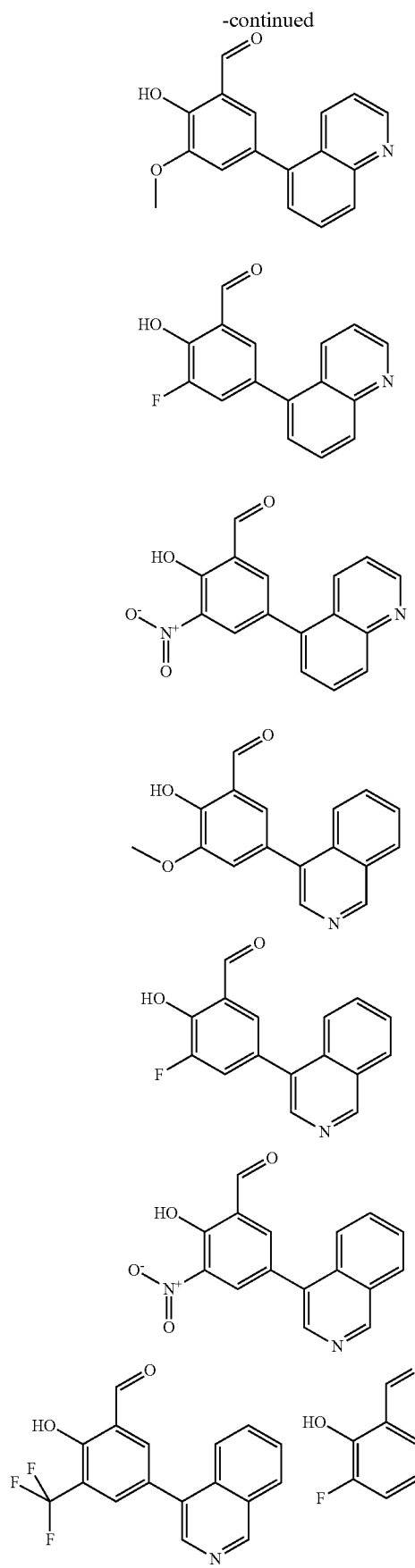
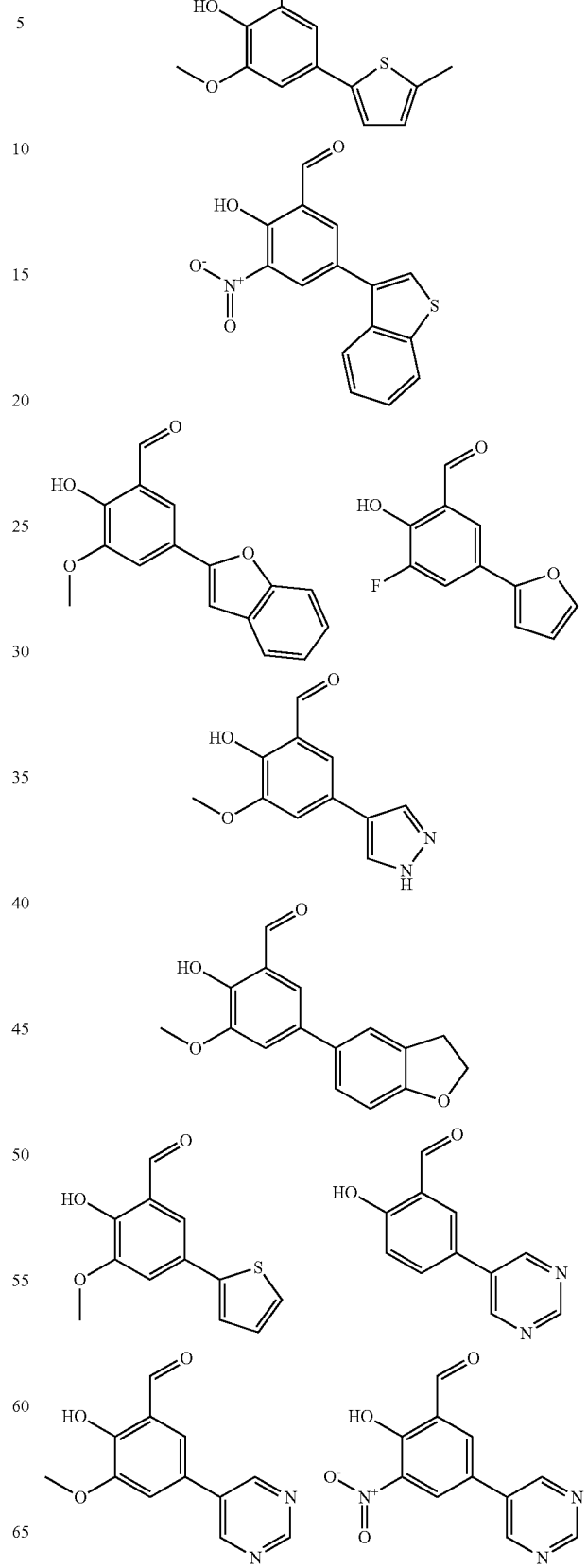

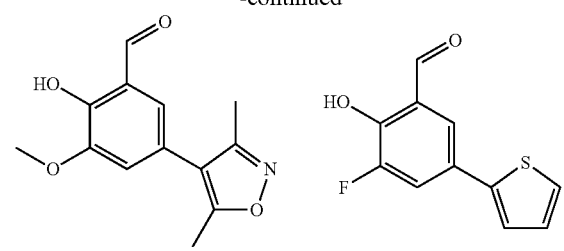
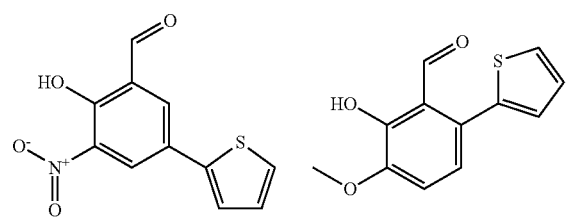
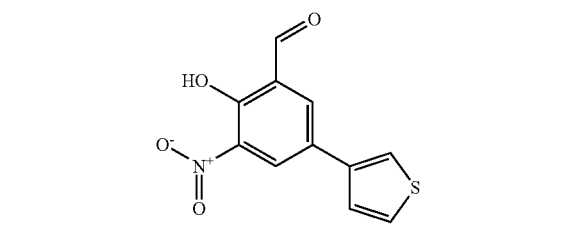
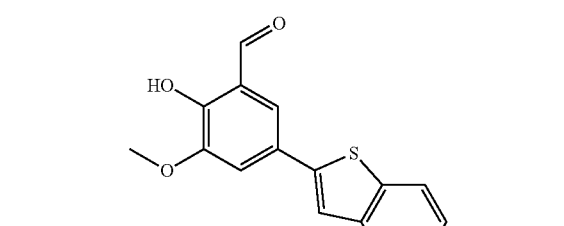
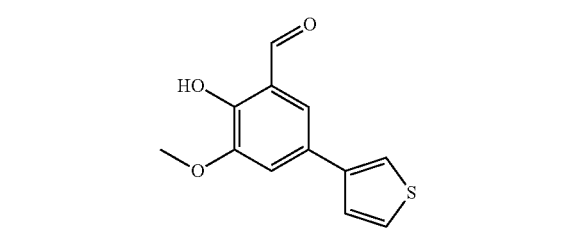
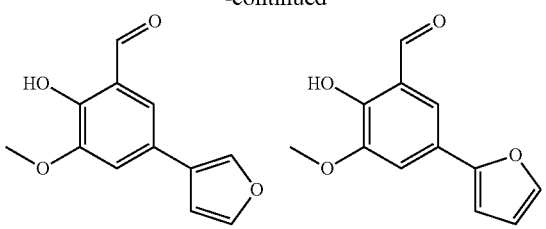
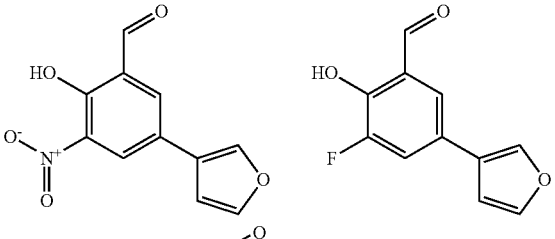
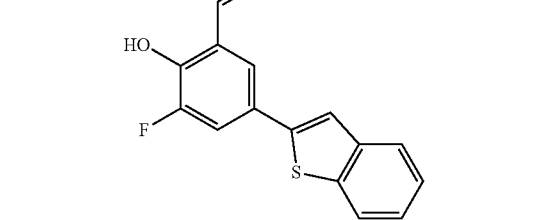
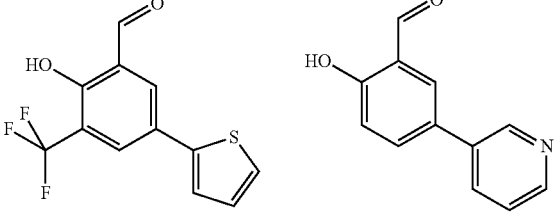
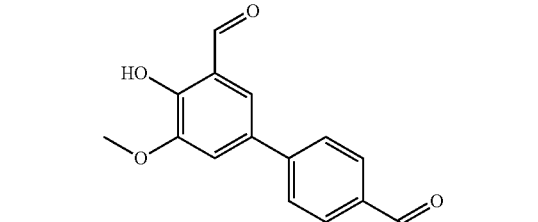
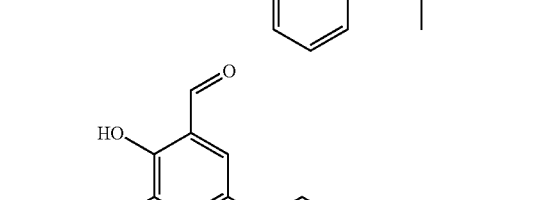
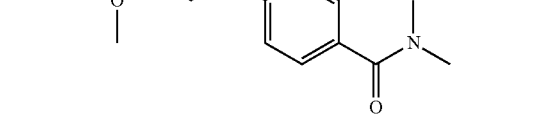

41
-continued
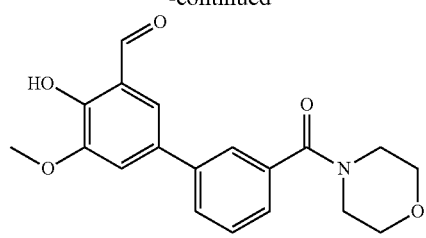
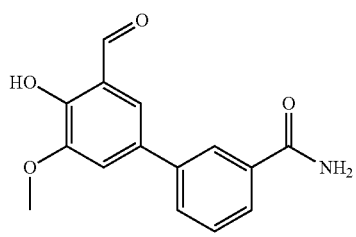
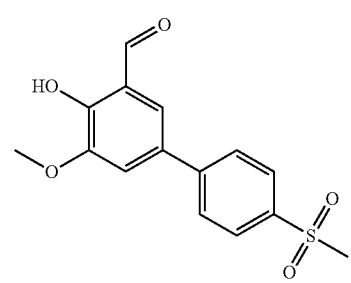
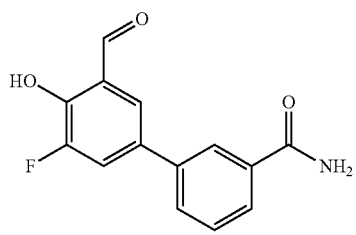
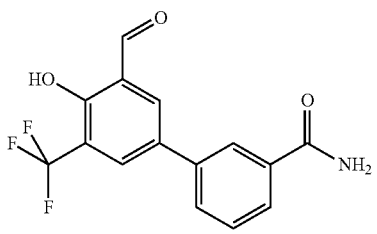
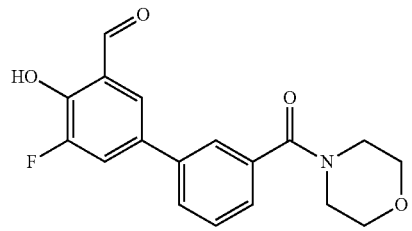
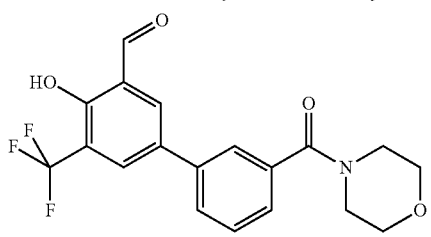
42
-continued
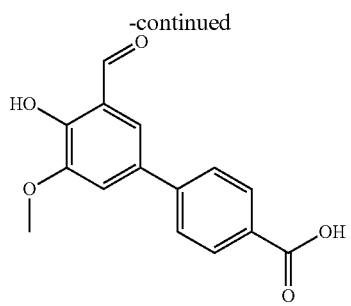
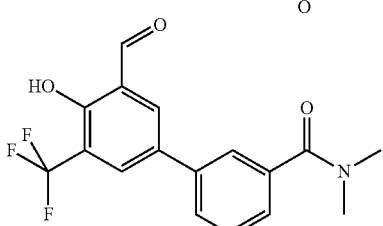
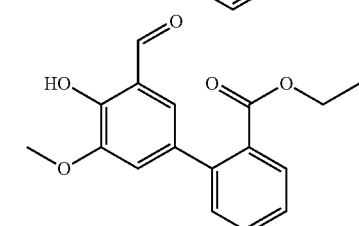
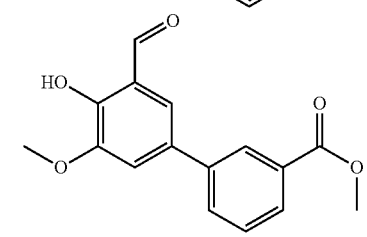
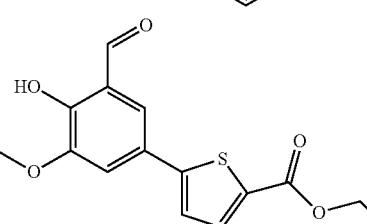
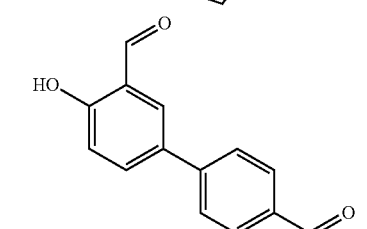
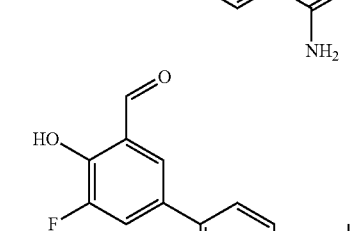
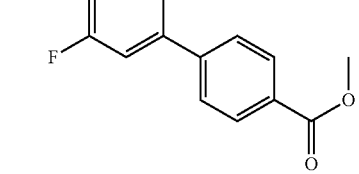

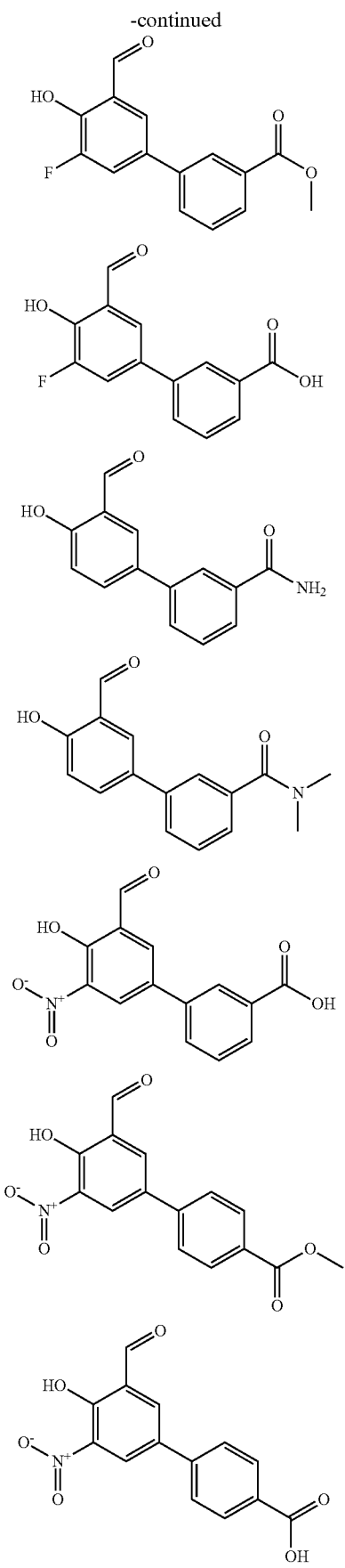
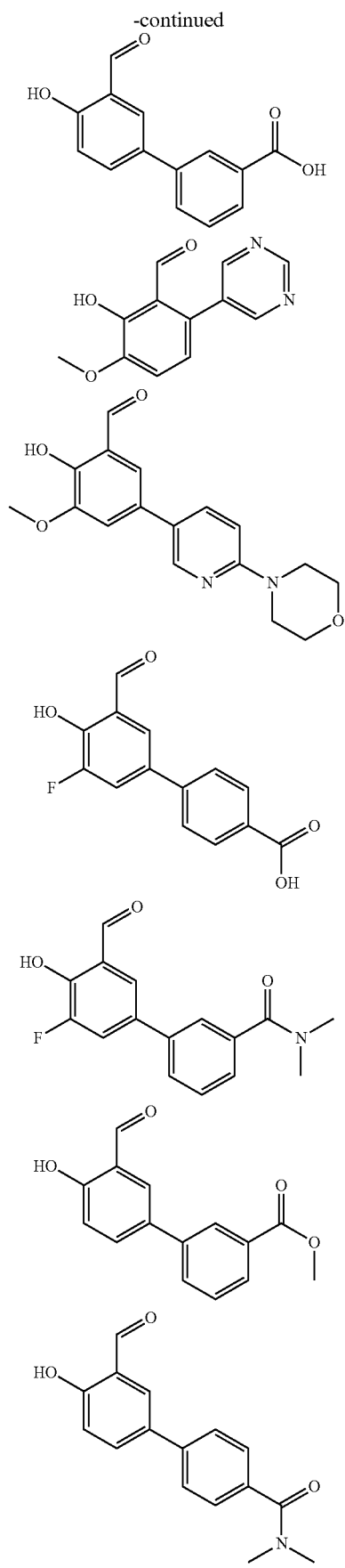

45
-continued
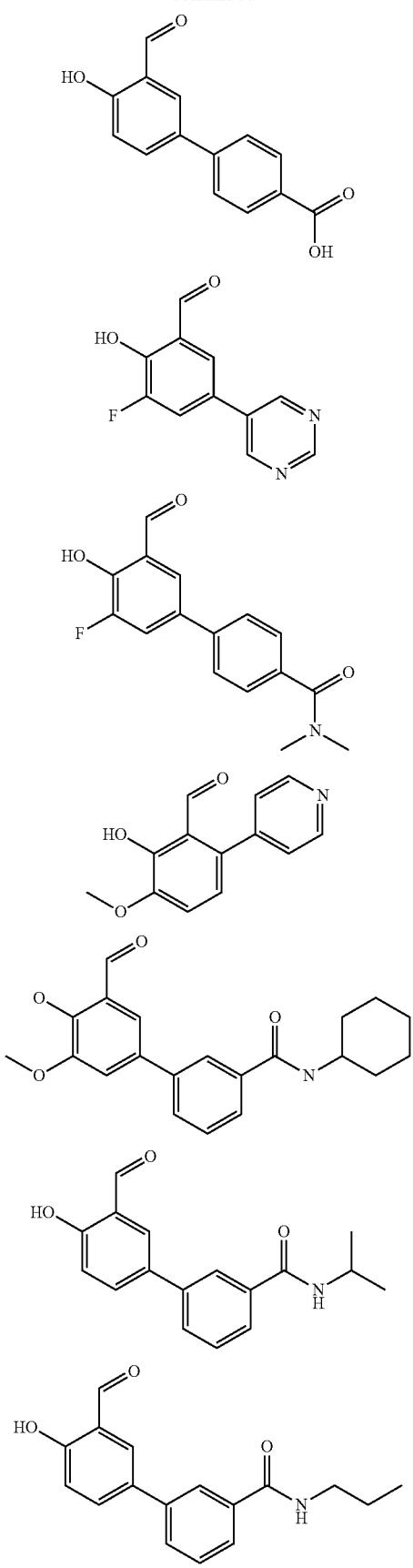
46
-continued
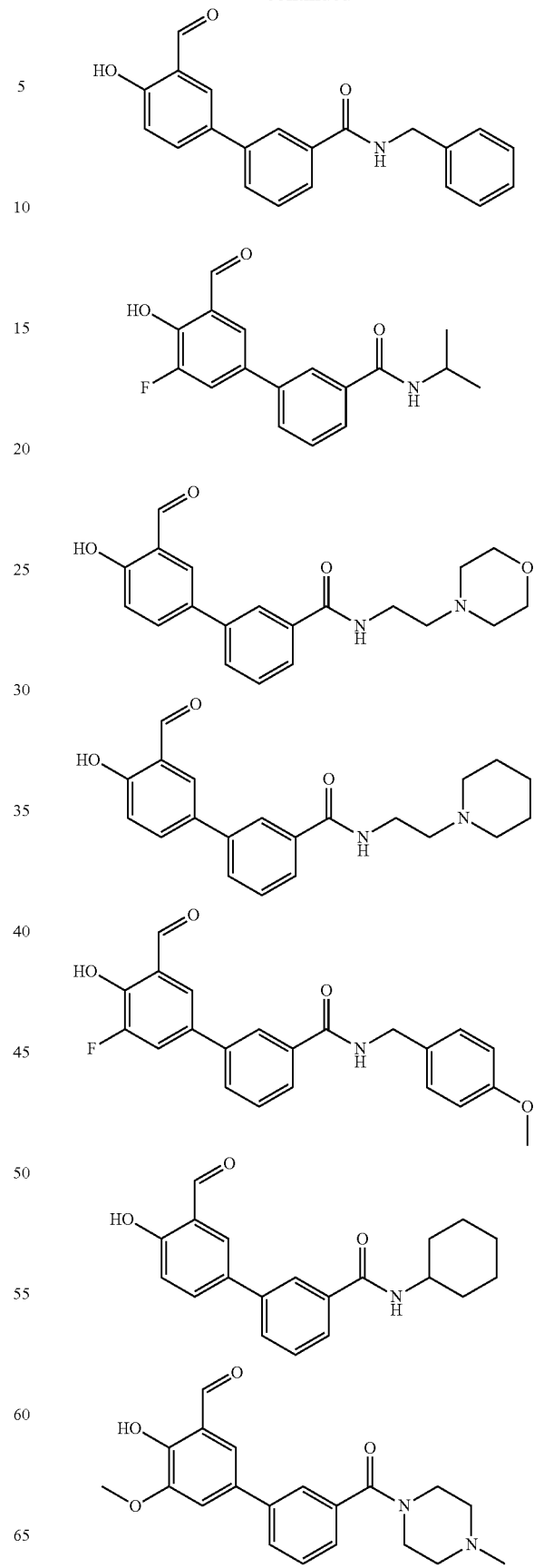

-continued
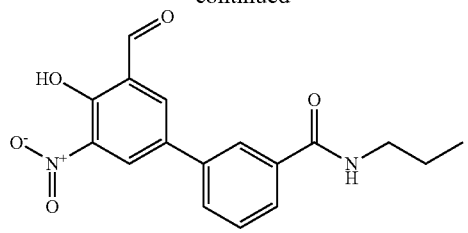
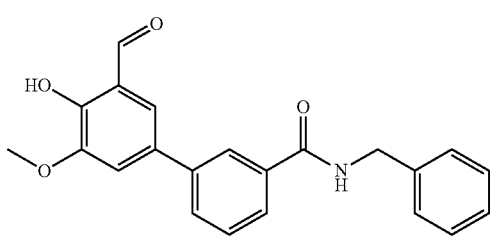
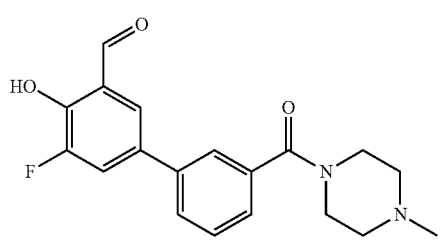
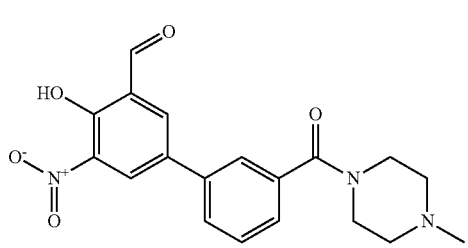
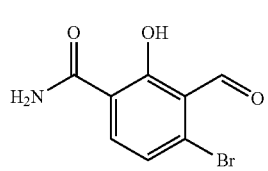
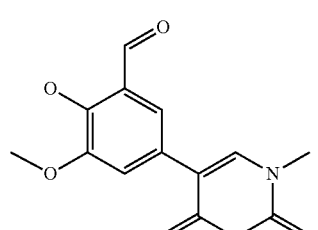
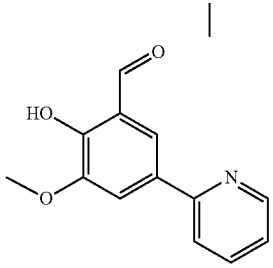
-continued
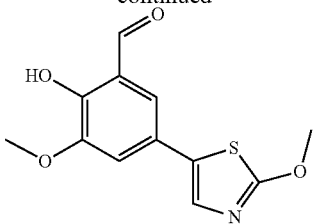
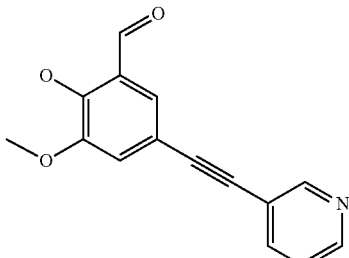
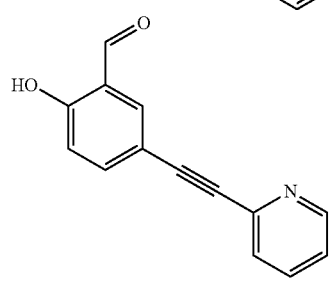
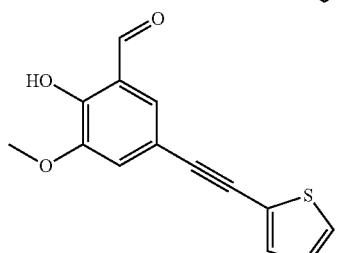
and
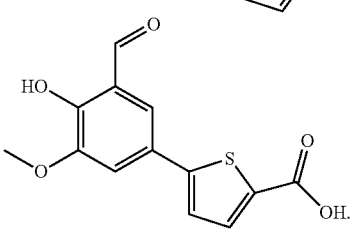
In some embodiments compounds are represented by structural formula (B), which falls within the scope of formula (I):
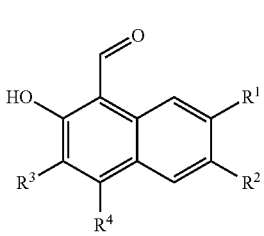
(B)
wherein:
$R^1$ and $R^2$ independently are hydrogen, phenyl or an optionally benzofused five- or six-membered heterocycle, wherein the phenyl or the optionally benzofused five- or six-membered heterocycle is optionally substituted with

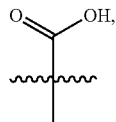

—$CH_2OH$, —CHO, —$OCH_3$, halogen, —OH, —$CH_3$,

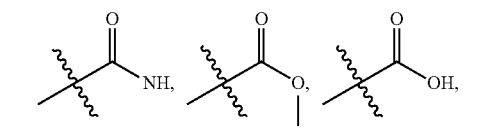

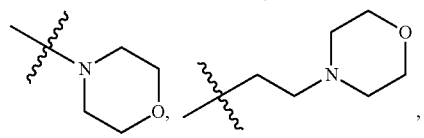

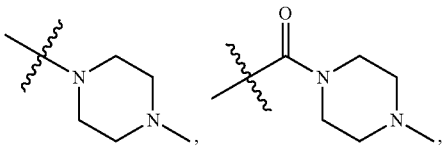

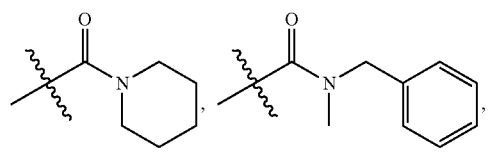

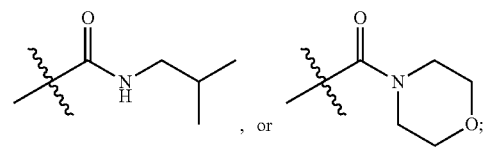

, or $R^3$ is hydrogen, halogen, —$NO_2$, $C_1$-$C_3$ linear or branched alkyl, $C_1$-$C_3$ linear or branched alkoxy, $C_1$-$C_3$ linear or branched hydroxyl alkyl,

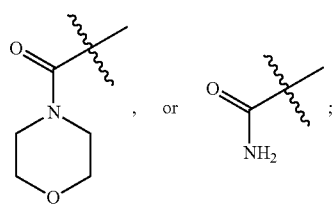

and
$R^4$ is hydrogen,

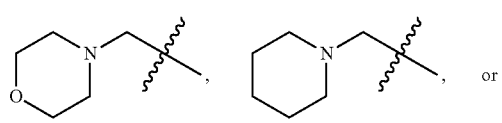, or

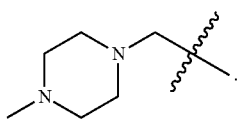

In some embodiments compounds have one of the following structural formulae:

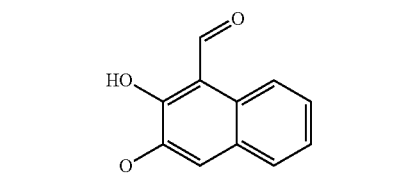

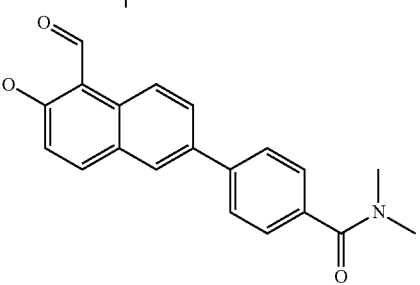

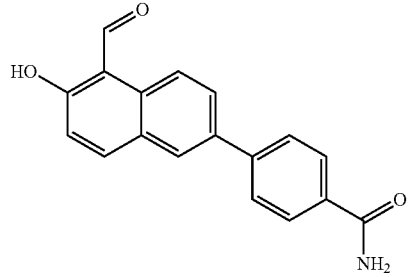

51
-continued
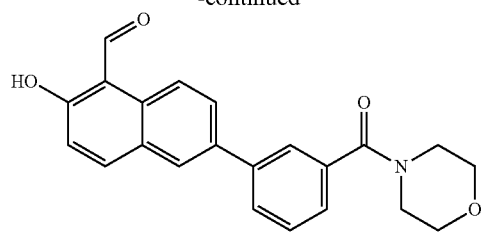
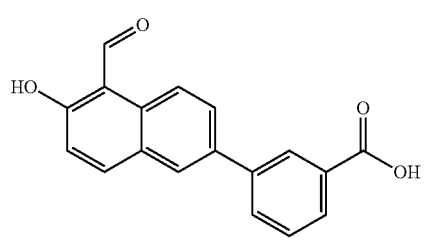
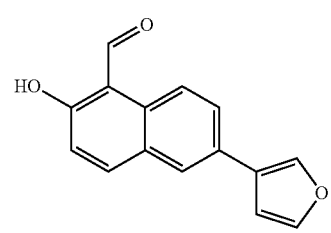
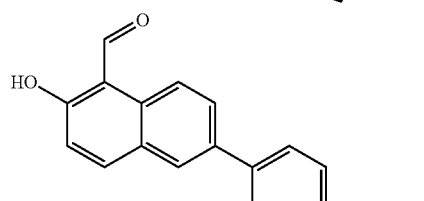
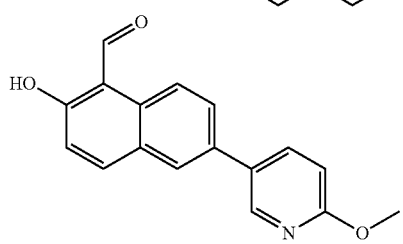
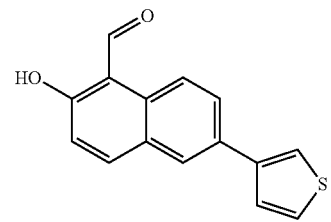
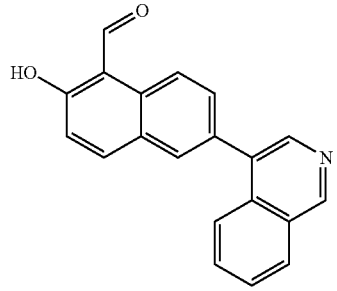
52
-continued
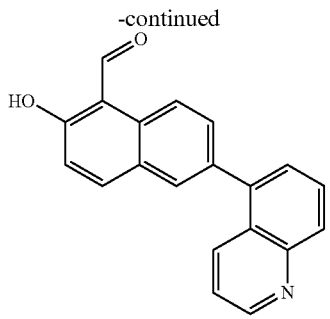
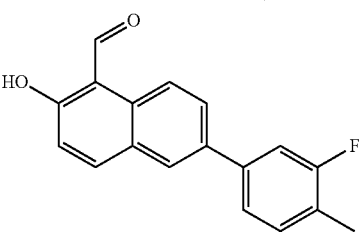
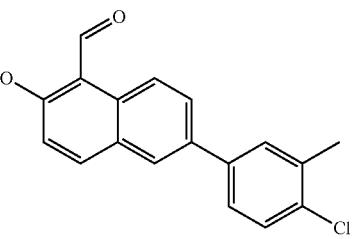
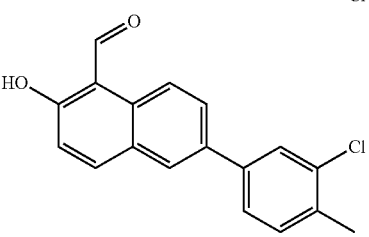

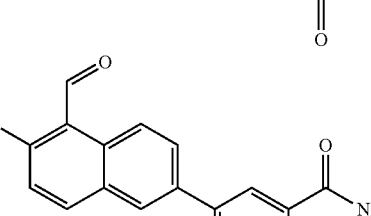
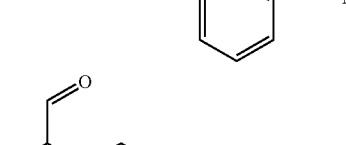
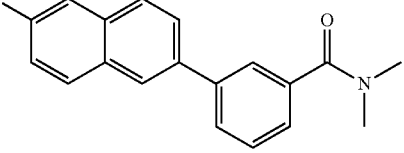

-continued
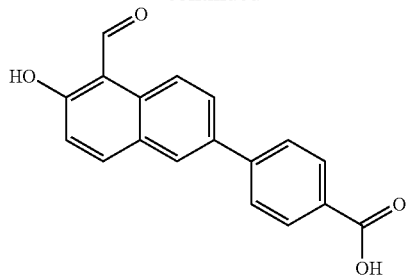
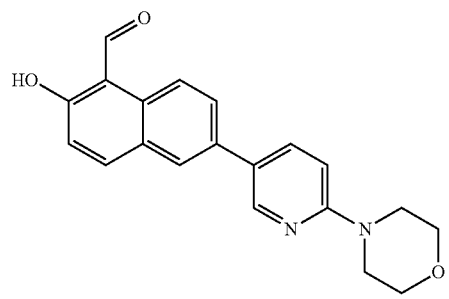
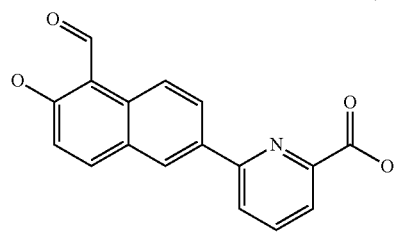
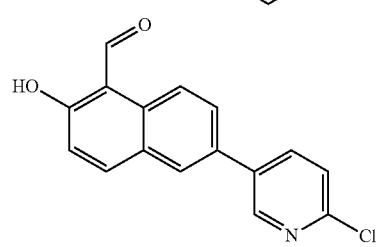
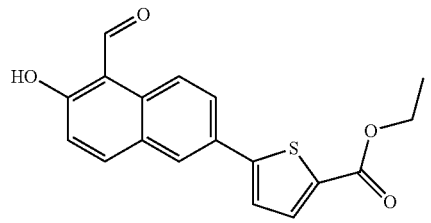
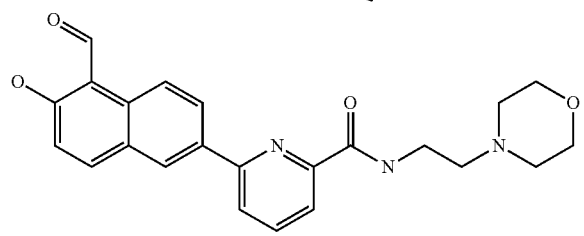
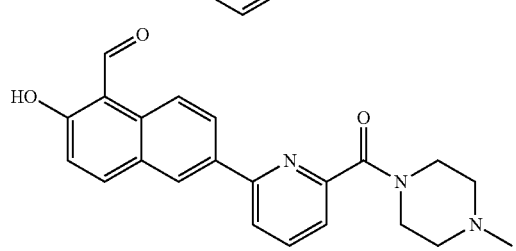
-continued
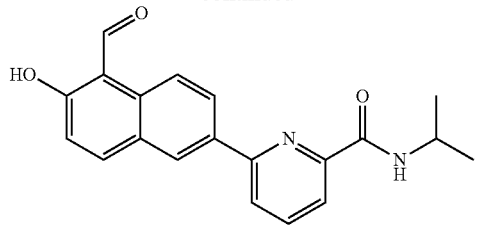
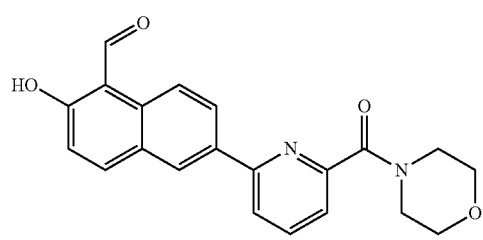
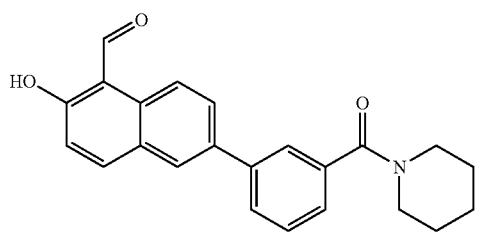
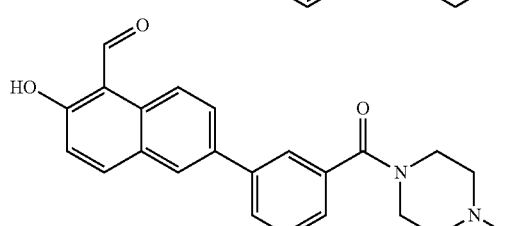
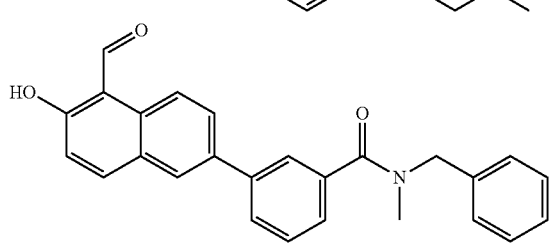
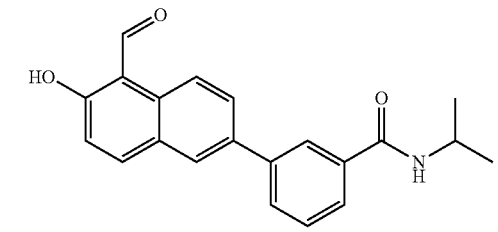
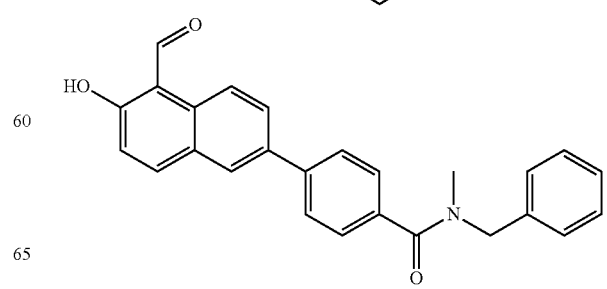

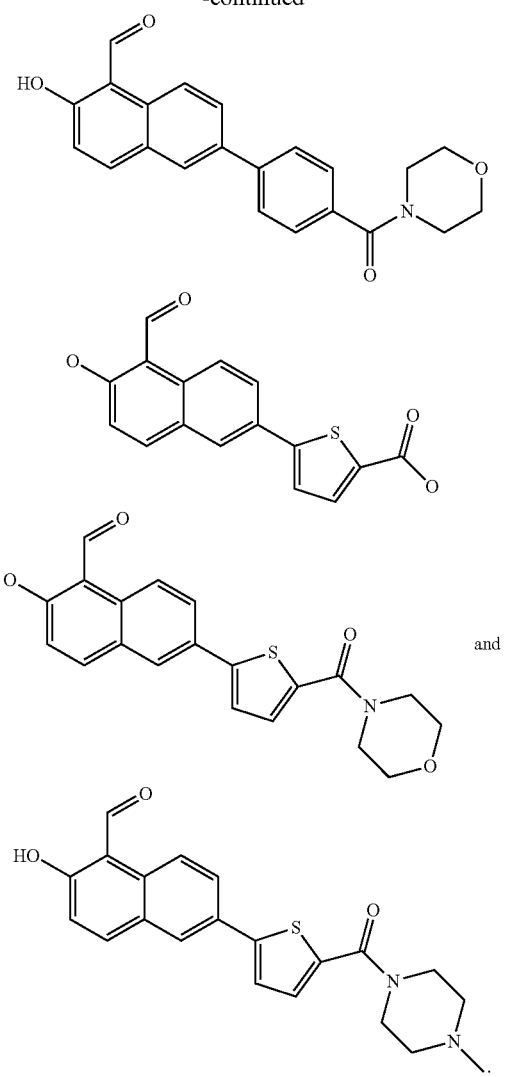

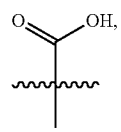

—CH$_2$OH, —CHO, —OCH$_3$, halogen, —OH, —CH$_3$,

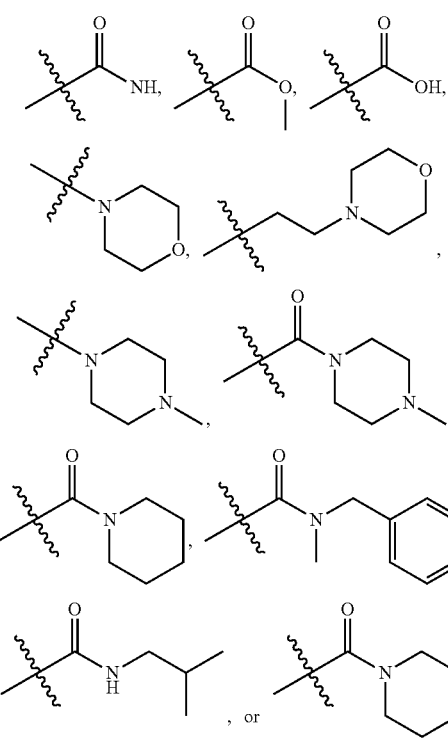

and the hydroxy substitutent in ring A is located ortho to the aldehyde substituent.

In some embodiments compounds represented by structural formula (C) have one of the following structures:

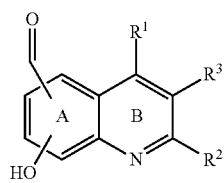

In some embodiments compounds are represented by structural formula (C), which falls within the scope of formula (I):

(C)

wherein:

R$^1$ is hydrogen, —CH$_3$, or —OH;

R$^2$ and R$^3$ independently are hydrogen, phenyl or an optionally benzofused five- or six-membered heterocycle, wherein the phenyl or the optionally benzofused five- or six-membered heterocycle is optionally substituted with In some embodiments compounds are represented by structural formula (D), which falls within the scope of formula (I):

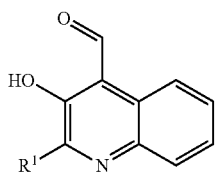

wherein $R^1$ is hydrogen, halogen, —$NO_2$, $C_1$-$C_3$ linear or branched alkyl, $C_1$-$C_3$ linear or branched alkoxy, $C_1$-$C_3$ linear or branched hydroxyl alkyl,

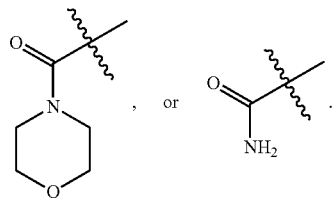

In one compound of structural formula (D), $R^1$ is methyl.

Other useful compounds according to the invention are shown in Tables 11-42.

Pharmaceutically Acceptable Salts; Stereoisomers; Tautomers

IRE-1α inhibitor compounds include both the free form of the compounds and the pharmaceutically acceptable salts and stereoisomers thereof. Some of the specific IRE-1α inhibitor compounds described herein are the protonated salts of amine compounds. The term "free form" refers to the amine compounds in non-salt form. The encompassed pharmaceutically acceptable salts not only include the salts described for the specific compounds disclosed herein, but also all the typical pharmaceutically acceptable salts of the free form of IRE-1α inhibitor compounds of Formulas I-VII and A-D and of the prodrugs of formulas E and F (below).

The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the disclosed IRE-1α inhibitor compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Pharmaceutically acceptable salts of IRE-1α inhibitor compounds include the conventional non-toxic salts of the compounds as formed by reacting a basic compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, benzenesulfonic, methanesulfonic, ethane disulfonic, oxalic, isethionic, trifluoroacetic and the like.

When an IRE-1α inhibitor compound is acidic, suitable pharmaceutically acceptable salts include salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular salts are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. The preparation of the pharmaceutically acceptable salts described above and other typical pharmaceutically acceptable salts is more fully described by Berg et al., "Pharmaceutical Salts," *J. Pharm. Sci.*, 1977:66:1-19.

Some IRE-1α compounds or prodrugs are potentially internal salts or zwitterions, because under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

IRE-1α inhibitor compounds or prodrugs thereof may have asymmetric centers, chiral axes, and chiral planes (as described in: E. L. Eliel and S. H. Wilen, Stereochemistry of Carbon Compounds, John Wiley & Sons, New York, 1994, pages 1119-1190), and may occur as racemates, racemic mixtures, and as individual diastereomers, with all possible isomers and mixtures thereof, including optical isomers, being included in the present invention.

An IRE-1α inhibitor compound or prodrug thereof may be of such a nature that its constituent atoms are capable of being arranged spatially in two or more ways, despite having identical bonds. As a consequence, this compound exists in the form of stereoisomers. Cis/trans isomerism is only one type of stereoisomerism. If the stereoisomers are image and mirror image which cannot be superimposed, they are enantiomers which have chirality or handedness since one or more asymmetric carbon atoms are present in the structure forming them. Enantiomers are optically active and therefore distinguishable since they rotate the plane of polarized light to an equal extent, but in opposite directions.

If two or more asymmetric carbon atoms are present in an IRE-1α compound, two possible configurations exist at each of these carbon atoms. If two asymmetric carbon atoms are present, four possible stereoisomers exist, for example. Furthermore, these four possible stereoisomers can be divided into six possible pairs of stereoisomers that differ from each other. In order for a pair of molecules with more than one asymmetric carbon to be enantiomers, they must have different configurations at each asymmetric carbon. Those pairs that do not behave as enantiomers have a different stereochemical relationship, which is known as a diastereomeric relationship. Stereoisomers that are not enantiomers are known as diastereoisomers, or, more frequently, diastereomers.

All of these well-known aspects of the stereochemistry of the compounds of the invention are considered to be part of the present invention. The present invention therefore covers IRE-1α inhibitor compounds which are stereoisomers, and, if these are enantiomers, the individual enantiomers, racemic mixtures of these enantiomers, and artificial, i.e. synthetic, mixtures comprising proportions of these enantiomers which are different from the proportions of these enantiomers observed in a racemic mixture. If an IRE-1α inhibitor compound has stereoisomers that are diastereomers, this compound includes the individual diastereomers as well as mixtures of any two or more of these diastereomers in any desired proportions.

The following is intended to serve for explanation: if a single asymmetric carbon atom exists in an IRE-1α inhibitor compound that results in the (−)(R) and (+)(S) enantiomers thereof, this an IRE-1α inhibitor compound includes all pharmaceutically acceptable salt forms, prodrugs and metabolites thereof which are therapeutically active and useful for the treatment of or preventing the diseases and conditions described further herein. If an IRE-1α inhibitor compound exists in the form of (−)(R) and (+)(S) enantiomers, this compound also includes the (+)(S) enantiomer alone or the (−)(R) enantiomer alone if all, substantially all or a predominant share of the therapeutic activity resides in only one of these enantiomers or undesired side effects reside in only one of these enantiomers. If essentially no difference exists between the biological properties of the two enantiomers, this compound of the invention furthermore includes the (+)(S) enantiomer and the (−)(R) enantiomer together as a racemic mixture or non-racemic mixture in any desired ratio of corresponding proportions.

The specific biological effects and/or physical and chemical properties of a pair or set of enantiomers of an IRE-1α inhibitor compound—if present—may make it obvious to use these enantiomers in certain ratios, for example to form a final therapeutic product. The following is intended to serve for illustration: if a pair of enantiomers exists, the enantiomers can be used in ratios such as 90% (R)-10% (S), 80% (R)-20% (S), 70% (R)-30% (S), 60% (R)-40% (S), 50% (R)-50% (S), 40% (R)-60% (S), 30% (R)-70% (S), 20% (R)-80% (S), and 10% (R)-90% (S). After evaluation of the properties of the various enantiomers of an IRE-1α inhibitor compound—if they exist—the corresponding amount of one or more of these enantiomers having certain desired properties which form the final therapeutic product can be determined in a simple manner.

For IRE-1α inhibitor compounds disclosed herein which may exist as tautomers, both tautomeric forms are encompassed within the invention, even though only one tautomeric structure is depicted. For example, a compound such as that below drawn as the keto tautomer includes the enol tautomer, and vice versa, as well as mixtures thereof

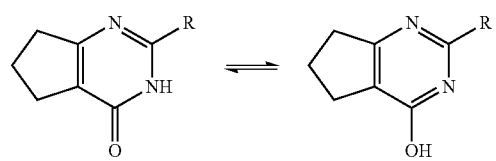

The invention also includes pharmaceutically usable stereoisomers, E/Z isomers, enantiomers, racemates, diastereomers, hydrates, and solvates of the disclosed compounds. "Solvates" are adductions of inert solvent molecules onto the compounds which form owing to their mutual attractive force. Solvates are, for example, monohydrates, dihydrates or alcoholates.

Prodrugs

The invention also provides prodrugs which are metabolized to active IRE-1α inhibitor compounds after administration. For example, IRE-1α inhibitor compounds disclosed herein can be modified, for example, with alkyl or acyl groups, sugars, or oligopeptides and which are rapidly cleaved in vivo to release the active IRE-1α inhibitor compounds.

Derivatives of the corresponding aromatic alcohols can serve as prodrugs for aromatic aldehydes because alcohols and aldehydes are metabolically interconvertible, according to the following general scheme:

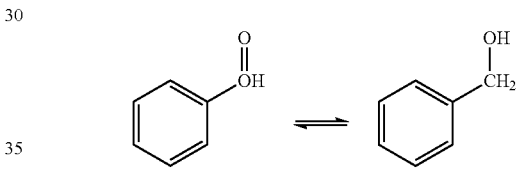

Scheline, 1972, *Xenobiotica*, 2, 227-36.

Examples of prodrugs of aldehydes, ketones, alcohols and other functional groups are described in Wermuth et al., 1996, *Designing Prodrugs and Bioprecursors I: Carrier Prodrugs. In The Practice of Medicinal Chemistry*, pp. 672-696; and in Wermuth, 1996, "Preparation of Water-Soluble Compounds by Covalent Attachment of Solubilizing Moieties," in Wermuth, ed., *The Practice of Medicinal Chemistry*, pp. 756-776. Other general aldehyde derivatives and alcohol derivatives that can perform prodrug functions as well as methods for their preparation are described in Cheronis et al., 1965, *Semimicro Qualitative Organic Analysis*, New York: Interscience, pp. 465-518.

Prodrugs of the invention includes compounds having the structural formula AA, BB, or CC, below, in which Q' is identical in all respects to Q as defined above, with the exception that the aldehyde substituent of Q is present in a prodrug form as shown below, and $R^a$ and $R^c$ are as defined above:

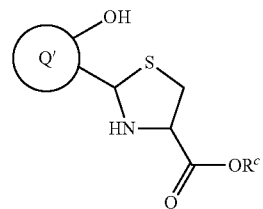

AA

-continued
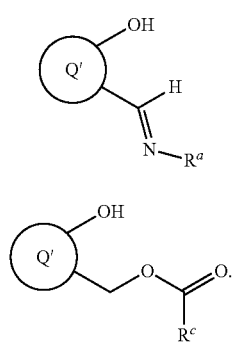
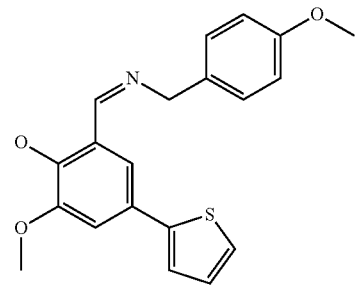
In some embodiments, prodrugs of IRE-1α inhibitor compounds are represented by structural formula (E):
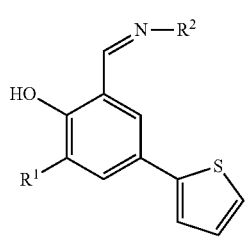
(E)
wherein:
R¹ is hydrogen or —OCH₃; and R² is
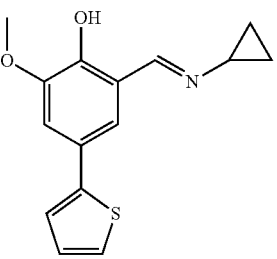
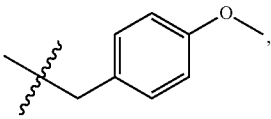
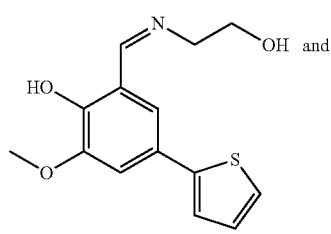
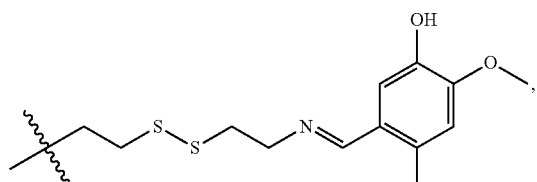
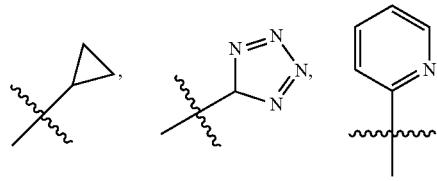
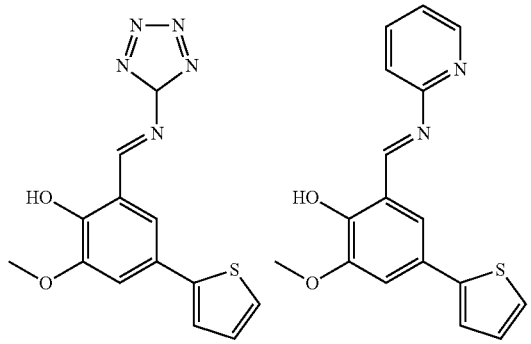
In some embodiments prodrugs represented by structural formula (E) have one of the following structural formulae:

In some embodiments IRE-1α inhibitor prodrugs are represented by structural formula (F):
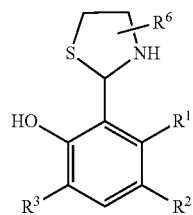  (F)
wherein:
R¹ is hydrogen or Br;
R² is hydrogen, Br, or
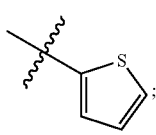 [SMILES: *c1cccs1];
and
R³ is hydrogen, —OCH₃, —COOH, or —OCH₂CH₃.
In some embodiments IRE-1α prodrugs represented by structural formula (F) have one of the following structural formulae:
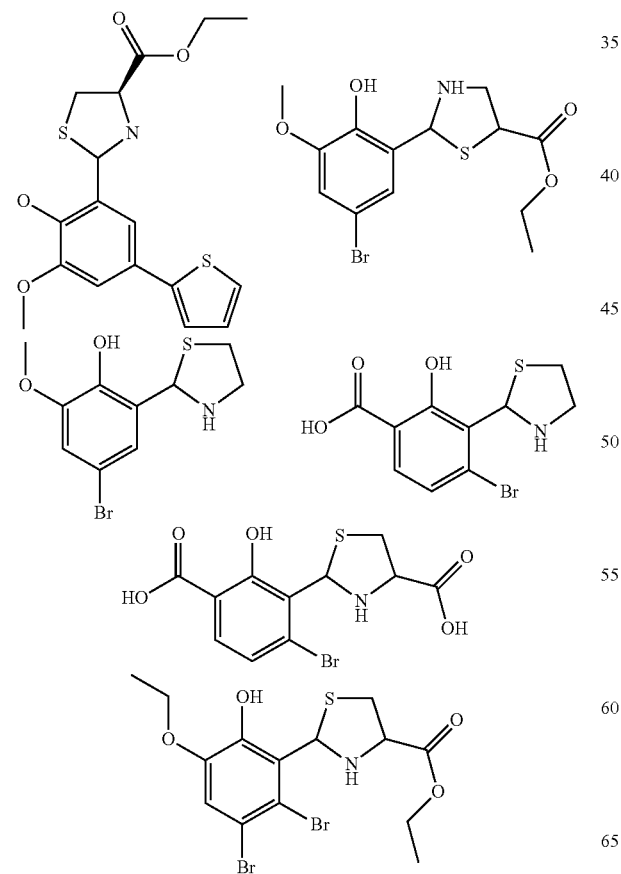
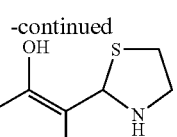
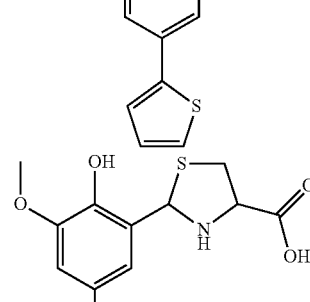
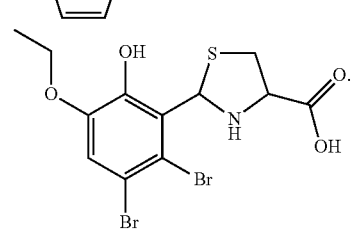
Other examples of IRE-1α inhibitor prodrugs include:
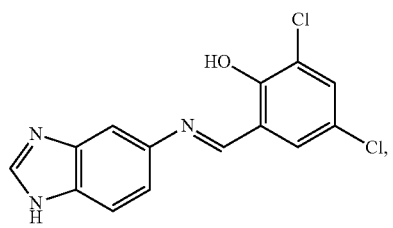
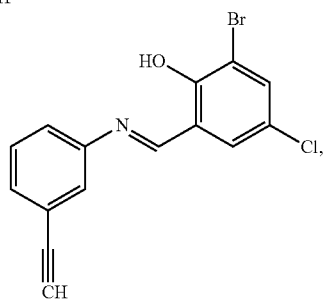
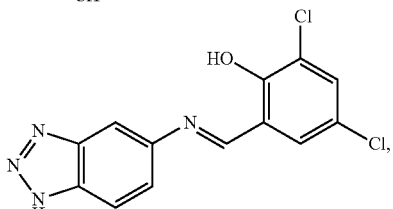
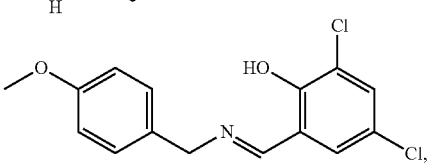

65
-continued
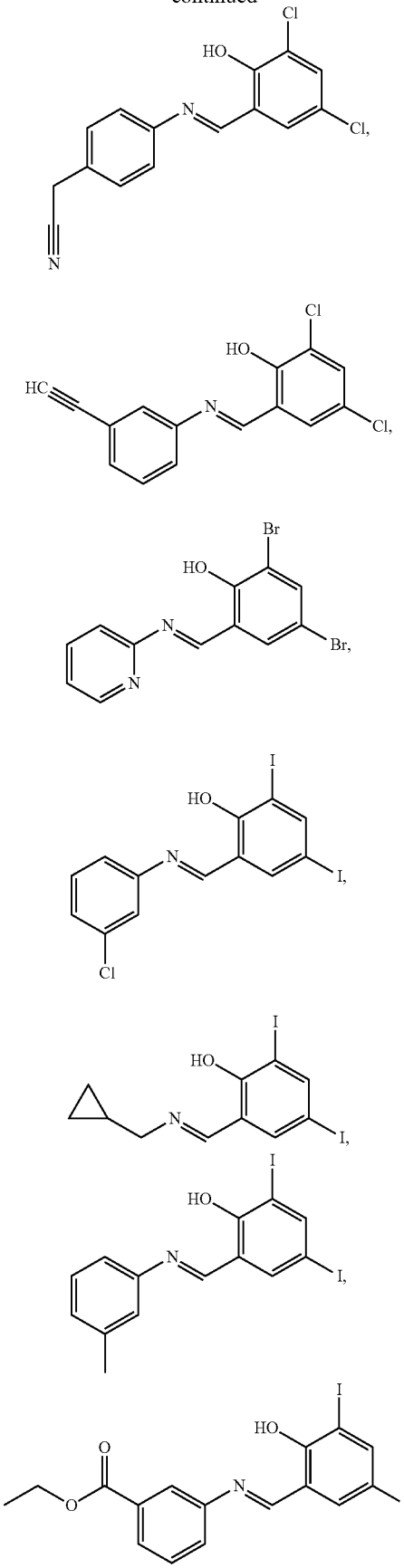
66
-continued
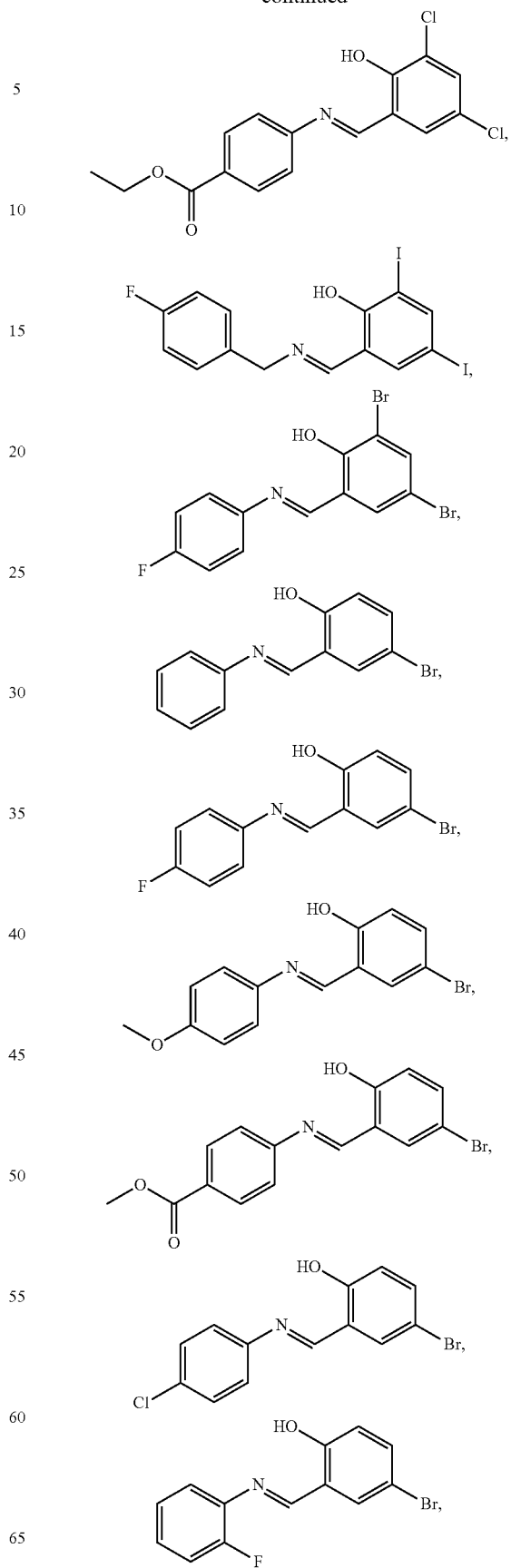

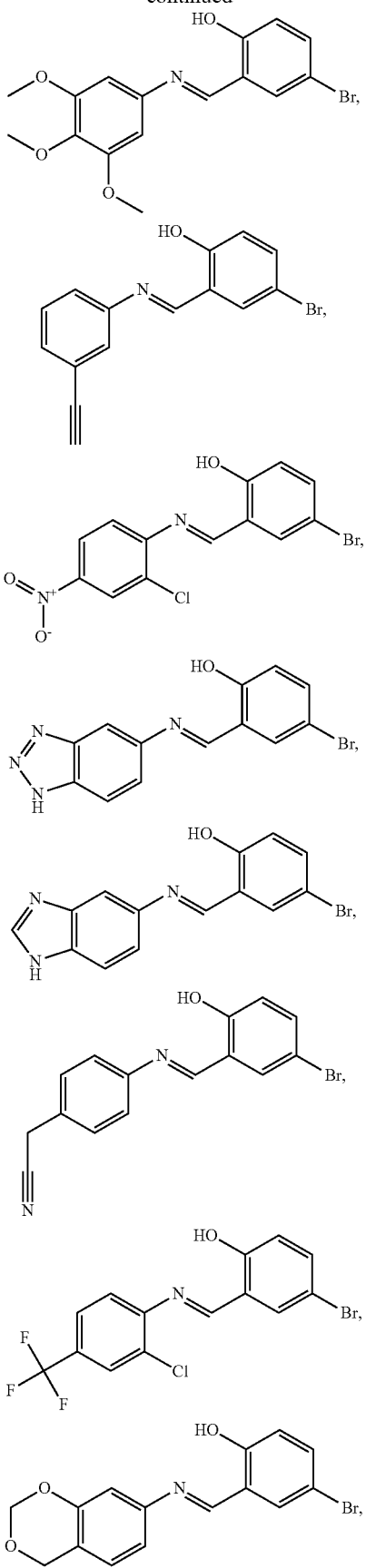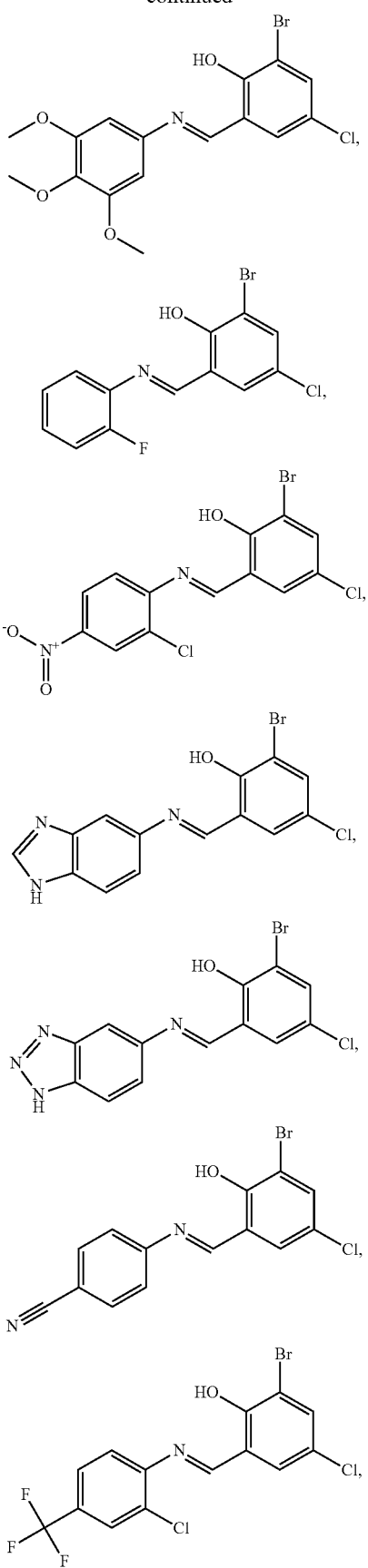

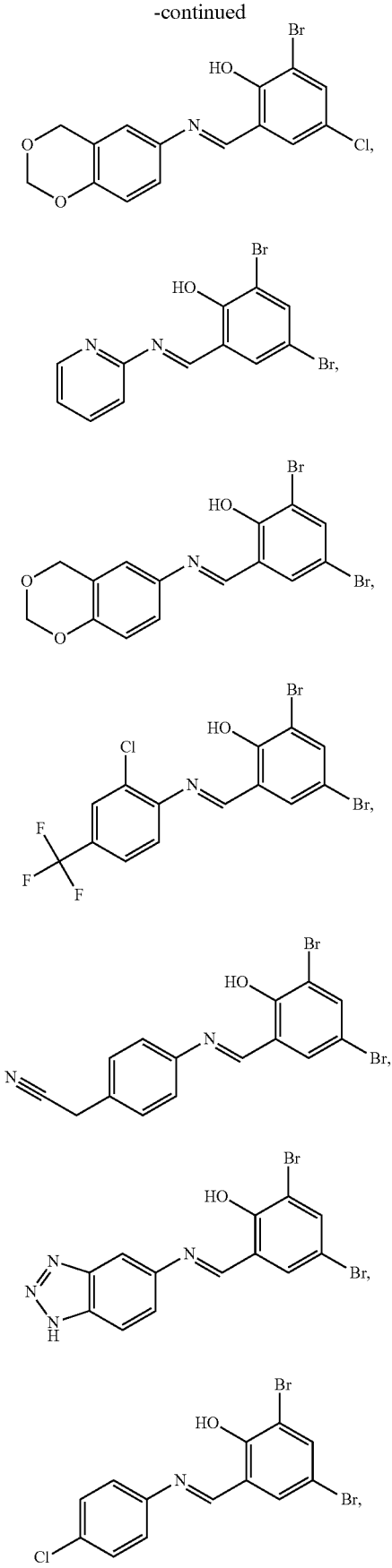
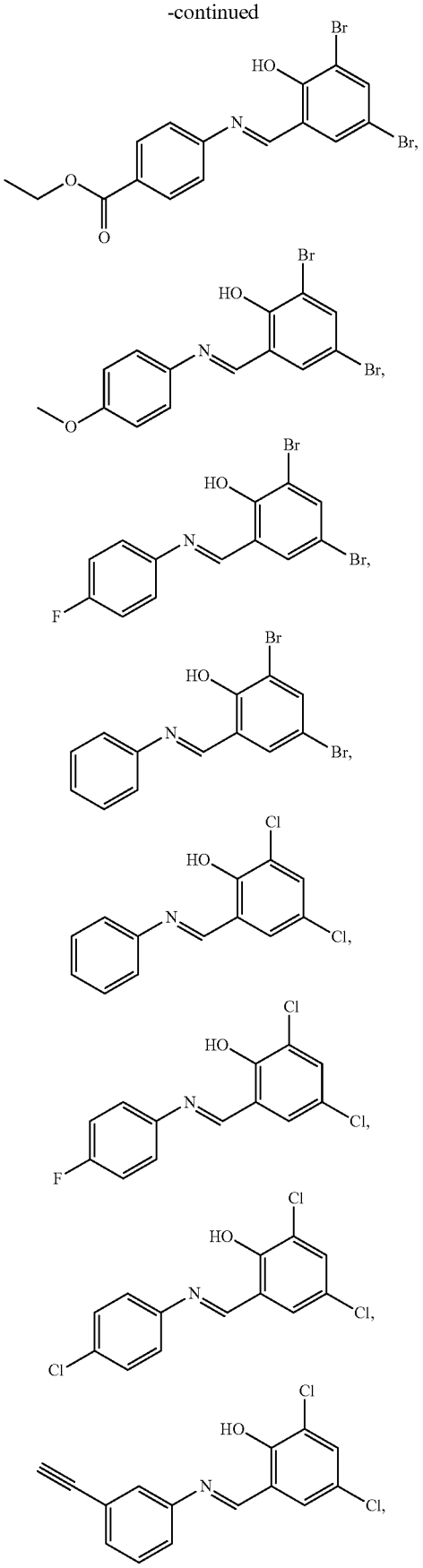

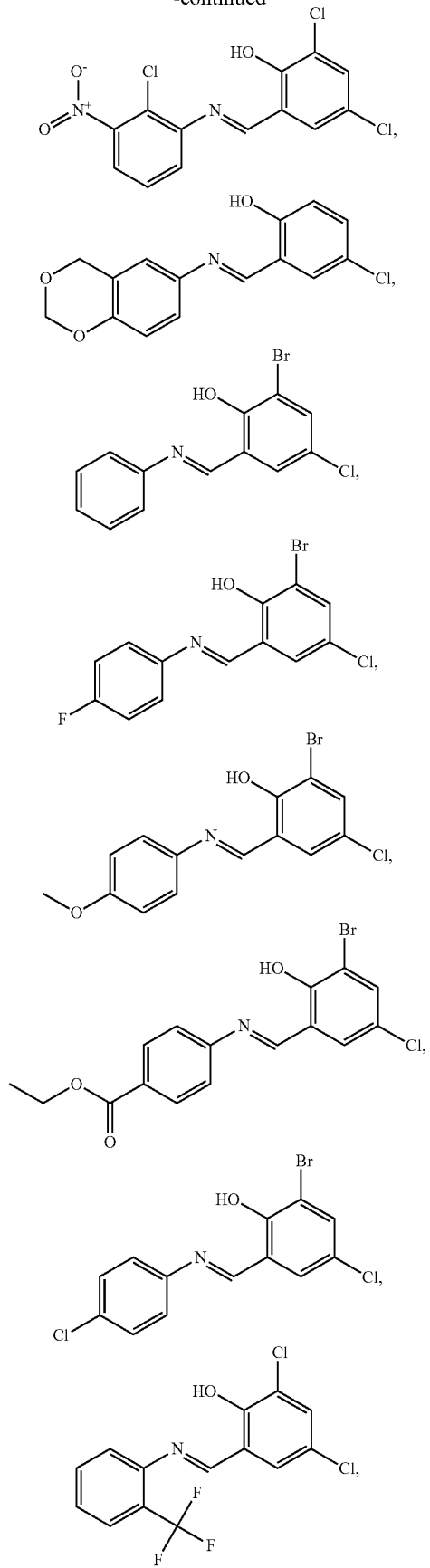
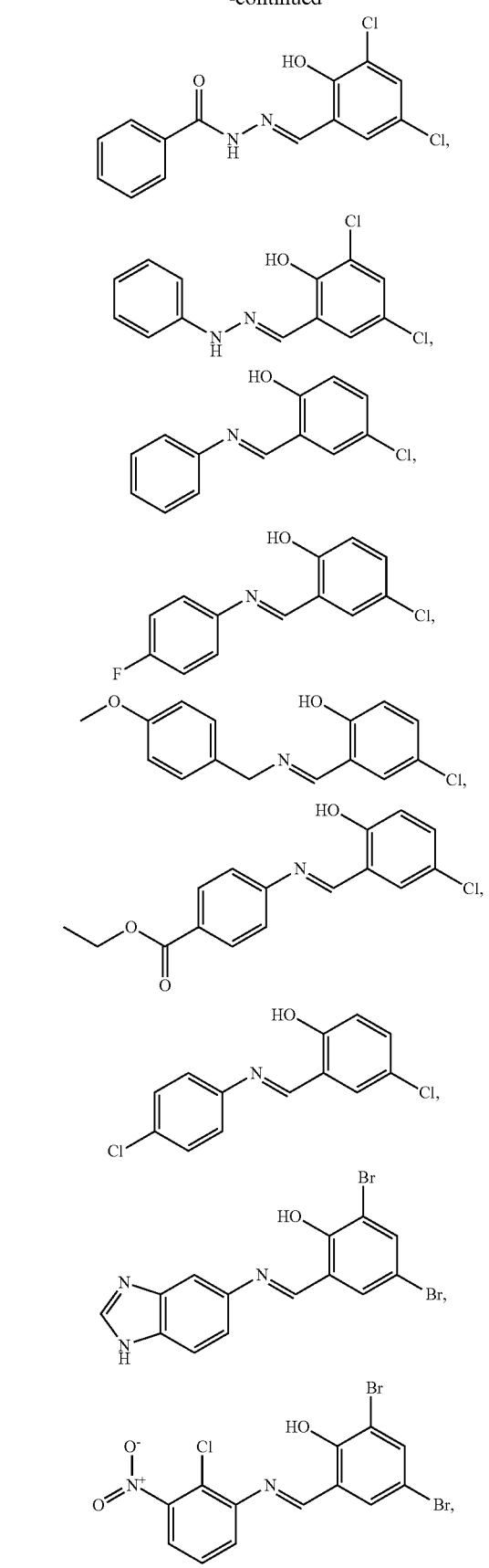

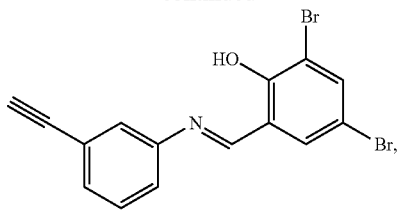
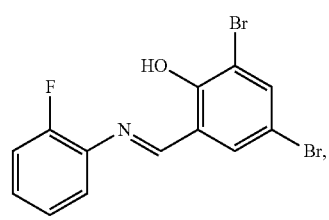
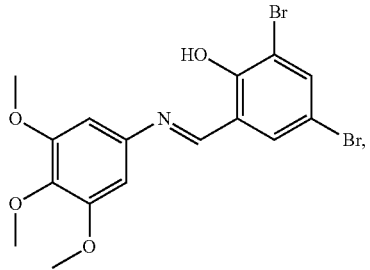
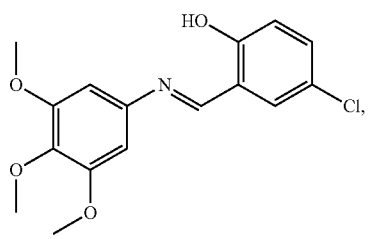
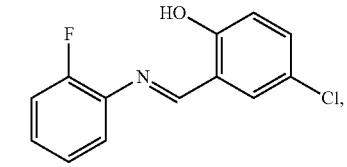
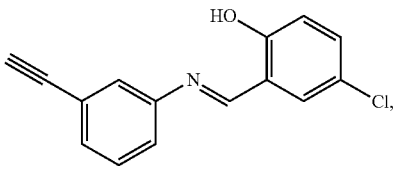
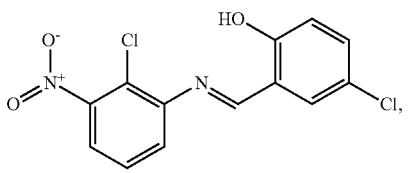
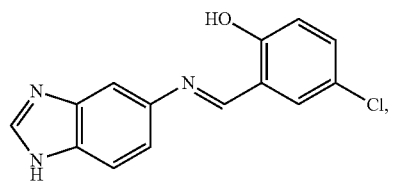
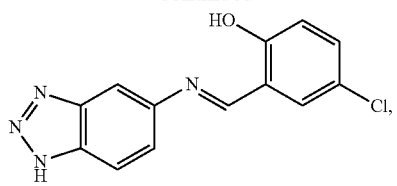
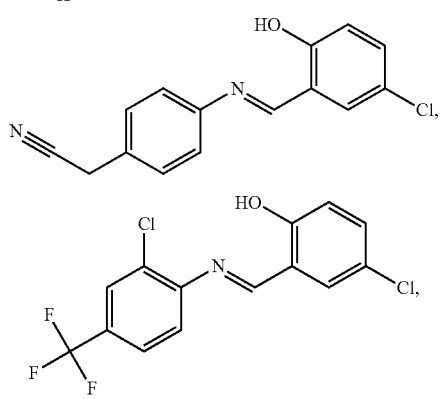
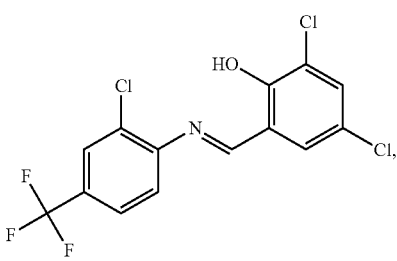
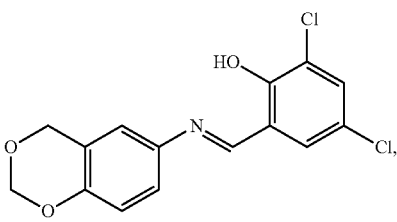
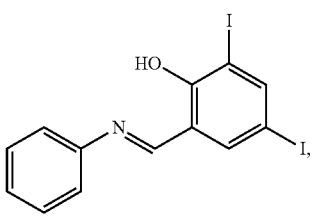
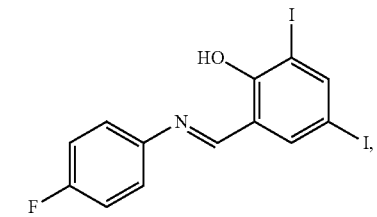
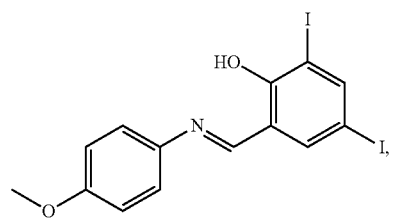

-continued

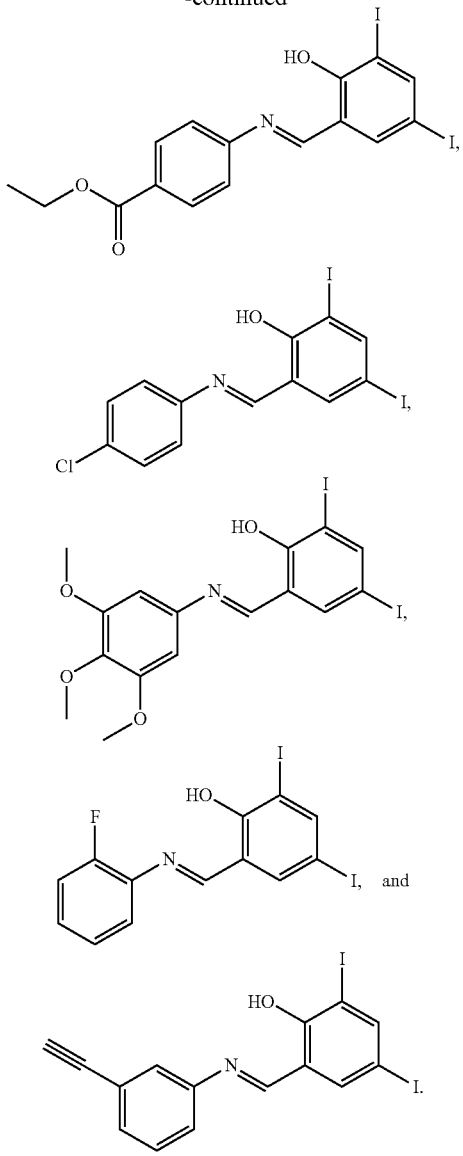

Provisos for Compound Claims

To the extent any of the following compounds are not novel, Applicants reserve the right to present compound and/or composition claims which include a proviso excluding the compounds and/or their pharmaceutically acceptable salts from the scope of the claims:

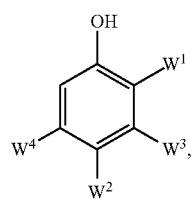

in which $W^2$ is halogen; an alkyl group having 1 to 4 carbon atoms; an alkoxy group having 1 to 4 carbon atoms; an acyloxy group having 2 to 4 carbon atoms; an acyl group having 2 to 4 carbon atoms; a carboxylic acid group; an ester group —COOW$^5$, wherein $W^5$ is a straight or branched chain alkyl radical having 1 to 4 carbon atoms; a nitrile group; an OH group; a —CHO group; an —NO$_2$ group; or an acetamido group; $W^1$ is hydrogen or one of the substituents defined under $W^2$; $W^3$ and $W^4$, which may be identical or different, are each a hydrogen atom or one of the substituents defined under $W^2$;

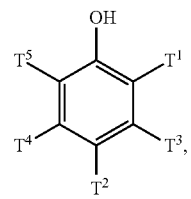

in which $T^1$, $T^2$, $T^3$, $T^4$, and $T^5$ are independently selected from hydroxyl groups, alkoxy groups containing from 1 to 6 carbon atoms; alkyl groups containing from 1 to 6 carbon atoms, a phenyl group, NO$_2$, COOH, COH, sulfonic acids, ketones containing from 1 to 6 carbon atoms, F, Cl, Br, I, hydrogen, or the salts of any of the preceding acids or alcohols, wherein at least two of the above T groups are hydrogen; or phenolic mixtures thereof;

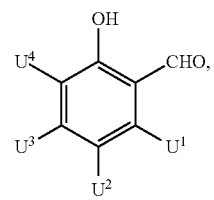

in which each of $U^1$, $U^2$, $U^3$, and $U^4$ independently represents a hydrogen or halogen atom or an alkyl, cycloalkyl, aralkyl, aryl, alkaryl, alkoxy, aryloxy, acyl or hydroxy group;

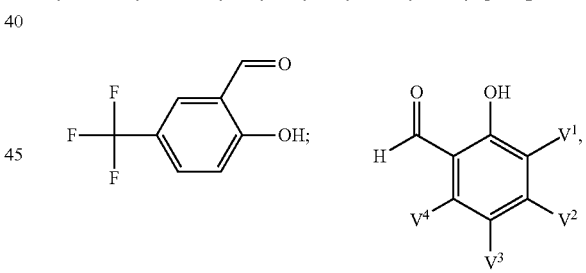

in which $V^1$, $V^2$, $V^3$, and $V^4$ represent hydrogen or halogen; or in which $V^2$ and $V^4$ are hydrogen and $V^1$ and $V^3$ are hydrogen or halogen;

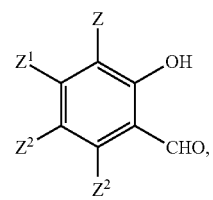

in which Z, $Z^1$, $Z^2$, and $Z^3$, which may be the same or different, represent a hydrogen atom; an alkyl, aryl, or cycloalkyl group; an alkoxyl, hydroxyl or acylamino group; or halogen;

2-hydroxybenzaldehyde (salicylic aldehyde); 2-hydroxy-3-methylbenzaldehyde; 2-hydroxy-3-tert.butylbenzaldehyde; 2-hydroxy-3-tert.butyl-5-methylbenzaldehyde; 2-hydroxy-3,5-ditert.butylbenzaldehyde; 2-hydroxy-3-isopropyl-6-methylbenzaldehyde; 2-hydroxy-3-cyclohexylbenzaldehyde; 2-hydroxy-4-tert.butyl-benzaldehyde; 2-hydroxy-4-chlorobenzaldehyde and 2-hydroxy-6-chlorobenz-aldehyde; 2-hydroxy-3-phenylbenzaldehyde; 2-hydroxy-5-methoxybenzaldehyde; 2-hydroxy-3-nonylbenzaldehyde; 2,5-dihydroxybenzaldehyde; and 2-hydroxy-4-acetylaminobenzaldehyde;

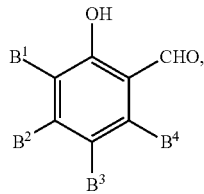

in which $B^1$, $B^2$, $B^3$, and $B^4$ are each a hydrogen atom, an alkyl, cycloalkyl, alkoxy or hydroxyl group or a halogen atom;

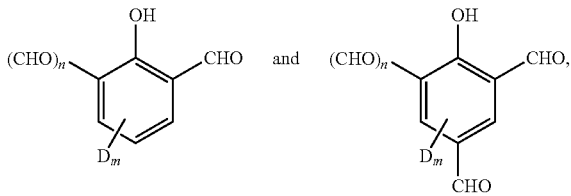

in which n is 0 or 1, m+n is at most 4 or 3, and D is alkyl, alkoxy, hydroxyalkyl, cycloalkyl, aryl, alkoxyalkyl, hydroxy, nitro, or halogen; salicylaldehyde, p-hydroxybenzaldehyde, 2,3-dihydroxybenzaldehyde, 2,6-dihydroxybenzaldehyde, 2-hydroxy-3-methoxybenzaldehyde (ortho-vanillin), 2,4-diformylphenol, 2,6-diformylphenol, 1,2-dihydroxy-3,5-diformylbenzene, 1,2-dihydroxy-4,6-diformylbenzene, 1-hydroxy-2-methoxy-4,6-diformylbenzene (4,6-diformylguaiacol), 1-hydroxy-2-ethoxy-4,6-diformylbenzene, 2,6-dihydroxy-benzaldehyde, and ortho-hydroxy-para-vanillin;

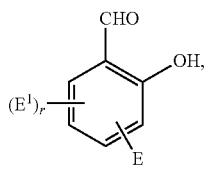

in which $E^1$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, or an alkylarylamino group; or $E^1$s may bond together to represent a 5- or 6-membered ring; E is positioned in the ortho or the para position with respect to the formyl group and represents a methylene group substituted by at least one selected from the group consisting of a hydroxyl group, a halogen atom, an alkoxy group, an aryloxy group, an alkylthio group, an arylthio group, an acyloxy group, a chlorocarbonyloxy group, an alkoxycarbonyloxy group, and an aminocarbonyloxy group; r is an integer of 0 to 3; and when r is 2 or more, $E^1$s are the same or different;

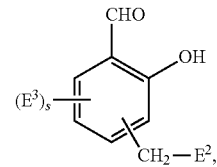

in which $E^3$ represents a hydroxyl group, an alkyl group, a cycloalkyl group, an aryl group, an alkoxy group, an aryloxy group, an acylamino group, a sulfonylamino group, an unsubstituted amino group, a monoalkylamino group, a dialkylamino group, an arylamino group, or an alkylarylamino group, or $E^3$s may bond together to represent a 5- or 6-membered ring; —$CH_2$— is positioned in the ortho or the para position with respect to the formyl group, $E^2$ represents an alkylthio group, an arylthio group, a chlorocarbonyloxy group, an alkoxycarbonyloxy group, or an aminocarbonyloxy group; s is 0 to 3, and when s is 2 or more, $E^3$s are the same or different;

2-hydroxybenzaldehyde, 3-methyl-2-hydroxybenzaldehyde, 3-ethyl-2-hydroxybenzaldehyde, 3-n-propyl-2-hydroxybenzaldehyde, 3-isopropyl-2-hydroxybenzaldehyde, 3-n-butyl-2-hydroxybenzaldehyde, 3-sec-butyl-2-hydroxybenzaldehyde, 3-tert-butyl-2-hydroxybenzaldehyde, 3-amyl-2-hydroxybenzaldehyde, 4-methyl-2-hydroxybenzaldehyde, 4-ethyl-2-hydroxybenzaldehyde, 4-n-propyl-2-hydroxybenzaldehyde, 4-isopropyl-2-hydroxybenzaldehyde, 4-n-butyl-2-hydroxybenzaldehyde, 4-sec-butyl-2-hydroxybenzaldehyde, 4-tert-butyl-2-hydroxybenzaldehyde, 4-amyl-2-hydroxybenzaldehyde, 5-methyl-2-hydroxybenzaldehyde, 5-ethyl-2-hydroxybenzaldehyde, 5-n-propyl-2-hydroxybenzaldehyde, 5-isopropyl-2-hydroxybenzaldehyde, 5-n-butyl-2-hydroxybenzaldehyde, 5-sec-butyl-2-hydroxybenzaldehyde, 5-tert-butyl-2-hydroxybenzaldehyde, 5-amyl-2-hydroxybenzaldehyde, 6-methyl-2-hydroxybenzaldehyde, 6-ethyl-2-hydroxybenzaldehyde, 6-n-propyl-2-hydroxybenzaldehyde, 6-isopropyl-2-hydroxybenzaldehyde, 6-n-butyl-2-hydroxybenzaldehyde, 6-sec-butyl-2-hydroxybenzaldehyde, 6-tert-butyl-2-hydroxybenzaldehyde, 6-amyl-2-hydroxybenzaldehyde, 3,5 dinitro-2-hydroxybenzaldehyde, 3,5 difluoro-2-hydroxybenzaldehyde, 3,4 diisobutyl-2-hydroxybenzaldehyde, 3,4 di-tert-butyl-2-hydroxybenzaldehyde, 3,6 di-tert-butyl-2-hydroxybenzaldehyde, 2-hydroxy-3,5-dichlorobenzaldehyde, 2,6-dihydroxybenzaldehyde, 2,4-dihydroxy-6-methylbenzaldehyde, 2,4,6-trihydroxybenzaldehyde, 5-chloro-2-hydroxybenzaldehyde, 2-hydroxy-5-bromobenzaldehyde, 2-hydroxy-3,5-diiodobenzaldehyde, 2,4-dihydroxy-3-methylbenzaldehyde, 2-hydroxy-3-methoxy-6-bromobenzaldehyde, 2,4-dihydroxy-5-propylbenzaldehyde, 2,4-dihydroxy-5-hexylbenzaldehyde, 2-formyl-3,6-dihydroxy-4,5-dimethylbenzaldehyde, 2,3,6-trihydroxybenzaldehyde, 2,4-dihydroxy-5-acetylbenzaldehyde, 2-formyl-3,6-dihydroxy-4,5-dipropylbenzaldehyde, 2-formyl-3-methoxy-4,5-dimethyl-6-hydroxybenzaldehyde, 2,3,5-trihydroxybenzaldehyde, 2-hydroxy-6-(oxy-4-methylpentanoic acid)benzaldehyde, 3-formyl-4,5-dihydroxybenzaldehyde, 2-ethyl-6-hydroxybenzaldehyde, 3-chloro-5-(3,7-dimethyl-2,6-octadienyl)-4,6-dihydroxy-2-methylbenzaldehyde, 2-hydroxy-6-(8-pentadecenyl)benzaldehyde, 2-4-dihydroxy-3-ethyl-6-(1-methylpentyl)

benzaldehyde, 2-pentanoic acid-3-formyl-4,5-dihydroxy benzaldehyde, 2-propanoic acid-3-formyl-4,5-dihydroxy benzaldehyde, 2,3,4-trihydroxy-5-methyl-6-hydroxymethylbenzaldehyde, 2-hydroxy-4-methoxybenzaldehyde, 2-hydroxy-5-carboxybenzaldehyde, 3-carboxy-4-hydroxybenzaldehyde, 2,3-dihydroxy-4-methoxybenzaldehyde, 2-hydroxy-6-methoxybenzaldehyde, 2,5-dihydroxybenzaldehyde, 2,3,4-trihydroxy-6-hydroxymethylbenzaldehyde, 2,3-dihydroxybenzaldehyde, 2-hydroxy-5-acetylbenzaldehyde, 2-hydroxy-5-carboxyethylbenzaldehyde, 2-hydroxy-5-carboxypropylbenzaldehyde, 2-hydroxy-5-carboxybutylbenzaldehyde, 2-hydroxy-3-iodo-5-carboxymethylbenzaldehyde, and 2-formyl-3,4,5-trihydroxybenzaldehyde;

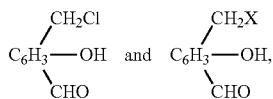

wherein X is halogen;

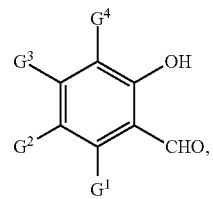

wherein $G^1$, $G^2$, $G^3$, and $G^4$ are independently hydrogen, straight-chain or branched $C_1$-$C_{10}$ alkyl, $C_3$-$C_8$ cycloalkyl, strain-chain or branched $C_1$-$C_{10}$ alkoxy, phenyl, or halogen, wherein alkyl or cycloalkyl may only be in the p-position to the hydroxyl group if they carry no a-H-atoms;

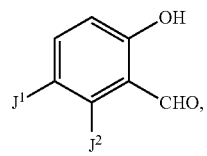

in which $J^1$ is $NO_2$ and $J^2$ is hydrogen; $J^1$ and $J^2$ are both chlorine; or $J^1$ is hydrogen and $J^2$ is fluorine;

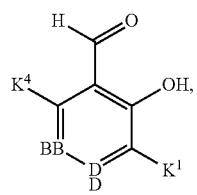

in which $K^1$ and $K^4$ are independently selected from the group consisting essentially of hydrogen; hydroxy; halo; nitro; cyano; trifluoromethyl; $(C_1$-$C_6)$alkyl; $(C_1$-$C_6)$alkoxy; $(C_3$-$C_6)$cycloalkyl; $(C_2$-$C_6)$alkenyl; —C(=O)OK$^7$; —OC(=O)K$^7$; —S(=O)$_2$; —S(=O)$_2$N(K$^7$)(K$^9$); —S(=O)$_2$K$^7$; —S(=O)$_2$OK$^7$; —C(=O)NK$^7$K$^9$; —C(=O)K$^9$; and —N(K$^7$)(K$^9$), where K$^7$ is hydrogen or $(C_1$-$C_4)$alkyl and K$^9$ is $(C_1$-$C_4)$ alkyl; wherein: said alkyl, cycloalkyl and alkenyl groups defining $K^1$ and $K^4$ may optionally be independently substituted by one or two substituents selected from the group consisting essentially of halo; hydroxy; $(C_1$-$C_2)$alkyl; $(C_1$-$C_2)$alkoxy; $(C_1$-$C_2)$alkoxy-$(C_1$-$C_2)$alkyl; $(C_1$-$C_2)$alkoxycarbonyl; carboxyl; $(C_1$-$C_2)$alkylcarbonyloxy; nitro; cyano; amino disubstituted by $(C_1$-$C_2)$alkyl; sulfonyl; and sulfonamido disubstituted by $(C_1$-$C_2)$alkyl; and DD and BB are independently N, or CHK$^2$ or CHK$^3$, respectively, where K$^2$ and K$^3$ are independently selected from the group consisting essentially of hydrogen; hydroxy; halo; nitro; cyano; trifluoromethyl; $(C_1$-$C_6)$alkyl; $(C_1$-$C_6)$alkoxy; $(C_3$-$C_6)$cycloalkyl; $(C_2$-$C_6)$alkenyl; —C(=O)OK$^{11}$; —OC(=O)K$^{11}$; —S(=O)$_2$; —S(=O)$_2$N(K$^{11}$)(K$^{13}$); and —N(K$^{11}$)(K$^{13}$), where K$^{11}$ is hydrogen or $(C_1$-$C_4)$alkyl and K$^{13}$ is $(C_1$-$C_4)$ alkyl; and wherein said alkyl, cycloalkyl and alkenyl groups defining K$^2$ and K$^3$ may optionally be independently substituted by one or two substituents selected from the group consisting essentially of halo; hydroxy; $(C_1$-$C_2)$alkyl; $(C_1$-$C_2)$alkoxy; $(C_1$-$C_2)$alkoxy-$(C_1$-$C_2)$alkyl; $(C_1$-$C_2)$alkoxycarbonyl; carboxyl; $(C_1$-$C_2)$alkylcarbonyl-oxy; nitro; cyano; amino disubstituted by $(C_1$-$C_2)$alkyl; sulfonyl; and sulfonamido disubstituted by $(C_1$-$C_2)$alkyl; in which K$^1$ and K$^4$ are independently hydrogen; hydroxy; trifluoromethyl; $(C_1$-$C_4)$ alkyl; $(C_1$-$C_4)$alkoxy-; —C(=O)OK$^7$; or —N(K$^7$)(K$^9$), where K$^7$ is hydrogen or $(C_1$-$C_2)$alkyl and K$^9$ is $(C_1$-$C_2)$; and more preferably K$^1$ and K$^4$ are independently hydrogen; hydroxy; $(C_1$-$C_2)$alkyl; $(C_1$-$C_2)$alkoxy; carboxyl or methylamino, in which case K$^7$ is hydrogen and K$^9$ is methyl; in which K$^1$ and K$^4$ are defined as alkyl and are substituted with a single substitutent selected from hydroxy; $(C_1$-$C_2)$alkoxy; carboxyl; amino disubstituted by $(C_1$-$C_2)$alkyl; and sulfonamido disubstituted by $(C_1$-$C_2)$alkyl; in which K$^1$ and K$^4$ are defined as alkyl and are substituted with a single substitutent selected from hydroxy, methoxy, and dimethylamino; in which one of DD or BB is N and the other is CHK$^2$, or CHK$^3$, respectively; in which DD is CHK$^2$ and BB is CHK$^3$, wherein K$^2$ and K$^3$ are independently hydrogen; hydroxy; halo; trifluoromethyl; $(C_1$-$C_4)$alkyl; $(C_1$-$C_4)$alkoxy; —C(=O)OK$^{11}$; —S(=O)$_2$N(K$^{11}$)(K$^{13}$); or —N(K$^{11}$)(K$^{13}$), where K$^{11}$ is hydrogen or $(C_1$-$C_2)$alkyl and K$^{13}$ is $(C_1$-$C_2)$alkyl; in which K$^2$ and K$^3$ are independently hydrogen; hydroxy; $(C_1$-$C_2)$ alkyl; $(C_1$-$C_2)$alkoxy; carboxyl; or methylamino, K$^{11}$ is hydrogen and K$^{13}$ is methyl; and in which K$^2$ and K$^3$ are defined as alkyl and are substituted, there is a single substituent selected from hydroxy; $(C_1$-$C_2)$alkoxy; carboxyl; amino disubstituted by $(C_1$-$C_2)$alkyl; and sulfonamido disubstituted by $(C_1$-$C_2)$alkyl.

o-vanillin; salicylaldehyde; 2,3-dihydroxybenzaldehyde; 2,6-dihydroxybenz-aldehyde; 2-hydroxy-3-ethoxybenzaldehyde; and pyridoxal;

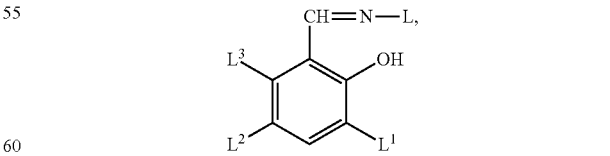

in which $L^1$ and $L^2$ represent halogen atoms, especially chlorine, bromine, or iodine atoms, $L^3$ represents a hydrogen or a halogen atom, especially chlorine, and L represents the hydroxyl group, an aryl or aralkyl residue which is substituted by at least one of the following substituents: a halogen atom, $CF_3$, $NO_2$, CN, alkyl, alkoxy, SCN, or a tertiary amino group;

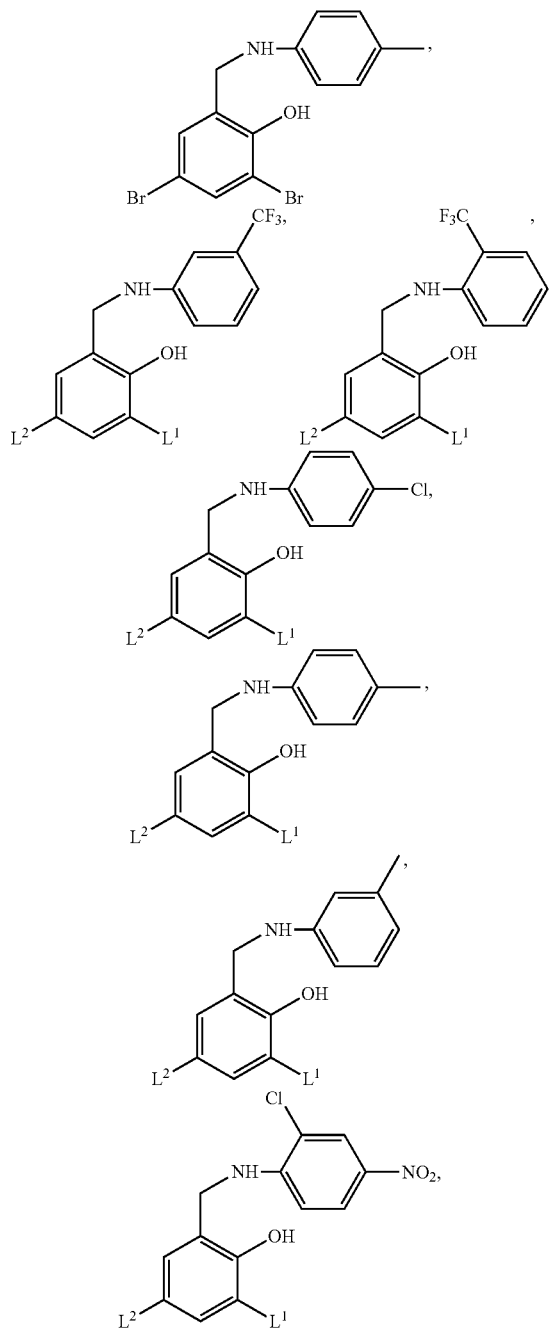

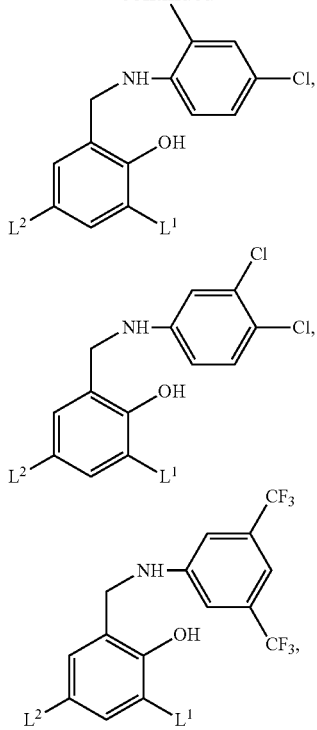

in which $L^1$ and $L^2$ are both Cl, both Br, or both I;

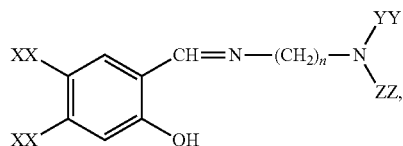

in which XX is halogen, n is 2 or 3, and YY and ZZ are identical or different lower alkyl radicals which may also form a heterocycle with the nitrogen atom and may contain another heteroatom of N, N, or S, as well as quaternary salts and metal chelates thereof; and

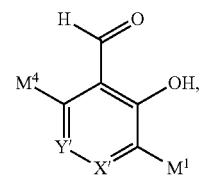

in which $M^1$, $M^4$, Y', and X' are as defined below:

| $M^1$ | $M^4$ | X' | Y' | $M^2$ | $M^3$ |
|---|---|---|---|---|---|
| H | H | $CHM^2$ | $CHM^3$ | H | H |
| H | OH | $CHM^2$ | $CHM^3$ | H | H |
| OH | H | $CHM^2$ | $CHM^3$ | H | H |
| $CF_3$ | H | $CHM^2$ | $CHM^3$ | H | H |
| $CH_3$ | H | $CHM^2$ | $CHM^3$ | H | H |

-continued

| $M^1$ | $M^4$ | X' | Y' | $M^2$ | $M^3$ |
|---|---|---|---|---|---|
| $CH_2CH_3$ | H | $CHM^2$ | $CHM^3$ | H | H |
| $OCH_3$ | H | $CHM^2$ | $CHM^3$ | H | H |
| C(=O)OH | H | $CHM^2$ | $CHM^3$ | H | H |
| $C(=O)OCH_3$ | H | $CHM^2$ | $CHM^3$ | H | H |
| $NHCH_3$ | H | $CHM^2$ | $CHM^3$ | H | H |
| $N(CH_3)_2$ | H | $CHM^2$ | $CHM^3$ | H | H |
| H | OH | $CHM^2$ | $CHM^3$ | H | H |
| H | $CH_3$ | $CHM^2$ | $CHM^3$ | H | H |
| H | $CF_3$ | $CHM^2$ | $CHM^3$ | H | H |
| H | $CH_2CH_3$ | $CHM^2$ | $CHM^3$ | H | H |
| H | $OCH_3$ | $CHM^2$ | $CHM^3$ | H | H |
| H | C(=O)OH | $CHM^2$ | $CHM^3$ | H | H |
| H | $C(=O)OCH_3$ | $CHM^2$ | $CHM^3$ | H | H |
| H | $NHCH_3$ | $CHM^2$ | $CHM^3$ | H | H |
| H | $N(CH_3)_2$ | $CHM^2$ | $CHM^3$ | H | H |
| OH | OH | $CHM^2$ | $CHM^3$ | H | H |
| $CF_3$ | $CF_3$ | $CHM^2$ | $CHM^3$ | H | H |
| $CH_3$ | $CH_3$ | $CHM^2$ | $CHM^3$ | H | H |
| $CH_2CH_3$ | $CH_2CH_3$ | $CHM^2$ | $CHM^3$ | H | H |
| $OCH_3$ | $OCH_3$ | $CHM^2$ | $CHM^3$ | H | H |
| C(=O)OH | C(=O)OH | $CHM^2$ | $CHM^3$ | H | H |
| $C(=O)OCH_3$ | $C(=O)OCH_3$ | $CHM^2$ | $CHM^3$ | H | H |
| $NHCH_3$ | $NHCH_3$ | $CHM^2$ | $CHM^3$ | H | H |
| $N(CH_3)_2$ | $N(CH_3)_2$ | $CHM^2$ | $CHM^3$ | H | H |
| H | H | $CHM^2$ | $CHM^3$ | OH | H |
| H | H | $CHM^2$ | $CHM^3$ | H | OH |
| H | H | $CHM^2$ | $CHM^3$ | OH | OH |
| H | H | $CHM^2$ | $CHM^3$ | $CH_3$ | H |
| H | H | $CHM^2$ | $CHM^3$ | H | $CH_3$ |
| H | H | $CHM^2$ | $CHM^3$ | $CH_3$ | $CH_3$ |
| H | H | $CHM^2$ | $CHM^3$ | $OCH_3$ | H |
| H | H | $CHM^2$ | $CHM^3$ | H | $OCH_3$ |
| H | H | $CHM^2$ | $CHM^3$ | $OCH_3$ | $OCH_3$ |
| H | H | $CHM^2$ | $CHM^3$ | $NHCH_3$ | H |
| H | H | $CHM^2$ | $CHM^3$ | H | $NHCH_3$ |
| H | H | $CHM^2$ | $CHM^3$ | $NHCH_3$ | $NHCH_3$ |
| H | H | $CHM^2$ | $CHM^3$ | $N(CH_3)_2$ | H |
| H | H | $CHM^2$ | $CHM^3$ | H | $N(CH_3)_2$ |
| H | H | $CHM^2$ | $CHM^3$ | $N(CH_3)_2$ | $N(CH_3)_2$ |
| $CH_3$ | H | $CHM^2$ | $CHM^3$ | $CH_3$ | H |
| H | $CH_3$ | $CHM^2$ | $CHM^3$ | H | $CH_3$ |
| $OCH_3$ | H | $CHM^2$ | $CHM^3$ | $OCH_3$ | H |
| $OCH_3$ | H | $CHM^2$ | $CHM^3$ | H | $CH_3$ |
| H | H | $CHM^2$ | $CHM^3$ | H | OH |
| H | OH | $CHM^2$ | $CHM^3$ | $CH_3$ | $CH_3$ |
| $OCH_3$ | H | $CHM^2$ | $CHM^3$ | $OCH_3$ | H |
| OH | H | $CHM^2$ | $CHM^3$ | $OCH_3$ | $OCH_3$ |
| $OCH_3$ | H | $CHM^2$ | $CHM^3$ | H | $NHCH_3$ |
| H | $NHCH_3$ | $CHM^2$ | $CHM^3$ | $NHCH_3$ | H |
| H | OH | $CHM^2$ | $CHM^3$ | H | $NHCH_3$ |
| H | OH | $CHM^2$ | $CHM^3$ | OH | H |
| H | OH | $CHM^2$ | $CHM^3$ | H | OH |
| $N(CH_3)_2$ | H | $CHM^2$ | $CHM^3$ | $OCH_3$ | H |
| $CH_3$ | H | $CHM^2$ | $CHM^3$ | H | $OCH_3$ |
| H | $CH_3$ | $CHM^2$ | $CHM^3$ | $N(CH_3)_2$ | H |
| H | $N(CH_3)_2$ | $CHM^2$ | $CHM^3$ | $CH_3$ | H |
| $OCH_3$ | H | $CHM^2$ | $CHM^3$ | H | $OCH_3$ |
| $OCH_3$ | H | $CHM^2$ | $CHM^3$ | $CH_3$ | $CH_3$ |
| $OCH_3$ | H | N | $CHM^3$ | — | H |
| $CH_3$ | H | N | $CHM^3$ | — | $CH_3$ |
| H | $N(CH_3)_2$ | N | $CHM^3$ | — | H |
| H | $CH_3$ | N | $CHM^3$ | — | $CH_3$ |
| $OCH_3$ | $OCH_3$ | N | $CHM^3$ | — | H |
| $CH_3$ | H | N | $CHM^3$ | — | $NHCH_3$ |
| $CH_3$ | $OCH_3$ | N | $CHM^3$ | — | H |
| $CH_3$ | $CH_2OH$ | N | $CHM^3$ | — | H |
| $CH_3$ | $CH_2OH$ | N | $CHM^3$ | — | $CH_3$ |
| $OCH_3$ | $CH_2OH$ | N | $CHM^3$ | — | H |

Methods of Preparing IRE-1α Inhibitor Compounds and Prodrugs of the Invention

Some of the IRE-1α inhibitor compounds for use in the disclosed methods are available commercially, for example from Fluorochem Ltd., Aurora Fine Chemicals, TCI America Organic Chemicals, AKos Consulting and Solutions, or Maybridge. Others and their starting materials can be prepared by appropriate modification of methods known in the art as described in the literature, for example in standard works such as Houben-Weyl, Methoden der organischen Chemie, Georg-Thieme-Verlag, Stuttgart. Methods may also be found by computer search in The MDL® CrossFire Beilstein database, in which the reaction domain details the preparation of substances. See also the specific Examples, below.

Pharmaceutical Preparations

Any of the IRE-1α inhibitor compounds and prodrugs disclosed herein can be formulated as pharmaceuticals using methods well known in the art. Pharmaceutical formulations of the invention typically comprise at least one IRE-1α inhibitor compound or prodrug thereof mixed with a carrier, diluted with a diluent, and/or enclosed or encapsulated by an ingestible carrier in the form of a capsule, sachet, cachet, paper or other container or by a disposable container such as an ampoule.

A carrier or diluent can be a solid, semi-solid or liquid material. Some examples of diluents or carriers which may be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, methyl cellulose, polyoxyethylene sorbitan monolaurate, ethyl lactate, propylhydroxybenzoate, sorbitan trioleate, sorbitan sesquioleate and oleyl alcohol.

Pharmaceutical compositions of the invention can be manufactured by methods well known in the art, including conventional mixing, dissolving, granulating, dragee-making, levigating, emulsifying, encapsulating, entrapping, or lyophilizing processes.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. If desired, any of the IRE-1α inhibitor compounds or prodrugs thereof disclosed herein can be provided in a pyrogen-free pharmaceutically acceptable vehicle.

For oral administration, an IRE-1α inhibitor compound or prodrug thereof can be combined with pharmaceutically acceptable carriers or vehicles which enable the IRE-1α inhibitor compound or prodrug thereof to be formulated as tablets, pills, dragees, capsules, liquids, gels, syrups, slurries, suspensions and the like. Fillers can be used, such as gelatin, sugars (e.g., lactose, sucrose, mannitol, or sorbitol); cellulose preparations (e.g., maize starch, wheat starch, rice starch, potato starch, gum tragacanth, methyl cellulose, hydroxypropylmethyl-cellulose, sodium carboxymethylcellulose); and/or polyvinylpyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an IRE-1α inhibitor compound or prodrug thereof may be dissolved or suspended in suitable liquids, such as fatty oils, liquid paraffin, or liquid polyethylene glycols. In addition, stabilizers may be added. All formulations for oral administration preferably are in dosages suitable for such administration.

For buccal administration, the compositions may take the form of tablets or lozenges formulated in conventional manner.

For administration by inhalation, pharmaceutical preparations of the invention can be delivered in the form of an aerosol sprays from pressurized packs or a nebulizer, with the use of a suitable propellant, e.g., dichlorodifluoromethane, trichlorofluoromethane, dichlorotetrafluoroethane, carbon dioxide, or other suitable gas. If desired, a valve can be used to deliver a metered amount. Capsules and cartridges of e.g., gelatin for use in an inhaler or insufflator, may be formulated containing a powder mix of an IRE-1α inhibitor compound or prodrug thereof and a suitable powder base such as lactose or starch.

IRE-1α inhibitor compounds or prodrugs thereof can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of an IRE-1α inhibitor compound or prodrug thereof. Additionally, a suspension of an IRE-1α inhibitor compound or prodrug thereof may be prepared as an appropriate oily injection suspension. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of an IRE-1α inhibitor compound or prodrug thereof to allow for the preparation of highly concentrated solutions.

Alternatively, an IRE-1α inhibitor compound or prodrug thereof may be in powder form for constitution with a suitable vehicle, e.g., sterile pyrogen-free water, before use.

IRE-1α inhibitor compounds or prodrugs thereof may also be formulated in rectal compositions such as suppositories or retention enemas, e.g., containing conventional suppository bases such as cocoa butter or other glycerides.

In addition to the formulations described previously, an IRE-1α inhibitor compound or prodrug thereof can also be formulated as a depot preparation. Such long acting formulations may be administered by implantation (for example subcutaneously or intramuscularly) or by intramuscular injection. Thus, for example, an IRE-1α inhibitor compound or prodrug thereof may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

In addition to the common dosage forms set out above, an IRE-1α inhibitor compound or prodrug thereof can be administered by controlled release means and/or delivery devices including ALZET® osmotic pumps, which are available from Alza Corporation. Suitable delivery devices are described in U.S. Pat. Nos. 3,845,770; 3,916,899; 3,536,809; 3,598,123; 3,944,064 and 4,008,719.

Therapeutic Methods

IRE-1α inhibitor compounds or prodrugs thereof can be administered to a patient, preferably a human patient, in pharmaceutical preparations as disclosed above, preferably with a pyrogen-free pharmaceutically acceptable vehicle, at doses effective to treat or ameliorate a symptom of a disorder associated with the unfolded protein response.

Disorders Associated with UPR

A fine balance exists between a cell's life and death depending on how protein folding stress is managed by the cell (proteostasis). Imbalances in proteostasis lead to many metabolic, oncological, neurodegenerative, inflammatory, cardiovascular disorders and infectious disease (Balch et al., Science 319, 916, 2008). The UPR relates specifically to the proteostasis of the endoplasmic reticulum where all secreted and membrane proteins are translated, folded and processed for delivery to their individual site of action. Therefore, activation of the UPR enhances protein folding in the ER allowing the cell to survive. If protein folding stress is not managed in the ER, the cells will initiate apoptosis.

Protein folding stress may be a natural hallmark of the type of cell for example insulin secreting β-islet cells or antibody secreting plasma cells. In both cases, the cell has fine tuned the machinery to deal with the stress by activating the UPR. Depending on the disease type, it may be therapeutically beneficial to induce or inhibit the UPR. For example, in type II diabetes or Alzheimer's disease, it may be therapeutically beneficial to activate the UPR in such a way where β-islet cells survive the stress of over producing insulin or neurons survive the apoptotic effects due to unfolded aggregates of β-amyloid protein. Diseases such as cancer, inflammation, and viral infection may be therapeutically modulated by inhibition of the UPR. In these types of conditions, cellular survival due to corruption of the UPR may be impacted. Protein folding in the ER is negatively impacted by such conditions in the tumor microenvironment as hypoxia, glucose starvation, amino acid deprivation, acidosis and mutant malfolded and oncogenic proteins. Additionally chemo-, bio-, and radio-therapy can lead to protein folding stress. It may be possible to induce apoptosis in these conditions by inhibiting the anti-apoptotic effects of the UPR. Myeloma derived from neoplastic antibody secreting plasma cells provides an example of a condition in which this approach can be applied.

Lastly, enveloped viruses must use and corrupt this system to ensure production of progeny from infected cells. Viruses often produce vast quantities of viral membrane glycoproteins which are folded and modified in the ER. Therefore, activation of the UPR by the virus for this purpose as a survival mechanism is entirely conceivable. It is therefore logical that inhibition of the UPR during viral infection can impact the outcome of the disease in a beneficial way.

Only specialized secretory cells and diseased cells activate the UPR for their own benefit. Most cells are not under such protein folding stress and therefore would not be impacted by a UPR inhibitor. Thus, "disorders associated with the UPR" as used herein means conditions for which pathogenesis can be advantageously impacted by inhibition of the UPR. In various embodiments of the invention such inhibition of the UPR is accomplished through inhibition of IRE-1α.

In some embodiments, the IRE-1α inhibitor compounds or prodrugs thereof are useful to treat or ameliorate a symptom of a B cell autoimmune disease, certain cancers, and infections of enveloped viruses that use the endoplasmic reticulum as a viral factory for expressing viral surface and spike proteins for budding and infection. IRE-1α inhibitors and prodrugs thereof can be used as single agents or in combination therapies, as described below.

B-cell autoimmune diseases which can be treated include, but are not limited to, Addison's disease, antiphospholipid syndrome, aplastic anemia, autoimmune hemolytic anemias, autoimmune hepatitis, autoimmune hypophysitis, autoimmune lymphoproliferative disorders, autoimmune myocarditis, Churg-Strauss syndrome, epidermolysis bullosa acquisita, giant cell arteritis, Goodpasture's syndrome, Graves' disease, Guillain-Barré syndrome, Hashimoto's thyroiditis, idiopathic thrombocytopenic purpura, IgA nephropathy, myasthenia gravis, pemphigus foliaceous, pemphigus vulgaris, polyarteritis nodosa, polymyositis/dermatomyositis, rheumatoid arthritis, scleroderma, Sjögren's syndrome, systemic lupus erythematosus, Takayasu's arteritis, and Wegener's granulomatosis.

Cancers which can be treated include solid tumors, such as tumors of the breast, bone, prostate, lung, adrenal gland (e.g., adrenocortical tumors), bile duct, bladder, bronchus, nervous tissue (including neuronal and glial tumors), gall bladder, stomach, salivary gland, esophagus, small intestine, cervix, colon, rectum, liver, ovary, pancreas, pituitary adenomas, and secretory adenomas. Methods of the invention are particularly useful for treating drug- or radiation-resistant solid tumors.

Cancers of the blood (e.g., lymphomas and leukemias) also can be treated including, but not limited to, multiple myeloma, Hodgkin's lymphoma, non-Hodgkin's lymphomas (e.g., cutaneous T cell lymphomas such as Sezary syndrome and Mycosis fungoides, diffuse large cell lymphoma, HTLV-1 associated T cell lymphoma, nodal peripheral T cell lymphoma, extranodal peripheral T cell lymphoma, central nervous system lymphoma, and AIDS-related lymphoma). Leukemias include acute and chronic types of both lymphocytic and myelogenous leukemia (e.g, acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia). Monoclonal gammopathy of undetermined significance (MGUS), the precursor of myeloma, also can be treated.

Viral infections which can be treated include infections of enveloped viruses which utilize the unfolded protein response pathway when they replicate and form infectious progeny (e.g., measles, pox viruses, Ebola, etc.). Infections also include those of Epstein Barr virus (EBV), cytomegalovirus (CMV), Flaviviruses (e.g., Japanese Encephalitis Virus and West Nile Virus), and Hepatitis C virus (HCV).

Combination Therapies

Various types of physiological stress induce the unfolded protein response including, but not limited to, hypoxia, nutrient starvation, acidosis, and genetic damage resulting in mutant or over-expressed misfolded proteins (oncogenic stress). One or more of these conditions are manifest in cancer cells, which may in part be mediated by the microenviroment of the tumor. It is likely the cytoprotective arm of the unfolded protein response (UPR) plays an anti-apototic role in tumor survival. In addition, bio- and chemotherapeutic drugs and radiation treatments may further impact the protein folding and degradation cycle in the ER thereby inducing the UPR as a protective resistance mechanism. Patients succumb to cancer because either the tumor is resistant to conventional therapies or returns in a resistant form after an initial response to treatment and, therefore, new treatments and treatment combinations are needed.

Angiogenesis inhibitors block tumor growth by inhibiting new blood vessel formation, a process that would enhance the stress effects of the tumor microenvironment. A promising approach to further reduce tumor burden would be to administer anti-angiogenesis agents in combination with IRE-1α/XBP-1 inhibitors to obtain a similar effect as that demonstrated by RNAi knockdown of GRP78, the major chaperone of the ER and target of XBP-1s (Dong et al., Cancer Res. 2007 Jul. 15; 67(14):6700-7). In addition, IRE-1α itself regulates angiogenesis by influencing the expression of VEGF.

Proteasome inhibitors and Hsp90 inhibitors are thought to act in part by blocking protein degradation and folding, respectively, inducing apoptosis (Davenport et al., Blood 2007 Oct. 1; 110(7):2641-9). Although it is clear that Hsp90 inhibitors induce XBP-1 splicing and activation of the UPR, it is less clear that proteasome inhibitors activate IRE-1α. Current scientific literature suggest that IRE-1α is not or is only minimally activated by proteasome inhibitors such as bortezomib or MG-132 (Davenport et al., Blood 2007 Oct. 1; 110(7):2641-9). However, the data shown in FIG. 6 demonstrates activation of this pathway in bortezomib-resistant RPMI8226 cells.

Interference with UPR may sensitize cancer cells to various chemotherapeutics that elevate the cellular stress and thus, IRE/XBP-1 inhibitors may become important therapies in conjunction with current and future standard of care in cancer.

Although the level of activation IRE-1α in solid tumors is currently not known, clearly, induction of the UPR in patient biopsies of drug resistant tumors is evidenced by induction of GRP78 (Moenner et al., Cancer Res. 2007 Nov. 15; 67(22): 10631-4; Lee, Cancer Res. 2007 Apr. 15; 67(8):3496-9).

Inhibition of XBP-1 splicing may have a greater effect than anticipated as the un-spliced form of XBP-1 may act as a dominant negative to XBP-1 and ATF-6 transcriptional activity. Further inhibitors which block the RNAse activity but not kinase activity of IRE-1α may have the added benefit of signaling through the JNK pathway, a signal that can have pro-apoptotic consequences.

In some embodiments an IRE-1α inhibitor compound or prodrug thereof is administered in combination with a therapeutic agent that induces or up-regulates IRE-1α expression (e.g., Hsp90 and or HDAC inhibitors, both of which induce IRE-1α activation and XBP-1 splicing) or a therapeutic agent which is less effective when IRE-1α is expressed (e.g., 17-AAG (TANESPIMYCIN®) and suberoylanilide hydroxamic acid (SAHA)).

In some embodiments an IRE-1α inhibitor compound or prodrug thereof is administered in combination with a cancer therapeutic agent, for example radiation therapy or a cancer therapeutic agent (e.g., a chemotherapeutic agent or a biotherapeutic agent) as described below. The cancer therapeutic agent can be administered separately or together with the IRE-1α inhibitor compound. The cancer therapeutic agent can be administered at essentially the same time as the IRE-1α inhibitor compound or can be administered either before or after the IRE-1α inhibitor compound.

Cancer therapeutic agents which can be used according to the invention include, but are not limited to, agents in the following categories (which may overlap):
  a. proteasome inhibitors, such as bortezomib ([(1R)-3-methyl-1-[[(2S)-1-oxo-3-phenyl-2-[(pyrazinylcarbonyl) amino]propyl]amino]butyl]boronic acid; MG-341; VELCADE®), MG-132 (N-[(phenylmethoxy)carbonyl]-L-leucyl-N-[(1S)-1-formyl-3-methylbutyl]-L-leucinamide);
  b. antimetabolites, such as:
     i. pyrimidine analogs (e.g., 5-fluorouracil, floxuridine, capecitabine, gemcitabine and cytarabine);
     ii. purine analogs,
     iii. folate antagonists and related inhibitors (e.g., mercaptopurine, thioguanine, pentostatin and 2-chlorodeoxyadenosine [cladribine]);
     iv. folic acid analogs (e.g., methotrexate);
  c. antimitotic agents, including:
     i. natural products such as vinca alkaloids (e.g., vinblastine, vincristine, and vinorelbine);
     ii. alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC);
  d. microtubule disruptors such as taxane (paclitaxel, docetaxel), vincristin, vinblastin, nocodazole, epothilones and navelbine, and epidipodophyllotoxins (e.g., teniposide);
  e. DNA damaging agents, such as actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16);
  f. antibiotics, such as dactinomycin (actinomycin D), daunorubicin, doxorubicin (adriamycin), idarubicin, anthracyclines, mitoxantrone, bleomycins, plicamycin (mithramycin) and mitomycin;
  g. enzymes, such as L-asparaginase;
  h. antiplatelet agents;
  i. platinum coordination complexes (e.g., cisplatin, carboplatin), procarbazine, hydroxyurea, mitotane, aminoglutethimide;
  j. hormones, hormone analogs (e.g., estrogen, tamoxifen, goserelin, bicalutamide, nilutamide);
  k. aromatase inhibitors (e.g., letrozole, anastrozole);
  l. anticoagulants (e.g., heparin, synthetic heparin salts and other inhibitors of thrombin);
  m. fibrinolytic agents (such as tissue plasminogen activator, streptokinase and urokinase), aspirin, COX-2 inhibitors, dipyridamole, ticlopidine, clopidogrel, abciximab;
  n. antimigratory agents;
  o. antisecretory agents (e.g., breveldin); immunosuppressives (e.g., cyclosporine, tacrolimus (FK-506), sirolimus (rapamycin), azathioprine, mycophenolate mofetil);
  p. anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors);
  q. angiotensin receptor blockers;
  r. nitric oxide donors;
  s. anti-sense oligonucleotides;
  t. antibodies (e.g., trastuzumab (HERCEPTIN®), AVASTIN®, ERBITUX®);
  u. cell cycle inhibitors and differentiation inducers (e.g., tretinoin);
  v. mTOR (mammalian target of rapamycin) inhibitors (e.g., everolimus, sirolimus);

w. topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan);
x. corticosteroids (e.g., cortisone, dexamethasone, hydrocortisone, methylpednisolone, prednisone, and prenisolone);
y. growth factor signal transduction kinase inhibitors;
z. mitochondrial dysfunction inducers;
aa. caspase activators; and
bb. chromatin disruptors.

In some embodiments the cancer therapeutic agent is selected from the group consisting of alemtuzumab, aminoglutethimide, amsacrine, anastrozole, asparaginase, beg, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, streptozocin, sunitinib, suramin, tamoxifen, temozolomide, teniposide, testosterone, thalidomide, thioguanine, thiotepa, titanocene dichloride, topotecan, tositumomab, trastuzumab, tretinoin, vatalanib, vinblastine, vincristine, vindesine, and vinorelbine.

Routes of Administration

Pharmaceutical preparations of the invention can be administered locally or systemically. Suitable routes of administration include oral, pulmonary, rectal, transmucosal, intestinal, parenteral (including intramuscular, subcutaneous, intramedullary routes), intranodal, intrathecal, direct intraventricular, intravenous, intraperitoneal, intranasal, intraocular, transdermal, topical, and vaginal routes. As described in more detail above, dosage forms include, but are not limited to, tablets, troches, dispersions, suspensions, suppositories, solutions, capsules, creams, patches, minipumps and the like. Targeted delivery systems also can be used (for example, a liposome coated with target-specific antibody).

Dosage

A pharmaceutical composition of the invention comprises at least one active ingredient (an IRE-1α inhibitor compound or prodrug thereof) in a therapeutically effective dose. A "therapeutically effective dose" is the amount of an IRE-1α inhibitor compound or prodrug thereof which, when administered to a patient over a treatment period, results in a measurable improvement in a characteristic of the disease being treated (e.g., improved laboratory values, retarded development of a symptom, reduced severity of a symptom, or improved levels of an appropriate biological marker).

Determination of therapeutically effective doses is well within the capability of those skilled in the art. A therapeutically effective dose initially can be estimated from in vitro enzyme assays, cell culture assays and/or animal models. For example, a dose can be formulated in an animal model to achieve a circulating concentration range at least as concentrated as the $IC_{50}$ as determined in an in vitro enzyme assay or in a cell culture (i.e., the concentration of the test compound which achieves a half-maximal inhibition of IRE-1α activity). Such information can be used to more accurately determine useful doses in humans. See the FDA guidance document "Guidance for Industry and Reviewers Estimating the Safe Starting Dose in Clinical Trials for Therapeutics in Adult Healthy Volunteers" (HFA-305), which provides an equation for use in calculating a human equivalent dose (HED) based on in vivo animal studies.

Appropriate animal models for the relevant diseases are known in the art. See, e.g., Lupus. 1996 October; 5(5):451-5 (antiphospholipid syndrome); Blood. 1974 July; 44(1):49-56 (aplastic anemia); Autoimmunity. 2001; 33(4):265-74 (autoimmune hypophysitis); Methods. 2007 January; 41(1):118-22 (autoimmune myocarditis); Clin Exp Rheumatol. 2003 November-December; 21(6 Suppl 32):S55-63 (Churg-Strauss syndrome, Wegener's granulomatosis); J Clin Invest. 2005 April; 115(4):870-8 (epidermolysis bullosa acquisita); Circulation. 2005 June 14; 111(23):3135-40. Epub 2005 Jun. 6 (giant cell arteritis; Takayusu's arteritis); Int J Immunopathol Pharmacol. 2005 October-December; 18(4):701-8 (IgA nephropathy); Vet Rec. 1984 May 12; 114(19):479 (pemphigus foliaceous); *J. Neuroimmunol.* 98, 130-35, 1999 (polymyositis); *Am. J. Pathol.* 120, 323-25, 1985 (dermatomyositis); *Cell. Mol. Immunol.* 2, 461-65, 2005 (myasthenia gravis); *Arthritis Rheum.* 50, 3250-59, 2004 (lupus erythymatosus); *Clin. Exp. Immunol.* 99, 294-302, 1995 (Grave's disease); *J. Clin. Invest.* 116, 961-973, 2006 (rheumatoid arthritis); *Exp Mol. Pathol.* 77, 161-67, 2004 (Hashimoto's thyroiditis); *Rheumatol.* 32, 1071-75, 2005 (Sjögren's syndrome); *Brain Pathol.* 12, 420-29, 2002 (Guillain-Barré syndrome); *Vet. Pathol.* 32, 337-45, 1995 (polyarteritis nodosa); *Immunol. Invest.* 3, 47-61, 2006 (pemphigus vulgaris); *Arch. Dermatol. Res.* 297, 333-44, 2006 (scleroderma); *J. Exp. Med.* 191, 899-906, 2000 (Goodpasture's syndrome); *Clin. Exp. Immunol.* 99, 294-302, 1995 (Grave's disease); *J. Clin. Invest.* 91, 1507-15, 1993 (membranous nephropathy); *J. Immunol.* 169, 4889-96, 2002 (autoimmune hepatitis); *Surgery* 128, 999-1006, 2000 (Addison's disease); *Eur. J. Immunol.* 32, 1147-56, 2002 (autoimmune hemolytic anemia); and *Haematologica* 88, 679-87, 2003 (autoimmune thrombocytopenic purpura).

$LD_{50}$ (the dose lethal to 50% of the population) and the $ED_{50}$ (the dose therapeutically effective in 50% of the population) can be determined by standard pharmaceutical procedures in cell cultures and/or experimental animals. Data obtained from cell culture assays or animal studies can be used to determine initial human doses. As is known in the art, the dosage may vary depending upon the dosage form and route of administration used.

Usual dosages for systemic administration to a human patient range from 1 µg/kg to 100 mg/kg (e.g., 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 5 mg/kg, 20 mg/kg, or 50 mg/kg). In some embodiments, the treatment schedule can require that a plasma concentration of an IRE-1α inhibitor compound be maintained for a period of time (e.g., several days or a week) and then allowed to decay by ceasing administration for a period of time (e.g., 1, 2, 3, or 4 weeks). The amount of composition administered will, of course, be dependent on the subject being treated, on the subject's weight, the severity of the disorder, the manner of administration and the judgment of the prescribing physician.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

IRE-1α Assay

A fusion protein comprising glutathione S transferase (GST) and human IRE-1α (GST-IRE-1α) was obtained from a 500 ml baculovirus-infected insect cell culture and used to measure IRE-1α activity in vitro.

Five μl of a reaction mixture comprising 1× reaction buffer (5× reaction buffer is 100 mM Hepes pH 7.5, 250 mM KOAc, 2.5 mM $MgCl_2$), 3 mM DTT, and 0.4% polyethylene glycol water were added to each well of 384 well plates. Twenty-five nanoliters of a 1 mM test compound solution were added to test wells. Three μl of a 128 ng/ml IRE-1α preparation were added to each test well and to positive control wells (final concentration 5.82 ng/well). Negative control wells contained only reaction mixture and test compound.

After spinning the plates at 1200 rpm for 30 seconds, 3 μl of an IRE-1α human mini-XBP-1 mRNA stem-loop substrate 5'-CAGUCCGCAGCACUG-3' (SEQ ID NO:1), labeled with the fluorescent dye Cy5 at the 5' end and Black Hole Quencher 2 (BH2) at the 3' end, were added to each well of a control plate. The plates were again spun at 1200 rpm for 30 seconds. Final concentrations for the assay were: 63 nM IRE-1α substrate, 5.82 ng IRE-1α protein, and 2.5 μM test compound.

The plates were covered with lids and incubated for one hour at 30° C. The plates were then transferred to an ACQUEST™ microplate reader. Data was analyzed using data analysis software, and the percent activity of IRE-1α was calculated.

EXAMPLE 2

Identification of IRE-1α Inhibitor Compounds

Compounds from the Maybridge library (Fisher) were screened using the assay described in Example 1. Approximately 60 compounds were selected as confirmed hits and repurified. These compounds were aryl imines or the Schiff base adduct of 2-hydroxy benzaldehyde analogues. There was no observable SAR relative to the R group. Upon re-purification by HPLC, however, it was noted that the compounds were breaking down into their constituent components: 2-hydroxy benzaldehyde derivatives and a primary amine linked to an R group, which suggested that the aldehyde derivative may be the active component of the compound.

Three purified 2-hydroxy benzaldehydes having halogens at the 3 and 5 positions (either Cl, Br or I) were then tested in the IRE-1α assay. All three were active. The most potent was 3,5 iodo 2-hydroxy benzaldehyde ($IC_{50}$ 0.35 μM), followed by 3,5 bromo 2-hydroxy benzaldehyde ($IC_{50}$ 0.46 μM) and last 3,5 chloro 2-hydroxy benzaldehyde (1.05 μM).

Approximately 20 benzaldehyde derivatives were then purchased and tested in the IRE-1α assay. The results of this testing indicated that compounds required the hydroxyl group at the ortho position relative to the aldehyde group but also required hydrophobic electron withdrawing groups at the 3, 5, or 6 positions of the benzene ring. Positions 3 and 5 can be a halogen or a methoxy or ethoxy. A nitro group is active at the 3 or 5 position but not both. The most potent compounds were the o-vanillins with a bromine substituent at the 5 or 6 position. Without wishing to be bound by the following explanation, the hydrogen of the ortho hydroxyl likely participates in hydrogen binding with the aldehyde oxygen which stabilizes the conformation.

EXAMPLE 3

Examples of o-vanillins with SAR and Selectivity for IRE-1α in in vitro Enzyme Assays IRE-1α, T1 RNase, and RNase A assays carried out in vitro with several o-vanillin derivatives to demonstrate selectivity of the derivatives for IRE-1α. IRE-1α assays were carried out as described in Example 1.

T1 RNase was assayed as follows. Five μl of a reaction mixture comprising 1× reaction buffer (5× reaction buffer is 100 mM Hepes pH 7.5, 250 mM KOAc, 2.5 mM $MgCl_2$), 3 mM DTT, and 0.4% polyethylene glycol water were added to each well of 384 well plates. Twenty-five nanoliters of a 1 mM test compound solution were added to test wells. Three μl of a 1/48,000 dilution of an approximately 200,000 U/ml RNase T1 (Worthington) preparation were added to each test well and to positive control wells (final concentration 49.5 pg/well). Negative control wells contained only reaction mixture and test compound.

After spinning the plates at 1200 rpm for 30 seconds, 3 μl of the mini-XBP-1 mRNA stem-loop substrate described in Example 1 were added to each well of a control plate. The plates were again spun at 1200 rpm for 30 seconds. Final concentrations for the assay were: 63 nM substrate, 49.5 pg RNase T1, and 2.5 μM test compound.

The plates were covered with lids and incubated for one hour at 30° C. The plates were then transferred to an ACQUEST™ microplate reader. Data was analyzed using data analysis software. The percent activity of RNase T1 was calculated.

RNase A was assayed as described for RNase T1. Final concentrations for the assay were: 63 nM substrate, 0.4 pg RNase A (Qiagen; 100 mg/ml or 7000 U/ml), and 2.5 μM test compound.

The tested compounds were selective for IRE-1, with $IC_{50}$ of 3 μM (o-vanillin), 1 μM (3-ethoxy o-vanillin), and 30 nm (6-bromo o-vanillin).

EXAMPLE 4

Cell-based IRE-1α XBP-1-specific Endoribonuclease Inhibition by 6-bromo o-vanillin Initial cell-based XBP-1 mRNA splicing assays confirmed IRE-1α inhibition with several potent 5-bromo and 6 bromo o-vanillins. HEK293 cells were incubated with compound either overnight or for 2 hours prior to IRE-1α activation with the UPR inducing reagent thapsigargin. IRE-1α mediated XBP-1 splicing was measured by RT-PCR using XBP-1 specific primers flanking the 26 bp intron excised by IRE-1α. The results are shown in FIG. 1. It can be observed that at the higher concentrations, there is relatively more of the unspliced XBP-1 (upper band: substrate) compared to the spliced form (lower band: product).

Without wishing to be bound by this explanation, the aldehyde apparently forms a reversible Schiff base with the primary amine of a lysine in the active site of the enzyme. The ortho-hydroxyl may accelerate and stabilize the Schiff base. In addition, the unpaired pair of electrons may act as a hydrogen bond acceptor with an additional amino acid of IRE-1α. The benzene ring and the various R groups may reside in a hydrophobic pocket of the enzyme linked via a Schiff base of the aldehyde moiety. The electron withdrawing and hydrophobic nature of the 3 and 5 position substitutes greatly facilitated potency. Due to the hydrophobic nature of the o-vanillins, these compounds may fit in a hydrophobic pocket in addition to forming Schiff bases.

EXAMPLE 5

Determination of $IC_{50}$ for Inhibition of IRE-1α

$IC_{50}$ for inhibition of IRE-1α of the compounds identified in Table 3 was measured as described in Example 1.

TABLE 3

| IRE-1α inhibitor compound | $IC_{50}$ (μM) |
|---|---|
| 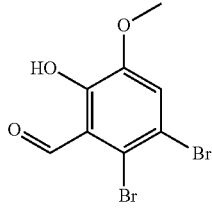 3-1 | 0.03 |
| 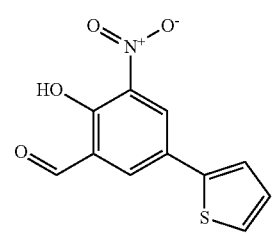 3-2 | 0.03 |
| 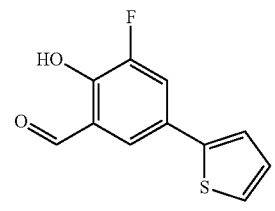 3-3 | 0.04 |
| 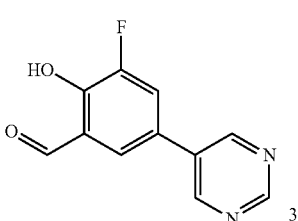 3-4 | 0.07 |

TABLE 3-continued

| IRE-1α inhibitor compound | $IC_{50}$ (μM) |
|---|---|
| 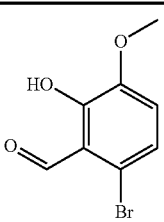 3-5 | 0.08 |
| 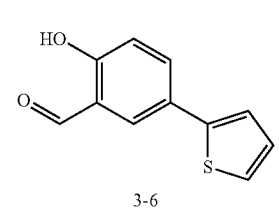 [SMILES: O=Cc1cc(-c2cccs2)ccc1O] 3-6 | 0.1 |
| 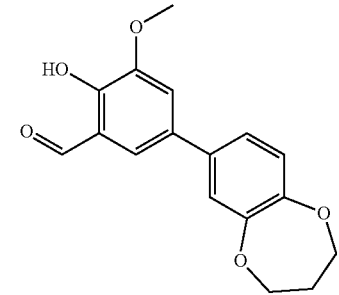 3-7 | 0.11 |
| 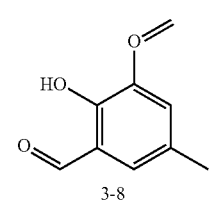 3-8 | 0.12 |
| 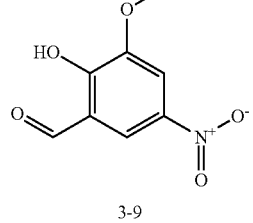 3-9 | 0.17 |
| 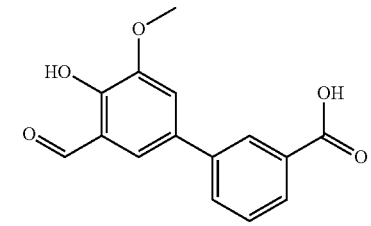 3-10 | 0.17 |

TABLE 3-continued
| IRE-1α inhibitor compound | IC$_{50}$ (μM) |
|---|---|
| 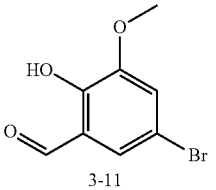 3-11 | 0.24 |
| 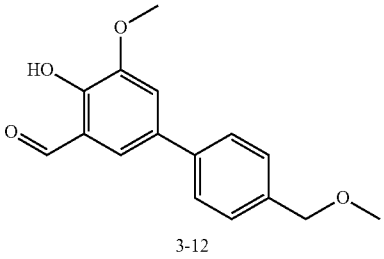 [SMILES: COCc1ccc(-c2cc(C=O)c(O)c(OC)c2)cc1] 3-12 | 0.24 |
| 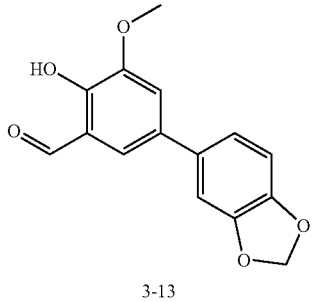 [SMILES: COc1cc(-c2ccc3c(c2)OCO3)cc(C=O)c1O] 3-13 | 0.25 |
| 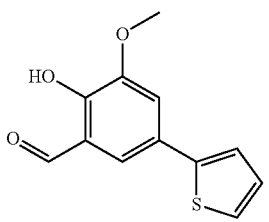 3-14 | 0.27 |
| 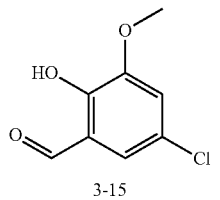 3-15 | 0.28 |
| 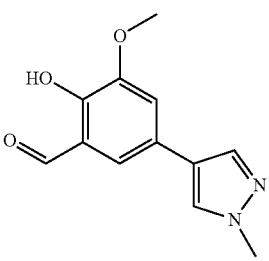 3-16 | 0.3 |
| 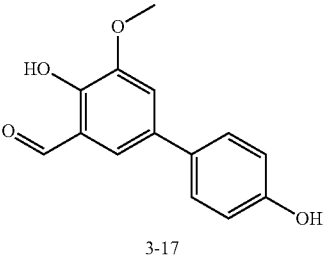 [SMILES: COc1cc(-c2ccc(O)cc2)cc(C=O)c1O] 3-17 | 0.35 |
| 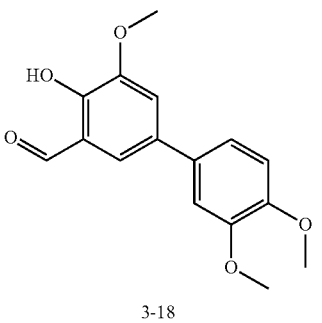 [SMILES: COc1ccc(-c2cc(C=O)c(O)c(OC)c2)cc1OC] 3-18 | 0.38 |
| 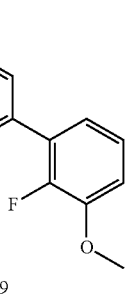 3-19 | 0.38 |
| 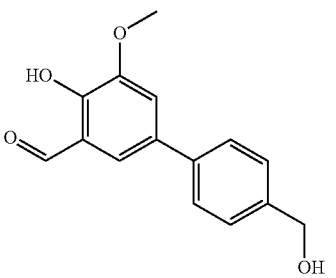 3-20 | 0.39 |
| 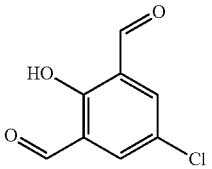 3-21 | 0.4 |

TABLE 3-continued
| IRE-1α inhibitor compound | IC$_{50}$ (μM) |
|---|---|
| 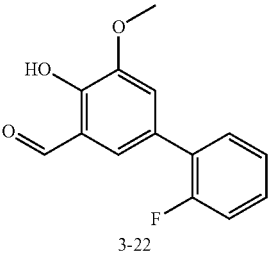 [SMILES: COc1cc(-c2ccccc2F)cc(C=O)c1O] 3-22 | 0.4 |
| 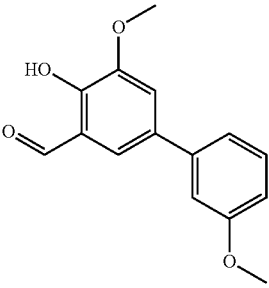 3-23 | 0.4 |
| 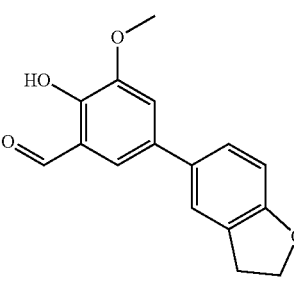 3-24 | 0.41 |
| 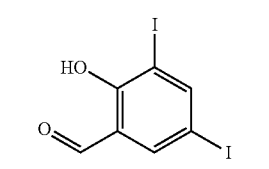 3-25 | 0.44 |
| 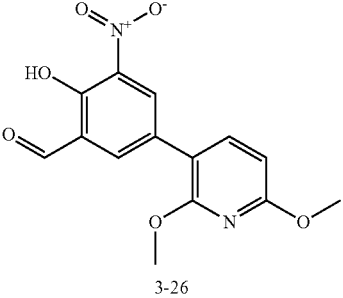 [SMILES: COc1ccc(-c2cc(C=O)c(O)c([N+](=O)[O-])c2)c(OC)n1] 3-26 | 0.51 |
TABLE 3-continued
| IRE-1α inhibitor compound | IC$_{50}$ (μM) |
|---|---|
| 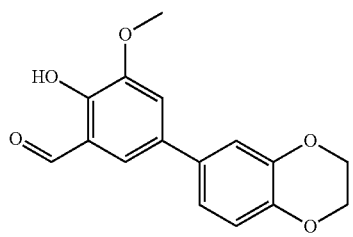 3-27 | 0.54 |
| 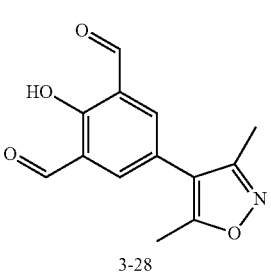 [SMILES: Cc1noc(C)c1-c1cc(C=O)c(O)c(C=O)c1] 3-28 | 0.55 |
| 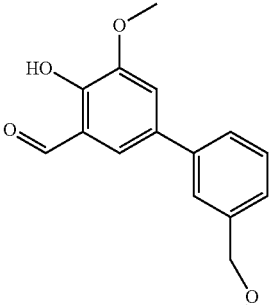 3-29 | 0.57 |
| 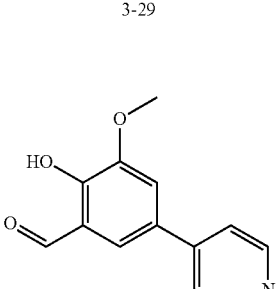 3-30 | 0.58 |
| 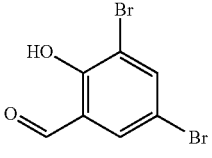 3-31 | 0.72 |

TABLE 3-continued
| IRE-1α inhibitor compound | IC$_{50}$ (μM) |
|---|---|
| 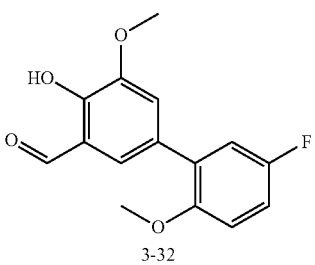 [SMILES: COc1ccc(F)cc1-c1cc(C=O)c(O)c(OC)c1] 3-32 | 0.75 |
| 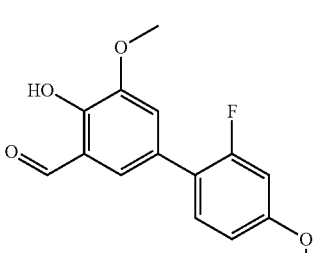 3-33 | 0.75 |
| 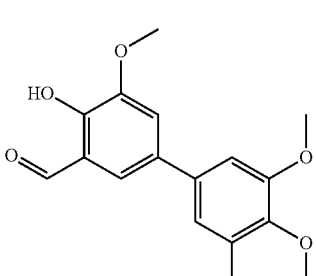 3-34 | 0.79 |
| 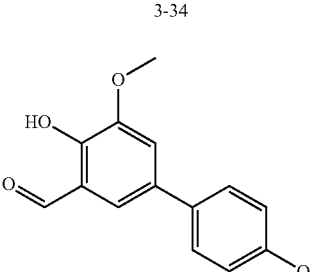 3-35 | 0.99 |
| 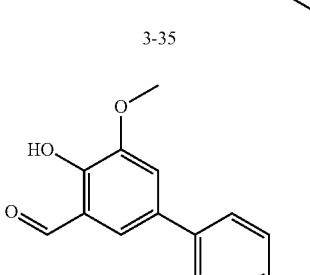 3-36 | 1.01 |
| 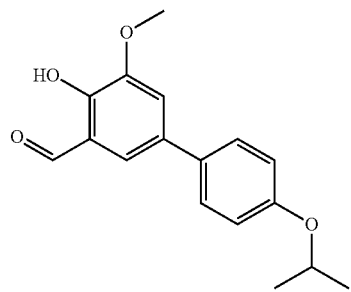 3-37 | 1.07 |
| 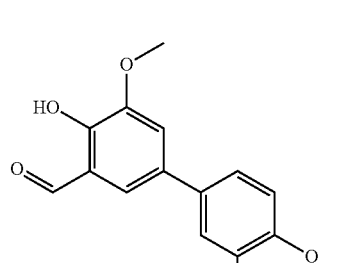 3-38 | 1.1 |
| 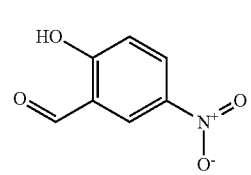 3-39 | 1.28 |
| 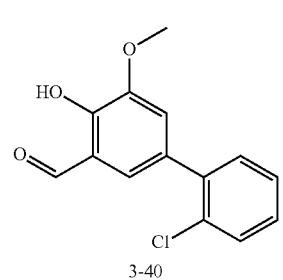 [SMILES: COc1cc(-c2ccccc2Cl)cc(C=O)c1O] 3-40 | 1.28 |
| 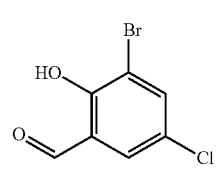 3-41 | 1.3 |

TABLE 3-continued
| IRE-1α inhibitor compound | IC$_{50}$ (μM) |
|---|---|
| 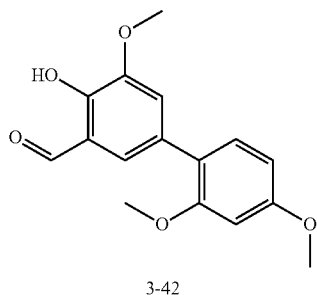 [SMILES: COc1ccc(-c2cc(C=O)c(O)c(OC)c2)c(OC)c1] 3-42 | 1.3 |
| 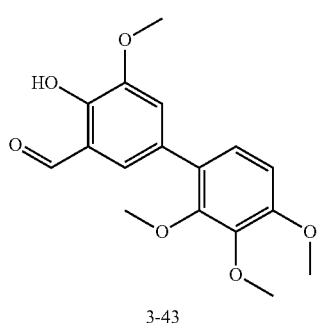 [SMILES: COc1cc(-c2ccc(OC)c(OC)c2OC)cc(C=O)c1O] 3-43 | 1.31 |
| 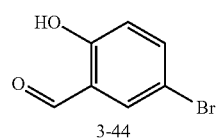 3-44 | 1.33 |
| 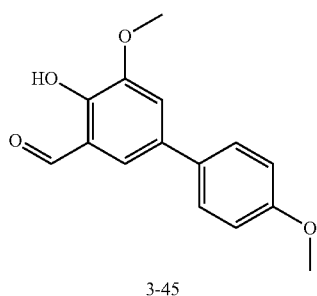 [SMILES: COc1ccc(-c2cc(C=O)c(O)c(OC)c2)cc1] 3-45 | 1.38 |
| 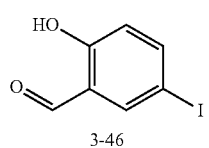 3-46 | 1.4 |
| 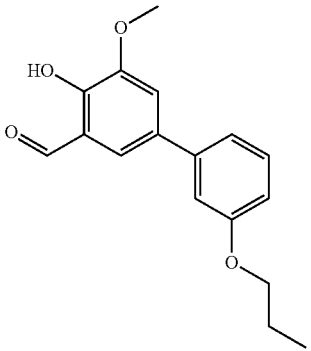 3-47 | 1.48 |
| 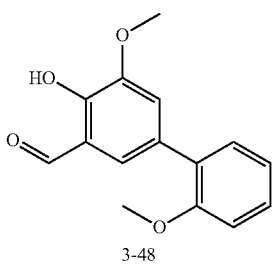 [SMILES: COc1ccccc1-c1cc(C=O)c(O)c(OC)c1] 3-48 | 1.59 |
| 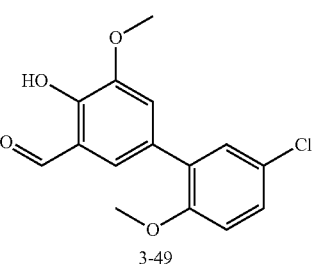 [SMILES: COc1ccc(Cl)cc1-c1cc(C=O)c(O)c(OC)c1] 3-49 | 1.64 |
| 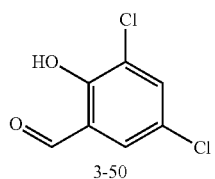 [SMILES: O=Cc1cc(Cl)cc(Cl)c1O] 3-50 | 1.75 |
| 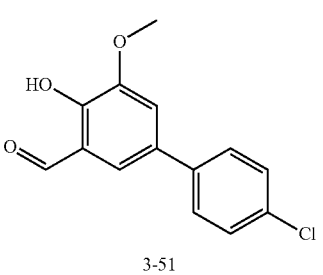 [SMILES: COc1cc(-c2ccc(Cl)cc2)cc(C=O)c1O] 3-51 | 1.83 |

TABLE 3-continued
| IRE-1α inhibitor compound | IC$_{50}$ (μM) |
|---|---|
| 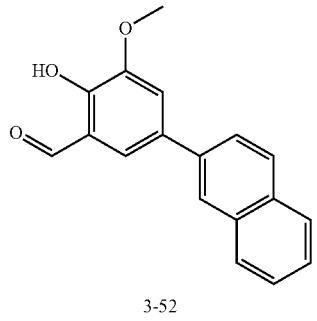 [SMILES: COc1cc(-c2ccc3ccccc3c2)cc(C=O)c1O]<br>3-52 | 1.92 |
| 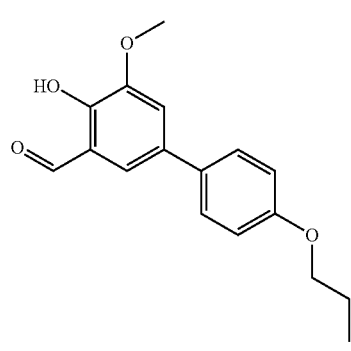<br>3-53 | 1.95 |
| 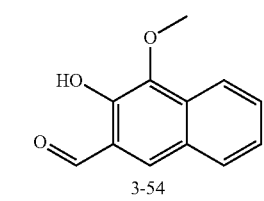<br>3-54 | 2.26 |
| 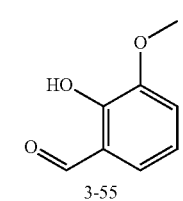<br>3-55 | 2.37 |
| 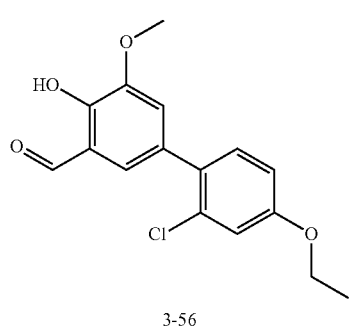 [SMILES: CCOc1ccc(-c2cc(C=O)c(O)c(OC)c2)c(Cl)c1]<br>3-56 | 2.7 |
| 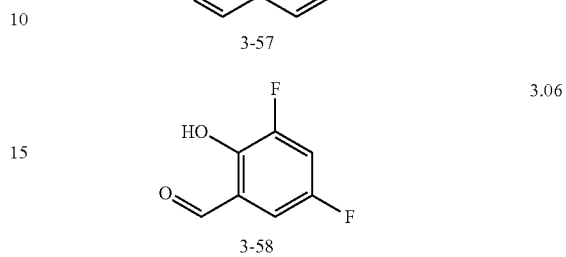<br>3-57 | 2.85 |
| 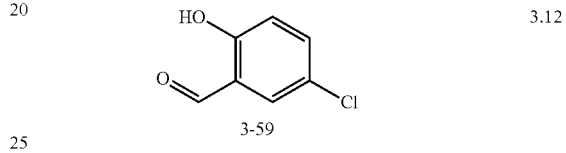<br>3-58 | 3.06 |
| 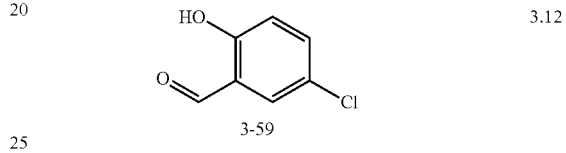<br>3-59 | 3.12 |
| 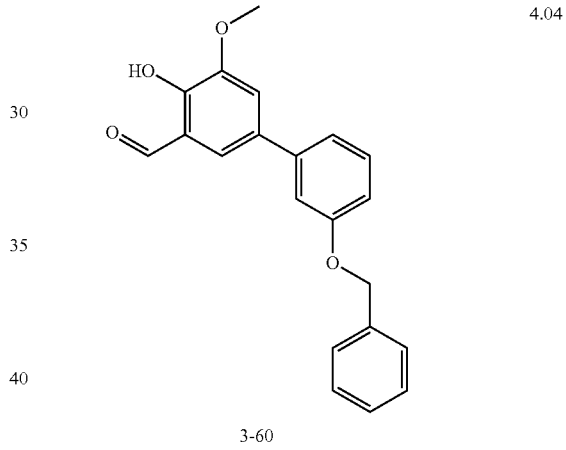<br>3-60 | 4.04 |
| 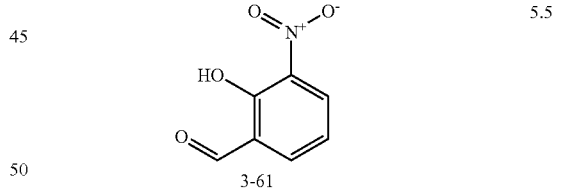<br>3-61 | 5.5 |
| 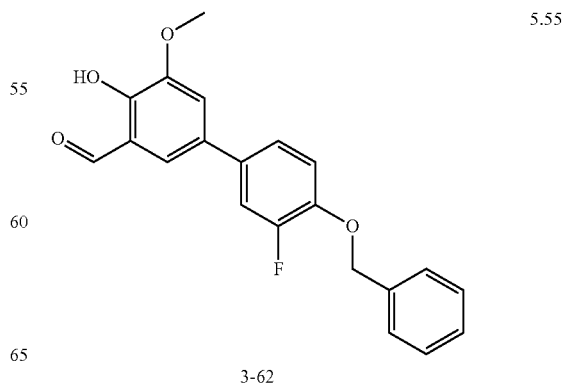<br>3-62 | 5.55 |

TABLE 3-continued
| IRE-1α inhibitor compound | IC$_{50}$ (μM) |
|---|---|
| 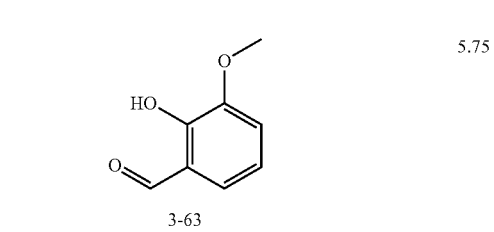 3-63 | 5.75 |
| 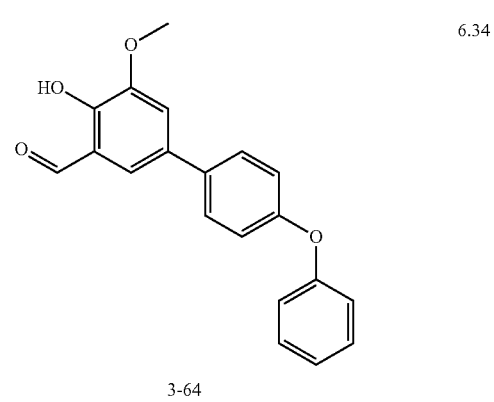 3-64 | 6.34 |
| 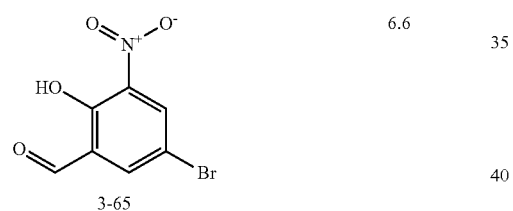 3-65 | 6.6 |
| 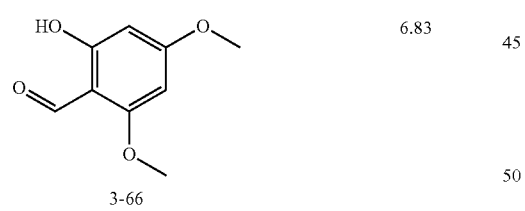 3-66 | 6.83 |
| 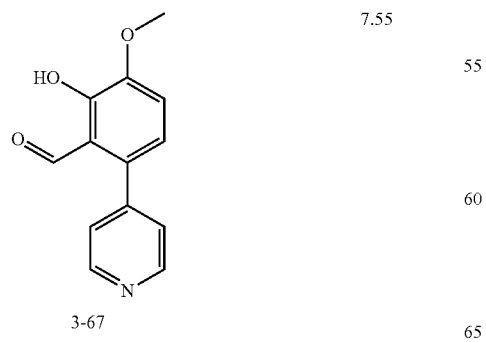 3-67 | 7.55 |
TABLE 3-continued
| IRE-1α inhibitor compound | IC$_{50}$ (μM) |
|---|---|
| 3-68 | 8.2 |
| 3-69 | 8.47 |
| 3-70 | 8.85 |
| 3-71 | 9.27 |
| 3-72 | 9.4 |

TABLE 3-continued

| IRE-1α inhibitor compound | IC$_{50}$ (μM) |
|---|---|
| 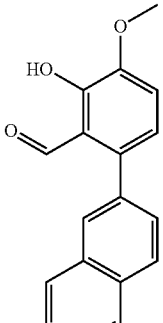 3-73 | 9.75 |
| 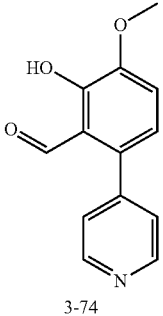 [SMILES: COc1ccc(-c2ccncc2)c(C=O)c1O] 3-74 | 17.71 |
| 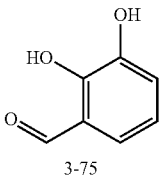 3-75 | 20.25 |

EXAMPLE 6

Kinase Selectivity Assays

The compounds shown below:

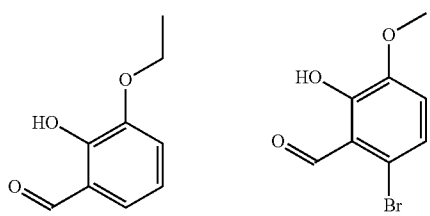

were assayed for their ability to inhibit 86 different kinases at a concentration of 10 μM, which is well above the IC$_{50}$ of each compound (3.71 and 0.027 μM, respectively). The results of the assays demonstrated that these compounds are selective for IRE-1α.

EXAMPLE 7

Synthesis of 2'-chloro-4-hydroxy-5-methoxybiphenyl-3-carbaldehyde

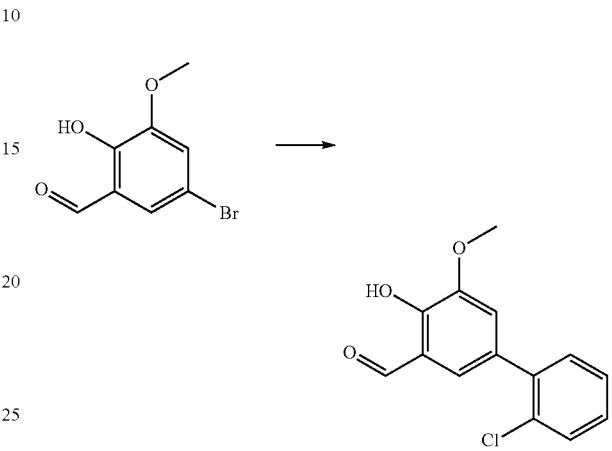

In a 5 ml microwave vial was added 2-chlorophenylboronic acid (54.73 mg, 0.35 mmol, 1.16 equiv), tetrakis(triphenylphosphine)palladium(0) (7 mg, 0.006 mmol, 2 mol %) as a catalyst and solution of 5-bromo-2-hydroxy-3-methoxybenzaldehyde (69.3 mg, 0.3 mmol, 1 equiv) in 1 ml of MeCN. To the resulting solution was added 1M solution K$_2$CO$_3$ (0.6 ml, 0.6 mmol, 2 equiv), followed by sealing. The reaction mixture was heated at 150° C. for 360 seconds in a Personal Chemistry Smith Creator Microwave. After completion, the organic layer was transferred to one well of a 96 well plate. The solvents were evaporated, and the residue was dissolved in 0.6 ml of 0.5% solution of TFA in DMSO and purified.

EXAMPLE 8

Synthesis of 2'-chloro-3-hydroxy-4-methoxybiphenyl-2-carbaldehyde

In a 5 ml microwave vial was added 2-chlorophenylboronic acid (54.73 mg, 0.35 mmol, 1.16 equiv), tetrakis(triphenylphosphine)palladium(0) (7 mg, 0.006 mmol, 2 mol %) as a catalyst and solution of 6-bromo-2-hydroxy-3-methoxybenzyldehyde (69.3 mg, 0.3 mmol, 1 equiv) in 1 ml of MeCN. To the resulting solution was added 1M solution K$_2$CO$_3$ (0.6 ml, 0.6 mmol, 2 equiv), followed by sealing. The reaction mixture was heated at 150° C. for 360 seconds in a Personal Chemistry Smith Creator Microwave. After completion, the organic layer was transferred to one well of a 96 well plate. The solvents were evaporated, and the residue was dissolved in 0.6 ml of 0.5% solution of TFA in DMSO and purified.

EXAMPLE 9

Synthesis of 4-Bromo-2-{[(E)-4-fluoro-phenylimino]-methyl}-phenol

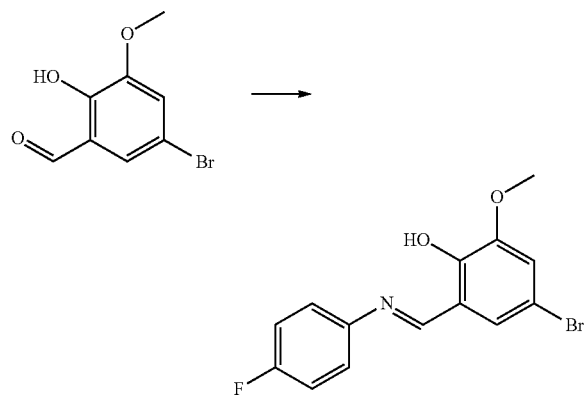

In a 20 ml scintillation vial was added 5-bromosalicaldehyde (100 mg, 0.50 mmol), toluene (5 ml), and activated molecular sieves (200 mg). To the resulting solution was added 4-fluoroaniline (56 mg, 0.50 mmol, 2 equiv). The reaction mixture was heated at 100° C. for 16 hours, after which the molecular sieves were filtered from solution and washed with dichloromethane. The product precipitated was collected by filtration and washed with hexane. After drying, the identity was confirmed by NMR and TLC.

EXAMPLE 10

Cell-based Assays

Human myeloma MM.1s cells were incubated with the indicated amounts of compound for 1.25 hours before stressing with 2 mM dithiothreitol (DTT). After an additional 45 minutes (2 hours total) with compound and DTT, the cells were harvested with TRIZOL® (a mono-phasic solution of phenol and guanidine isothiocyanate), and total RNA was prepared as directed by the manufacturer (Invitrogen). Human XBP-1 was amplified by RT-PCR with the following primers, which flank the 26 base unconventional intron excised by IRE-1α:

```
CCTGGTTGCTGAAGAGGAGG    (SEQ ID NO: 2)    (forward)
and

CCATGGGGAGATGTTCTGGAG   (SEQ ID NO: 3)    (reverse).
```

Figure 2:
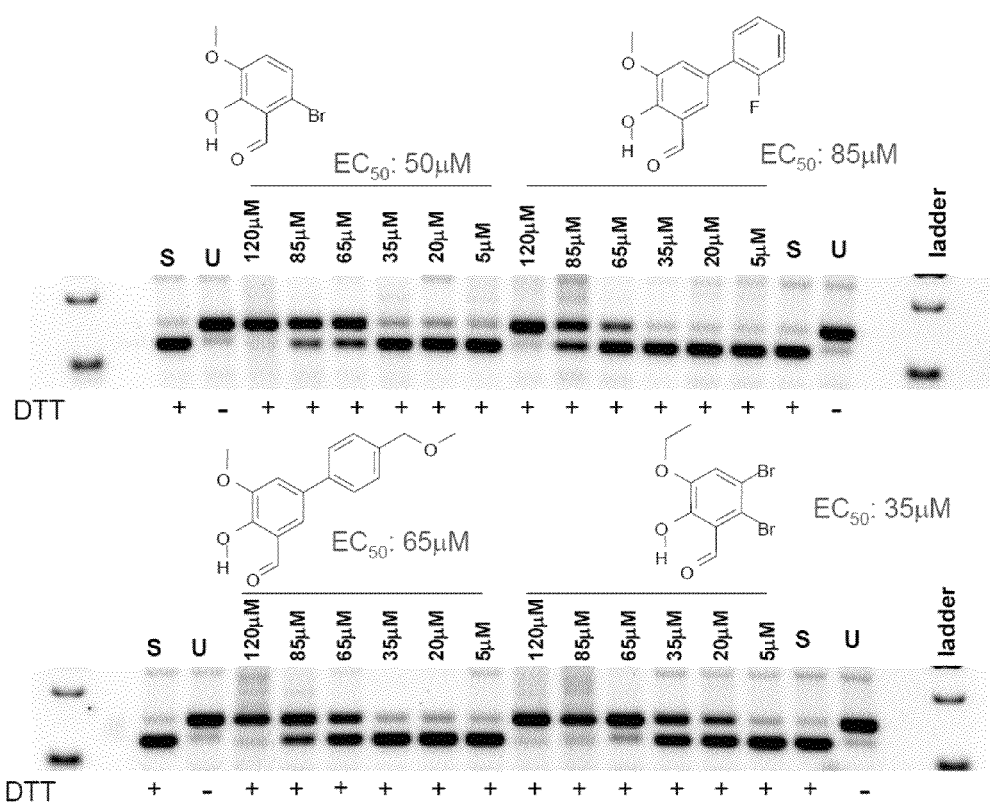
FIG. 2. Results of cell-based IRE-1α XBP-1-specific endoribonuclease inhibition in human myeloma cells.

The results are shown in FIG. 2. In unstressed cells, IRE-1α is inactive and hence, the 26 base intron is left in the XBP-1 mRNA. RT-PCR of unstressed (U) cells then generates the upper band. When cells are stressed (S) with the endoplasmic reticulum (ER) stressing agent DTT, IRE-1α is activated due to accumulating unfolded protein and the resulting RT-PCR product is 26 base pairs shorter (lower band). Increasing amounts of compound block IRE-1α mediated XBP-1 splicing as demonstrated by the shift from the lower band to the upper band. Compound potency reflects SAR in the in vitro enzyme assay.

Determination of Cellular $ED_{50}$ for IRE-1α Inhibitors

Compounds which pass specificity assays are assayed for cellular $EC_{50}$ using endogenous XBP-1 splicing in myeloma cells. XBP-1 is regulated through the excision of a 26 nucleotide intron from the XBP-1 mRNA by the highly specific endoribonuclease activity of IRE-1α. This splicing event induces a frame shift in the ORF of the C-terminus of XBP-1 leading to the translation of the larger 54 kD active transcription factor rather than the inactive 33 kD form. This splicing event is used to measure IRE-1α activity on XBP-1 mRNA in cells and tissues.

Figure 3:
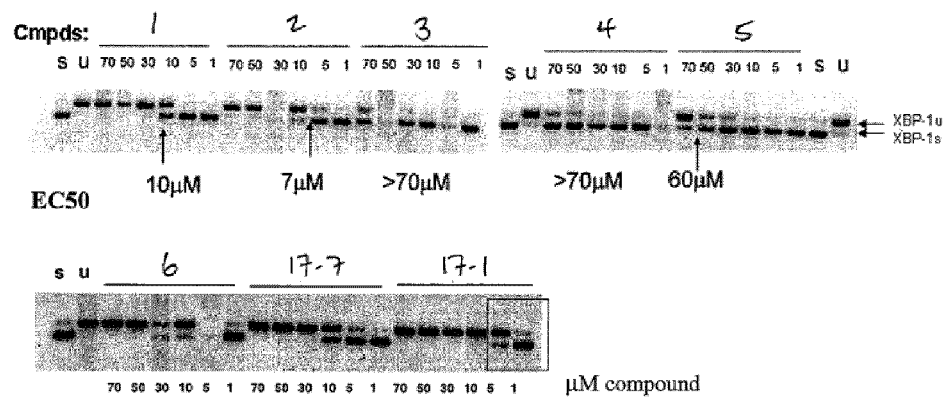
FIG. 3. Scans of agarose gels displaying PCR products from cell-based assays of IRE-1α inhibitors, demonstrating dose-dependent inhibition of cellular XBP-1 splicing for various IRE-1α inhibitors. XBP-1α, unspliced XBP-1; XBP-1s, spliced SBP-1; $EC_{50}$, concentration (μM) at which IRE-1α inhibitors inhibit DTT-induced cellular XBP-1 splicing by 50%. The numbers above the lanes indicate the concentration of each compound in μM. MM.1s myeloma cells were treated with active or inactive compounds for two hours and then treated with DTT for 1 hour. RT-PCR was performed using human XBP-1 specific primers flanking the intron region. DTT induced UPR stress (S) resulted in the removal of a 26 nucleotide fragment resulting in the appearance of the lower band compared to unstressed cells (U) (upper band). $EC_{50}$ was determined as the 50 percent inhibition of spliced XBP-1 induced by DTT. The $EC_{50}$ of compound 17-1 is approximately 2-3 μM.
Figure 5:
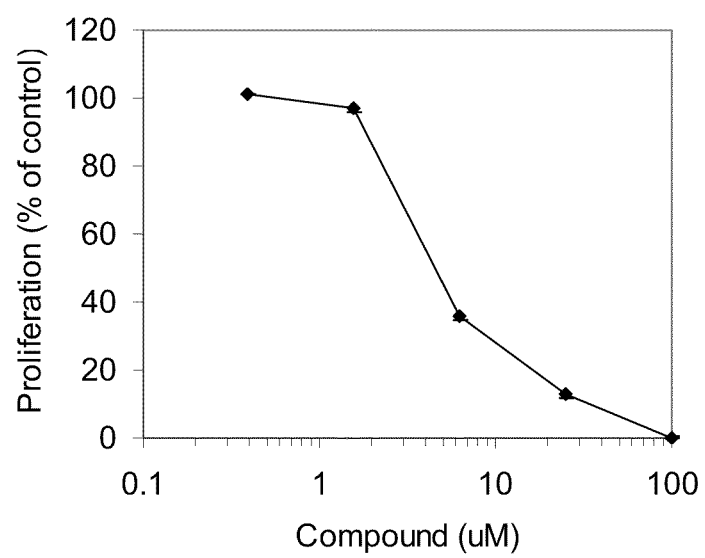
FIG. 5. Graph showing inhibition of proliferation of multiple myeloma cells by IRE-1α inhibitor 11-28 (Example 11). RPMI-8226 multiple myeloma cells were seeded at 20,000 cells per well in RPMI culture medium containing 1% FBS and the required antibiotics. The plate was incubated overnight at 37° C., 95% air, 5% $CO_2$. The following day, compound 11-28 or medium alone was added to wells, resulting in a final volume of 100 μl per well. The compound concentration ranged from 100 μM to 0 μM, with compounds diluted by a factor of 4. After addition of compound, the plate was incubated at 37° C., 95% air, 5% $CO_2$ for 24 hours. Cell proliferation was measured using the CellTiter-Glo assay (Promega), following the manufacturer's instructions.
Figure 7:
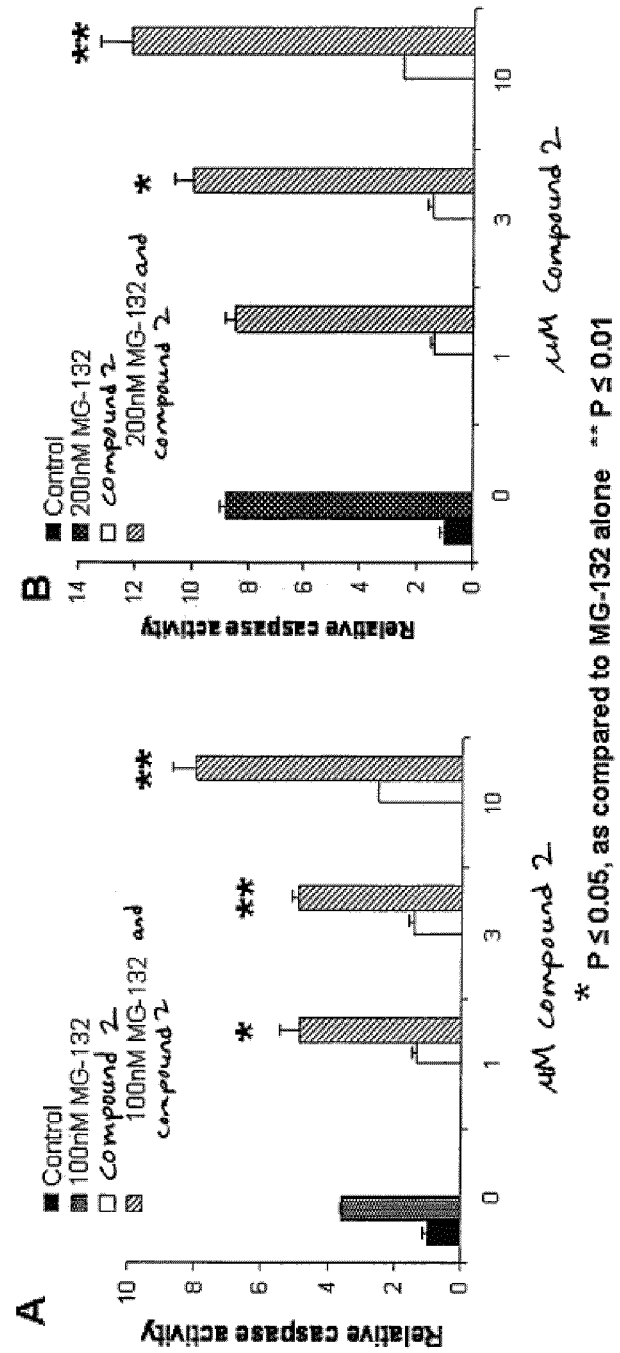
FIG. 7. Graphs showing potentiation of apoptosis in myeloma cells using the proteasome inhibitor MG-132 (N-[(phenylmethoxy)carbonyl]-L-leucyl-N-[(1S)-1-formyl-3-methylbutyl]-L-leucinamide) and an IRE-1α/XBP-1 specific inhibitor as reflected by relative caspase activity (the total of caspase 3 and caspase 7 activities).

Briefly, compounds are incubated in the presence or absence of an ER stress agent (e.g., DTT), and the ratio of XBP-1u (unspliced) to XBP-1s (spliced) is quantified by RT-PCR. The $ED_{50}$ is determined as the 50% XBP-1s to total XPB-1 levels (FIG. 3). Compounds which have $EC_{50}$s equal to or below 10 μM are used in standard apoptosis assays, including Annexin V staining and CASPASE-GLO® (FIG. 5 and FIG. 7).

Figure 6:
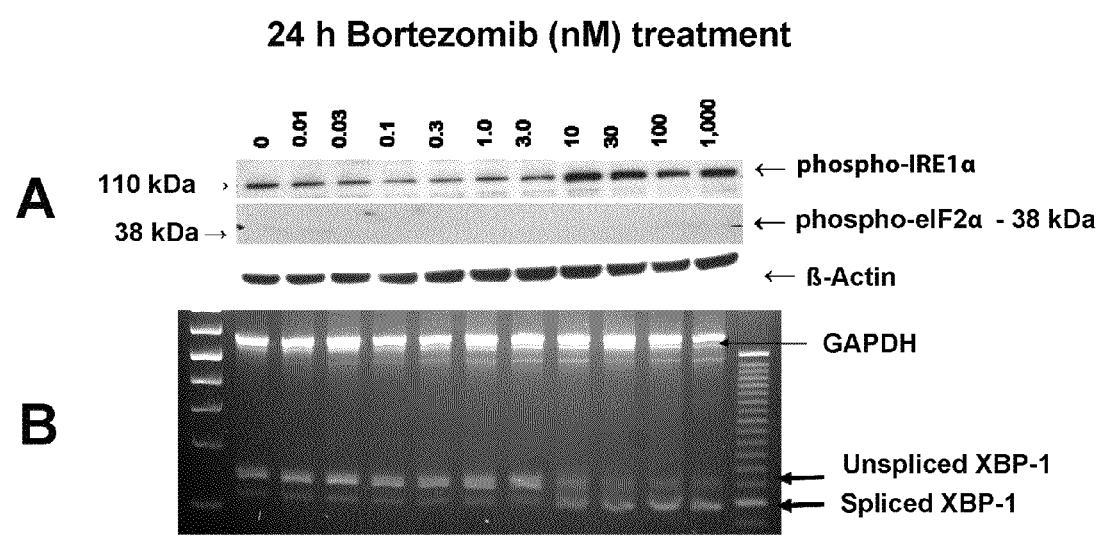
FIG. 6. Western blot (FIG. 6A) and agarose gel (FIG. 6B) demonstrating that 24 hour treatment of RPMI8226 cells with bortezomib (MG-341; VELCADE®) increases the levels of phosphorylated IRE-1α and XBP1-splicing. The numbers indicate the concentration of bortezomib in nM.

Proliferation assays using myeloma cell lines (U266, RPMI8226 and MM.1s) are used to determine $ED_{50}$. Compounds are used as single agents and in combination with other chemotherapeutic drugs. As shown in FIG. 5, IRE-1α inhibitor 11-28 compound inhibits the proliferation of RPMI8226 myeloma cells, which have endogenous activation of the pathway and are further induced by the addition of bortezomib (FIG. 6). When IRE-1α inhibitor compound 2 is used in combination with MG-132, increased apoptosis is observed with U266 myeloma cells (FIG. 7).

EXAMPLE 11

Synthesis of 3'-formyl-4'-hydroxy-5'-methoxybiphenyl-3-carboxylic acid

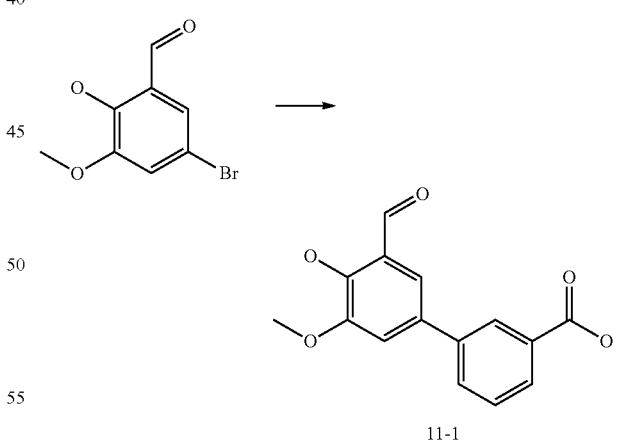

11-1

5-bromo-2-hydroxy-3-methoxybenzaldehyde (3.00 g, 13.0 mmol), 3-carboxy-phenylboronic acid (2.37 g, 14.3 mmol), sodium carbonate (8.27 g, 78.0 mmol), and tetrakis (triphenylphosphine)palladium (0.728 g, 0.65 mmol) were dissolved in a mixture of 200 mL DMF and 200 mL water. The reaction was stirred at 105° C. under argon for 5 h. 200 ml, 1N sodium hydroxide was added, and the solution was extracted with dichloromethane (3×100 mL). The aqueous layer was acidified with 6N hydrochloric acid and the precipitated material was filtered off, washed with water then diethyl ether to afford 11-1 (1.70 g, 6.25 mmol, 48%). $^1$H NMR (400 MHz, DMSO-d$_6$) δ ppm 13.07 (br. s, 1H), 10.34 (s, 1H), 10.44 (br. s, 1H), 8.18 (t, J=1.6 Hz, 1H), 7.90-7.97 (m, 2H), 7.59 (t, J=7.8 Hz, 1H), 7.55 (s, 2H), 3.97 (s, 3H).

The following compounds were made by the above procedure using the corresponding aryl bromide and aryl boronic acid and characterized by LC/MS using a Waters UPLC/MS with UV detector (220 nM) and MS detector (ESI). HPLC column: Acquity BEH C18 1.7 μm (Waters) 2.1 mm×50 mm. HPLC Gradient: 0.6 mL/min, from 95:5 20 mM ammonium formate buffer (brought to pH 7.4 with ammonium hydroxide): acetonitrile to 20:80 ammonium formate buffer: acetonitrile in 1.5 min, maintaining for 1.3 min.

TABLE 4

| No. | CHEMISTRY | MW | MH+ | Rt |
|---|---|---|---|---|
| 11-2 | | 229.1 | 230.2 | 0.95 |
| 11-3 | | 232.1 | 233.2 | 0.96 |
| 11-4 | | 199.1 | 200.1 | 1.03 |
| 11-5 | | 217.1 | 218.2 | 0.86 |
| 11-6 | | 229.1 | 230.2 | 1.01 |

TABLE 4-continued

| No. | CHEMISTRY | MW | MH+ | Rt |
|---|---|---|---|---|
| 11-7 | | 259.1 | 260.3 | 1.26 |
| 11-8 | | 235.1 | 236.3 | 1.02 |
| 11-9 | | 267.1 | 268.3 | 1.13 |
| 11-10 | | 264.0 | 265.11 | 1.00 |
| 11-11 | | 247.1 | 248.3 | 1.21 |
| 11-12 | | 276.0 | 277.2 | 1.20 |
| 11-13 | | 274.1 | 275.3 | 0.84 |

TABLE 4-continued

| No. | CHEMISTRY | MW | MH+ | Rt |
|---|---|---|---|---|
| 11-14 | | 279.1 | 280.3 | 1.22 |
| 11-15 | | 267.1 | 268.3 | 1.14 |
| 11-16 | | 294.1 | 295.3 | 0.86 |
| 11-17 | | 279.1 | 280.3 | 1.23 |
| 11-18 | | 267.1 | 268.3 | 1.21 |
| 11-19 | | 294.1 | 295.3 | 0.90 |
| 11-20 | | 317.1 | 318.3 | 1.43 |
| 11-21 | | 220.1 | 221.2 | 0.99 |
| 11-22 | | 248.1 | 248.2 | 1.54 |
| 11-23 | | 299.0 | 299.2 | 1.21 |
| 11-24 | | 268.1 | 268.2 | 1.56 |

TABLE 4-continued

| No. | CHEMISTRY | MW | MH+ | Rt |
|---|---|---|---|---|
| 11-25 | (3-fluoro-4-hydroxy-5-(furan-2-yl)benzaldehyde) | 206.0 | 205.1 | 1.26 |
| 11-26 | (4-hydroxy-3-methoxy-5-(1H-pyrazol-4-yl)benzaldehyde) | 218.1 | 217.97 | 0.86 |

The following compounds were made by the above procedure using the corresponding aryl bromide and aryl boronic acid and characterized by NMR.

TABLE 5

| No. | CHEMISTRY | NMR |
|---|---|---|
| 11-27 | (5-(2,3-dihydrobenzofuran-5-yl)-4-hydroxy-3-methoxybenzaldehyde) | $^1$H NMR (400 M Hz, DMSO-d$_6$) δ ppm 10.30 (s, 1H), 10.28 (br. s, 1H), 7.55 (d, J = 1.5 Hz, 1H), 7.41 - 7.45 (m, 2H), 7.39 (dd, J = 8.3, 2.3 Hz, 1H), 6.82 (d, J = 8.5 Hz, 1H), 4.56 (t, J = 8.6 Hz, 2H), 3.94 (s, 3H), 3.23 (t, J = 8.7 Hz, 2H). |
| 11-28 | (4-hydroxy-3-methoxy-5-(thiophen-2-yl)benzaldehyde) | $^1$H NMR (400 M Hz, DMSO-d$_6$) δ ppm 11.05 (s, 1H), 9.96 (s, 1H), 7.39 (d, J = 2.0 Hz, 1H), 7.31 (d, J = 2.0 Hz, 1H), 7.28 (dd, J = 5.1, 1.1 Hz, 1H), 7.24 (dd, J = 3.6, 1.1 Hz, 1H), 7.09 (dd, J = 5.0, 3.5 Hz, 1H), 3.98 (s, 3H). |
| 11-29 | (4-hydroxy-3-(pyrimidin-5-yl)benzaldehyde) | $^1$H NMR (400 M Hz, DMSO-d$_6$) δ ppm 11.03 (br. s, 1H), 10.32 (s, 1H), 9.14 (s, 1H), 9.10 (s, 2H), 8.06 (d, J = 2.5 Hz, 1H), 7.97 (dd, J = 8.5, 2.5 Hz, 1H), 7.16 (d, J = 8.8 Hz, 1H). |
| 11-30 | (4-hydroxy-3-methoxy-5-(pyrimidin-5-yl)benzaldehyde) | $^1$H NMR (400 M Hz, DMSO-d$_6$) δ ppm 10.55 (br. s, 1H), 10.34 (s, 1H), 9.12-9.22 (m, 3H), 7.67 (d, J = 2.3 Hz, 1H), 7.65 (d, J = 2.3 Hz, 1H), 3.98 (s, 3H). |

TABLE 5-continued

| No. | CHEMISTRY | NMR |
|---|---|---|
| 11-31 | | $^1$H NMR (400 M Hz, DMSO-d$_6$) δ ppm 10.25 (s, 1H), 8.98-9.04 (m, 3H), 8.26 (d, J = 3.0 Hz, 1H), 7.89 (d, J = 3.0 Hz, 1H). |
| 11-32 | | $^1$H NMR (400 M Hz, DMSO-d$_6$) δ ppm 10.40 (br. s, 1H), 10.30 (s, 1H), 7.22 (d, J = 2.3 Hz, 1H), 7.19 (d, J = 2.0 Hz, 1H), 3.89 (s, 3H), 2.39 (s, 3H), 2.22 (s, 3H). |
| 11-33 | | $^1$H NMR (400 M Hz, DMSO-d$_6$) δ ppm 11.08 (br. s, 1H), 10.31 (s, 1H), 7.89 (dd, J = 12.0, 2.3 Hz, 1H), 7.68 (dd, J = 2.3, 1.3 Hz, 1H), 7.54 (dd, J = 5.0, 1.3 Hz, 1H), 7.51 (dd, J = 3.6, 1.1 Hz, 1H), 7.13 (dd, J = 5.1, 3.6 Hz, 1H). |
| 11-34 | | $^1$H NMR (400 M Hz, DMSO-d$_6$) δ ppm 11.76 (br. s, 1H), 10.31 (s, 1H), 8.45 (d, J = 2.5 Hz, 1H), 8.22 (d, J = 2.5 Hz, 1H), 7.60-7.66 (m, 2H), 7.17 (dd, J = 5.0, 3.5 Hz, 1H). |
| 11-35 | | $^1$H NMR (400 M Hz, DMSO-d$_6$) δ ppm 11.78 (s, 1H), 10.00 (s, 1H), 7.67 (dd, J = 5.0, 1.3 Hz, 1H), 7.33 (d, J = 8.3 Hz, 1H), 7.21 (dd, J = 3.5, 1.3 Hz, 1H), 7.17 (dd, J = 5.0, 3.5 Hz, 1H), 6.99 (d, J = 8.3 Hz, 1H), 3.86 (s, 3H). |
| 11-36 | | $^1$H NMR (400 M Hz, DMSO-d$_6$) δ ppm 10.31 (s, 1H), 8.54 (d, J = 2.5 Hz, 1H), 8.35 (d, J = 2.5 Hz, 1H), 8.06 (dd, J = 2.9, 1.4 Hz, 1H), 7.69 (dd, J = 5.0, 3.0 Hz, 1H), 7.64 (dd, J = 5.2, 1.5 Hz, 1H). |
| 11-37 | | $^1$H NMR (400 M Hz, DMSO-d$_6$) δ ppm 10.56 (br. s, 1H), 10.34 (s, 1H), 7.96 (d, J = 7.8 Hz, 1H), 7.87 (s, 1H), 7.82 (d, J = 7.0 Hz, 1H), 7.66 (d, J = 2.3 Hz, 1H), 7.54 (d, J = 2.3 Hz, 1H), 7.39 (td, J = 7.7, 1.4 Hz, 1H), 7.34 (td, J = 7.7, 1.4 Hz, 1H). |

TABLE 5-continued

| No. | CHEMISTRY | NMR |
|-----|-----------|-----|
| 11-38 | | $^1$H NMR (400 M Hz, DMSO-d$_6$) δ ppm 10.36 (s, 1H), 10.40 (br. s, 1H), 8.07 (dd, J = 7.2, 2.3 Hz, 1H), 7.92 (dd, J = 7.2, 2.3 Hz, 1H), 7.84 (s, 1H), 7.41-7.50 (m, 4H), 3.95 (s, 3H). |
| 11-39 | | $^1$H NMR (400 M Hz, DMSO-d$_6$) δ ppm 10.30 (s, 1H), 10.26 (br. s, 1H), 7.85 (dd, J = 2.9, 1.4 Hz, 1H), 7.63 (dd, J = 5.0, 3.0 Hz, 1H), 7.52-7.60 (m, 3H), 3.94 (s, 3H). |
| 11-40 | | $^1$H NMR (400 M Hz, DMSO-d$_6$) δ ppm 10.85 (br. s, 1H), 10.30 (s, 1H), 7.79 (dd, J = 12.3, 2.3 Hz, 1H), 7.70 (s, 1H), 7.55 (s, 1H), 7.39 (dd, J = 8.3, 1.8 Hz, 1H), 6.82 (d, J = 8.3 Hz, 1H), 4.56 (t, J = 8.7 Hz, 2H), 3.22 (t, J = 8.7 Hz, 2H). |
| 11-41 | | $^1$H NMR (400 M Hz, DMSO-d$_6$) δ ppm 10.28 (s, 1H), 7.79-7.88 (m, 2H), 7.72-7.77 (m, 1H), 7.61 (dd, J = 5.0, 2.8 Hz, 1H), 7.52 (dd, J = 5.0, 1.5 Hz, 1H). |
| 11-42 | | $^1$H NMR (400 M Hz, DMSO-d$_6$) δ ppm 10.29 (s, 1H), 10.24 (br. s, 1H), 8.18 (dd, J = 2.0, 1.0 Hz, 1H), 7.72 (t, J = 1.6 Hz, 1H), 7.46 (d, J = 2.1 Hz, 1H), 7.44 (d, J = 2.1 Hz, 1H), 6.96 (dd, J = 2.0, 1.0 Hz, 1H), 3.92 (s, 3H). |
| 11-43 | | $^1$H NMR (400 M Hz, DMSO-d$_6$) δ ppm 10.37 (br. s, 1H), 10.31 (s, 1H), 7.71 (d, J = 1.3 Hz, 1H), 7.53 (dd, J = 14.1, 2.0 Hz, 2H), 6.92 (d, J = 3.0 Hz, 1H), 6.58 (dd, J = 3.5, 1.8 Hz, 1H), 3.93 (s, 3H). |

TABLE 5-continued

| No. | CHEMISTRY | NMR |
|---|---|---|
| 11-44 | 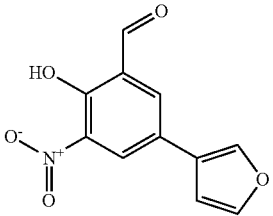 [SMILES: O=Cc1cc(-c2ccoc2)cc([N+](=O)[O-])c1O] | $^1$H NMR (400 M Hz, DMSO-d$_6$) δ ppm 11.45 (br. s, 1H), 10.30 (s, 1H), 8.46 (d, J = 2.5 Hz, 1H), 8.36 (t, J = 1.0 Hz, 1H), 8.25 (d, J = 2.5 Hz, 1H), 7.78 (t, J = 1.8 Hz, 1H), 7.08 (dd, J = 2.0, 1.0 Hz, 1H). |
| 11-45 | 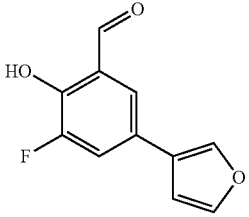 [SMILES: O=Cc1cc(-c2ccoc2)cc(F)c1O] | $^1$H NMR (400 M Hz, DMSO-d$_6$) δ ppm 10.90 (br. s, 1H), 10.29 (s, 1H), 8.21 (s, 1H), 7.84 (dd, J = 12.3, 2.3 Hz, 1H), 7.68-7.75 (m, 2H), 6.98 (dd, J = 1.9, 0.9 Hz, 1H). |
| 11-46 | 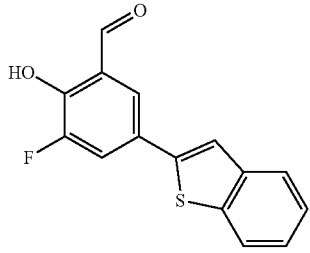 [SMILES: O=Cc1cc(-c2cc3ccccc3s2)cc(F)c1O] | $^1$H NMR (400 M Hz, DMSO-d$_6$) δ ppm 11.27 (br. s, 1H), 10.34 (s, 1H), 8.03 (dd, J = 11.8, 2.3 Hz, 1H), 7.97 (d, J = 7.8 Hz, 1H), 7.88 (s, 1H), 7.83 (d, J = 7.0 Hz, 1H), 7.78-7.81 (m, 1H), 7.34-7.43 (m, 2H). |
| 11-47 | 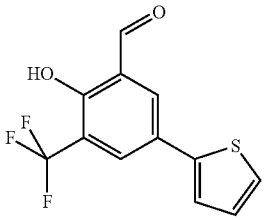 [SMILES: O=Cc1cc(-c2cccs2)cc(C(F)(F)F)c1O] | $^1$H NMR (400 M Hz, DMSO-d$_6$) δ ppm 11.62 (br. s, 1H), 10.17 (s, 1H), 8.29 (d, J = 2.3 Hz, 1H), 8.10 (d, J = 2.0 Hz, 1H), 7.57-7.65 (m, 2H), 7.17 (dd, J = 5.1, 3.6 Hz, 1H). |
| 11-48 | 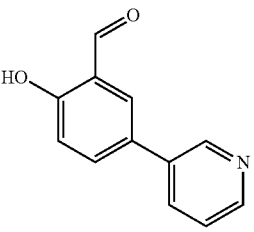 [SMILES: O=Cc1cc(-c2cccnc2)ccc1O] | $^1$H NMR (400 M Hz, DMSO-d$_6$) δ ppm 10.93 (br. s, 1H), 10.32 (s, 1H), 8.86 (br. s, 1H), 8.54 (d, J = 3.8 Hz, 1H), 8.02-8.07 (m, 1H), 7.98 (d, J = 2.5 Hz, 1H), 7.91 (dd, J = 8.5, 2.5 Hz, 1H), 7.46 (dd, J = 7.8, 4.0 Hz, 1H), 7.14 (d, J = 8.5 Hz, 1H). |
| 11-49 | 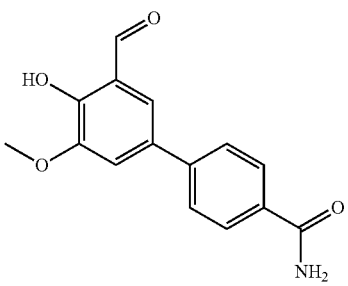 [SMILES: COc1cc(-c2ccc(C(N)=O)cc2)cc(C=O)c1O] | $^1$H NMR (400 M Hz, DMSO-d$_6$) δ ppm 10.36 (br. s, 1H), 10.33 (s, 1H), 8.00 (br. s, 1H), 7.96 (d, J = 8.5 Hz, 2H), 7.78 (d, J = 8.5 Hz, 2H), 7.60 (d, J = 2.0 Hz, 1H), 7.58 (d, J = 2.0 Hz, 1H), 7.35 (br. s, 1H), 3.97 (s, 3H). |

TABLE 5-continued

| No. | CHEMISTRY | NMR |
|---|---|---|
| 11-50 | 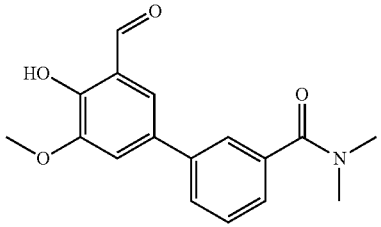 | $^1$H NMR (400 M Hz, CDCl$_3$) δ ppm 11.06 (s, 1H), 9.99 (s, 1H), 7.58-7.64 (m, 2H), 7.48 (t, J = 7.7 Hz, 1H), 7.37-7.42 (m, 1H), 7.40 (d, J = 2.0 Hz, 1H), 7.33 (d, J = 1.8 Hz, 1H), 3.99 (s, 3H), 3.15 (br. s, 3H), 3.03 (br. s, 3H). |
| 11-51 | 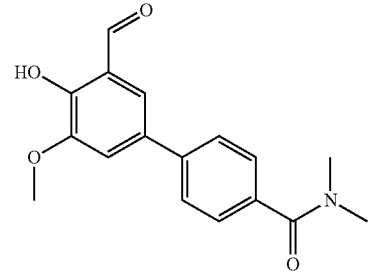 [SMILES: COc1cc(-c2ccc(C(=O)N(C)C)cc2)cc(C=O)c1O] | $^1$H NMR (400 M Hz, CDCl$_3$) δ ppm 11.08 (s, 1H), 10.00 (s, 1H), 7.57-7.63 (m, 2H), 7.50-7.55 (m, 2H), 7.40 (d, J = 2.0 Hz, 1H), 7.33 (d, J = 2.0 Hz, 1H), 4.00 (s, 3H), 3.14 (br. s, 3H), 3.05 (br. s, 3H). |
| 11-52 | 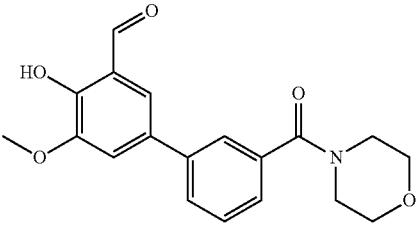 [SMILES: COc1cc(-c2cccc(C(=O)N3CCOCC3)c2)cc(C=O)c1O] | $^1$H NMR (400 M Hz, CDCl$_3$) δ ppm 11.09 (s, 1H), 10.00 (s, 1H), 7.62 (d, J = 1.8 Hz, 1H), 7.61-7.65 (m, 1H), 7.50 (t, J = 8.0 Hz, 1H), 7.40 (d, J = 2.0 Hz, 1H), 7.36 (ddd, J = 7.7, 1.4, 1.3 Hz, 1H), 7.33 (d, J = 2.0 Hz, 1H), 4.00 (s, 3H), 3.67 (br. s, 8H). |
| 11-53 | 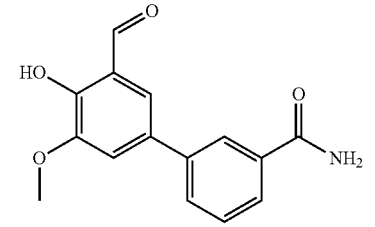 [SMILES: COc1cc(-c2cccc(C(N)=O)c2)cc(C=O)c1O] | $^1$H NMR (400 M Hz, DMSO-d$_6$) δ ppm 10.39 (s, 1H), 10.35 (s, 1H), 8.14 (t, J = 1.6 Hz, 1H), 8.13 (br. s, 1H), 7.81-7.88 (m, 2H), 7.59 (dd, J = 10.0, 2.3 Hz, 2H), 7.53 (t, J = 7.7 Hz, 1H), 7.45 (br. s, 1H), 3.98 (s, 3H). |
| 11-54 | 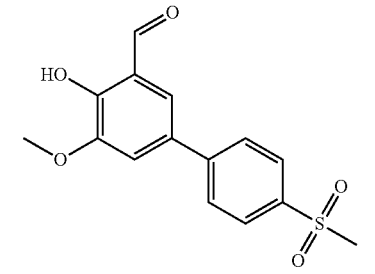 | $^1$H NMR (400 M Hz, CDCl$_3$) δ ppm 11.16 (s, 1H), 10.03 (s, 1H), 8.01-8.05 (m, 2H), 7.74-7.78 (m, 2H), 7.44 (d, J = 2.3 Hz, 1H), 7.33 (d, J = 2.0 Hz, 1H), 4.02 (s, 3H), 3.11 (s, 3H). |
| 11-55 | 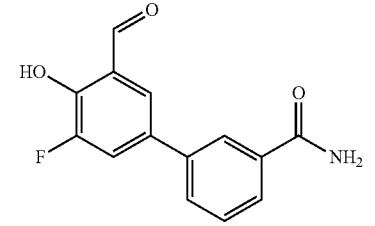 [SMILES: NC(=O)c1cccc(-c2cc(F)c(O)c(C=O)c2)c1] | $^1$H NMR (400 M Hz, DMSO-d$_6$) δ ppm 11.06 (br. s, 1H), 10.34 (s, 1H), 8.17 (s, 1H), 8.11 (br. s, 1H), 7.98 (dd, J = 12.3, 2.3 Hz, 1H), 7.88 (s, 1H), 7.81-7.88 (m, 2H), 7.54 (t, J = 7.7 Hz, 1H), 7.42 (br. s, 1H). |

TABLE 5-continued

| No. | CHEMISTRY | NMR |
|---|---|---|
| 11-56 | | $^1$H NMR (400 M Hz, DMSO-d$_6$) δ ppm 11.66 (br. s, 1H), 10.19 (s, 1H), 8.45 (d, J = 2.3 Hz, 1H), 8.21 (d, J = 2.3 Hz, 1H), 8.03 (br. s, 1H), 7.97-8.01 (m, 2H), 7.82-7.87 (m, 2H), 7.39 (br. s, 1H). |
| 11-57 | | $^1$H NMR (400 M Hz, CDCl$_3$) δ ppm 10.96 (s, 1H), 10.00 (d, J = 2.0 Hz, 1H), 7.58-7.63 (m, 4H), 7.51 (t, J = 7.5 Hz, 1H), 7.39 (dt, J = 7.8, 1.3 Hz, 1H), 3.73 (br. s, 6H), 3.48 (br. s, 2H). |
| 11-58 | | $^1$H NMR (400 M Hz, CDCl$_3$) δ ppm 11.71 (s, 1H), 10.03 (s, 1H), 8.04 (d, J = 2.0 Hz, 1H), 7.96 (d, J = 2.3 Hz, 1H), 7.60-7.65 (m, 1H), 7.63 (d, J = 1.8 Hz, 1H), 7.53 (t, J = 7.8 Hz, 1H), 7.41 (dt, J = 7.8, 1.3 Hz, 1H), 3.67 (br. s, 6H), 3.51 (br. s, 2H). |
| 11-59 | | $^1$H NMR (400 M Hz, DMSO-d$_6$) δ ppm 12.93 (br. s, 1H), 10.46 (br. s, 1H), 10.34 (s, 1H), 7.96-8.04 (m, 1H), 7.80-7.85 (m, 2H), 7.61 (d, J = 2.3 Hz, 1H), 7.59 (d, J = 2.3 Hz, 1H), 3.98 (s, 3H). |
| 11-60 | | $^1$H NMR (400 M Hz, CDCl$_3$) δ ppm 11.70 (s, 1H), 10.03 (s, 1H), 8.04 (d, J = 2.5 Hz, 1H), 7.97 (d, J = 2.5 Hz, 1H), 7.63 (t, J = 1.5 Hz, 1H), 7.58-7.62 (m, 1H), 7.51 (t, J = 7.7 Hz, 1H), 7.43 (ddd, J = 7.7, 1.4, 1.3 Hz, 1H), 3.15 (br. s, 3H), 3.03 (br. s, 3H). |
| 11-61 | | $^1$H NMR (400 M Hz, CDCl$_3$) δ ppm 11.10 (s, 1H), 9.93 (s, 1H), 7.87 (dd, J = 7.8, 1.0 Hz, 1H), 7.55 (td, J = 7.5, 1.5 Hz, 1H), 7.45 (td, J = 7.5, 1.3 Hz, 1H), 7.36 (dd, J = 7.5, 1.0 Hz, 1H), 7.14 (d, J = 2.0 Hz, 1H), 7.08 (d, J = 2.0 Hz, 1H), 4.15 (q, J = 7.0 Hz, 2H), 3.92 (s, 3H), 1.11 (t, J = 7.2 Hz, 3H). |

TABLE 5-continued

| No. | CHEMISTRY | NMR |
|---|---|---|
| 11-62 | | $^1$H NMR (400 M Hz, CDCl$_3$) δ ppm 11.09 (s, 1H), 10.01 (s, 1H), 8.24 (t, J = 1.5 Hz, 1H), 8.03 (dt, J = 7.8, 1.4 Hz, 1H), 7.75 (ddd, J = 7.7, 1.9, 1.1 Hz, 1H), 7.53 (td, J = 7.8, 0.5 Hz, 1H), 7.43 (d, J = 2.3 Hz, 1H), 7.35 (d, J = 2.0 Hz, 1H), 4.01 (s, 3H), 3.97 (s, 3H). |
| 11-63 | | $^1$H NMR (400 M Hz, CDCl$_3$) δ ppm 11.13 (s, 1H), 9.97 (s, 1H), 7.76 (d, J = 3.8 Hz, 1H), 7.45 (d, J = 2.0 Hz, 1H), 7.32 (d, J = 2.0 Hz, 1H), 7.23 (d, J = 4.0 Hz, 1H), 4.38 (q, J = 7.0 Hz, 2H), 3.99 (s, 3H), 1.40 (t, J = 7.0 Hz, 3H). |
| 11-64 | | $^1$H NMR (400 M Hz, DMSO-d$_6$) δ ppm 10.91 (br. s, 1H), 10.33 (s, 1H), 7.90-8.04 (m, 5H), 7.72 (d, J = 8.5 Hz, 2H), 7.34 (br. s, 1H), 7.12 (d, J = 8.5 Hz, 1H). |
| 11-65 | | $^1$H NMR (400 M Hz, CDCl$_3$) δ ppm 10.99 (br. s, 1H), 10.02 (d, J = 1.8 Hz, 1H), 8.13 (d, J = 8.8 Hz, 2H), 7.60-7.66 (m, 4H), 3.95 (s, 3H). |
| 11-66 | | $^1$H NMR (400 M Hz, CDCl$_3$) δ ppm 10.97 (s, 1H), 10.03 (d, J = 2.0 Hz, 1H), 8.23 (t, J = 1.5 Hz, 1H), 8.05 (dd, J = 7.8, 1.8 Hz, 1H), 7.73 (dd, J = 7.8, 2.0 Hz, 1H), 7.62-7.67 (m, 2H), 7.55 (t, J = 7.8 Hz, 1H), 3.97 (s, 3H). |
| 11-67 | | $^1$H NMR (400 M Hz, DMSO-d$_6$) δ ppm 13.03 (br. s, 1H), 11.20 (br. s, 1H), 10.33 (s, 1H), 8.18 (t, J = 1.6 Hz, 1H), 7.92-7.98 (m, 3H), 7.81-7.85 (m, 1H), 7.59 (t, J = 7.8 Hz, 1H). |

TABLE 5-continued

| No. | CHEMISTRY | NMR |
|---|---|---|
| 11-68 | | $^1$H NMR (400 M Hz, DMSO-d$_6$) δ ppm 10.87 (br. s, 1H), 10.34 (s, 1H), 8.13 (t, J = 1.6 Hz, 1H), 8.10 (br. s, 1H), 8.02 (d, J = 2.5 Hz, 1H), 7.92 (dd, J = 8.5, 2.5 Hz, 1H), 7.83 (dt, J = 7.8, 1.0 Hz, 1H), 7.79 (ddd, J = 7.8, 2.1, 1.3 Hz, 1H), 7.53 (t, J = 7.8 Hz, 1H), 7.40 (br. s, 1H), 7.12 (d, J = 8.5 Hz, 1H). |
| 11-69 | | $^1$H NMR (400 M Hz, CDCl$_3$) δ ppm 11.01 (s, 1H), 9.98 (s, 1H), 7.78 (d, J = 2.3 Hz, 1H), 7.62 (t, J = 1.5 Hz, 1H), 7.58-7.61 (m, 1H), 7.48 (td, J = 7.7, 0.5 Hz, 1H), 7.37-7.41 (m, 2H), 7.09 (d, J = 9.5 Hz, 1H), 3.14 (br. s, 3H), 3.03 (br. s, 3H). |
| 11-70 | | $^1$H NMR (400 M Hz, DMSO-d$_6$) δ ppm 13.11 (br. s, 2H), 10.33 (br. s, 1H), 8.47 (d, J = 2.5 Hz, 1H), 8.27 (d, J = 2.8 Hz, 1H), 8.19-8.22 (m, 1H), 7.91-8.00 (m, 3H). |
| 11-71 | | $^1$H NMR (400 M Hz, CDCl$_3$) δ ppm 11.40 (s, 1H), 10.50 (s, 1H), 8.61 (d, J = 2.5 Hz, 1H), 8.38 (d, J = 2.5 Hz, 1H), 8.16 (d, J = 8.8 Hz, 2H), 7.67 (d, J = 8.8 Hz, 2H), 3.96 (s, 3H). |
| 11-72 | | $^1$H NMR (400 M Hz, DMSO-d$_6$) δ ppm 12.99 (br. s, 1H), 10.34 (s, 1H), 8.58 (d, J = 2.5 Hz, 1H), 8.40 (d, J = 2.5 Hz, 1H), 8.04 (d, J = 8.5 Hz, 2H), 7.89 (d, J = 8.5 Hz, 2H). |
| 11-73 | | $^1$H NMR (400 M Hz, DMSO-d$_6$) δ ppm 13.07 (br. s, 1H), 11.02 (br. s, 1H), 10.33 (s, 1H), 8.15 (t, J = 1.6 Hz, 1H), 7.97 (d, J = 2.3 Hz, 1H), 7.88-7.95 (m, 4H), 7.58 (t, J = 7.8 Hz, 1H). |

TABLE 5-continued

| No. | CHEMISTRY | NMR |
|---|---|---|
| 11-74 | | $^1$H NMR (400 M Hz, DMSO-d$_6$) δ ppm 11.11 (br. s, 1H), 10.11 (s, 1H), 9.17 (s, 1H), 8.79 (s, 2H), 7.36 (d, J = 8.3 Hz, 1H), 6.89 (d, J = 8.3 Hz, 1H), 3.90 (s, 3H). |
| 11-75 | | $^1$H NMR (400 M Hz, CDCl$_3$) δ ppm 11.01 (s, 1H), 9.98 (s, 1H), 8.42 (d, J = 2.5 Hz, 1H), 7.70 (dd, J = 8.8, 2.8 Hz, 1H), 7.29 (d, J = 2.0 Hz, 1H), 7.25 (d, J = 2.0 Hz, 1H), 6.72 (d, J = 8.8 Hz, 1H), 3.98 (s, 3H), 3.83-3.88 (m, 4H), 3.56-3.60 (m, 4H). |
| 11-76 | | $^1$H NMR (400 M Hz, DMSO-d$_6$) δ ppm 12.93 (br. s, 1H), 11.16 (br. s, 1H), 10.33 (s, 1H), 7.97-8.04 (m, 3H), 7.88 (dd, J = 2.4, 1.1 Hz, 1H), 7.83 (d, J = 8.8 Hz, 2H). |
| 11-77 | | $^1$H NMR (400 M Hz, CDCl$_3$) δ ppm 10.95 (s, 1H), 10.00 (d, J = 2.0 Hz, 1H), 7.56-7.63 (m, 4H), 7.49 (t, J = 7.7 Hz, 1H), 7.41 (td, J = 7.5, 1.3 Hz, 1H), 3.14 (br. s, 3H), 3.03 (br. s, 3H). |
| 11-78 | | $^1$H NMR (400 M Hz, CDCl$_3$) δ ppm 11.03 (s, 1H), 10.00 (s, 1H), 8.24 (t, J = 1.6 Hz, 1H), 8.03 (dd, J = 9.4, 1.1 Hz, 1H), 7.78-7.84 (m, 2H), 7.75 (dd, J = 7.8, 2.0 Hz, 1H), 7.53 (t, J = 7.8 Hz, 1H), 7.10 (d, J = 9.8 Hz, 1H), 3.96 (s, 3H). |
| 11-79 | | $^1$H NMR (400 M Hz, DMSO-d$_6$) δ ppm 10.89 (br. s, 1H), 10.32 (s, 1H), 7.98 (d, J = 2.5 Hz, 1H), 7.90 (dd, J = 8.7, 2.6 Hz, 1H), 7.70 (d, J = 8.5 Hz, 2H), 7.48 (d, J = 8.5 Hz, 2H), 7.12 (d, J = 8.5 Hz, 1H), 2.98 (br. s, 6H). |

TABLE 5-continued

| No. | CHEMISTRY | NMR |
|---|---|---|
| 11-80 | | $^1$H NMR (400 M Hz, DMSO-$d_6$) δ ppm 12.97 (br. s, 1H), 11.10 (br. s, 1H), 10.33 (s, 1H), 7.98-8.04 (m, 3H), 7.92 (dd, J = 8.5, 2.5 Hz, 1H), 7.77 (d, J = 8.5 Hz, 2H), 7.13 (d, J = 8.5 Hz, 1H). |
| 11-81 | | $^1$H NMR (400 M Hz, DMSO-$d_6$) δ ppm 11.25 (br. s, 1H), 10.33 (s, 1H), 9.10-9.23 (m, 3H), 8.09 (dd, J = 12.1, 2.3 Hz, 1H), 7.93 (dd, J = 2.4, 1.1 Hz, 1H). |
| 11-82 | | $^1$H NMR (400 M Hz, CDCl$_3$) δ ppm 10.96 (s, 1H), 10.01 (d, J = 2.0 Hz, 1H), 7.59-7.63 (m, 2H), 7.56-7.59 (m, 2H), 7.51-7.54 (m, 2H), 3.14 (br. s, 3H), 3.04 (br. s, 3H). |
| 11-83 | | $^1$H NMR (400 M Hz, DMSO-$d_6$) δ ppm 13.64 (br. s, 1H), 9.95 (br. s, 1H), 8.60 (dd, J = 4.4, 1.6 Hz, 2H), 8.06 (d, J = 10.8 Hz, 1H), 7.33 (dd, J = 4.4, 1.6 Hz, 2H), 6.81 (d, J = 7.8 Hz, 1H), 6.27 (d, J = 7.8 Hz, 1H), 3.73 (s, 3H). |

EXAMPLE 12

Synthesis of N-cyclohexyl-3'-formyl-4'-hydroxy-5'-methoxybiphenyl-3-carboxamide

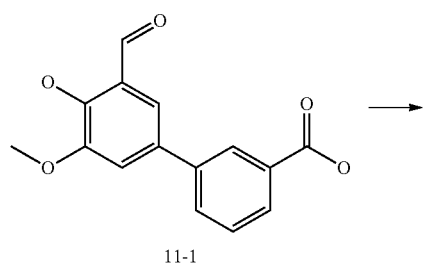

11-1

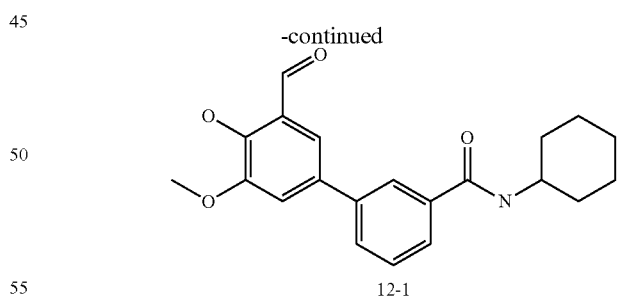

12-1

N-(3-Dimethylaminopropyl)-N'-ethylcarbodiimide hydrochloride (42 mg, 0.22 mmol), 1-hydroxybenzotriazole (30 mg, 0.22 mmol), triethylamine (140 μL, 1 mmol) and cyclohexylamine (50 μL, 0.44 mmol) were added to a solution of 11-1 (54 mg, 0.2 mmol) in 2 mL THF at room temperature. After 2 h, the reaction was diluted with 2 mL 2N hydrochloric acid and stirred for 2 h, then evaporated to dryness. The residue was dissolved in 2 mL chloroform, and extracted with water (1×1.5 mL), 1N hydrochloric acid (1×1.5 mL), water (1×1.5 mL), satd. sodium bicarbonate (1×1.5 mL) and water (1×1.5 mL). The organic phase was evaporated, and the crude product was purified with prep. HPLC, then recrystallized from diethyl ether to give 12-1 (16 mg, 0.05 mmol, 25%). ¹H NMR (400 MHz, CDCl₃) δ ppm 11.07 (s, 1H), 10.00 (s, 1H), 8.00 (t, J=1.8 Hz, 1H), 7.64-7.69 (m, 2H), 7.50 (t, J=7.8 Hz, 1H), 7.42 (d, J=2.3 Hz, 1H), 7.35 (d, J=2.0 Hz, 1H), 6.01 (d, J=7.8 Hz, 1H), 3.97-4.06 (m, 4H), 2.03-2.11 (m, 2H), 1.73-1.82 (m, 2H), 1.63-1.71 (m, 1H), 1.40-1.51 (m, 2H), 1.23-1.32 (m, 3H).

The following compounds were made by the above procedure, using the corresponding aryl acid and amine and characterized by NMR.

TABLE 6

| No. | CHEMISTRY | NMR |
|---|---|---|
| 12-2 | | ¹H NMR (400 M Hz, CDCl₃) δ ppm 11.03 (br. s, 1H), 9.99 (s, 1H), 7.99 (d, J = 3.3 Hz, 1H), 7.78-7.82 (m, 2H), 7.64-7.69 (m, 2H), 7.50 (t, J = 7.7 Hz, 1H), 7.09 (d, J = 8.5 Hz, 1H), 5.98 (d, J = 6.5 Hz, 1H), 4.27-4.38 (m, 1H), 1.29 (d, J = 6.5 Hz, 6H) |
| 12-3 | | ¹H NMR (400 M Hz, CDCl₃) δ ppm 11.03 (br. s, 1H), 9.98 (s, 1H), 8.01 (t, J = 1.6 Hz, 1H), 7.77-7.82 (m, 2H), 7.66-7.72 (m, 2H), 7.50 (t, J = 7.5 Hz, 1H), 7.09 (d, J = 8.5 Hz, 1H), 6.20 (br. s, 1H), 3.46 (td, J = 7.1, 5.9 Hz, 2H), 1.62-1.72 (m, 2H), 1.01 (t, J = 7.4 Hz, 3H). |
| 12-4 | | ¹H NMR (400 M Hz, CDCl₃) δ ppm 11.02 (br. s, 1H), 9.98 (s, 1H), 8.04 (t, J = 1.8 Hz, 1H), 7.76-7.81 (m, 2H), 7.71 (d, J = 7.8 Hz, 1H), 7.68 (d, J = 7.8 Hz, 1H), 7.50 (t, J = 7.8 Hz, 1H), 7.28-7.40 (m, 5H), 7.09 (d, J = 8.0 Hz, 1H), 6.47 (br. s, 1H), 4.68 (d, J = 5.5 Hz, 2H). |
| 12-5 | | ¹H NMR (400 M Hz, CDCl₃) δ ppm 10.96 (br. s, 1H), 10.01 (d, J = 2.0 Hz, 1H), 7.99 (t, J = 1.6 Hz, 1H), 7.67-7.70 (m, 1H), 7.61-7.67 (m, 3H), 7.51 (t, J = 7.9 Hz, 1H), 5.98 (d, J = 6.5 Hz, 1H), 4.27-4.38 (m, 1H), 1.30 (d, J = 6.5 Hz, 6H). |
| 12-6 | | ¹H NMR (400 M Hz, DMSO-d₆) δ ppm 10.95 (br. s, 1H), 10.71 (br. s, 1H), 10.35 (s, 1H), 9.02 (t, J = 5.5 Hz, 1H), 8.19 (t, J = 1.6 Hz, 1H), 8.03 (d, J = 2.5 Hz, 1H), 7.96 (dd, J = 8.5, 2.5 Hz, 1H), 7.88 (d, J = 8.3 Hz, 1H), 7.82 (d, J = 8.5 Hz, 1H), 7.56 (t, J = 7.8 Hz, 1H), 7.16 (d, J = 8.8 Hz, 1H), 3.93-4.03 (m, 2H), 3.76-3.86 (m, 2H), 3.72 (q, J = 6.1 Hz, 2H), 3.50-3.61 (m, 2H), 3.36-3.40 (m, 2H, overlapped), 3.08-3.20 (m, 2H). |
| 12-7 | | ¹H NMR (400 M Hz, DMSO-d₆) δ ppm 10.91 (br. s, 1H), 10.35 (s, 1H), 8.96 (br. s, 1H), 8.17 (br. s, 1H), 8.03 (d, J = 2.5 Hz, 1H), 7.95 (dd, J = 8.8, 2.5 Hz, 1H), 7.86 (d, J = 8.0 Hz, 1H), 7.82 (d, J = 8.5 Hz, 1H), 7.56 (t, J = 7.8 Hz, 1H), 7.16 (d, J = 8.5 Hz, 1H), 3.66 (br. s, 2H), 3.08 (br. s, 6H), 1.75 (br. s, 4H), 1.49 (br. s, 2H). |

TABLE 6-continued

| No. | CHEMISTRY | NMR |
|---|---|---|
| 12-8 | (structure) | ¹H NMR (400 M Hz, DMSO-d₆) δ ppm 11.01 (br. s, 1H), 10.34 (s, 1H), 9.09 (t, J = 5.9 Hz, 1H), 8.16 (t, J = 1.6 Hz, 1H), 7.97 (dd, J = 12.3, 2.3 Hz, 1H), 7.82-7.90 (m, 3H), 7.55 (t, J = 7.8 Hz, 1H), 7.27 (d, J = 8.8 Hz, 2H), 6.90 (d, J = 8.8 Hz, 2H), 4.45 (d, J = 6.0 Hz, 2H), 3.73 (s, 3H). |
| 12-9 | (structure) | ¹H NMR (400 M Hz, CDCl₃) δ ppm 11.03 (s, 1H), 9.99 (s, 1H), 7.98 (t, J= 1.6 Hz, 1H), 7.77-7.83 (m, 2H), 7.67-7.69 (m, 2H), 7.50 (t, J = 7.9 Hz, 1H), 7.09 (d, J = 8.5 Hz, 1H), 6.01 (d, J = 8.0 Hz, 1H), 3.96-4.07 (m, 1H), 2.02-2.11 (m, 2H), 1.73-1.82 (m, 2H), 1.63-1.72 (m, 1H), 1.39-1.51 (m, 2H), 1.17-1.32 (m, 3H). |
| 12-10 | (structure) | ¹H NMR (400 M Hz, CDCl₃) δ ppm 11.07 (br. s, 1H), 10.00 (s, 1H), 7.59-7.65 (m, 2H), 7.49 (t, J = 7.5 Hz, 1H), 7.40 (d, J = 2.0 Hz, 1H), 7.36 (dt, J = 7.5, 1.4 Hz, 1H), 7.33 (d, J = 2.0 Hz, 1H), 4.00 (s, 3H), 3.83 (br. s, 2H), 3.59 (br. s, 2H), 2.52 (br. s, 2H), 2.43 (br. s, 2H), 2.36 (s, 3H). |
| 12-11 | (structure) | ¹H NMR (400 M Hz, CDCl₃) δ ppm 11.40 (s, 1H), 10.49 (s, 1H), 8.60 (d, J = 2.3 Hz, 1H), 8.38 (d, J = 2.5 Hz, 1H), 8.04 (t, J = 1.6 Hz, 1H), 7.77 (d, J = 6.8 Hz, 1H), 7.72 (d, J = 8.5 Hz, 1H), 7.56 (t, J = 7.3 Hz, 1H), 6.26 (br. s, 1H), 3.43-3.52 (m, 2H), 1.65-1.74 (m, 2H), 1.02 (t, J = 7.4 Hz, 3H). |
| 12-12 | (structure) | ¹H NMR (400 M Hz, CDCl₃) δ ppm 11.07 (s, 1H), 9.99 (s, 1H), 8.06 (s, 1H), 7.70 (t, J = 7.2 Hz, 2H), 7.51 (t, J = 7.7 Hz, 1H), 7.29-7.43 (m, 7H), 6.49 (br. s, 1H), 4.69 (d, J = 5.5 Hz, 2H), 3.99 (s, 3H). |
| 12-13 | (structure) | ¹H NMR (400 M Hz, CDCl₃) δ ppm 10.97 (br. s, 1H), 10.00 (d, J = 2.0 Hz, 1H), 7.57-7.63 (m, 4H), 7.50 (t, J = 7.5 Hz, 1H), 7.39 (dt, J = 7.5, 1.4 Hz, 1H), 3.83 (br. s, 2H), 3.48 (br. s, 2H), 2.50 (br. s, 2H), 2.39 (br. s, 2H), 2.33 (s, 3H). |

TABLE 6-continued

| No. | CHEMISTRY | NMR |
|---|---|---|
| 12-14 | 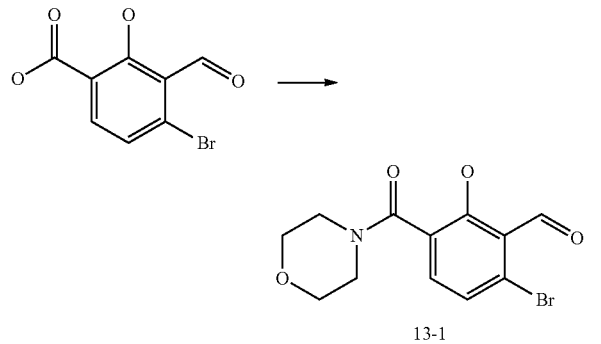 | $^1$H NMR (400 M Hz, CDCl$_3$) δ ppm 10.48 (s, 1H), 8.57 (d, J = 2.3 Hz, 1H), 8.35 (d, J = 2.5 Hz, 1H), 7.60-7.69 (m, 2H), 7.53 (t, J = 7.5 Hz, 1H), 7.43 (dt, J = 7.8, 1.4 Hz, 1H), 3.85 (br. s, 2H), 3.48 (br. s, 2H), 2.51 (br. s, 2H), 2.40 (br. s, 2H), 2.34 (s, 3H). |

EXAMPLE 13

Synthesis of 6-bromo-2-hydroxy-3-(morpholine-4-carbonyl)benzaldehyde

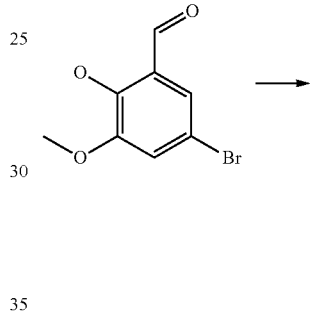

4-Bromo-3-formyl-2-hydroxybenzoic acid (122 mg, 0.5 mmol) was dissolved in 5 mL of dry THF. Phosphorus pentachloride (115 mg, 0.55 mmol) was added at 0° C., and the mixture was stirred for 20 minutes. This mixture was added dropwise to a solution of morpholine (433 µL, 5 mmol) in 20 mL of dry THF at −10° C. The reaction was warmed to room temperature and stirred for 30 min. The volatiles were evaporated and the residue taken up in 15 mL of 1N hydrochloric acid and extracted with ethyl acetate. The organic layer was evaporated and the resulting crude product was purified by column chromatography to afford 13-1 (25 mg, 0.08 mmol, 16%). $^1$H NMR (400 MHz, CDCl$_3$) δ ppm 12.33 (s, 1H), 10.34 (s, 1H), 7.41 (d, J=8.0 Hz, 1H), 7.25 (d, J=8.0 Hz, 1H), 3.78 (br. s, 4H), 3.66 (br. s, 2H), 3.32 (br. s, 2H).

The following compound was made by the above procedure and characterized by LC/MS.

TABLE 7

| No. | CHEMISTRY | MW | MH+ | Rt |
|---|---|---|---|---|
| 13-2 | 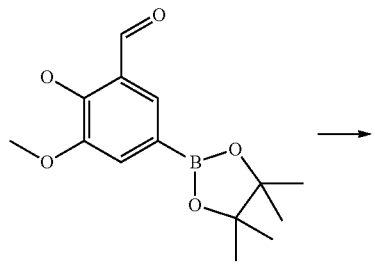 | 243.0 | 244.08 | 0.77 |

EXAMPLE 14

Synthesis of 5-(1,3-dimethyl-2,4-dioxo-1,2,3,4-tetrahydropyrimidin-5-yl)-2-hydroxy-3-methoxybenzaldehyde

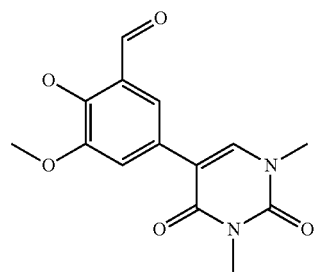

5-bromo-2-hydroxy-3-methoxybenzaldehyde (3.00 g; 13.0 mmol), bis-pinacolato-diboron (3.63 g; 14.3 mmol), potassium acetate (3.80; 39.0 mmol) and Pd(dppf)C12 (1.10 g; 1.50 mmol) were dissolved in dioxane and heated at reflux under argon for 4 h. The reaction mixture was cooled, filtered, and the filtrate was evaporated to dryness under reduced pressure. The solid residue was purified by column chromatography on silica with dichloromethane as eluent. The collected light yellow solid was triturated with diisopropyl ether to give the 14a (1.45 g, 5.22 mmol, 40%). $^1$H NMR (400 MHz, CDCl$_3$) δ ppm 11.36 (s, 1 H), 9.93 (s, 1 H), 7.69 (d, J=1.3 Hz, 1 H), 7.49 (s, 1 H), 3.96 (s, 3 H), 1.36 (s, 12 H).

5-bromo-1,3-dimethyluracil (88 mg, 0.4 mmol), 14a (117 mg, 0.4 mmol) and anhydrous sodium carbonate (254 mg, 2.4 mmol) were dissolved in a mixture of 6 mL of DMF and 6 mL of water. Tetrakis(triphenylphosphine)palladium (22 mg, 0.02 mmol) was added, and the reaction heated to 110° C. under argon for 1 h. 40 mL satd. sodium chloride solution was added, and the mixture was extracted with chloroform (2×40 mL). The organic layer was dried, evaporated, and the residue purified with column chromatography to give 14-1 (37 mg, 0.13 mmol, 32%). $^1$H NMR (400 MHz, CDCl$_3$) δ ppm 11.00 (s, 1H), 9.95 (s, 1H), 7.35 (d, J=1.8 Hz, 1H), 7.33 (dd, J=9.3, 2.0 Hz, 2H), 3.96 (s, 3H), 3.51 (s, 3H), 3.44 (s, 3H).

The following compounds was made by the above procedure using the corresponding aryl bromide and characterized by LC/MS.

TABLE 8

| No. | CHEMISTRY | MW | MH+ | Rt |
|---|---|---|---|---|
| 14-2 | | 229.1 | 230.2 | 1.09 |

The following compound was made by the above procedure using the corresponding aryl bromide and characterized by NMR.

TABLE 9

| No. | CHEMISTRY | NMR |
|---|---|---|
| 14-3 | | $^1$H NMR (400 MHz, CDCl$_3$) δ ppm 11.10 (s, 1H), 9.98 (s, 1H), 7.67 (d, J = 1.8 Hz, 1H), 7.56 (d, J = 2.0 Hz, 1H), 6.80 (s, 1H), 4.16 (s, 3H), 3.99 (s, 3H). |

EXAMPLE 15

Synthesis of 2-hydroxy-3-methoxy-5-(pyridin-3-ylethynyl)benzaldehyde

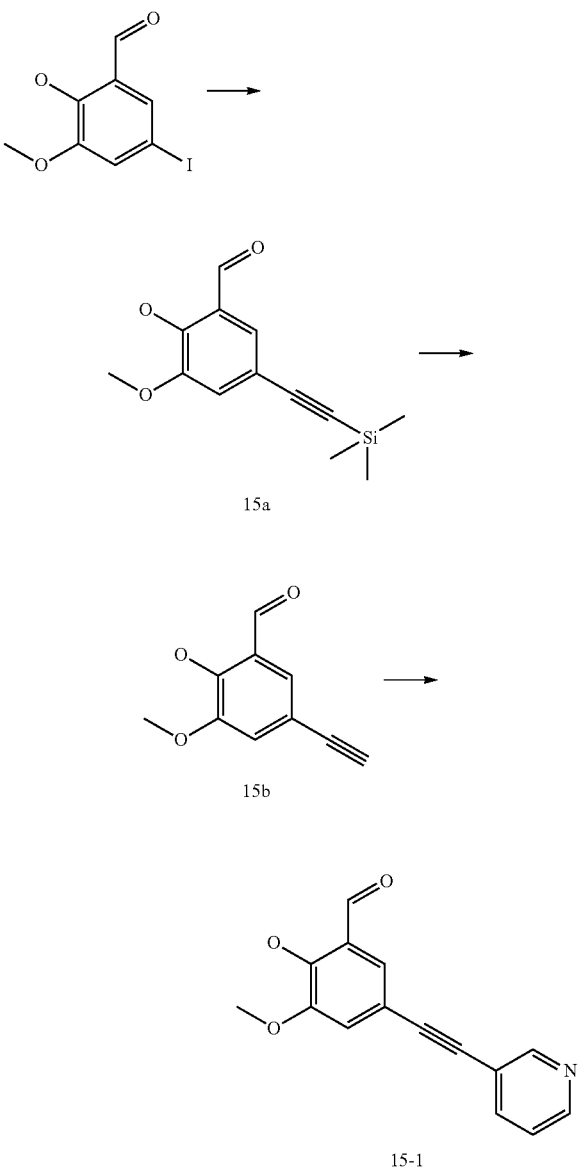

2-Hydroxy-5-iodo-3-methoxybenzaldehyde (2.08 g; 7.5 mmol), ethynyl-trimethylsilane (2.65 mL, 1.8 mmol), Pd(PPh$_3$)$_2$Cl$_2$ (158 mg; 0.23 mmol) and copper(I) iodide (43 mg; 0.23 mmol) were dissolved in 40 mL triethylamine and was heated at 60° C. for 4 h. The mixture was cooled to room temperature, filtered, and the filtrate was evaporated. The solid residue was purified by column chromatography on silica with toluene as eluent to give 15a (0.7 g, 3.9 mmol, 49%). $^1$H NMR (400 MHz, CDCl$_3$) δ ppm 11.20 (s, 1H), 9.87 (s, 1H), 7.35 (d, J=1.8 Hz, 1H), 7.16 (d, J=1.8 Hz, 1H), 3.92 (s, 3H), 0.26 (s, 9H).

Compound 15a (2.00 g; 8.06 mmol) was dissolved in 150 mL of methanol. Sodium carbonate (2.3 g, 21.7 mmol) was added and the mixture was stirred overnight at room temperature. The reaction was evaporated and the residue partitioned between water and dichloromethane. The organic layer was dried, evaporated and the solid residue was chromatographed on silica with toluene as the eluent to give 15b as a white powder (0.70 g, 4 mmol, 50%). $^1$H NMR (400 MHz, CDCl$_3$) δ ppm 11.22 (s, 1H), 9.88 (s, 1H), 7.37 (d, J=1.8 Hz, 1H), 7.18 (d, J=1.8 Hz, 1H), 3.92 (s, 3H), 3.04 (s, 1H).

Compound 15b (70 mg, 0.4 mmol), 3-iodopyridine (90 mg, 0.44 mmol), Pd(dppf)Cl$_2$ (15 mg, 0.02 mmol) and copper(I) iodide (5 mg, 0.02 mmol) were dissolved in 5 mL triethylamine and 5 mL DMF, and heated to 80° C. After 4 h, 20 mL 1N hydrochloric acid was added, and the mixture was extracted with dichloromethane. The organic layer was evaporated, and the solid residue was purified by column chromatography to afford 15-1 (9 mg, 0.04 mmol, 9%). $^1$H NMR (400 MHz, CDCl$_3$) δ ppm 11.24 (s, 1H), 9.93 (s, 1H), 8.77 (s, 1H), 8.57 (d, J=3.5 Hz, 1H), 7.81 (ddd, J=7.9, 1.9, 1.8 Hz, 1H), 7.44 (d, J=2.0 Hz, 1H), 7.30 (dd, J=7.9, 4.9 Hz, 1H), 7.24 (d, J=1.8 Hz, 1H), 3.97 (s, 3H).

The following compound was made by the above procedure, using the corresponding aryl bromide and characterized by LC/MS.

TABLE 10

| No. | CHEMISTRY | MW | MH+ | Rt |
|---|---|---|---|---|
| 15-2 | 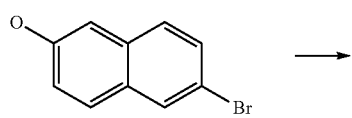 | 223.1 | 224.2 | 1.21 |

The following compound was made by the above procedure using the corresponding aryl bromide and characterized by NMR.

TABLE 11

| No. | CHEMISTRY | NMR |
|---|---|---|
| 15-3 | (structure shown) | $^1$H NMR (400 MHz, CDCl$_3$) δ ppm 11.23 (s, 1H), 9.90 (s, 1H), 7.39 (d, J = 1.8 Hz, 1H), 7.31 (dd, J = 5.1, 1.1 Hz, 1H), 7.28 (dd, J = 3.6, 1.1 Hz, 1H), 7.21 (d, J = 1.8 Hz, 1H), 7.02 (dd, J = 5.3, 3.5 Hz, 1H), 3.95 (s, 3H). |

EXAMPLE 16

Synthesis of 6-bromo-2-hydroxy-1-naphthaldehyde

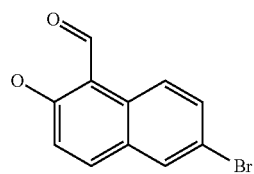

16-1

A solution of titanium tetrachloride (231 μL, 2.1 mmol) and dichloromethyl methyl ether (97 μL, 1.1 mmol) in 1 mL of dichloromethane was stirred at 0° C. for 15 min. A solution of 6-bromo-2-hydroxy-naphthalene (223 mg, 1 mmol) in 3 mL of dichloromethane was added dropwise, the solution was allowed to warm up to room temperature, and stirred for 12 hours. 10 mL of 1 N hydrochloric acid was added, and the mixture was extracted with dichloromethane. The organic layer was washed with water, dried, and evaporated to give 16-1 (206 mg, 0.82 mmol, 82%). $^1$H NMR (400 MHz, DMSO-$d_6$) δ ppm 11.90 (s, 1H), 10.76 (s, 1H), 8.92 (d, J=9.3 Hz, 1H), 8.16 (d, J=2.0 Hz, 1H), 8.10 (d, J=9.3 Hz, 1H), 7.72 (dd, J=9.0, 2.3 Hz, 1H), 7.30 (d, J=9.0 Hz, 1H).

The following compound was made by the above procedure and characterized by NMR.

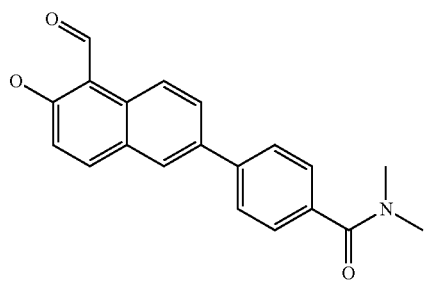

17-1

TABLE 12

| No. | CHEMISTRY | NMR |
|---|---|---|
| 16-2 | 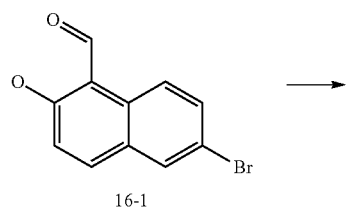 | $^1$H NMR (400 MHz, DMSO-$d_6$) δ ppm 11.88 (br. s, 1 H), 10.82 (s, 1 H), 8.80 (d, J = 8.5 Hz, 1 H), 7.81 (dd, J = 7.9, 1.4 Hz, 1 H), 7.67 (s, 1 H), 7.47 (ddd, J = 8.5, 7.0, 1.5 Hz, 1 H), 7.40 (ddd, J = 8.3, 7.0, 1.3 Hz, 1 H), 3.98 (s, 3 H). |

EXAMPLE 17

Synthesis of 4-(5-formyl-6-hydroxynaphthalen-2-yl)-N,N-dimethylbenzamide

Compound 16-1 (251 mg, 1 mmol), 4-(N,N-dimethylaminocarbonyl)phenylboronic acid (222 mg, 1.2 mmol) and anhydrous sodium carbonate (424 mg, 4 mmol) were dissolved in a mixture of 20 mL of DMF and 12 mL of water. Tetrakis(triphenylphosphine)palladium (56 mg, 0.05 mmol) was added, and the reaction was heated at 105° C. under argon, for 25 min. 50 mL satd. sodium chloride solution and 900 μL of acetic acid were added, and the mixture was extracted with chloroform. The organic layer was evaporated, and the crude product was purified with column chromatography to afford 17-1 (186 mg, 0.58 mmol, 58%). $^1$H NMR (400 MHz, CDCl$_3$) δ ppm 13.15 (s, 1H), 10.85 (s, 1H), 8.44 (d, J=9.0 Hz, 1H), 8.05 (d, J=9.0 Hz, 1H), 8.01 (d, J=2.0 Hz, 1H), 7.88 (dd, J=8.8, 2.0 Hz, 1H), 7.71-7.75 (m, 2H), 7.56 (d, J=8.5 Hz, 2H), 7.19 (d, J=9.0 Hz, 1H), 3.15 (br. s, 3H), 3.07 (br. s, 3H).

The following compounds were made by the above procedure using the corresponding aryl boronic acid and characterized by NMR.

TABLE 13

| No. | CHEMISTRY | NMR |
|---|---|---|
| 17-2 | | $^1$H NMR (400 MHz, DMSO-d$_6$) δ ppm 11.99 (br. s, 1H), 10.83 (s, 1H), 9.04 (d, J = 9.0 Hz, 1H), 8.30 (d, J = 2.0 Hz, 1H), 8.23 (d, J = 9.0 Hz, 1H), 7.97-8.08 (m, 4H), 7.90 (d, J = 8.5 Hz, 2H), 7.37 (br. s, 1H), 7.30 (d, J = 9.0 Hz, 1H). |
| 17-3 | | $^1$H NMR (400 MHz, CDCl$_3$) δ ppm 13.16 (s, 1H), 10.86 (s, 1H), 8.96 (d, J = 1.8 Hz, 1H), 8.65 (dd, J = 4.8, 1.3 Hz, 1H), 8.47 (d, J = 9.3 Hz, 1H), 8.07 (d, J = 9.0 Hz, 1H), 8.01 (d, J = 2.0 Hz, 1H), 7.98 (dt, J = 7.8, 2.0 Hz, 1H), 7.86 (dd, J = 8.8, 2.0 Hz, 1H), 7.42 (dd, J = 7.5, 4.5 Hz, 1H), 7.22 (d, J = 9.3 Hz, 1H). |
| 17-4 | | $^1$H NMR (400 MHz, CDCl$_3$) δ ppm 13.20 (s, 1H), 10.86 (s, 1H), 9.26 (s, 1H), 9.07 (s, 2H), 8.52 (d, J = 9.3 Hz, 1H), 8.09 (d, J = 9.3 Hz, 1H), 8.02 (d, J = 2.0 Hz, 1H), 7.85 (dd, J = 8.8, 2.0 Hz, 1H), 7.25 (d, J = 9.3 Hz, 1H). |
| 17-5 | | $^1$H NMR (400 MHz, CDCl$_3$) δ ppm 13.15 (s, 1H), 10.85 (s, 1H), 8.44 (d, J = 9.3 Hz, 1H), 8.38 (t, J = 1.6 Hz, 1H), 8.01-8.10 (m, 3H), 7.90 (td, J = 8.5, 2.0 Hz, 2H), 7.57 (t, J = 7.8 Hz, 1H), 7.20 (d, J = 9.3 Hz, 1H), 3.98 (s, 3H). |
| 17-6 | | $^1$H NMR (400 MHz, CDCl$_3$) δ ppm 13.15 (s, 1H), 10.85 (s, 1H), 8.44 (d, J = 9.3 Hz, 1H), 8.04 (d, J = 9.3 Hz, 1H), 8.01 (d, J = 2.0 Hz, 1H), 7.87 (dd, J = 8.8, 2.0 Hz, 1H), 7.73-7.78 (m, 2H), 7.54 (t, J = 8.3 Hz, 1H), 7.40 (dt, J = 7.5, 1.4 Hz, 1H), 7.20 (d, J = 9.0 Hz, 1H), 3.40-4.02 (m, 8H). |
| 17-7 | | $^1$H NMR (400 MHz, DMSO-d$_6$) δ ppm 12.90 (br. s, 1H), 12.11 (br. s, 1H), 10.83 (s, 1H), 9.05 (d, J = 9.0 Hz, 1H), 8.33 (s, 1H), 8.24-8.30 (m, 2H), 8.06 (d, J = 7.8 Hz, 1H), 7.98 (t, J = 9.0 Hz, 1H), 7.99 (d, J = 9.0 Hz, 1H), 7.64 (t, J = 7.8 Hz, 1H), 7.29 (d, J = 9.0 Hz, 1H). |

TABLE 13-continued

| No. | CHEMISTRY | NMR |
|---|---|---|
| 17-8 | 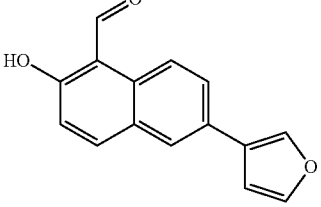 | $^1$H NMR (400 MHz, CDCl$_3$) δ ppm 13.08 (s, 1H), 10.82 (s, 1H), 8.35 (d, J = 9.0 Hz, 1H), 7.98 (d, J = 9.0 Hz, 1H), 7.87 (d, J = 1.8 Hz, 1H), 7.83 (s, 1H), 7.75 (dd, J = 8.8, 2.0 Hz, 1H), 7.53 (t, J = 1.6 Hz, 1H), 7.16 (d, J = 9.0 Hz, 1H), 6.80 (d, J = 1.0 Hz, 1H). |
| 17-9 | 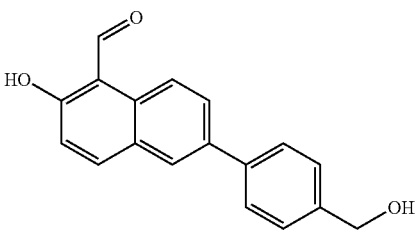 [SMILES: O=Cc1c(O)ccc2cc(-c3ccc(CO)cc3)ccc12] | $^1$H NMR (400 MHz, CDCl$_3$) δ ppm 13.13 (s, 1H), 10.84 (s, 1H), 8.41 (d, J = 9.3 Hz, 1H), 8.04 (d, J = 9.0 Hz, 1H), 7.99 (d, J = 1.8 Hz, 1H), 7.88 (dd, J = 8.8, 2.0 Hz, 1H), 7.69 (d, J = 8.5 Hz, 2H), 7.50 (d, J = 8.5 Hz, 2H), 7.18 (d, J = 9.3 Hz, 1H), 4.78 (d, J = 5.3 Hz, 2H), 1.72 (t, J = 5.8 Hz, 1H). |
| 17-10 | 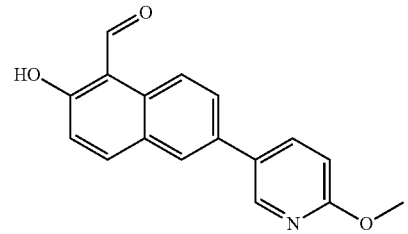 [SMILES: COc1ccc(-c2ccc3c(C=O)c(O)ccc3c2)cn1] | $^1$H NMR (400 MHz, CDCl$_3$) δ ppm 13.13 (s, 1H), 10.84 (s, 1H), 8.49 (dd, J = 2.8, 0.8 Hz, 1H), 8.43 (d, J = 9.3 Hz, 1H), 8.04 (d, J = 9.0 Hz, 1H), 7.92 (d, J = 2.0 Hz, 1H), 7.89 (dd, J = 8.7, 2.6 Hz, 1H), 7.81 (dd, J = 8.5, 2.0 Hz, 1H), 7.19 (d, J = 9.0 Hz, 1H), 6.87 (dd, J = 8.7, 0.6 Hz, 1H), 4.01 (s, 3H). |
| 17-11 | 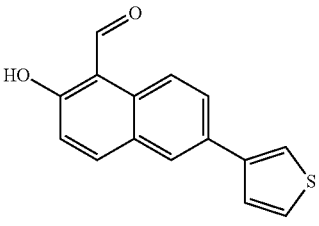 | $^1$H NMR (400 MHz, CDCl$_3$) δ ppm 13.10 (s, 1H), 10.83 (s, 1H), 8.38 (d, J = 9.3 Hz, 1H), 8.01 (d, J = 9.3 Hz, 1H), 7.99 (d, J = 2.0 Hz, 1H), 7.88 (dd, J = 8.8, 2.0 Hz, 1H), 7.56 (dd, J = 2.9, 1.4 Hz, 1H), 7.50 (dd, J = 5.0, 1.5 Hz, 1H), 7.45 (dd, J = 5.0, 3.0 Hz, 1H), 7.17 (d, J = 9.0 Hz, 1H). |
| 17-12 | 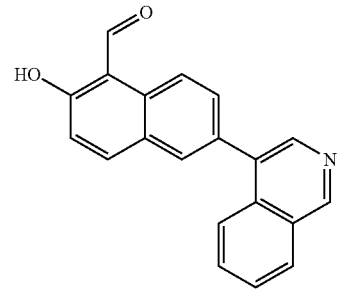 [SMILES: O=Cc1c(O)ccc2cc(-c3cncc4ccccc34)ccc12] | $^1$H NMR (400 MHz, CDCl$_3$) δ ppm 13.20 (s, 1H), 10.91 (s, 1H), 9.33 (br. s, 1H), 8.58 (br. s, 1H), 8.51 (d, J = 9.3 Hz, 1H), 8.05-8.12 (m, 2H), 7.96 (d, J = 2.0 Hz, 1H), 7.92 (d, J = 7.5 Hz, 1H), 7.80 (dd, J = 8.7, 1.9 Hz, 1H), 7.64-7.73 (m, 2H), 7.24 (d, J = 9.3 Hz, 1H). |
| 17-13 | 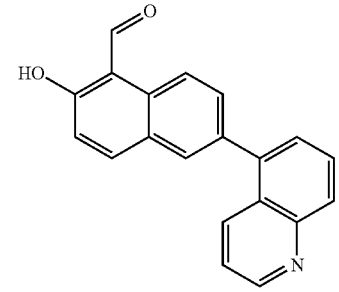 [SMILES: O=Cc1c(O)ccc2cc(-c3cccc4ncccc34)ccc12] | $^1$H NMR (400 MHz, CDCl$_3$) δ ppm 13.19 (s, 1H), 10.91 (s, 1H), 8.96 (dd, J = 4.1, 1.4 Hz, 1H), 8.49 (d, J = 9.0 Hz, 1H), 8.24 (d, J = 8.5 Hz, 1H), 8.18 (d, J = 8.5 Hz, 1H), 8.05 (d, J = 9.0 Hz, 1H), 7.91 (d, J = 2.0 Hz, 1H), 7.81 (dd, J = 8.5, 7.0 Hz, 1H), 7.75 (dd, J = 8.5, 1.8 Hz, 1H), 7.59 (dd, J = 7.0, 1.0 Hz, 1H), 7.38 (dd, J = 8.7, 4.1 Hz, 1H), 7.24 (d, J = 9.0 Hz, 1H). |

TABLE 13-continued

| No. | CHEMISTRY | NMR |
|---|---|---|
| 17-14 | | ¹H NMR (400 MHz, CDCl₃) δ ppm 13.12 (s, 1H), 10.84 (s, 1H), 8.40 (d, J = 9.0 Hz, 1H), 8.03 (d, J = 9.0 Hz, 1H), 7.93 (d, J = 1.8 Hz, 1H), 7.82 (dd, J = 8.8, 2.0 Hz, 1H), 7.48-7.52 (m, 1H), 7.43-7.48 (m, 1H), 7.18 (d, J = 9.0 Hz, 1H), 7.11 (t, J = 9.0 Hz, 1H), 2.38 (d, J = 1.8 Hz, 3H). |
| 17-15 | | ¹H NMR (400 MHz, CDCl₃) δ ppm 13.13 (s, 1H), 10.84 (s, 1H), 8.41 (d, J = 9.0 Hz, 1H), 8.04 (d, J = 9.0 Hz, 1H), 7.96 (d, J = 1.8 Hz, 1H), 7.83 (dd, J = 8.8, 2.0 Hz, 1H), 7.55 (s, 1H), 7.45 (d, J = 1.3 Hz, 2H), 7.18 (d, J = 9.0 Hz, 1H), 2.48 (s, 3H). |
| 17-16 | | ¹H NMR (400 MHz, CDCl₃) δ ppm 13.13 (s, 1H), 10.84 (s, 1H), 8.41 (d, J = 9.0 Hz, 1H), 8.03 (d, J = 9.0 Hz, 1H), 7.96 (d, J = 1.8 Hz, 1H), 7.84 (dd, J = 8.8, 2.0 Hz, 1H), 7.68 (d, J = 2.0 Hz, 1H), 7.48 (dd, J = 7.8, 1.8 Hz, 1H), 7.34 (d, J = 8.0 Hz, 1H), 7.18 (d, J = 9.0 Hz, 1H), 2.44 (s, 3H). |
| 17-17 | | ¹H NMR (400 MHz, DMSO-d₆) δ ppm 12.00 (br. s, 1H), 10.83 (s, 1H), 9.05 (d, J = 9.0 Hz, 1H), 8.32 (d, J = 2.0 Hz, 1H), 8.24 (d, J = 8.8 Hz, 1H), 8.08 (d, J = 8.5 Hz, 2H), 8.03 (dd, J = 8.9, 2.1 Hz, 1H), 7.97 (d, J = 8.8 Hz, 2H), 7.30 (d, J = 9.0 Hz, 1H), 3.89 (s, 3H). |
| 17-18 | | ¹H NMR (400 MHz, DMSO-d₆) δ ppm 11.99 (br. s, 1H), 10.84 (s, 1H), 9.05 (d, J = 8.8 Hz, 1H), 8.30 (t, J = 1.6 Hz, 1H), 8.29 (d, J = 2.0 Hz, 1H), 8.24 (d, J = 9.0 Hz, 1H), 8.11 (br. s, 1H), 8.03 (dd, J = 8.8, 2.0 Hz, 1H), 7.96 (ddd, J = 7.8, 1.8, 1.3 Hz, 1H), 7.89 (ddd, J = 7.5, 1.5, 1.0 Hz, 1H), 7.59 (t, J = 7.8 Hz, 1H), 7.44 (br. s, 1H), 7.30 (d, J = 9.0 Hz, 1H). |
| 17-19 | | ¹H NMR (400 MHz, CDCl₃) δ ppm 13.14 (s, 1H), 10.85 (s, 1H), 8.43 (d, J = 9.3 Hz, 1H), 8.04 (d, J = 9.0 Hz, 1H), 8.01 (d, J = 2.0 Hz, 1H), 7.88 (dd, J = 8.8, 2.0 Hz, 1H), 7.68-7.77 (m, 2H), 7.50-7.54 (m, 1H), 7.35-7.46 (m, 1H), 7.19 (d, J = 9.0 Hz, 1H), 3.16 (br. s, 3H), 3.05 (br. s, 3H). |

TABLE 13-continued

| No. | CHEMISTRY | NMR |
|---|---|---|
| 17-20 | | $^1$H NMR (400 MHz, DMSO-$d_6$) δ ppm 12.97 (br. s, 1H), 12.05 (br. s, 1H), 10.82 (s, 1H), 9.07 (d, J = 9.0 Hz, 1H), 8.31 (d, J = 2.0 Hz, 1H), 8.23 (d, J = 9.0 Hz, 1H), 8.06 (d, J = 8.8 Hz, 2H), 8.02 (dd, J = 8.9, 2.1 Hz, 1H), 7.94 (d, J = 8.8 Hz, 2H), 7.37 (d, J = 9.0 Hz, 1H). |
| 17-21 | | $^1$H NMR (400 MHz, CDCl$_3$) δ ppm 13.11 (s, 1H), 10.84 (s, 1H), 8.56 (d, J = 1.8 Hz, 1H), 8.41 (d, J = 9.3 Hz, 1H), 8.02 (d, J = 9.3 Hz, 1H), 7.91 (d, J = 2.0 Hz, 1H), 7.79-7.86 (m, 2H), 7.17 (d, J = 9.0 Hz, 1H), 6.75 (d, J = 8.8 Hz, 1H), 3.86-3.89 (m, 4H), 3.58-3.62 (m, 4H). |

EXAMPLE 18

Synthesis of 6-(5-formyl-6-hydroxynaphthalen-2-yl)picolinic acid

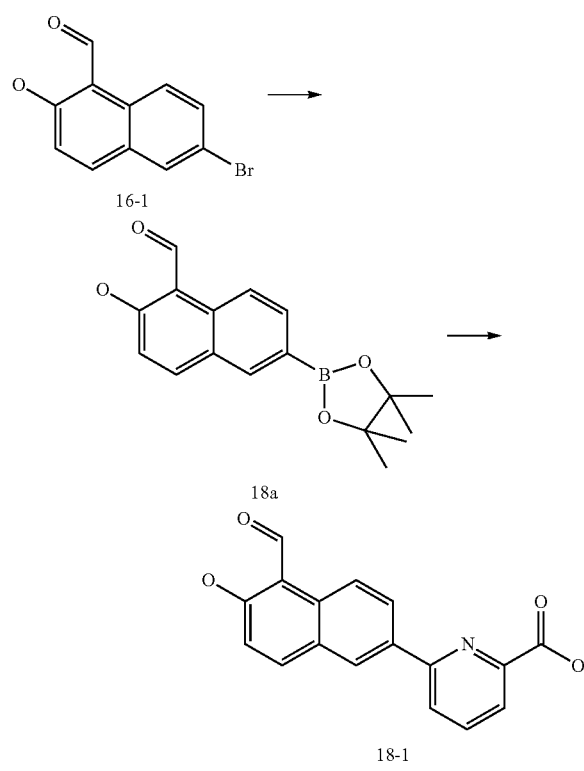 [SMILES: O=Cc1c(O)ccc2cc(Br)ccc12 ; CC1(C)OB(c2ccc3c(C=O)c(O)ccc3c2)OC1(C)C ; O=Cc1c(O)ccc2cc(-c3cccc(C(=O)O)n3)ccc12]

Compound 16-1 (5.00 g; 19.9 mmol) bis-pinacolatodiboron (5.57 g; 21.9 mmol), potassium acetate (5.86 g; 59.8 mmol) and Pd(dppf)Cl$_2$ (1.75 g; 2.39 mmol) were heated at reflux in dioxane under argon for 4 h. The reaction mixture was cooled to room temperature, filtered, and the filtrate was evaporated to dryness under reduced pressure. The solid residue was purified by column chromatography on silica with dichloromethane as the eluent. The collected light yellow solid was triturated with diisopropyl ether to give 18a (3.56 g; 11.9 mmol, 60%). $^1$H NMR (400 MHz, CDCl$_3$) δ ppm 13.23 (s, 1H), 10.82 (s, 1H), 8.33 (d, J=8.8 Hz, 1H), 8.29 (s, 1H), 8.02 (d, J=9.0 Hz, 1H), 7.98 (dd, J=8.5, 1.3 Hz, 1H), 7.13 (d, J=9.0 Hz, 1H), 1.39 (s, 12H).

6-bromopicolinic acid (81 mg, 0.4 mmol), 18a (119 mg, 0.4 mmol) and anhydrous sodium carbonate (339 mg, 3.2 mmol) were dissolved in a mixture of 8 mL of DMF and 8 mL of water. Tetrakis(triphenylphosphine)palladium (22 mg, 0.02 mmol) was added and the reaction was stirred under argon for 3 h at 110° C. 40 mL 1N sodium hydroxide solution was added, and the aqueous layer was extracted with chloroform (2×40 mL). The aqueous layer was acidified with 6N hydrochloric acid to pH 5, the white precipitate was filtered, washed with water, dried under vacuum, and recrystallized from diethyl ether to give 100 mg 18-1 (0.34 mmol, 84%). $^1$H NMR (400 MHz, DMSO-$d_6$) δ ppm 13.15 (br. s, 1H), 12.08 (br. s, 1H), 10.84 (s, 1H), 9.07 (d, J=9.0 Hz, 1H), 8.73 (d, J=2.0 Hz, 1H), 8.44 (dd, J=9.0, 2.0 Hz, 1H), 8.33 (dd, J=7.9, 0.9 Hz, 1H), 8.28 (d, J=9.0 Hz, 1H), 8.11 (t, J=7.8 Hz, 1H), 8.02 (dd, J=7.8, 0.8 Hz, 1H), 7.34 (d, J=9.0 Hz, 1H).

The following compound was made by the above procedure using the corresponding aryl boronic acid and characterized by LC/MS.

TABLE 14

| No. | CHEMISTRY | MW | MH+ | Rt | IC$_{50}$ (nM) | EC$_{50}$ (nM) |
|---|---|---|---|---|---|---|
| 18-2 | ![structure] | 283.0 | 283.6 | 1.59 | 5616 | |

The following compound was made by the above procedure using the corresponding aryl boronic acid and characterized by NMR.

TABLE 15

| No. | CHEMISTRY | NMR |
|---|---|---|
| 18-3 | ![structure] | $^1$H NMR (400 MHz, CDCl$_3$) δ ppm 13.14 (s, 1H), 10.82 (s, 1H), 8.38 (d, J = 9.3 Hz, 1H), 8.05 (d, J = 2.0 Hz, 1H), 8.01 (d, J = 9.0 Hz, 1H), 7.88 (dd, J = 8.8, 2.0 Hz, 1H), 7.80 (d, J = 3.8 Hz, 1H), 7.39 (d, J = 3.8 Hz, 1H), 7.20 (d, J = 9.3 Hz, 1H), 4.39 (q, J = 7.3 Hz, 2H), 1.41 (t, J = 7.2 Hz, 3H). |

EXAMPLE 19

Synthesis of 6-(5-formyl-6-hydroxynaphthalen-2-yl)-N-(2-morpholinoethyl)picolinamide

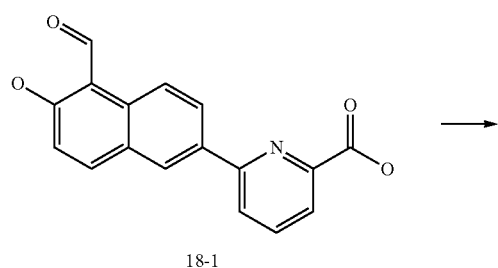

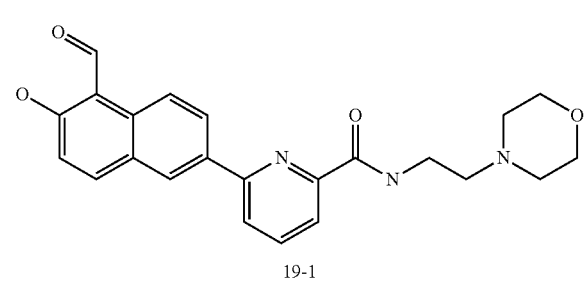

N-(3-Dimethylaminopropyl)-N'-ethylcarbodiimide hydrochloride (42 mg, 0.22 mmol), 1-hydroxybenzotriazole (30 mg, 0.22 mmol), triethylamine (140 µL, 1 mmol) and 1-(2-aminoethyl)morpholine (57 µL, 0.44 mmol) were added to a solution of 18-1 (59 mg, 0.2 mmol) in 2 mL THF at room temperature. After 2 h, 2 mL 2N hydrochloric acid was added, and the reaction was stirred for 2 h. The mixture was evaporated, and the residue was dissolved in 2 mL chloroform and washed with satd. sodium bicarbonate (1×1.5 mL) and water (1×1.5 mL). The organic phase was evaporated and the crude product was purified by column chromatography to give 7 mg of 19-1 (0.02 mmol, 9%). $^1$H NMR (400 MHz, CDCl$_3$) δ ppm 13.20 (br. s, 1H), 10.89 (s, 1H), 8.71 (br. s, 1H), 8.49 (d, J=8.8 Hz, 1H), 8.46 (d, J=2.0 Hz, 1H), 8.38 (dd, J=8.8, 2.0 Hz, 1H), 8.19 (dd, J=7.2, 1.6 Hz, 1H), 8.10 (d, J=9.0 Hz, 1H), 8.01 (dd, J=8.0, 1.5 Hz, 1H), 7.97 (t, J=7.8 Hz, 1H), 7.23 (d, J=9.0 Hz, 1H), 3.78-3.86 (m, 4H), 3.66 (q, J=6.0 Hz, 2H), 2.69 (t, J=6.1 Hz, 2H), 2.56-2.65 (m, 4H).

The following compounds were made by the above procedure, using the corresponding aryl acid and amine and characterized by NMR.

TABLE 16

| No. | CHEMISTRY | NMR |
|---|---|---|
| 19-2 | 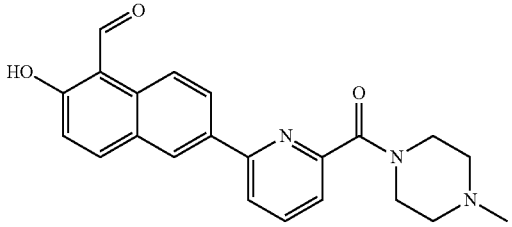 [SMILES: CN1CCN(C(=O)c2cccc(-c3ccc4c(C=O)c(O)ccc4c3)n2)CC1] | ¹H NMR (400 MHz, CDCl₃) δ ppm 13.18 (br. s, 1H), 10.86 (s, 1H), 8.44-8.49 (m, 2H), 8.30 (dd, J = 8.9, 1.9 Hz, 1H), 8.09 (d, J = 9.0 Hz, 1H), 7.92 (s, 1H), 7.91 (d, J = 1.9 Hz, 1H), 7.60-7.66 (m, 1H), 7.20 (d, J = 9.0 Hz, 1H), 3.85-3.95 (m, 2H), 3.73-3.81 (m, 2H), 2.55-2.62 (m, 2H), 2.47-2.54 (m, 2H), 2.37 (s, 3H). |
| 19-3 | 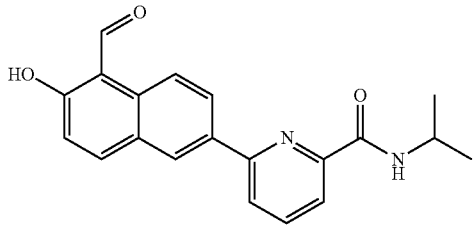 [SMILES: CC(C)NC(=O)c1cccc(-c2ccc3c(C=O)c(O)ccc3c2)n1] | ¹H NMR (400 MHz, CDCl₃) δ ppm 13.19 (s, 1H), 10.87 (s, 1H), 8.50 (d, J = 9.3 Hz, 1H), 8.40 (d, J = 2.0 Hz, 1H), 8.29 (dd, J = 8.8, 2.0 Hz, 1H), 8.21 (dd, J = 5.1, 3.6 Hz, 1H), 8.12 (d, J = 9.0 Hz, 1H), 7.97 (s, 1H), 7.96 (d, J = 1.5 Hz, 1H), 7.90 (d, J = 5.5 Hz, 1H), 7.22 (d, J = 9.3 Hz, 1H), 4.34 (s, 1H), 1.35 (d, J = 6.5 Hz, 6H). |
| 19-4 | 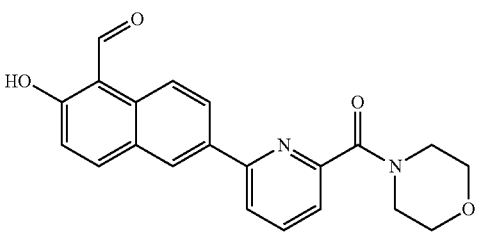 [SMILES: O=Cc1c(O)ccc2cc(-c3cccc(C(=O)N4CCOCC4)n3)ccc12] | ¹H NMR (400 MHz, CDCl₃) δ ppm 13.19 (s, 1H), 10.86 (s, 1H), 8.41-8.51 (m, 1H), 8.29 (dd, J = 8.8, 2.0 Hz, 1H), 8.09 (d, J = 9.0 Hz, 1H), 7.92 (d, J = 4.3 Hz, 2H), 7.67 (t, J = 4.3 Hz, 1H), 7.18-7.23 (m, 2H), 3.83-3.92 (m, 4H), 3.75-3.83 (m, 4H). |
| 19-5 | 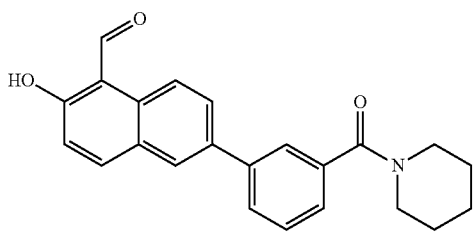 [SMILES: O=Cc1c(O)ccc2cc(-c3cccc(C(=O)N4CCCCC4)c3)ccc12] | ¹H NMR (400 MHz, CDCl₃) δ ppm 13.14 (s, 1H), 10.85 (s, 1H), 8.43 (d, J = 8.8 Hz, 1H), 8.04 (d, J = 9.0 Hz, 1H), 8.01 (d, J = 2.0 Hz, 1H), 7.88 (dd, J = 8.8, 2.0 Hz, 1H), 7.70-7.76 (m, 2H), 7.51 (t, J = 7.8 Hz, 1H), 7.39 (dt, J = 7.5, 1.3 Hz, 1H), 7.19 (d, J = 9.3 Hz, 1H), 3.76 (br. s, 2H), 3.42 (br. s, 2H), 1.70 (br. s, 4H), 1.56 (br. s, 2H). |
| 19-6 | 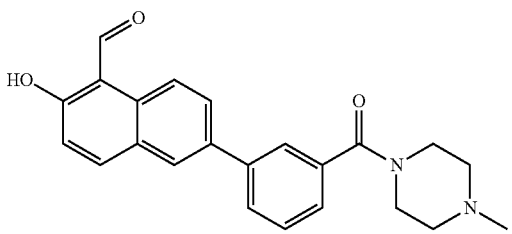 [SMILES: CN1CCN(C(=O)c2cccc(-c3ccc4c(C=O)c(O)ccc4c3)c2)CC1] | ¹H NMR (400 MHz, CDCl₃) δ ppm 13.15 (br. s, 1H), 10.85 (s, 1H), 8.44 (d, J = 9.0 Hz, 1H), 8.04 (d, J = 8.8 Hz, 1H), 8.01 (d, J = 2.0 Hz, 1H), 7.88 (dd, J = 8.7, 2.1 Hz, 1H), 7.72-7.76 (m, 2H), 7.53 (t, J = 7.5 Hz, 1H), 7.40 (dt, J = 7.8, 1.3 Hz, 1H), 7.19 (d, J = 9.0 Hz, 1H), 3.85 (br. s, 2H), 3.48 (br. s, 2H), 2.50 (br. s, 2H), 2.41 (br. s, 2H), 2.34 (s, 3H). |
| 19-7 | 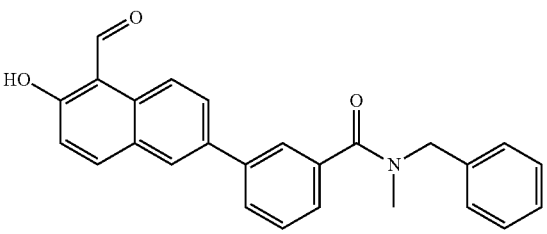 [SMILES: CN(Cc1ccccc1)C(=O)c1cccc(-c2ccc3c(C=O)c(O)ccc3c2)c1] | ¹H NMR (400 MHz, CDCl₃) δ ppm 13.14 (s, 1H), 10.84 (s, 1H), 8.39 (br. s, 1H), 7.94-8.07 (m, 1H), 7.70-7.90 (m, 3H), 7.45-7.54 (m, 2H), 7.30-7.42 (m, 4H), 7.16-7.27 (m, 3H), 4.80 (br. s, 1H), 4.60 (br. s, 1H), 3.07 (br. s, 3H). |

TABLE 16-continued

| No. | CHEMISTRY | NMR |
|---|---|---|
| 19-8 | | ¹H NMR (400 MHz, CDCl₃) δ ppm 13.15 (s, 1H), 10.85 (s, 1H), 8.43 (d, J = 8.8 Hz, 1H), 8.12 (t, J = 1.8 Hz, 1H), 8.02 -8.08 (m, 2H), 7.90 (dd, J = 8.8, 2.0 Hz, 1H), 7.81 (d, J = 7.8 Hz, 1H), 7.71 (d, J = 7.8 Hz, 1H), 7.54 (t, J = 7.7 Hz, 1H), 7.19 (d, J = 9.3 Hz, 1H), 6.01 (br. s, 1H), 4.27- 4.41 (m, 1H), 1.31 (d, J = 6.5 Hz, 6H). |
| 19-9 | | ¹H NMR (400 MHz, CDCl₃) δ ppm 13.14 (s, 1H), 10.85 (s, 1H), 8.43 (d, J = 8.8 Hz, 1H), 8.04 (d, J = 9.0 Hz, 1H), 8.00 (br. s, 1H), 7.88 (br. s, 1H), 7.71 (br. s, 2H), 7.59 (d, J = 8.3 Hz, 2H), 7.29-7.42 (m, 4H), 7.17-7.25 (m, 2H), 4.70 (br. s, 2H), 3.01 (br. s, 3H). |
| 19-10 | | ¹H NMR (400 MHz, CDCl₃) δ ppm 13.15 (s, 1H), 10.85 (s, 1H), 8.44 (d, J = 9.3 Hz, 1H), 8.01 (d, J = 2.0 Hz, 1H), 8.05 (d, J = 9.3 Hz, 1H), 7.87 (dd, J = 8.8, 2.0 Hz, 1H), 7.74 (d, J = 8.5 Hz, 2H), 7.55 (d, J = 8.5 Hz, 2H), 7.20 (d, J = 9.0 Hz, 1H), 3.74 (br. s, 8H). |

EXAMPLE 20

Synthesis of 2-hydroxy-6-(5-(morpholine-4-carbonyl)thiophen-2-yl)-1-naphthaldehyde

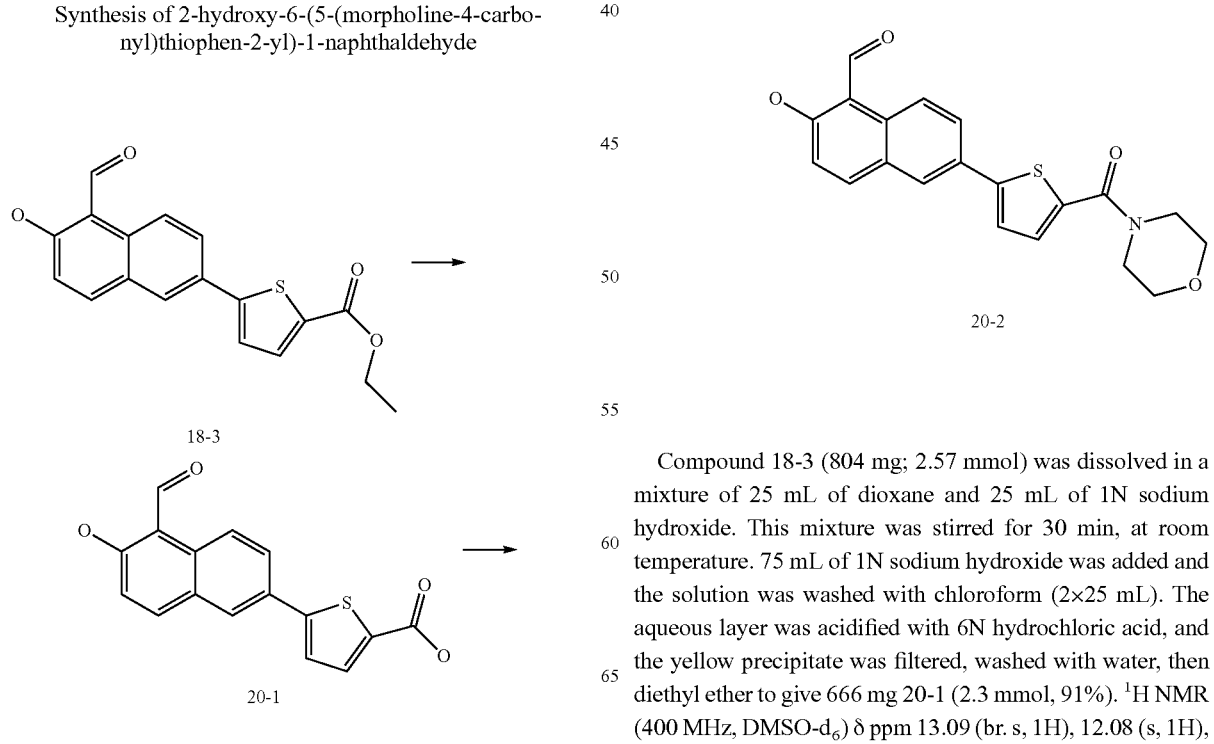

Compound 18-3 (804 mg; 2.57 mmol) was dissolved in a mixture of 25 mL of dioxane and 25 mL of 1N sodium hydroxide. This mixture was stirred for 30 min, at room temperature. 75 mL of 1N sodium hydroxide was added and the solution was washed with chloroform (2×25 mL). The aqueous layer was acidified with 6N hydrochloric acid, and the yellow precipitate was filtered, washed with water, then diethyl ether to give 666 mg 20-1 (2.3 mmol, 91%). ¹H NMR (400 MHz, DMSO-d₆) δ ppm 13.09 (br. s, 1H), 12.08 (s, 1H), 10.78 (s, 1H), 9.04 (d, J=8.8 Hz, 1H), 8.28 (d, J=2.0 Hz, 1H), 8.20 (d, J=9.0 Hz, 1H), 7.98 (dd, J=8.8, 2.0 Hz, 1H), 7.76 (d, J=3.8 Hz, 1H), 7.67 (d, J=3.8 Hz, 1H), 7.41 (d, J=9.0 Hz, 1H).

N-(3-Dimethylaminopropyl)-N'-ethylcarbodiimide hydrochloride (42 mg, 0.22 mmol), 1-hydroxybenzotriazole (30 mg, 0.22 mmol), triethylamine (140 μL, 1 mmol) and morpholine (38 μL, 0.44 mmol) were added to a solution of 20-1 (54 mg, 0.2 mmol) in 2 mL THF at room temperature. After 2 h, 2 mL 2N hydrochloric acid was added, and the reaction was stirred for 2 h. The mixture was evaporated to dryness, the residue dissolved in 2 mL chloroform, and extracted with water (1×1.5 mL), 1N hydrochloric acid (1×1.5 mL), water (1×1.5 mL), satd. sodium bicarbonate (1×1.5 mL), and water (1×1.5 mL). The organic phase was evaporated and the crude product was purified by column chromatography to afford 20-2 (20 mg, 0.05 mmol, 27%). $^1$H NMR (400 MHz, CDCl$_3$) δ ppm 13.13 (s, 1H), 10.82 (s, 1H), 8.38 (d, J=9.0 Hz, 1H), 7.96-8.06 (m, 2H), 7.86 (dd, J=8.8, 2.0 Hz, 1H), 7.34 (d, J=3.8 Hz, 1H), 7.32 (d, J=3.8 Hz, 1H), 7.19 (d, J=9.3 Hz, 1H), 3.80-3.85 (m, 4H), 3.74-3.79 (m, 4H).

The following compounds were made by the above procedure using the corresponding aryl ester and amine, if present, and characterized by NMR.

3-hydroxyquinoline (145 mg, 1 mmol) was added to a well stirred mixture of 5 mL chloroform, water (72 μL, 4 mmol), sodium hydroxide (100 mg, 2.5 mmol) and tetrabutylammonium hydroxide (50 μL, 20% in water) at room temperature. The resulting suspension was heated to 60° C. and stirred for 3 h. Sodium hydroxide was added hourly in 100 mg portions. The reaction mixture was diluted with 5 mL chloroform, acidified to pH 6 with 10 mL 1N hydrochloric acid and extracted with chloroform (3×10 mL). The combined organic phases were dried and evaporated. The crude material was purified by column chromatography to afford 21-1 (24 mg, 0.14 mmol, 14%). $^1$H NMR (400 MHz, DMSO-d$_6$) δ ppm 10.70 (s, 1H), 9.06 (s, 1H), 8.75 (d, J=6.3 Hz, 1H), 8.43 (d, J=6.0 Hz, 1H), 8.16 (d, J=8.8 Hz, 1H), 7.23 (d, J=9.3 Hz, 1H).

The following compounds were made by the above procedure and characterized by NMR.

TABLE 17

| No. | CHEMISTRY | NMR |
| --- | --- | --- |
| 20-3 | ![structure] | $^1$H NMR (400 MHz, CDCl$_3$) δ ppm 13.13 (br. s, 1H), 10.82 (s, 1H), 8.37 (d, J = 9.0 Hz, 1H), 7.97-8.05 (m, 2H), 7.86 (dd, J = 8.8, 2.0 Hz, 1H), 7.30-7.35 (m, 2H), 7.19 (d, J = 9.0 Hz, 1H), 3.78-3.88 (m, 4H), 2.45-2.55 (m, 4H), 2.35 (s, 3H). |
| 20-4 | ![structure] | $^1$H NMR (400 MHz, DMSO-d$_6$) δ ppm 13.46 (br. s, 1H), 10.95 (br. s, 1H), 10.30 (s, 1H), 7.70 (d, J = 4.0 Hz, 1H), 7.56 (d, J = 4.0 Hz, 1H), 7.47-7.55 (m, 2H), 3.95 (s, 3H). |

EXAMPLE 21

Synthesis of 3-hydroxyquinoline-4-carbaldehyde

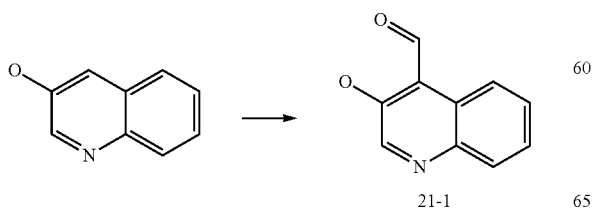

21-1

TABLE 18

| No. | CHEMISTRY | NMR |
|---|---|---|
| 21-2 | 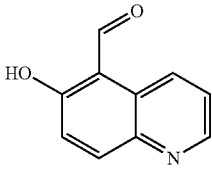 [SMILES: O=Cc1c(O)ccc2ncccc12] | $^1$H NMR (400 MHz, CDCl$_3$) δ ppm 13.05 (s, 1H), 10.77 (s, 1H), 8.85 (dd, J = 4.3, 1.5 Hz, 1H), 8.68 (d, J = 8.5 Hz, 1H), 8.27 (d, J = 9.3 Hz, 1H), 7.53 (dd, J = 8.8, 4.3 Hz, 1H), 7.40 (d, J = 9.5 Hz, 1H). |
| 21-3 | 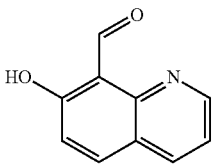 [SMILES: O=Cc1c(O)ccc2cccnc12] | $^1$H NMR (400 MHz, CDCl$_3$) δ ppm 13.15 (s, 1H), 11.25 (s, 1H), 8.90 (dd, J = 4.3, 1.8 Hz, 1H), 8.08 (dd, J = 8.0, 1.8 Hz, 1H), 7.94 (d, J = 9.3 Hz, 1H), 7.37 (dd, J = 8.3, 4.3 Hz, 1H), 7.22 (d, J = 9.3 Hz, 1H). |
| 21-5 | 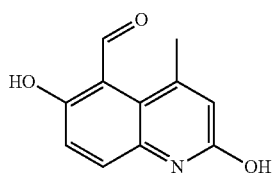 | $^1$H NMR (400 MHz, DMSO-d$_6$) δ ppm 11.72 (br. s, 1H), 11.54 (br. s, 1H), 10.68 (s, 1H), 7.49 (d, J = 9.0 Hz, 1H), 7.20 (d, J = 9.0 Hz, 1H), 6.51 (s, 1H), 2.43 (s, 3H). |

EXAMPLE 22

Synthesis of 3-hydroxy-2-methylquinoline-4-carbaldehyde

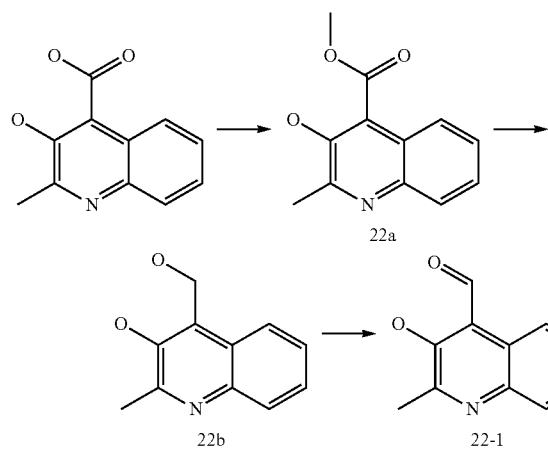

2-methyl-3-hydroxyquinoline-4-carboxylic acid (1.016 g, 5 mmol) was dissolved in 10 mL methanol. Thionyl chloride (730 µL, 10 mmol) was added at −10° C., and the mixture was heated at reflux for 20 h, with additions of 365 µL thionyl chloride (5 mmol) every 4 h. The reaction mixture was evaporated, taken up in satd. sodium bicarbonate and the mixture was extracted with ethyl acetate. The organic layer was evaporated and the crude product recrystallized from hexane to give 22a (258 mg, 1.1 mmol, 24%), ESI MS m/e 218 ([M+H]$^+$).

Compound 22a (0.163 mg, 0.75 mmol) was dissolved in 3 mL dry THF, and a 1M solution of DIBAL in THF (3.3 mL, 3.3 mmol) was added at −10° C. After 2 h, 5 mL of a 1M potassium dihydrogen phosphate solution was added, and the mixture was extracted with chloroform to afford 22b (59 mg, 0.3 mmol, 42%) %), ESI MS m/e 191 ([M+H]$^+$).

3-hydroxy-4-hydroxymethylquinoline, 22b, (63 mg, 0.33 mmol) was added to a suspension of manganese dioxide (86 mg, 1 mmol) in 12 mL acetone. The mixture was stirred at room temperature for 48 h, with additional portions (86 mg, 1 mmol) of manganese dioxide added at 12 h intervals. The suspension was filtered, evaporated, and the crude product was purified with column chromatography to give 22-1 (15 mg, 0.08 mmol, 24%). $^1$H NMR (400 MHz, CDCl$_3$) δ ppm 12.57 (s, 1H), 10.91 (s, 1H), 8.28-8.34 (m, 1H), 8.00-8.08 (m, 1H), 7.58-7.64 (m, 2H), 2.73 (s, 3H).

EXAMPLE 23

Synthesis of ethyl 2-(2-hydroxy-3-methoxy-5-(thiophen-2-yl)phenyl)thiazolidine-4-carboxylate

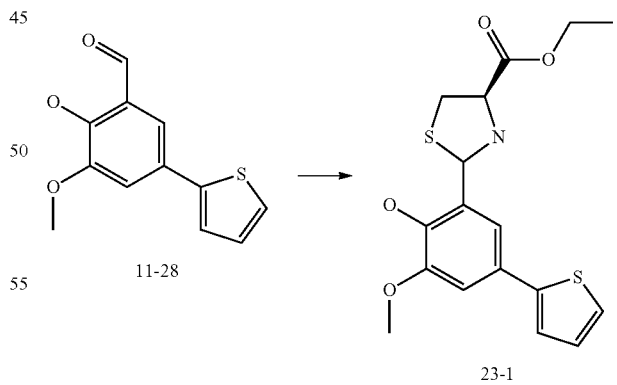

Compound 11-28 (120 mg, 0.5 mmol), L-cysteine ethyl ester hydrochloride (90 mg, 0.5 mmol) and diisopropylethylamine (85 µL, 0.5 mmol) were dissolved in 3 mL ethanol and stirred at room temperature for 1 h. The mixture was filtered to give 23-1 as a yellow solid (147 mg, 0.4 mmol, 80%). $^1$H NMR (400 MHz, DMSO-d$_6$, stereoisomers) δ ppm 9.43 (s, 0.4 H), 9.26 (s, 0.6 H), 7.44 (dd, J=5.0, 1.0 Hz, 0.4 H), 7.42

(dd, J=5.0, 1.0 Hz, 0.6 H), 7.39 (dd, J=3.5, 1.3 Hz, 0.4 H), 7.37 (dd, J=3.5, 1.3 Hz, 0.6 H), 7.30 (d, J=2.0 Hz, 0.4 H), 7.24 (d, J=2.0 Hz, 0.6 H), 7.15 (d, J=2.0 Hz, 0.4 H), 7.11 (d, J=2.0 Hz, 0.6 H), 7.07-7.10 (m, 1H), 5.87 (d, J=11.5 Hz, 0.6), 5.72 (d, J=11.5 Hz, 0.4), 4.32-4.39 (m, 0.6H), 4.19 (qd, J=2.0, 7.0 Hz, 0.4 H), 4.17 (q, J=7.0 Hz, 0.6 H), 3.92-4.01 (m, 0.6+0.4 H), 3.87 (s, 1.2 H), 3.87 (s, 1.8H), 3.76 (t, J=11.3), 3.33 (m, 0.4 H, overlapped), 3.26 (dd, J=7.0, 10.3 Hz, 0.6 H), 3.08 (dd, J=4.8, 10.3 Hz, 0.6 H), 3.04 (dd, J=8.8, 10.0 Hz, 0.4 H), 1.24 (t, J=7.0 Hz, 1.2 H), 1.23 (t, J=7.0 Hz, 1.8 H).

The following compounds were made by the above procedure and characterized by NMR.

TABLE 19

| No. | CHEMISTRY | NMR |
|---|---|---|
| 23-2 | 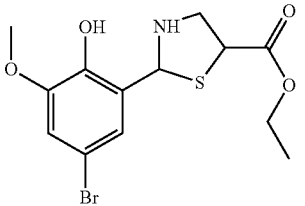 [SMILES: CCOC(=O)C1CNC(c2cc(Br)cc(OC)c2O)S1] | $^1$H NMR (400 MHz, DMSO-$d_6$, stereoisomers) δ ppm 9.47 (s, 0.4H), 9.31 (s, 0.6H), 7.25 (s, 0.4H), 7.11 (s, 0.6H), 7.06 (s, 0.4H), 7.02 (s, 0.6H), 5.82 (d, J = 9.3 Hz, 0.6H), 5.67 (d, J = 11.3 Hz, 0.4H), 4.23-4.30 (m, 0.6H), 4.11-4.21 (m, 2H), 3.86-4.01 (m, 0.6 + 0.4H), 3.80 (br.s, 3H), 3.71 (t, J = 11.3 Hz, 0.4H), 3.28-3.31 (m, 0.4 H, overlapped), 3.18-3.25 (m, 0.6H), 2.98-3.06 (m, 1H), 1.16-1.32 (m, 3H). |
| 23-3 | 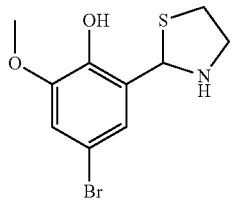 | $^1$H NMR (400 MHz, DMSO-$d_6$) δ ppm 9.39 (br. s, 1H), 7.11 (d, J = 2.0 Hz, 1H), 7.00 (d, J = 2.3 Hz, 1H), 5.65 (s, 1H), 3.79 (s, 3H), 2.99-3.17 (m, 1H), 2.83-2.97 (m, 3H). |
| 23-4 | 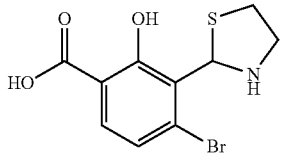 | $^1$H NMR (400 MHz, DMSO-$d_6$) δ ppm 10.50 (br. s, 1H), 7.58 (d, J = 8.3 Hz, 1H), 6.77 (d, J = 8.5 Hz, 1H), 6.00 (s, 1H), 3.93-4.05 (m, 1H), 3.42-3.52 (m, 1H), 3.36 (ddd, J = 18.7, 10.0, 6.9 Hz, 2H). |
| 23-5 | 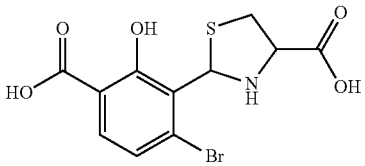 [SMILES: O=C(O)c1ccc(Br)c(C2NC(C(=O)O)CS2)c1O] | $^1$H NMR (400 MHz, DMSO-$d_6$, stereoisomers) δ ppm 11.8 (br. s, 1H), 7.64 (d, J = 8.3 Hz, 0.6H), 7.61 (d, J = 8.5 Hz, 0.4H), 7.02 (d, J = 8.5 Hz, 0.6H), 6.95 (d, J = 8.5 Hz, 0.4H), 6.17 (s, 0.4H), 6.05 (s, 0.6H), 5.01 (dd, J = 6.4, 2.6 Hz, 0.4H), 4.23 (t, J = 7.5 Hz, 0.6H), 3.43-3.57 (m, 1.2H), 3.18 (t, J = 9.5 Hz, 0.8H). |
| 23-6 | 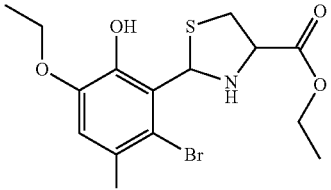 | $^1$H NMR (400 MHz, CDCl$_3$, stereoisomers) δ ppm 7.08 (s, 0.3H), 7.03 (s, 0.7H), 6.24 (s, 0.7H), 6.20 (s, 0.3H), 4.06-4.10 (m, 0.3 H, overlapped), 4.46 (dd, J = 6.1, 3.1 Hz, 0.7H), 4.24-4.33 (m, 2H), 3.99-4.10 (m, 2H), 3.49 (dd, J = 11.3, 6.0 Hz, 0.7H), 3.41 (td, J = 6.5, 1.0 Hz, 0.3H), 3.38 (dd, J = 11.3, 3.0 Hz, 0.7H), 3.26 (td, J = 9.5, 1.0 Hz, 0.3H), 1.45 (t, J = 6.9 Hz, 0.9H), 1.46 (t, J = 6.9 Hz, 2.1H), 1.32 (t, J = 7.0 Hz, 0.9H), 1.33 (t, J = 7.0 Hz, 2.1H). |
| 23-7 | 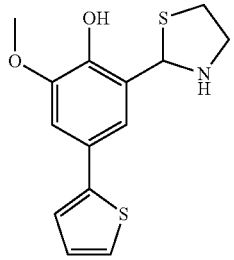 | $^1$H NMR (400 MHz, DMSO-$d_6$) δ ppm 9.43 (br. s, 1H), 7.42 (dd, J = 5.1, 1.1 Hz, 1H), 7.35 (dd, J = 3.5, 1.3 Hz, 1H), 7.23 (d, J = 1.8 Hz, 1H), 7.08 (d, J = 3.5 Hz, 1H), 7.09 (t, J = 3.0 Hz, 1H), 5.70 (s, 1H), 3.86 (s, 3H), 3.35-3.42 (m, 1H), 2.98-3.11 (m, 1H), 2.88-2.96 (m, 2H). |

TABLE 19-continued

| No. | CHEMISTRY | NMR |
|---|---|---|
| 23-8 | 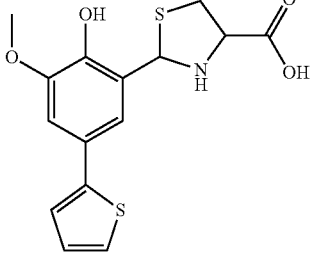 | $^1$H NMR (400 MHz, DMSO-$d_6$, stereoisomers) δ ppm 9.53 (br. s, 1H), 7.43 (t, J = 5.3 Hz, 1H), 7.38 (dd, J = 14.1, 3.5 Hz, 1H), 7.28 (d, J = 2.0 Hz, 0.4H), 7.22 (d, J = 1.8 Hz, 0.6H), 7.15 (d, J = 1.8 Hz, 0.4H), 7.11 (d, J = 2.0 Hz, 0.6H), 7.07-7.10 (m, 1H), 5.88 (s, 0.6H), 5.71 (s, 0.4H), 4.25 (t, J = 5.9 Hz, 0.6H), 3.83-3.91 (m, 0.4 H, overlapped), 3.83-3.91 (m, 3H), 3.34 (dd, J = 9.9, 6.9 Hz, 0.6H), 3.24 (dd, J = 10.3, 6.8 Hz, 0.6H), 3.05 (dd, J = 10.3, 5.3 Hz, 0.4H), 3.01 (t, J = 9.3 Hz, 0.4H). |
| 23-9 | 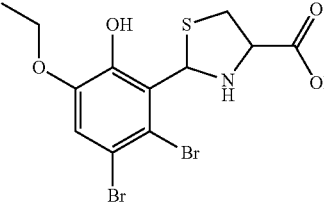 [SMILES: CCOC(=O)C1CSC(c2c(O)c(OCC)cc(Br)c2Br)N1] | $^1$H NMR (400 MHz, DMSO-$d_6$, stereoisomers) δ ppm 12.71 (br. s, 1H), 7.23 (s, 0.6H), 7.18 (s, 0.4H), 6.13 (s, 0.4H), 5.98 (s, 0.6H), 4.54 (br. s, 0.4H), 3.93-3.99 (m, 0.6 H, overlapped), 3.94-4.12 (m, 2H), 3.32-3.40 (m, 1.6H), 3.07 (t, J = 9.5 Hz, 0.8H), 1.23-1.38 (m, 3H). |

EXAMPLE 24

Synthesis of 2-methoxy-6-((4-methoxybenzylimino)methyl)-4-(thiophen-2-yl)phenol

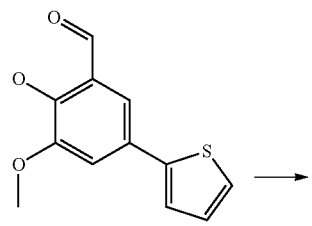

11-28

Compound 11-28 (117 mg; 0.50 mmol) and 4-methoxybenzylamine (65 µl; 0.50 mmol) were dissolved in 4 mL ethanol and stirred at room temperature for 4 h. The mixture was filtered to give 24-1 (113 mg, 0.32 mmol, 64%). $^1$H NMR (400 MHz, DMSO-$d_6$) δ ppm 13.82 (br. s, 1H), 8.70 (s, 1H), 7.43 (ddd, J=14.3, 4.3, 1.3 Hz, 2H), 7.25-7.32 (m, 4H), 7.10 (dd, J=5.1, 3.6 Hz, 1H), 6.92-6.97 (m, 2H), 4.75 (s, 2H), 3.84 (s, 3H), 3.75 (s, 3H).

The following compounds were made by the above procedure and characterized by NMR.

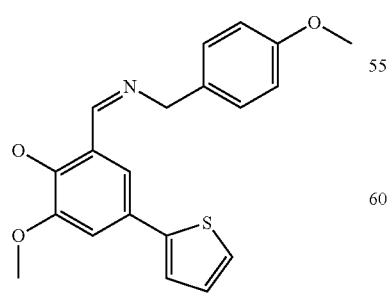

24-1

TABLE 20

| No. | CHEMISTRY | NMR |
|---|---|---|
| 24-2 | 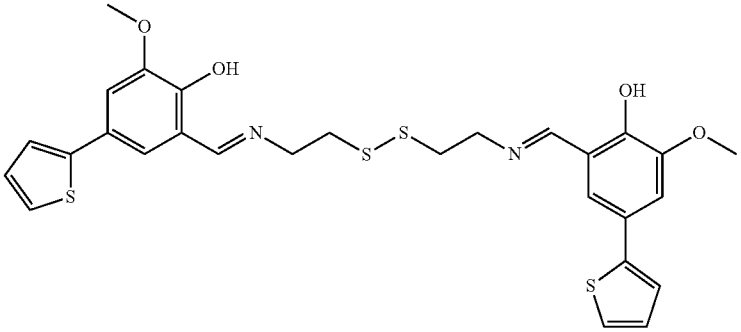 [SMILES: COc1cc(-c2cccs2)cc(/C=N/CCSSCC/N=C/c2cc(-c3cccs3)cc(OC)c2O)c1O] | $^1$H NMR (400 MHz, DMSO-d$_6$) δ ppm 13.63 (br. s, 2H), 8.62 (s, 2H), 7.42 (ddd, J = 16.7, 4.3, 1.1 Hz, 4H), 7.29 (d, J = 2.3 Hz, 2H), 7.25 (d, J = 2.3 Hz, 2H), 7.09 (dd, J = 5.0, 3.5 Hz, 2H), 3.92 (t, J = 6.4 Hz, 4H), 3.85 (s, 6H), 3.11 (t, J = 6.4 Hz, 4H). |
| 24-3 | 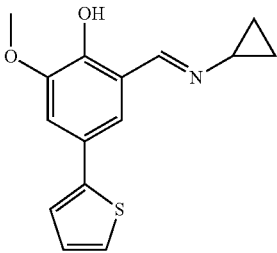 [SMILES: COc1cc(-c2cccs2)cc(/C=N/C2CC2)c1O] | $^1$H NMR (400 MHz, DMSO-d$_6$) δ ppm 12.89 (br. s, 1H), 8.75 (s, 1H), 7.46 (dd, J = 5.1, 1.1 Hz, 1H), 7.42 (dd, J = 3.6, 1.1 Hz, 1H), 7.29 (d, J = 2.0 Hz, 1H), 7.26 (d, J = 2.0 Hz, 1H), 7.10 (dd, J = 5.1, 3.6 Hz, 1H), 3.86 (s, 3H), 3.15 (tt, J = 6.9, 3.4 Hz, 1H), 0.97-1.06 (m, 2H), 0.85-0.90 (m, 2H). |
| 24-4 | 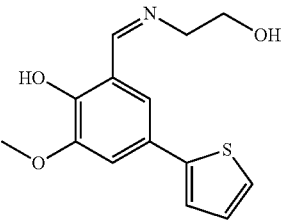 [SMILES: COc1cc(-c2cccs2)cc(/C=N\CCO)c1O] | $^1$H NMR (400 MHz, DMSO-d$_6$) δ ppm 13.96 (br. s, 1H), 8.53 (s, 1H), 7.42 (dd, J = 5.1, 1.1 Hz, 1H), 7.38 (dd, J = 3.5, 1.1 Hz, 1H), 7.27 (d, J = 2.3 Hz, 1H), 7.21 (d, J = 2.0 Hz, 1H), 7.09 (dd, J = 5.0, 3.5 Hz, 1H), 4.84 (br. s, 1H), 3.84 (s, 3H), 3.66 (s, 4H). |
| 24-5 | 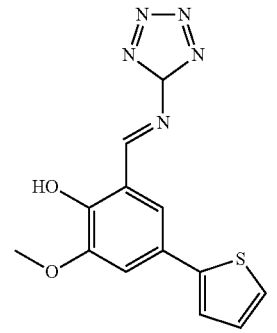 [SMILES: COc1cc(-c2cccs2)cc(/C=N/C2N=NN=N2)c1O] | $^1$H NMR (400 MHz, DMSO-d$_6$) δ ppm 11.07 (br. s, 1H), 9.57 (s, 1H), 7.75 (d, J = 1.8 Hz, 1H), 7.50 (dd, J = 7.4, 1.6 Hz, 2H), 7.52 (br. s, 1H), 7.14 (t, J = 4.5 Hz, 1H), 3.96 (s, 3H). |
| 24-6 | 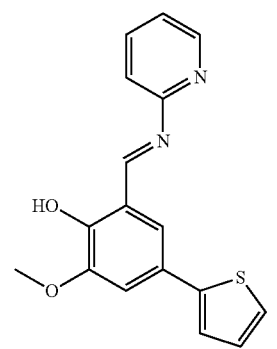 [SMILES: COc1cc(-c2cccs2)cc(/C=N/c2ccccn2)c1O] | $^1$H NMR (400 MHz, DMSO-d$_6$) δ ppm 13.20 (br. s, 1H), 9.54 (s, 1H), 8.55 (d, J = 3.5 Hz, 1H), 7.94 (td, J = 7.7, 1.8 Hz, 1H), 7.66 (d, J = 2.0 Hz, 1H), 7.46-7.52 (m, 3H), 7.34-7.42 (m, 2H), 7.12 (t, J = 4.0 Hz, 1H), 3.92 (s, 3H). |

EXAMPLE 25

Synthesis of 3-hydroxy-4-(morpholinomethyl)-2-naphthaldehyde

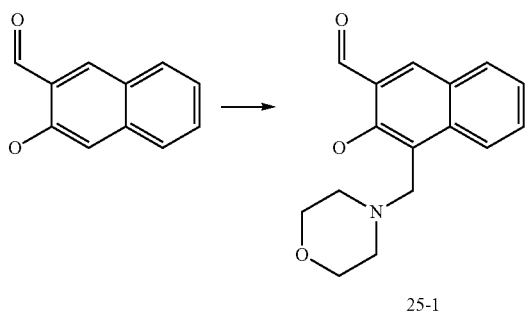 [SMILES: O=Cc1cc2ccccc2cc1O ; O=Cc1cc2ccccc2c(CN2CCOCC2)c1O]

25-1

3-hydroxy-2-naphthaldehyde (20 mg, 0.12 mmol), morpholine (63 μL, 0.72 mmol), and formaldehyde (37 μL, 37% in water) were dissolved in 2 mL acetic acid. After evaporation the solid residue was partitioned between chloroform and saturated sodium bicarbonate solution. The organic layer was washed with water and dried over sodium sulfate. The solvent was removed and the solid residue was recrystallized from diisopropyl ether to give 25-1 (18 mg, 0.07 mmol, 55%). $^1$H NMR (400 MHz, CDCl$_3$) δ ppm 11.79 (br. s, 1H), 10.41 (s, 1H), 8.22 (s, 1H), 7.96 (d, J=8.8 Hz, 1H), 7.87 (d, J=8.3 Hz, 1H), 7.57 (ddd, J=8.5, 7.0, 1.4 Hz, 1H), 7.36 (td, J=7.5, 1.0 Hz, 1H), 4.11 (s, 2H), 3.76 (t, J=4.5 Hz, 4H), 2.66 (t, J=4.5 Hz, 4H).

The following compounds were made by the above procedure and characterized by NMR.

TABLE 21

| No. | CHEMISTRY | NMR |
|---|---|---|
| 25-2 | (piperidinylmethyl-3-hydroxy-2-naphthaldehyde structure) | $^1$H NMR (400 MHz, CDCl$_3$) δ ppm 8.25 (s, 1H), 7.85 (d, J = 8.3 Hz, 1H), 7.80 (d, J = 8.8 Hz, 1H), 7.48-7.55 (m, 1H), 7.28-7.33 (m, 1H), 4.13 (s, 2H), 2.63 (br. s, 4H), 1.65-1.75 (m, 4H), 1.55 (br. s, 2H). |
| 25-3 | (N-methylpiperazinylmethyl-3-hydroxy-2-naphthaldehyde structure) | $^1$H NMR (400 MHz, CDCl$_3$) δ ppm 10.52 (s, 1H), 8.25 (s, 1H), 7.87 (d, J = 9.5 Hz, 2H), 7.52-7.57 (m, 1H), 7.30-7.36 (m, 1H), 4.15 (s, 2H), 2.73 (br. s, 4H), 2.53 (br. s, 4H), 2.33 (s, 4H). |

EXAMPLE 26

Activities of Compounds

Results of IC$_{50}$ and EC$_{50}$ assays are shown in Tables 26-42.

TABLE 26

| compound | IC50_avg (nM) | EC50_avg (nM) |
|---|---|---|
| (4-hydroxy-3-methoxy-5-(pyridin-4-yl)benzaldehyde) | 104 | 70000 |
| (4-hydroxy-3-methoxy-5-(1-methyl-1H-pyrazol-4-yl)benzaldehyde) | 772 | 30000 |

TABLE 26-continued

| compound | IC50_avg (nM) | EC50_avg (nM) |
|---|---|---|
| (3-formyl-2-hydroxy-4-(pyrimidin-5-yl)benzoic acid) | >20000 | 80000 |
| (2-hydroxy-5-(pyridin-4-yl)benzaldehyde) | 147 | 80000 |
| (3-fluoro-2-hydroxy-5-(pyridin-3-yl)benzaldehyde) | 163 | 80000 |
| (2-hydroxy-3-methoxy-5-(pyridin-3-yl)benzaldehyde) | 149 | 30000 |
| (2-hydroxy-3-methoxy-5-(5-methylthiophen-2-yl)benzaldehyde) | 743 | 50000 |
| (3-fluoro-2-hydroxy-5-(6-methoxypyridin-3-yl)benzaldehyde) | 168 | 80000 |

TABLE 26-continued

| compound | IC50_avg (nM) | EC50_avg (nM) |
|---|---|---|
| (5-(5-acetylthiophen-2-yl)-2-hydroxy-3-methoxybenzaldehyde) | 97 | 30000 |
| (2-hydroxy-5-(6-methoxypyridin-3-yl)-3-nitrobenzaldehyde) | 346 | 70000 |
| (2-hydroxy-3-methoxy-5-(quinolin-5-yl)benzaldehyde) | 932 | 70000 |
| (3-fluoro-2-hydroxy-5-(quinolin-5-yl)benzaldehyde) | 305 | 80000 |
| (2-hydroxy-3-nitro-5-(quinolin-5-yl)benzaldehyde) | 3333 | 70000 |
| (2-hydroxy-5-(isoquinolin-4-yl)-3-methoxybenzaldehyde) | 100 | 50000 |

TABLE 26-continued
| compound | IC50_avg (nM) | EC50_avg (nM) |
|---|---|---|
| 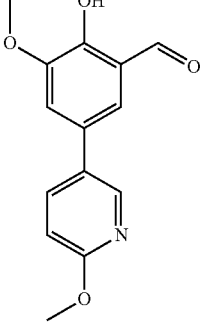 | 74 | 30000 |
| 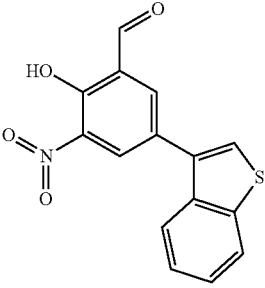 [SMILES: O=Cc1cc(-c2csc3ccccc23)cc([N+](=O)[O-])c1O] | 2369 | 80000 |
| 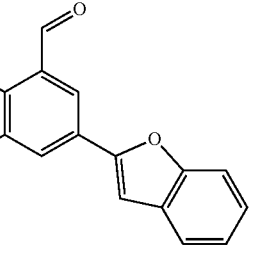 | 82 | 80000 |
| 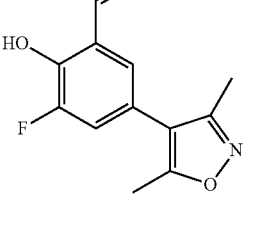 | 994 | 80000 |
| 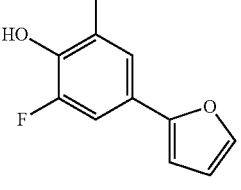 | 190 | 80000 |
TABLE 26-continued
| compound | IC50_avg (nM) | EC50_avg (nM) |
|---|---|---|
| 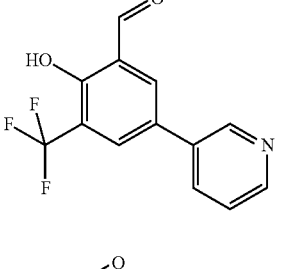 | 800 | 80000 |
| 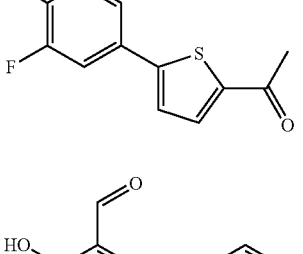 | 46 | 80000 |
| 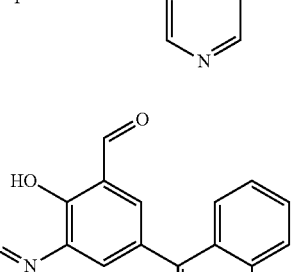 | 104 | 50000 |
| 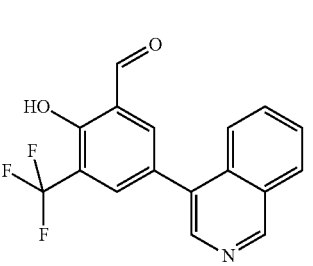 [SMILES: O=Cc1cc(-c2cncc3ccccc23)cc(C(F)(F)F)c1O] | 754 | 80000 |
| 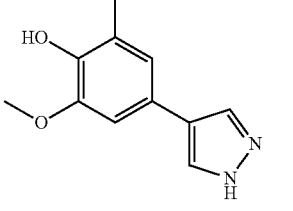 | 164 | 50000 |
| 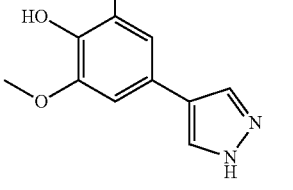 | 310 | 80000 |

TABLE 26-continued
| compound | IC50_avg (nM) | EC50_avg (nM) |
|---|---|---|
| 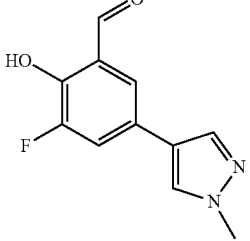 | 236 | 80000 |
| 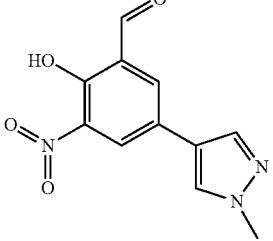 | 535 | 80000 |
TABLE 43
| compound | IC50_avg (nM) | EC50_avg (nM) |
|---|---|---|
| 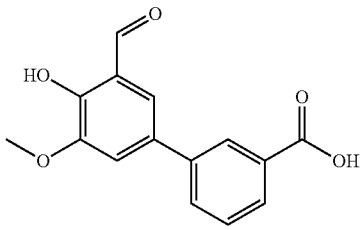 [SMILES: COc1cc(-c2cccc(C(=O)O)c2)cc(C=O)c1O] | 102 | 70000 |
| 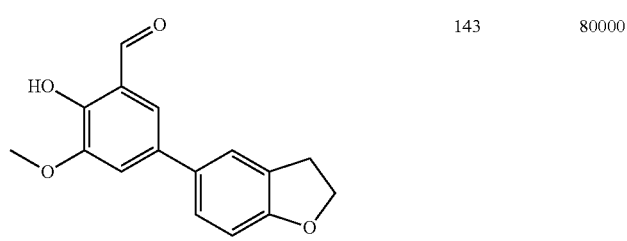 | 143 | 80000 |
| 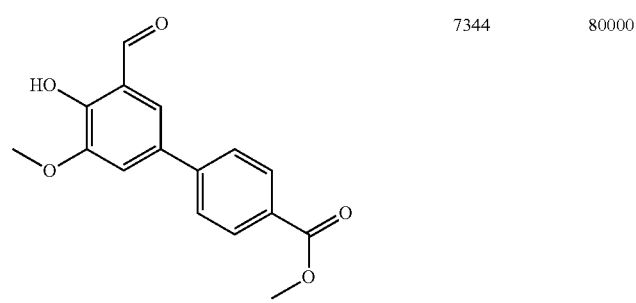 | 7344 | 80000 |
| 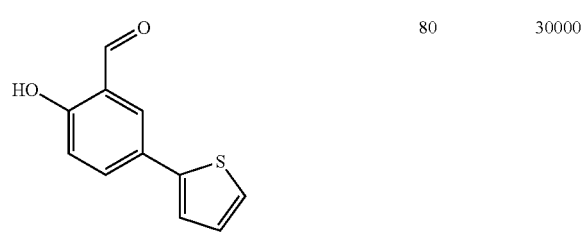 | 80 | 30000 |

TABLE 43-continued

| compound | IC50_avg (nM) | EC50_avg (nM) |
|---|---|---|
| (structure) | 22 | 30000 |
| (structure) | 170 | 80000 |
| (structure) | 39 | 30000 |
| (structure) | 331 | 80000 |
| (structure) | 1112 | 80000 |
| (structure) | 34 | 70000 |

TABLE 43-continued

| compound | IC50_avg (nM) | EC50_avg (nM) |
|---|---|---|
| 2-hydroxy-3-nitro-5-(thiophen-2-yl)benzaldehyde | 42 | 70000 |
| 2-hydroxy-3-methoxy-6-(thiophen-2-yl)benzaldehyde | 351 | 30000 |
| 2-hydroxy-3-nitro-5-(thiophen-3-yl)benzaldehyde | 401 | 50000 |
| 5-(benzo[b]thiophen-2-yl)-2-hydroxy-3-methoxybenzaldehyde | 3906 | 50000 |
| 5-(benzo[b]thiophen-3-yl)-2-hydroxy-3-methoxybenzaldehyde | 1472 | 70000 |
| 2-hydroxy-3-methoxy-5-(thiophen-3-yl)benzaldehyde | 199 | 30000 |

TABLE 43-continued
| compound | IC50_avg (nM) | EC50_avg (nM) |
|---|---|---|
| 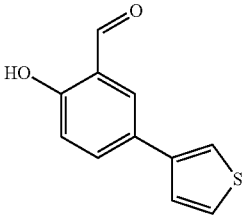 | 699 | 70000 |
| 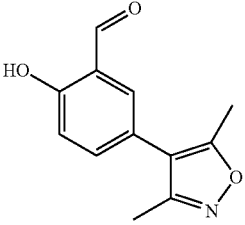 [SMILES: Cc1noc(C)c1-c1ccc(O)c(C=O)c1] | 1011 | 80000 |
| 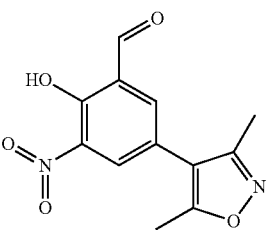 [SMILES: Cc1noc(C)c1-c1cc(C=O)c(O)c([N+](=O)[O-])c1] | 3059 | 80000 |
| 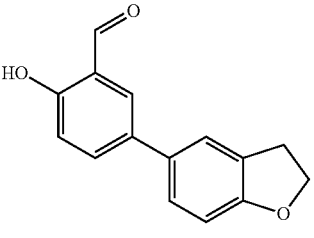 [SMILES: O=Cc1cc(-c2ccc3c(c2)CCO3)ccc1O] | 1797 | 80000 |
| 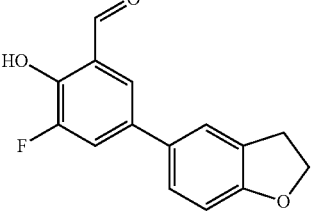 | 381 | 80000 |
| 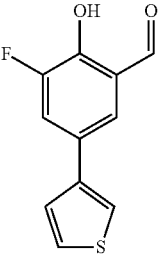 [SMILES: O=Cc1cc(-c2ccsc2)cc(F)c1O] | 74 | 80000 |

TABLE 43-continued
| compound | IC50_avg (nM) | EC50_avg (nM) |
|---|---|---|
| 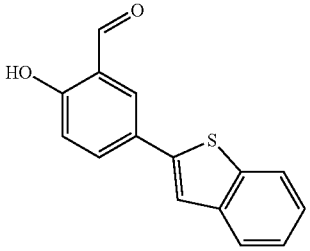 [SMILES: O=Cc1cc(-c2cc3ccccc3s2)ccc1O] | <20000 | 80000 |
| 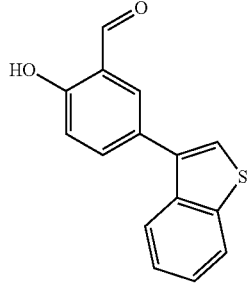 [SMILES: O=Cc1cc(-c2csc3ccccc23)ccc1O] | 4503 | 80000 |
| 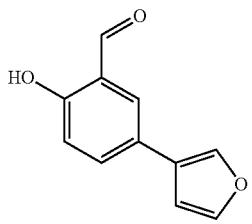 [SMILES: O=Cc1cc(-c2ccoc2)ccc1O] | 441 | 80000 |
| 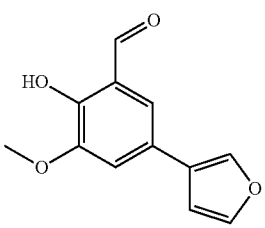 [SMILES: COc1cc(-c2ccoc2)cc(C=O)c1O] | 114 | 80000 |
| 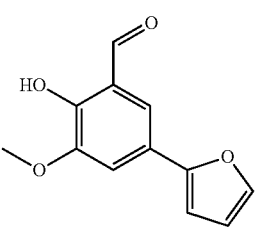 [SMILES: COc1cc(-c2ccco2)cc(C=O)c1O] | 61 | 30000 |
| 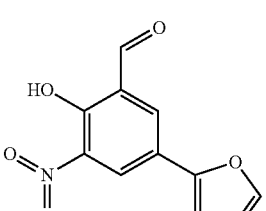 | 223 | 80000 |

TABLE 43-continued
| compound | IC50_avg (nM) | EC50_avg (nM) |
|---|---|---|
| 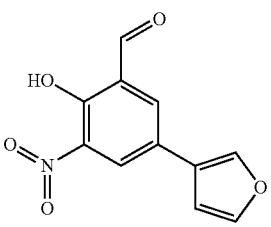 [SMILES: O=Cc1cc(-c2ccoc2)cc([N+](=O)[O-])c1O] | 81 | 80000 |
| 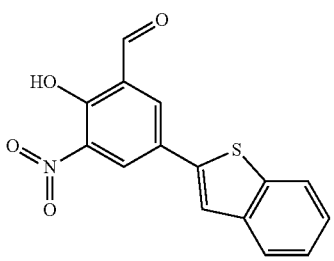 [SMILES: O=Cc1cc(-c2cc3ccccc3s2)cc([N+](=O)[O-])c1O] | 420 | 80000 |
| 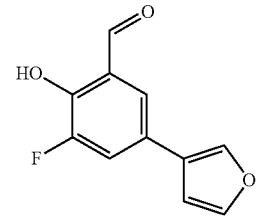 [SMILES: O=Cc1cc(-c2ccoc2)cc(F)c1O] | 88 | 80000 |
| 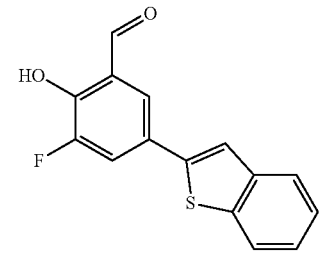 [SMILES: O=Cc1cc(-c2cc3ccccc3s2)cc(F)c1O] | 1622 | 80000 |
| 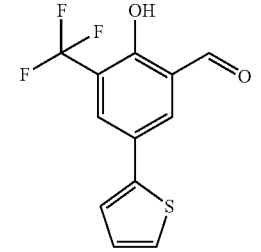 [SMILES: O=Cc1cc(-c2cccs2)cc(C(F)(F)F)c1O] | 704 | 70000 |
| 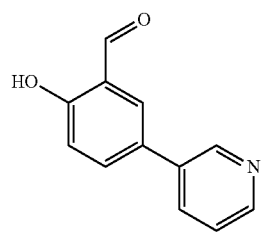 [SMILES: O=Cc1cc(-c2cccnc2)ccc1O] | 141 | 80000 |

TABLE 43-continued

| compound | IC50_avg (nM) | EC50_avg (nM) |
|---|---|---|
| (3-fluoro-4-hydroxy-5-(benzothiophen-3-yl)benzaldehyde) | 461 | 50000 |
| (4'-carbamoyl-4-hydroxy-5-methoxybiphenyl-3-carbaldehyde) | 82 | 80000 |
| (3'-(N,N-dimethylcarbamoyl)-4-hydroxy-5-methoxybiphenyl-3-carbaldehyde) | 413 | 80000 |
| (4'-(N,N-dimethylcarbamoyl)-4-hydroxy-5-methoxybiphenyl-3-carbaldehyde) | 162 | 80000 |
| (3'-(morpholine-4-carbonyl)-4-hydroxy-5-methoxybiphenyl-3-carbaldehyde) | 795 | 80000 |
| (3'-carbamoyl-4-hydroxy-5-methoxybiphenyl-3-carbaldehyde) | 173 | 80000 |

TABLE 43-continued

| compound | IC50_avg (nM) | EC50_avg (nM) |
|---|---|---|
| | 379 | 80000 |
| | 46 | 80000 |
| | 235 | 80000 |
| | 1202 | 80000 |
| | 2795 | 80000 |
| | 410 | 80000 |

TABLE 43-continued

| compound | IC50_avg (nM) | EC50_avg (nM) |
|---|---|---|
| (biphenyl with CHO, OH, CF3 and morpholine amide) | 348 | 80000 |
| (biphenyl with CHO, OH, OMe and carboxylic acid) | 540 | 80000 |
| (biphenyl with CHO, OH, CF3 and N,N-dimethyl amide) | 3670 | 80000 |
| (biphenyl with CHO, OH, OMe and ethyl ester) | 3309 | 80000 |
| (biphenyl with CHO, OH, OMe and methyl ester) | 192 | 80000 |
| (biphenyl with CHO, OH, NO2 and methyl ester) | 736 | 80000 |

TABLE 43-continued

| compound | IC50_avg (nM) | EC50_avg (nM) |
|---|---|---|
| (structure) | 4784 | 80000 |
| (structure) | 1711 | 80000 |
| (structure) | 230 | 80000 |
| (structure) | 131 | 30000 |
| (structure) | 213 | 80000 |

TABLE 43-continued

| compound | IC50_avg (nM) | EC50_avg (nM) |
|---|---|---|
| (structure) | 471 | 80000 |
| (structure) | 495 | 60000 |
| (structure) | 197 | 50000 |
| (structure) | 147 | 50000 |
| (structure) | 132 | 80000 |
| (structure) | 21 | 60000 |

TABLE 43-continued

| compound | IC50_avg (nM) | EC50_avg (nM) |
|---|---|---|
| | 32 | 80000 |
| | 154 | 80000 |
| | 1242 | 80000 |
| | 101 | 80000 |
| | 371 | 80000 |
| | 351 | 30000 |

TABLE 43-continued

| compound | IC50_avg (nM) | EC50_avg (nM) |
| --- | --- | --- |
| (4-methoxy-3-hydroxy-2-formylphenyl, pyrimidin-5-yl) | 20111 | 80000 |
| (4-hydroxy-3-formylphenyl, furan-2-yl) | 223 | 80000 |
| (4-hydroxy-3-methoxy-5-formylphenyl, 6-morpholinopyridin-3-yl) | 367 | 30000 |
| (4-hydroxy-3-fluoro-5-formylphenyl, 4-carboxyphenyl) | 214 | 60000 |
| (4-hydroxy-3-fluoro-5-formylphenyl, 4-carbamoylphenyl) | 85 | 60000 |
| (4-hydroxy-3-fluoro-5-formylphenyl, 3-(N,N-dimethylcarbamoyl)phenyl) | 633 | 60000 |

TABLE 43-continued
| compound | IC50_avg (nM) | EC50_avg (nM) |
| --- | --- | --- |
| 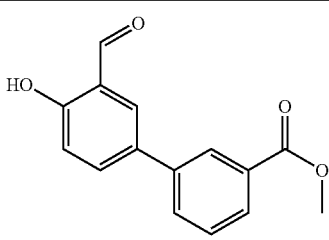 | 421 | 3000 |
| 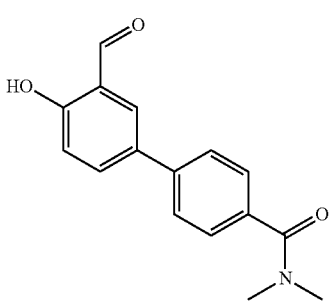 [SMILES: CN(C)C(=O)c1ccc(-c2ccc(O)c(C=O)c2)cc1] | 420 | 60000 |
| 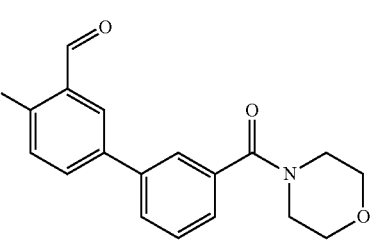 | 657 | 60000 |
| 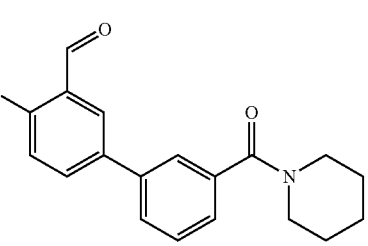 | 398 | 50000 |
| 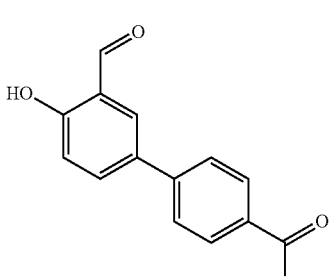 | 172 | no |
| 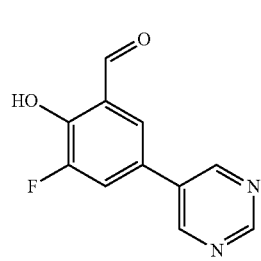 [SMILES: O=Cc1cc(-c2cncnc2)cc(F)c1O] | 79 | 80000 |

TABLE 43-continued
| compound | IC50_avg (nM) | EC50_avg (nM) |
|---|---|---|
| 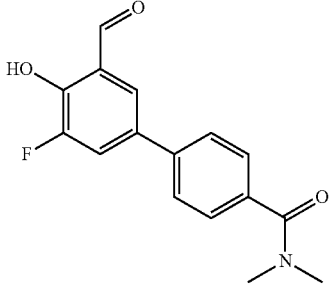 [SMILES: CN(C)C(=O)c1ccc(-c2cc(F)c(O)c(C=O)c2)cc1] | 455 | 80000 |
| 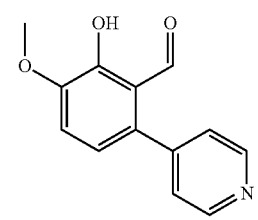 [SMILES: COc1ccc(-c2ccncc2)c(C=O)c1O] | 10000 | 80000 |
| 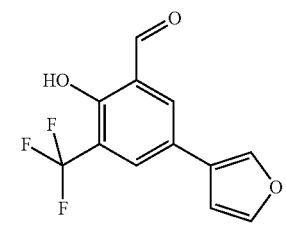 [SMILES: O=Cc1cc(-c2ccoc2)cc(C(F)(F)F)c1O] | 800 | 30000 |
TABLE 28
| compound | IC50_avg (nM) |
|---|---|
| 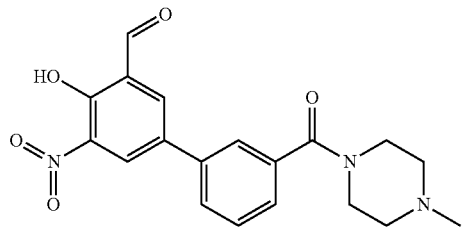 [SMILES: CN1CCN(C(=O)c2cccc(-c3cc(C=O)c(O)c([N+](=O)[O-])c3)c2)CC1] | 1940 |
| 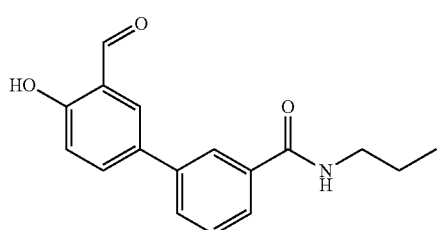 | 491 |
| 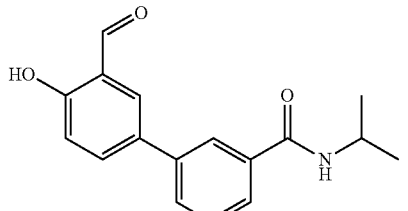 | 158 |
TABLE 28-continued
| compound | IC50_avg (nM) |
|---|---|
| 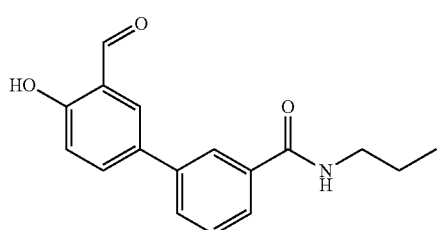 | 100 |
| 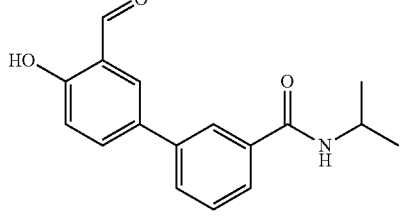 | 106 |

TABLE 28-continued
| compound | IC50_avg (nM) |
|---|---|
| 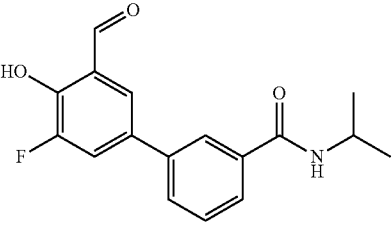 [SMILES: CC(C)NC(=O)c1cccc(-c2cc(F)c(O)c(C=O)c2)c1] | 253 |
| 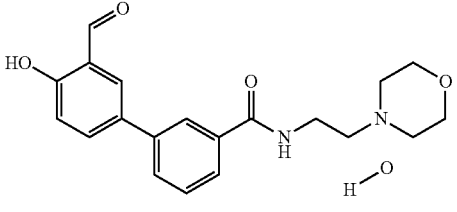 | 84 |
| 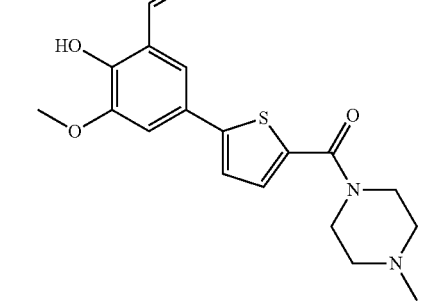 | 389 |
| 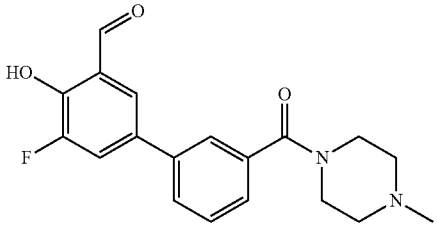 [SMILES: CN1CCN(C(=O)c2cccc(-c3cc(F)c(O)c(C=O)c3)c2)CC1] | 393 |
| 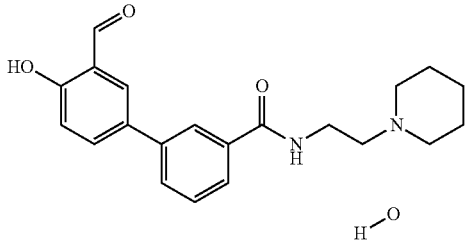 [SMILES: O=Cc1cc(-c2cccc(C(=O)NCCN3CCCCC3)c2)ccc1O ; O] | 66 |
| 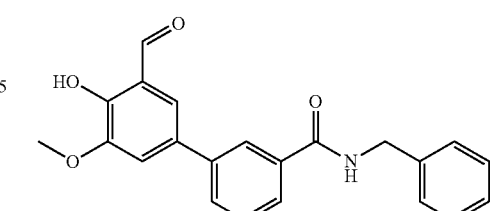 | 40 |
TABLE 28-continued
| compound | IC50_avg (nM) |
|---|---|
| 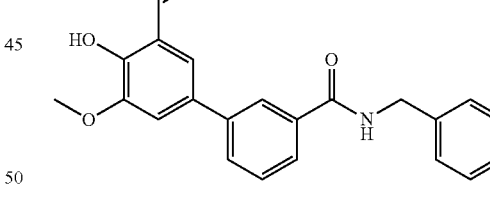 | 19 |
| 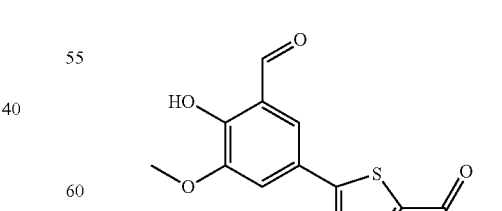 | 396 |
| 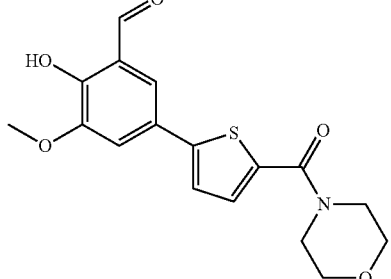 | 94 |
| 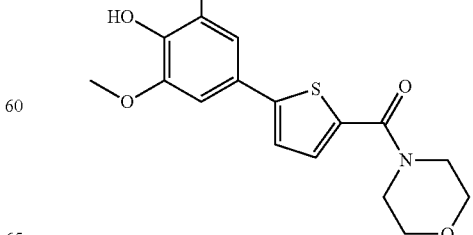 | 6 |
| 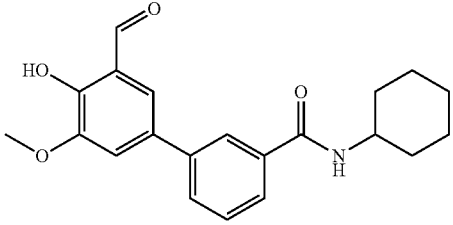 [SMILES: COc1cc(-c2cccc(C(=O)NC3CCCCC3)c2)cc(C=O)c1O] | 645 |

TABLE 29

| compound | IC50_avg(nM) | EC50_avg(nM) |
|---|---|---|
| (methyl 3-(6-hydroxy-5-formyl-naphthalen-2-yl)benzoate) | 5665 | 10000 |
| (6-(pyridin-3-yl)-2-hydroxy-1-naphthaldehyde) | 23 | 5000 |
| (6-(pyrimidin-5-yl)-2-hydroxy-1-naphthaldehyde) | 66 | 4000 |
| (6-(3-(morpholine-4-carbonyl)phenyl)-2-hydroxy-1-naphthaldehyde) | 74 | 5000 |
| (3-(6-hydroxy-5-formyl-naphthalen-2-yl)benzoic acid) | 79 | 10000 |
| (4-(6-hydroxy-5-formyl-naphthalen-2-yl)-N,N-dimethylbenzamide) | 36 | 3000 |

TABLE 29-continued

| compound | IC50_avg(nM) | EC50_avg(nM) |
| --- | --- | --- |
| (2-hydroxy-6-(furan-3-yl)naphthalene-1-carbaldehyde) | 4202 | 7000 |
| (6-(4-(hydroxymethyl)phenyl)-2-hydroxynaphthalene-1-carbaldehyde) | 2016 | 10000 |
| (2-hydroxy-6-(6-methoxypyridin-3-yl)naphthalene-1-carbaldehyde) | 8737 | 30000 |
| (2-hydroxy-6-(thiophen-3-yl)naphthalene-1-carbaldehyde) | 9371 | 20000 |
| (2-hydroxy-6-(isoquinolin-4-yl)naphthalene-1-carbaldehyde) | 12122 | 15000 |
| (2-hydroxy-6-(quinolin-5-yl)naphthalene-1-carbaldehyde) | 6277 | 30000 |

TABLE 29-continued
| compound | IC50_avg(nM) | EC50_avg(nM) |
| --- | --- | --- |
| 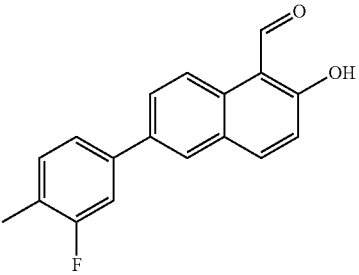 | >20000 | 50000 |
| 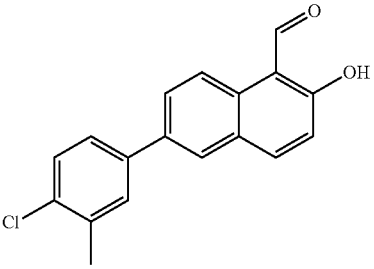 | >20000 | >80000 |
| 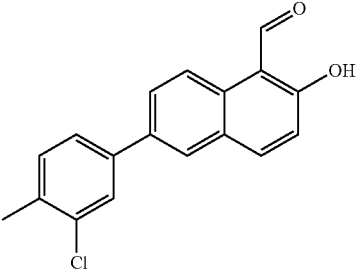 [SMILES: Cc1ccc(-c2ccc3c(C=O)c(O)ccc3c2)cc1Cl] | >20000 | >80000 |
| 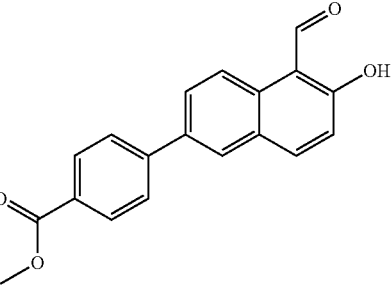 | >20000 | no |
| 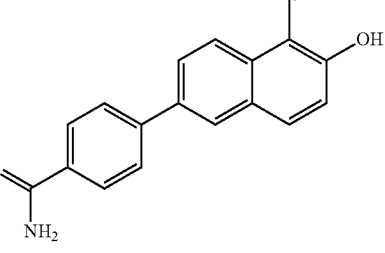 | 878 | 10000 |

TABLE 29-continued

| compound | IC50_avg(nM) | EC50_avg(nM) |
|---|---|---|
| *(structure: 6-(3-carbamoylphenyl)-2-hydroxy-1-naphthaldehyde)* | 26 | 1000 |
| *(structure: 6-(3-(dimethylcarbamoyl)phenyl)-2-hydroxy-1-naphthaldehyde)* | 125 | 3000 |
| *(structure: 6-(4-carboxyphenyl)-2-hydroxy-1-naphthaldehyde)* | 594 | 30000 |
| *(structure: 6-(6-morpholinopyridin-3-yl)-2-hydroxy-1-naphthaldehyde)* | >20000 | 50000 |

TABLE 30

| compound | IC50_avg(nM) |
|---|---|
| (6-chloropyridin-3-yl naphthalene with CHO and OH) | 5616 |

TABLE 31

| compound | IC50_avg (nM) |
|---|---|
| (ethyl thiophene-2-carboxylate naphthalene with CHO and OH) | 15564 |
| (naphthalene-pyridine-2-carboxylic acid with CHO and OH) | 125 |

TABLE 32

| compound | IC50_avg(nM) | EC50_avg(nM) |
|---|---|---|
| (phenyl-piperidine amide naphthalene with CHO and OH) | 1345 | 50000 |
| (phenyl-4-methylpiperazine amide naphthalene with CHO and OH) | 157 | 50000 |

TABLE 32-continued

| compound | IC50_avg(nM) | EC50_avg(nM) |
|---|---|---|
| | 2808 | 50000 |
| | 3 | 50000 |
| | 3797 | 30000 |
| | 47 | 60000 |
| | 645 | 60000 |

TABLE 32-continued

| compound | IC50_avg(nM) | EC50_avg(nM) |
|---|---|---|
|  | 67 | 60000 |
|  | 48 | 60000 |
|  | 389 | 60000 |
|  | 157 | 60000 |
|  | 5 | 60000 |

TABLE 32-continued

| compound | IC50_avg(nM) | EC50_avg(nM) |
| --- | --- | --- |
| (ethyl 5-(6-hydroxy-5-formylnaphthalen-2-yl)thiophene-2-carboxylate) | 15564 | 80000 |
| (6-(6-hydroxy-5-formylnaphthalen-2-yl)picolinic acid) | 125 | 10000 |

TABLE 33

| compound | IC50_avg (nM) |
| --- | --- |
| (5-(6-hydroxy-5-formylnaphthalen-2-yl)thiophene-2-carboxylic acid) | 151 |
| (morpholino-thiophene-naphthalene aldehyde) | 157 |
| (4-methylpiperazinyl-thiophene-naphthalene aldehyde) | 5 |

TABLE 34

| compound | IC50_avg(nM) | EC50_avg(nM) |
| --- | --- | --- |
| (6-hydroxyquinoline-5-carbaldehyde) | 170 | 7000 |
| (3-hydroxyquinoline-4-carbaldehyde) | 45 | 60000 |
| (7-hydroxyquinoline-8-carbaldehyde) | 1240 | 10000 |

TABLE 35

| compound | IC50_avg(nM) | EC50_avg(nM) |
| --- | --- | --- |
| (6-hydroxyisoquinoline-5-carbaldehyde) | 427 | 20000 |

TABLE 35-continued

| compound | IC50_avg(nM) | EC50_avg(nM) |
|---|---|---|
| (4-methyl-quinoline with OH groups) | 915 | >80000 |

TABLE 36

| compound | IC50_avg (nM) | EC50_avg (nM) |
|---|---|---|
| (methoxy-bromo-phenyl thiazolidine carboxylic acid) | 8796 | >80000 |
| (methoxy-bromo-phenyl thiazolidine ethyl ester) | 17662 | >80000 |
| (methoxy-bromo-phenyl thiazolidine) | 4146 | >80000 |
| (methoxy-hydroxy-thiophenyl-phenyl thiazolidine ethyl ester) | >20000 | >80000 |
| (carboxy-hydroxy-bromo-phenyl thiazolidine) | >20000 | >80000 |
| (carboxy-hydroxy-bromo-phenyl thiazolidine carboxylic acid) | >20000 | >80000 |

TABLE 36-continued

| compound | IC50_avg (nM) | EC50_avg (nM) |
|---|---|---|
| (ethoxy-hydroxy-dibromo-phenyl thiazolidine ethyl ester) | >20000 | >80000 |
| (methoxy-hydroxy-thiophenyl-phenyl thiazolidine) | >20000 | >80000 |
| (methoxy-hydroxy-thiophenyl-phenyl thiazolidine carboxylic acid) | >20000 | >80000 |
| (ethoxy-hydroxy-dibromo-phenyl thiazolidine carboxylic acid) | >20000 | >80000 |

TABLE 37

| compound | IC50_avg (nM) | EC50_avg (nM) |
|---|---|---|
| (hydroxy-formyl-phenyl ethynyl-pyridine) | 155 | >80000 |

TABLE 37-continued

| compound | IC50_avg (nM) | EC50_avg (nM) |
|---|---|---|
| (5-methoxy-2-hydroxy-3-((pyridin-3-yl)ethynyl)benzaldehyde) | 303 | 70000 |
| (5-methoxy-2-hydroxy-3-((thiophen-2-yl)ethynyl)benzaldehyde) | 799 | >80000 |

TABLE 38

| compound | IC50_avg(nM) | EC50_avg(nM) |
|---|---|---|
| bis-bromomethoxysalicylidene ethyl disulfide | 2117 | 50000 |
| 5-bromo-3-methoxy-2-hydroxy-N-(4-methoxybenzyl)benzaldimine | 221 | 50000 |
| 5-bromo-3-methoxy-2-hydroxy-N-cyclopropylbenzaldimine | 110 | 50000 |
| bis-(thiophen-2-yl)methoxysalicylidene ethyl disulfide | 1348 | 50000 |
| 3-methoxy-2-hydroxy-5-(thiophen-2-yl)-N-cyclopropylbenzaldimine | 34 | 50000 |

TABLE 38-continued
| compound | IC50_avg(nM) | EC50_avg(nM) |
|---|---|---|
| 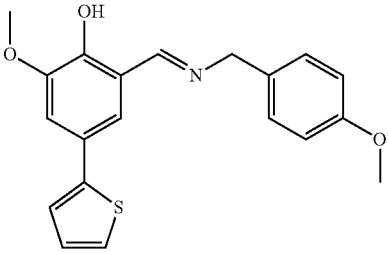 [SMILES: COc1ccc(C/N=C/c2cc(-c3cccs3)cc(OC)c2O)cc1] | 23 | 50000 |
| 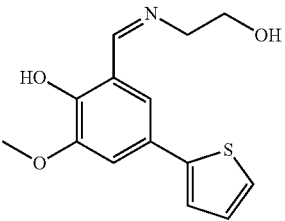 [SMILES: COc1cc(-c2cccs2)cc(/C=N\CCO)c1O] | 15 | 30000 |
| 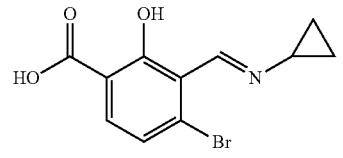 [SMILES: O=C(O)c1ccc(Br)c(/C=N/C2CC2)c1O] | 9523 | ND |
| 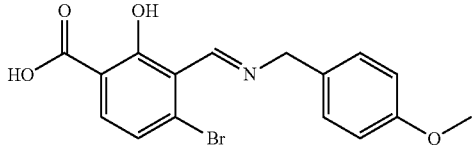 [SMILES: COc1ccc(C/N=C/c2c(Br)ccc(C(=O)O)c2O)cc1] | >20000 | ND |
| 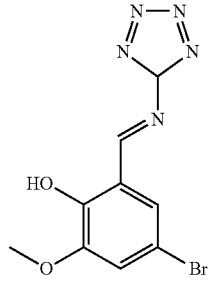 [SMILES: COc1cc(Br)cc(/C=N/C2N=NN=N2)c1O] | 587 | 75000 |
| 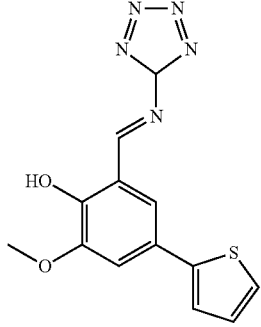 [SMILES: COc1cc(-c2cccs2)cc(/C=N/C2N=NN=N2)c1O] | 157 | 70000 |

TABLE 38-continued
| compound | IC50_avg(nM) | EC50_avg(nM) |
|---|---|---|
| 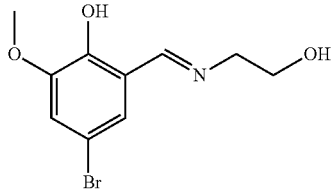 | 154 | 80000 |
| 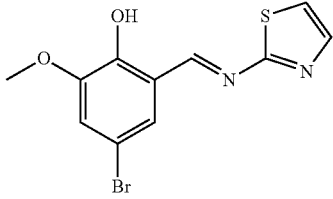 [SMILES: COc1cc(Br)cc(/C=N/c2nccs2)c1O] | 641 | 80000 |
| 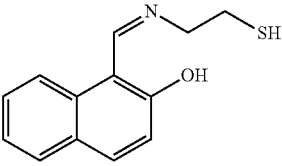 [SMILES: Oc1ccc2ccccc2c1/C=N\CCS] | >20000 | ND |
| 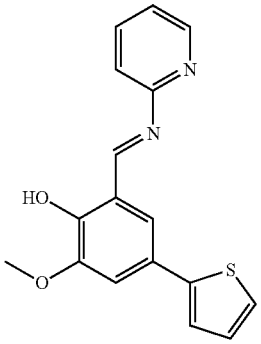 [SMILES: COc1cc(-c2cccs2)cc(/C=N/c2ccccn2)c1O] | >20000 | 30000 |
| 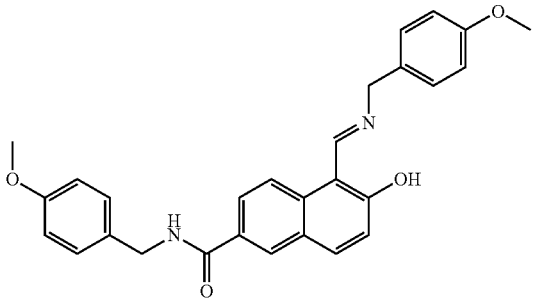 [SMILES: COc1ccc(C/N=C/c2c(O)ccc3cc(C(=O)NCc4ccc(OC)cc4)ccc23)cc1] | >20000 | ND |

TABLE 38-continued

| compound | IC50_avg(nM) | EC50_avg(nM) |
|---|---|---|
| [structure] | >20000 | ND |

TABLE 39

| compound | IC50_avg(nM) | EC50_avg(nM) |
|---|---|---|
| [structure - morpholine] | 1523 | 80000 |
| [structure - piperidine] | 11375 | 70000 |
| [structure - N-methylpiperazine] | 12217 | no |

TABLE 40

| compound | IC50_avg(nM) |
|---|---|
| [structure] | 47 |
| [structure] | 526 |

TABLE 41

| compound | IC50_avg (nM) | EC50_avg (nM) |
|---|---|---|
| [structure] | 108 | 60000 |

TABLE 41-continued

| compound | IC50_avg (nM) | EC50_avg (nM) |
|---|---|---|
| (3-fluoro-5-(4-(morpholine-4-carbonyl)phenyl)-4-hydroxybenzaldehyde) | 221 | >80000 |
| (4-hydroxy-3-methoxy-5-(1,3-dimethyl-2,4-dioxo-1,2,3,4-tetrahydropyrimidin-5-yl)benzaldehyde) | 1581 | 50000 |

TABLE 41-continued

| compound | IC50_avg (nM) | EC50_avg (nM) |
|---|---|---|
| (4-hydroxy-3-methoxy-5-(2-methoxythiazol-5-yl)benzaldehyde) | 128 | 30000 |

TABLE 42

| compound | IC50_avg(nM) | EC50_avg(nM) |
|---|---|---|
| (4-hydroxy-3-methoxy-5-(3-carboxyphenyl)benzaldehyde) | 102 | |
| (4-hydroxy-3-methoxy-5-(3-(cyclohexylcarbamoyl)phenyl)benzaldehyde) | 19 | |
| (6-bromo-2-hydroxy-1-naphthaldehyde) | 509 | 10000 |

TABLE 42-continued
| compound | IC50_avg(nM) | EC50_avg(nM) |
|---|---|---|
| 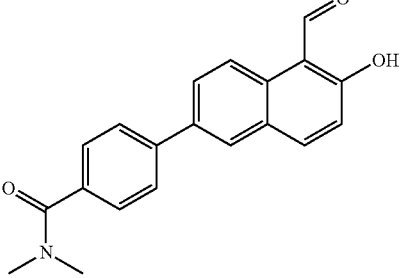 | 36 | 3000 |
| 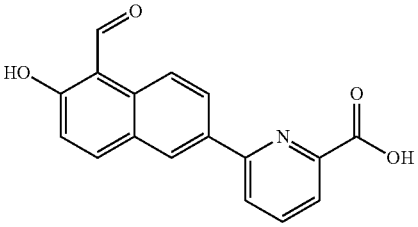 [SMILES: O=Cc1c(O)ccc2cc(-c3cccc(C(=O)O)n3)ccc12] | 125 | |
| 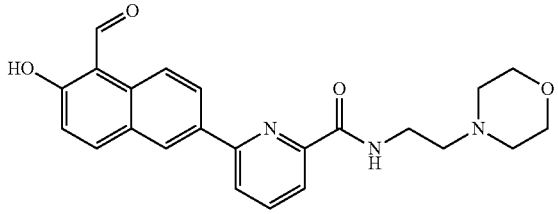 [SMILES: O=Cc1c(O)ccc2cc(-c3cccc(C(=O)NCCN4CCOCC4)n3)ccc12] | 48 | |
| 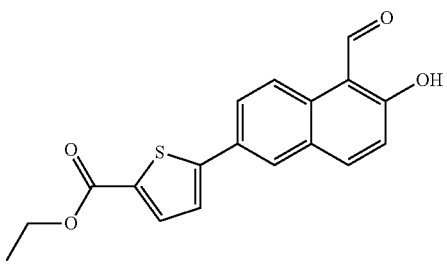 [SMILES: CCOC(=O)c1ccc(-c2ccc3c(C=O)c(O)ccc3c2)s1] | 15564 | |
| 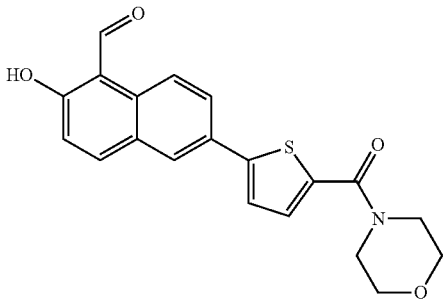 [SMILES: O=Cc1c(O)ccc2cc(-c3ccc(C(=O)N4CCOCC4)s3)ccc12] | 157 | |
| 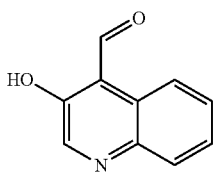 [SMILES: O=Cc1c(O)cnc2ccccc12] | 45 | 60000 |

TABLE 42-continued
| compound | IC50_avg(nM) | EC50_avg(nM) |
|---|---|---|
| 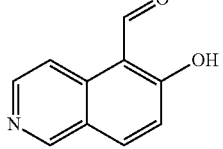 | 427 | 20000 |
| 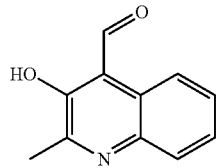 | 36370 | 50000 |
| 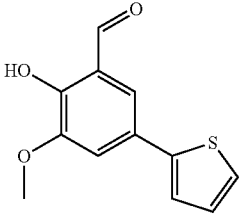 [SMILES: COc1cc(-c2cccs2)cc(C=O)c1O] | 22 | 19365 |
| 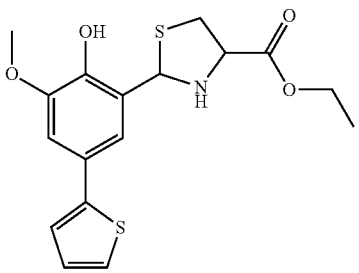 [SMILES: CCOC(=O)C1CSC(c2cc(-c3cccs3)cc(OC)c2O)N1] | >20000 | |
| 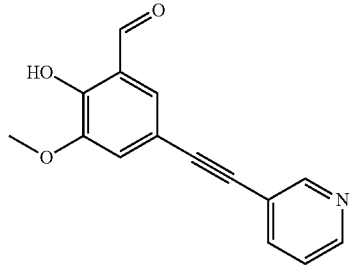 [SMILES: COc1cc(C#Cc2cccnc2)cc(C=O)c1O] | 303 | |
| 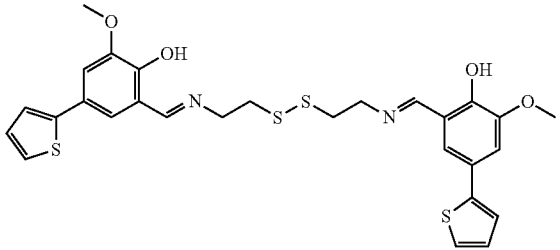 [SMILES: COc1cc(-c2cccs2)cc(/C=N/CCSSCC/N=C/c2cc(-c3cccs3)cc(OC)c2O)c1O] | 1348 | 50000 |

TABLE 42-continued

| compound | IC50_avg(nM) | EC50_avg(nM) |
|---|---|---|
| [structure: morpholinomethyl-hydroxynaphthaldehyde] | 1523 | 80000 |
| [structure: morpholine carbonyl hydroxy bromo benzaldehyde] | 526 | |
| [structure: hydroxy methoxy phenyl dimethyl pyrimidinedione benzaldehyde] | 1581 | 50000 |

EXAMPLE 27

Optimization Assay Strategy

A series of in vitro ADME assays (Absorption-Distribution-Metabolism-Excretion assays, testing properties such as plasma stability, liver microsome stability, solubility, $CaCO_2$ permeability) are used to optimize IRE-1α inhibitor compounds for pharmacological characteristics. The strategy is executed in a sequential pattern of assays in stages depending on the activity of compound analogs. In early stage optimization, in vitro potency, cellular on-target XBP-1 mRNA splicing, apoptosis Caspase 3 and 7, and proteasome inhibitor potentiation assays are employed with a set of compound characteristics assays: solubility, serum stability, and log P. Activity assays are used together with assays for pharmacological characteristics, such as serum protein binding, membrane permeability, cellular permeability, and microsome stability. Finally, in vitro toxicology and pharmacokinetic assays are employed, such as P450, AMES, hERG, and receptor profiling assays.

EXAMPLE 28

Animal Model/Preclinical Validation Studies

Figure 8D:
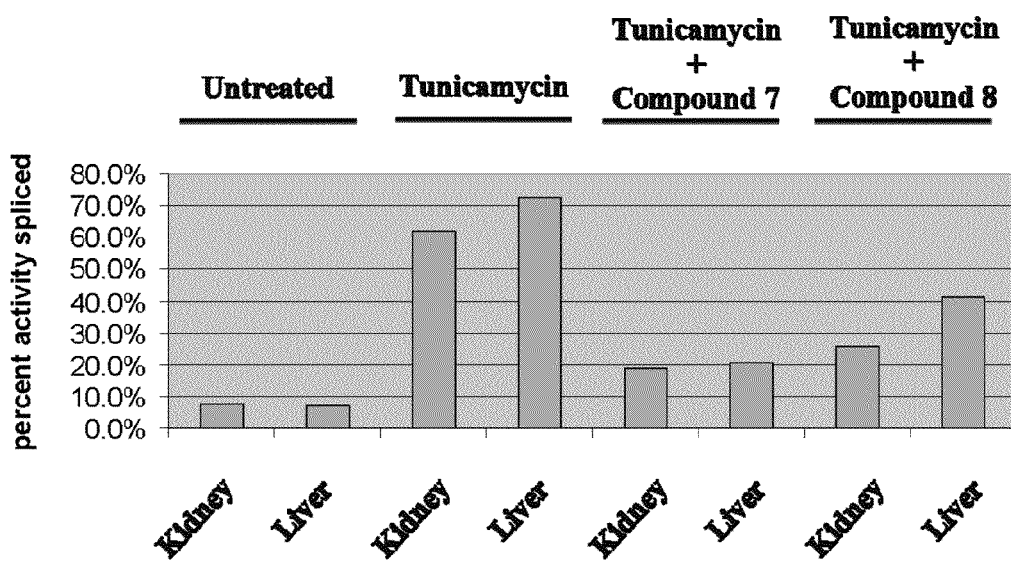
FIG. 8D, graphical representation of the average relative percentage of spliced XBP-1 over total XBP-1 from the two mice per group in FIGS. 8B and 8C. The numbers above the brackets in FIG. 8B and FIG. 8C are mouse numbers (mouse 3, mouse 4, etc.).
Figure 9:
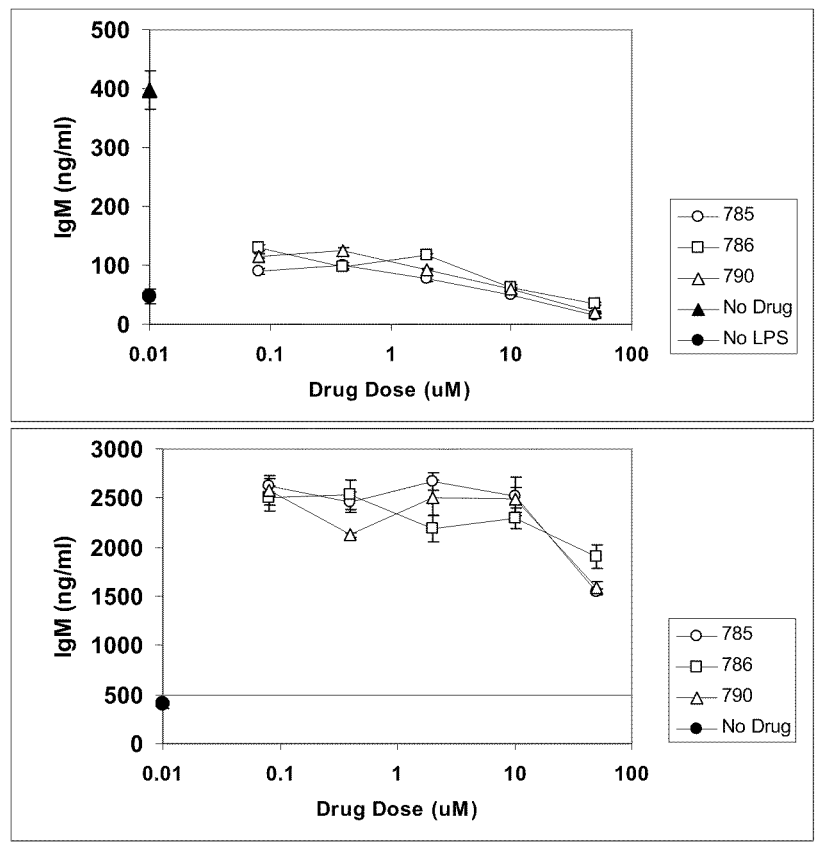
FIG. 9. Inhibition of IgM secretion after LPS stimulation of primary murine B cells with selected IRE-1α inhibitors. Compound 17-1 blocked IgM secretion at all doses tested down to 100 nM when added at beginning of stimulation and again at 24 hours post stimulation. However, compounds had little effect when at added after 40 hours of stimulation; only slight inhibition at the highest dose. Methods were performed as previously described by Iwakoshi et al., *Nature* 4, 321-29, 2003 for B cell stimulation, plasma cell differentiation and IgM secretion. Primary B cells were Isolated from BALB/c splenocytes using mouse CD43 Microbeads (Miltenyi cat# 130-049-801) with $1 \times 10^6$ cells per treatment. Purified B cells were stimulated in B Cell Media at a final density of $1 \times 10^6$/ml/well in 24-well plates with 20 μg/ml LPS (Sigma cat# L4391). IRE-1α inhibitor compound 17-1 was added at various concentrations (50 μM, 10 μM, 2 μM, 0.4 μM and 0.08 μM) at specified time points (t=0, t=24 hr, t=40 hr, etc.) Cells were incubated for 48 hr at 37° C. At end of the incubation, cells were spun in a plate at 1500 rpm/3 min. Supernatants were collected for quantitation for IgM secretion using a mouse IgM ELISA Kit (Bethyl Labs cat# E90-101). B Cell

The preclinical validation strategy employs a set of animal models representing normal tissues under chemical stress and multiple myeloma xenographs. The normal animal model is employed as a surrogate model where dose-related on-target activity of compounds can be confirmed in tissues sensitive to standard UPR inducing agents such as tunicamycin (Wu et al., Dev Cell. 2007 September; 13(3):351-64). As demonstrated in FIG. 8, normal mouse tissues are not under ER stress, and therefore the XBP-1 mRNA remains as the inactive, unspliced form. Upon induction with tunicamycin, tissues induce active XBP-1 mRNA splicing, and this activity is suppressed by IRE-1α inhibitors. This on-target ER stress animal model is a useful screening and early pharmacokinetic tool.

Antibody production is evaluated in a second surrogate model. However, in cell-based models, IRE-1α inhibitors have been shown to potently inhibit antibody production.

Final efficacy studies are performed in myeloma xenograft models, as described below.

EXAMPLE 29

RPMI8226 Xenograft Efficacy Model

SCID mice are evaluated for their ability to support implantation of desired tumor cells in support of model development and characterization. Mice are injected intravenously (IV) or implanted either subcutaneously (SC) or intraperitoneally (IP). To generate a relevant animal model mimicking human disease, it is desirable that all three approaches are evaluated for improved implantation rates and relevant disease progression, as is well known in the art. SC injections provide an easy way to measure tumor growth and efficacy, and IV and IP injections represent a more physiologically relevant model of human tumor spread. SC injections are given primarily in the flank, while IV injections are administered in the tail vein. Mice are manually restrained for SC and IP injections, and a Broome mouse restrainer is used for IV injections.

EXAMPLE 30

Evaluation of IRE-1α Inhibitor Compounds in a Xenograft Efficacy Model

SCID mice are implanted with tumor cells (human RPMI8226 myeloma cells) via IP, IV or SC routes based on the results from the xenograft model development studies (above). Mice are treated with compound or mock treated (vehicle) for a period of up to 4-5 weeks. Compound administration can be via IV, IP, PO or SC routes. In some cases, tunicamycin is administered via IP injection in order to stimulate stress in the animal. This stress mimics the stress an animal may undergo during times of tumor growth. The tunicaymycin injection mimics tumor growth during times of stress and permits evaluation of biomarkers which indicate the effectiveness of a compound (such as XBP-1 splicing) by RT-PCR, immunohistochemistry, or Western blots.

Mice are monitored for tumor growth, regression and general health. Tumors are collected and characterized by immunohistochemistry and/or FACS analysis. Tumor growth is measured by calipers, ultrasound, or by abdominal lavage. Biomarkers in the blood or tumor can evaluated (primarily XBP-1 splicing).

In some experiments, blood samples are collected at various time points during the dosing (i.e., day 1 or week 4 etc.) to evaluate the pharmacokinetic profile. The time points of blood collection vary depending on the pharmacokinetic properties of the drug being tested. The volume of blood sample is 100 microliters/per time point, and mice are bled twice after drug administration within a 24 hour period via retro-orbital sinus. If the same mouse is used, blood samples are collected once from each eye during 24 hours.

Tumor cells are cultured and injected IP, IV (tail vein) or SC (flank) in the mouse using a 21G needle in a volume of approx 100 pt. Mice are treated with compounds or vehicle alone as a control by IV, IP, SC or PO routes 5 days per week for up to 4-5 weeks. Blood is collected via retroorbital bleed (100 μl) at 2 time points (different eyes). The endpoint of the study depends on the overall health of the mice: while mice are euthanized at the end of 4-5 weeks in most studies, mice are maintained until day 40 in a few studies if their general health will allow. The reason for maintaining studies for 40 days is to determine if the tested compounds have a long term effect on inhibiting tumor growth. Euthanization of mice in which tumor regression is observed will depend on the experimental design. In screening mode, the experiment will end with tumors in the control/untreated group reach 1.5 cm, are ulcerated or when loss of motility is observed in that group. In follow up experiments, mice in which tumor regression is observed may be maintained longer, until they show signs of tumor growth of ill health.

Therapeutic dosing with bortezomib 0.75 mg/kg IV twice weekly of SCID mice bearing human myeloma RPMI8226 tumor xenografts resulted in suppression of tumor growth. However, after cessation of bortezomib therapy, tumors often recurred and grew into large masses. Therefore, mice will be treated in combination as with both bortezomib (as indicated) and twice daily with 10-60 mg/kg IRE-1α/XBP-1 inhibitors such as compound 17-1 by oral, IP or IV administration. Compounds which reduce the incidence of tumor recurrence are identified.

EXAMPLE 31

Combination Therapies

The spliced form of XBP-1, as a homodimer and heterodimer with ATF-6, transcriptionally regulates genes involved in adapting to ER stress (Wu et al., Dev Cell. 2007 September; 13(3):351-64). Many of these downstream targets are major chaperones, co-chaperones and ERAD components of the ER. Chaperones such as GRP78 and GRP94 are stable and long lived proteins with half lives on the order of days (Wu et al., Dev Cell. 2007 September; 13(3):351-64). Therefore, treatment of cancer with an IRE-1α/XBP-1 inhibitor may require up to 5 to 6 days of treatment in each cycle.

In some embodiments, combination therapy given in cycles such as with proteasome inhibitors involves giving the patient 2 days of pretreatment with IRE-1α/XBP-1 inhibitor and then simultaneously with the chemotherapeutic agent until a pharmacodynamic effect is achieved (typically 24 hours post bortezomib infusion). Bortezomib is typically administered on three week cycles, every 1, 4, 8 and 11 days (of 21). Dosing is 1.3 mg/m$^2$ by IV administration. IRE-1α/XBP-1 inhibitors can be administered 2 day prior and 24 hours post infusion of bortezomib at 10 to 100 mg/kg by the IV or oral route once, twice or three times daily depending on the PK/PD relationship.

A similar protocol can be employed with Hsp90 and or HDAC inhibitors. Alternatively, both agents are administered simultaneously for the duration of each cycle depending on the PK/PD relation of the inhibitor. IRE-1α/XBP-1 inhibitors can be given to breast cancer patients in combination with Tamoxifen (Gomez et al., FASEB J. 2007 December; 21(14): 4013-27) or in combination with Sorafinib to various other cancers including kidney carcinoma and hepatocellular carcinoma (Rahmani et al., Mol Cell Biol. 2007 August; 27(15): 5499-513).

In general, because many kinase inhibitors often are not selective on their targeted kinase and often affect many additional kinases; they may cause non-specific cellular stress which may activate the UPR. Therefore, combination approaches may be useful using IRE-1α/XBP-1 inhibitors as sensitizing agents.

The invention claimed is:

1. A method of inhibiting IRE-1α activity, comprising contacting IRE-1α with a compound represented by structural formula (I):

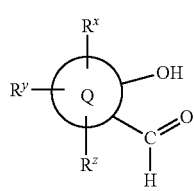

(I)

wherein:
   the OH substituent is located ortho to the aldehyde substituent;
   Q is an aromatic isocyclic or heterocyclic ring system selected from benzene, naphthalene, pyridine, pyridine N-oxide, thiophene, benzo[b]thiophene, benzo[c]thiophene, furan, pyrrole, pyridazine, pyrmidine, pyrazine, triazine, isoxazoline, oxazoline, thiazoline, pyrazoline, imidazoline, fluorenyl, biphenyl, quinoline, isoquinoline, cinnoline, phthalazine, quinazoline, quinoxaline, benzofuran, indole, isoindole, isobenzofuran, benzimidazole, 1,2-benzisoxazole, and carbazole;
   $R^x$ and $R^z$ can be present or absent and are independently selected from hydrogen, aryl, heterocyclic, -A"$R^a$, —OH, —OA"$R^a$, —NO$_2$, —NH$_2$, —NHA"$R^a$, —N(A"$R^a$)(A'''$R^b$), —NHCOA"$R^a$, —NHCOOA"$R^a$, —NHCONH$_2$, —NHCONHA"$R^a$, —NHCON(A"$R^a$)(A'''$R^b$), halogen, —COOH, —COOA"$R^a$, —CONH$_2$, —CONHA"$R^a$, —CON(A"$R^a$)(A'''$R^b$), and

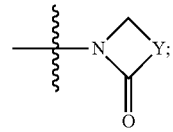

$R^y$ can be present or absent and is selected from hydrogen, aryl, heterocyclic, -A"$R^a$, —OA"$R^a$, —NO$_2$, —NH$_2$, —NHA"$R^a$, —N(A"$R^a$)(A'''$R^b$), —NHCOA"$R^a$, —NHCOOA"$R^a$, —NHCONH$_2$, —NHCONHA"$R^a$, —NHCON(A"$R^a$)(A'''$R^b$), halogen, —COOH, —COOA"$R^a$, —CONH$_2$, —CONHA"$R^a$, —CON(A"$R^a$)(A'''$R^b$), and

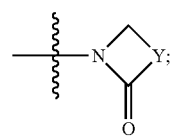

$R^a$ is hydrogen, —COOH, —COOA, —CONH$_2$, —CONHA, —CONAA', —NH$_2$, —NHA, —NAA', —NCOA, —NCOOA, or —OA;

$R^b$ is hydrogen, —COOH, —COOA, —CONH$_2$, —CONHA, —CONAA', —NH$_2$, —NHA, —NAA', —NCOA, —NCOOA, —OH, or —OA;

Y is $C_1$-$C_{10}$ alkylene or $C_2$-$C_8$ alkenylene, in which (a) one, two or three CH$_2$ groups may be replaced by O, S, SO, SO$_2$, NH, or NR$^c$ and/or (b) 1-7 H atoms may be independently replaced by F or Cl;

A and A' are:
   (a) independently $C_1$-$C_{10}$ alkyl or $C_2$-$C_8$ alkenyl, in which (i) one, two or three CH$_2$ groups may be replaced by O, S, SO, SO$_2$, NH, or NR$^c$ and/or (ii) 1-7

H atoms may be independently replaced by F or Cl, aryl or heterocyclic; or (b) A and A' together are alternatively $C_2$-$C_7$ alkylene, in which one, two or three $CH_2$ groups may be replaced by O, S, SO, $SO_2$, NH, $NR^c$, $NCOR^c$ or $NCOOR^c$, to form, for example, an alkylenedioxy group;

A", A''' are independently (a) absent, (b) $C_1$-$C_{10}$ alkylene, $C_2$-$C_8$ alkenylene, or $C_3$-$C_7$ cycloalkyl in which one, two or three $CH_2$ groups may be replaced by O, S, SO, $SO_2$, NH or $NR^c$ and/or 1-7 H atoms may be replaced by F and/or Cl; or (c) together are $C_2$-$C_7$ alkyl in which one, two or three $CH_2$ groups may be replaced by O, S, SO, $SO_2$, NH, $NR^c$, $NCOR^c$ or $NCOOR^c$, $R^c$ is $C_1$-$C_{10}$ alkyl, $C_3$-$C_7$ cycloalkyl, $C_4$-$C_8$ alkylenecycloalkyl, or $C_2$-$C_8$ alkenyl in which one, two or three $CH_2$ groups may be replaced by O, S, SO, $SO_2$, NH, NMe, NEt and/or by —CH=CH— groups, 1-7 H atoms may be replaced by F and/or Cl, and/or 1 H atom may be replaced by $R^a$;

aryl is phenyl, benzyl, naphthyl, fluorenyl or biphenyl, each of which is unsubstituted or monosubstituted, disubstituted or trisubstituted by halogen, —$CF_3$, —$R^f$, —$OR^d$, —$N(R^d)_2$, —$NO_2$, —CN, —$COOR^d$, $CON(R^d)_2$, —$NR^dCOR^e$, —$NR^dCON(R^e)_2$, —$NR^dSO_2$A, —$COR^d$, —$SO_2N(R^d)_2$, —$S(O)_mR^f$, AA' together, or —O(aryl), $R^d$ and $R^e$ are independently H or $C_1$-$C_6$ alkyl;

$R^f$ is $C_1$-$C_6$ alkyl;

heterocyclic is a monocyclic or bicyclic saturated, unsaturated or aromatic heterocyclic ring having 1 to 2 N, O and/or S atoms, which may be unsubstituted or monosubstituted or disubstituted by carbonyl oxygen, halogen, $R^f$, —$OR^d$, —$N(R^d)_2$, —$NO_2$, —CN, —$COOR^d$, —$CON(R^d)_2$, —$NR^dCOR^e$, —$NR^dCON(R^e)_2$, —$NR^fSO_2R^e$, —$COR^d$, —$SO_2NR^d$ and/or —$S(O)_mR^f$; and m is 0, 1 or 2, provided that the compound is not salicylaldehyde.

2. The method of claim 1 wherein the IRE-1α is in a cell.

3. The method of claim 1 wherein the cell has an activated unfolded protein response.

4. The method of claim 2 wherein the cell is a cancer cell.

5. The method of claim 2 wherein the cell is a myeloma cell.

6. The method of claim 2 wherein inhibition of the IRE-1α activity inhibits cell proliferation.

7. The method of claim 2 wherein inhibition of the IRE-1α activity induces apoptosis.

8. The method of claim 2 further comprising contacting the cell with an agent that induces or up-regulates IRE-1α expression.

9. The method of claim 2 further comprising contacting the cell with a biotherapeutic agent, a chemotherapeutic agent, or radiation.

10. The method of claim 2 further comprising contacting the cell with a proteasome inhibitor.

11. The method of claim 1 wherein the compound is provided in the form of a pharmaceutically acceptable salt.

12. A method of inhibiting IRE-1α activity, comprising contacting IRE-1α with a compound represented by structural formula (B):

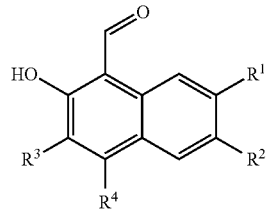

(B)

wherein:

$R^1$ and $R^2$ independently are hydrogen, phenyl or an optionally benzofused five- or six-membered heterocycle, wherein the phenyl or the optionally benzofused five- or six-membered heterocycle is optionally substituted with

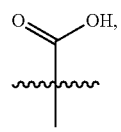

—$CH_2OH$, —CHO, —$OCH_3$, halogen, —OH, —$CH_3$,

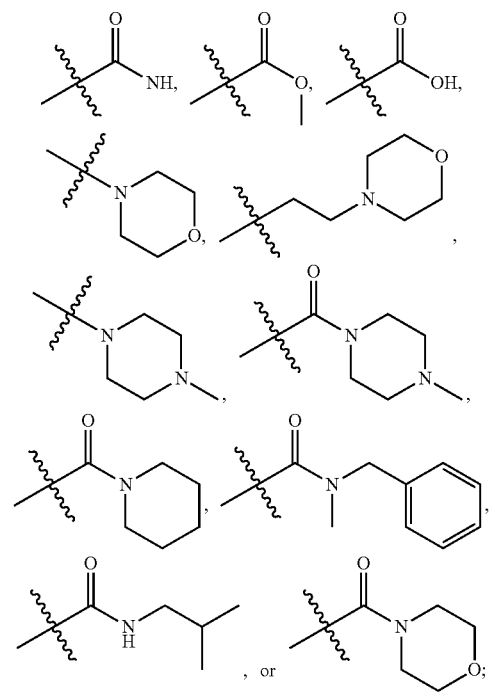

, or and either:

(1) $R^3$ is hydrogen, halogen, —$NO_2$, $C_1$-$C_3$ linear or branched alkyl, $C_1$-$C_3$ linear or branched alkoxy, $C_1$-$C_3$ linear or branched hydroxyl alkyl,

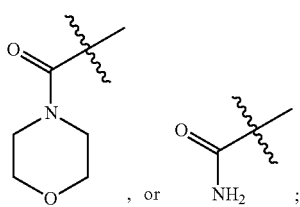, or and R⁴ is

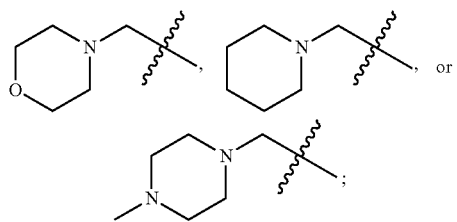

or (2) R³ is halogen, —NO₂, C₁-C₃ linear or branched alkyl, C₁-C₃ linear or branched alkoxy, C₁-C₃ linear or branched hydroxyl alkyl,

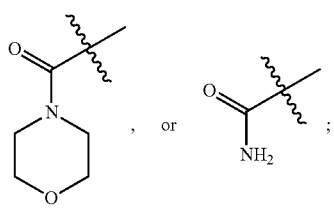

and R⁴ is hydrogen,

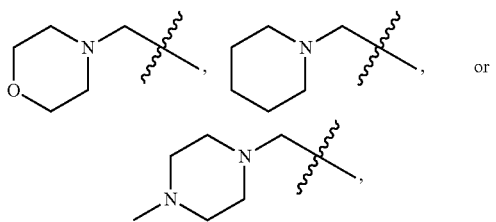

wherein the IRE-1α is in a cell.

13. A method of inhibiting IRE-1α activity, comprising contacting IRE-1α with a compound represented by structural formula (A):

(A)

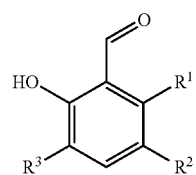

wherein:

R¹ is hydrogen, halogen, or a 5- or 6-membered heterocyclic containing one or two heteroatoms independently selected from nitrogen, oxygen, and sulfur;

R² is hydrogen,

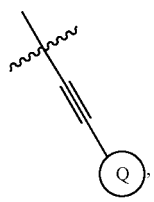

phenyl, or a 5- or 6-membered heterocyclic containing 1 or 2 heteroatoms independently selected from nitrogen, oxygen, and sulfur, wherein the heterocyclic is optionally benzofused and wherein the heterocyclic is optionally substituted by 1, 2, or 3 substituents independently selected from

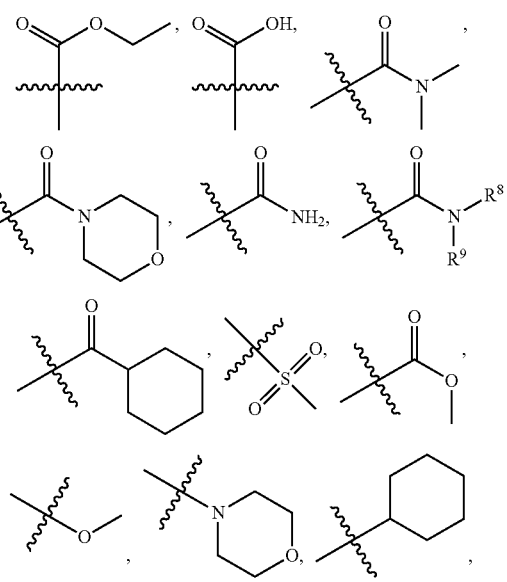

C₁-C₃ linear or branched alkyl,

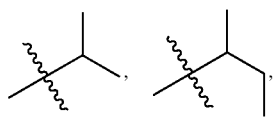

C₁-C₃ phenylalkyl, C₁-C₃ alkoxyphenylalkyl,

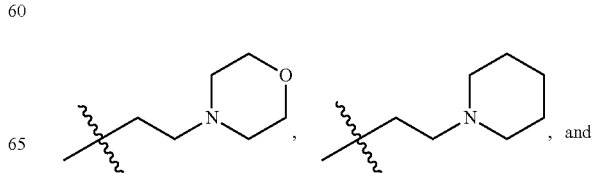, and

-continued

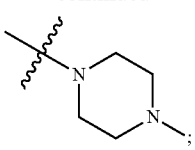

$R^3$ is hydrogen, halogen, —$NO_2$, $C_1$-$C_3$ linear or branched alkoxy, $C_1$-$C_3$ linear or branched hydroxyl alkyl,

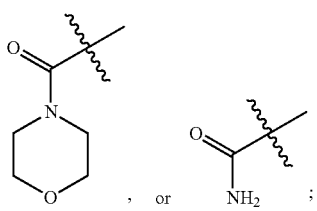

and

Q is a five- or six-membered heterocycle, provided that structural formula (A) does not encompass salicylaldehyde.

14. A method of inhibiting IRE-1α activity, comprising contacting IRE-1α with a compound represented by structural formula (C):

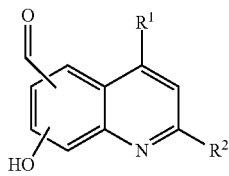
(C)

wherein:

$R^1$ and $R^2$ are independently hydrogen, —$CH_3$, or —OH; and the hydroxy substitutent in ring A is located ortho to the aldehyde substituent.

15. A method of inhibiting IRE-1α activity, comprising contacting IRE-1α with a compound represented by structural formula (D):

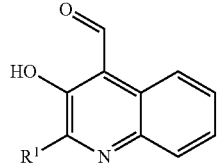
(D)

wherein $R^1$ is hydrogen, halogen, —$NO_2$, $C_1$-$C_3$ linear or branched alkyl, $C_1$-$C_3$ linear or branched alkoxy, $C_1$-$C_3$ linear or branched hydroxyl alkyl,

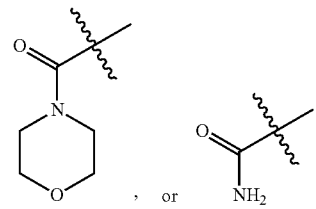

16. The method of claim 12, wherein the cell has an activated unfolded protein response.

17. The method of claim 12, wherein the cell is a cancer cell.

18. The method of claim 12, wherein the cell is a myeloma cell.

19. The method of claim 12, wherein inhibition of the IRE-1α activity inhibits cell proliferation.

20. The method of claim 12, wherein inhibition of the IRE-1α activity induces apoptosis.

21. The method of claim 13, further comprising contacting the cell with an agent that induces or up-regulates IRE-1α expression.

22. The method of claim 12, further comprising contacting the cell with a biotherapeutic agent, a chemotherapeutic agent, or radiation.

23. The method of claim 12 further comprising contacting the cell with a proteasome inhibitor.

24. The method of claim 12 wherein the compound is provided in the form of a pharmaceutically acceptable salt.

25. The method of claim 13, wherein the IRE-1α is in a cell.

26. The method of claim 25, wherein the cell has an activated unfolded protein response.

27. The method of claim 25, wherein the cell is a cancer cell.

28. The method of claim 25, wherein the cell is a myeloma cell.

29. The method of claim 25, wherein inhibition of the IRE-1α activity inhibits cell proliferation.

30. The method of claim 25, wherein inhibition of the IRE-1α activity induces apoptosis.

31. The method of claim 25, further comprising contacting the cell with an agent that induces or up-regulates IRE-1α expression.

32. The method of claim 25, further comprising contacting the cell with a biotherapeutic agent, a chemotherapeutic agent, or radiation.

33. The method of claim 25, further comprising contacting the cell with a proteasome inhibitor.

34. The method of claim 25 wherein the compound is provided in the form of a pharmaceutically acceptable salt.

35. The method of claim 14, wherein the IRE-1α is in a cell.

36. The method of claim 35, wherein the cell has an activated unfolded protein response.

37. The method of claim 35, wherein the cell is a cancer cell.

38. The method of claim 35, wherein the cell is a myeloma cell.

39. The method of claim 35, wherein inhibition of the IRE-1α activity inhibits cell proliferation.

40. The method of claim 35, wherein inhibition of the IRE-1α activity induces apoptosis.

41. The method of claim 35, further comprising contacting the cell with an agent that induces or up-regulates IRE-1α expression.

42. The method of claim 35, further comprising contacting the cell with a biotherapeutic agent, a chemotherapeutic agent, or radiation.

43. The method of claim 35, further comprising contacting the cell with a proteasome inhibitor.

44. The method of claim 35, wherein the compound is provided in the form of a pharmaceutically acceptable salt.

45. The method of claim 15, wherein the IRE-1α is in a cell.

46. The method of claim 45, wherein the cell has an activated unfolded protein response.

47. The method of claim 45, wherein the cell is a cancer cell.

48. The method of claim 45, wherein the cell is a myeloma cell.

49. The method of claim 45, wherein inhibition of the IRE-1α activity inhibits cell proliferation.

50. The method of claim 45, wherein inhibition of the IRE-1α activity induces apoptosis.

51. The method of claim 45, further comprising contacting the cell with an agent that induces or up-regulates IRE-1α expression.

52. The method of claim 45, further comprising contacting the cell with a biotherapeutic agent, a chemotherapeutic agent, or radiation.

53. The method of claim 45, further comprising contacting the cell with a proteasome inhibitor.

54. The method of claim 45, wherein the compound is provided in the form of a pharmaceutically acceptable salt.

55. A method of inhibiting IRE-1α activity, comprising contacting IRE-1α with a compound represented by structural formula (B):

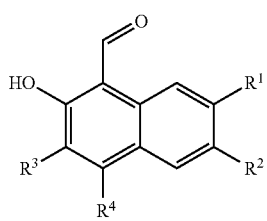

(B)

wherein:

$R^1$ and $R^2$ independently are hydrogen, phenyl or an optionally benzofused five- or six-membered heterocycle, wherein the phenyl or the optionally benzofused five- or six-membered heterocycle is optionally substituted with

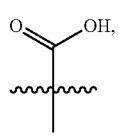 [SMILES: *C(=O)O]

—CH$_2$OH, —CHO, —OCH$_3$, halogen, —OH, —CH$_3$,

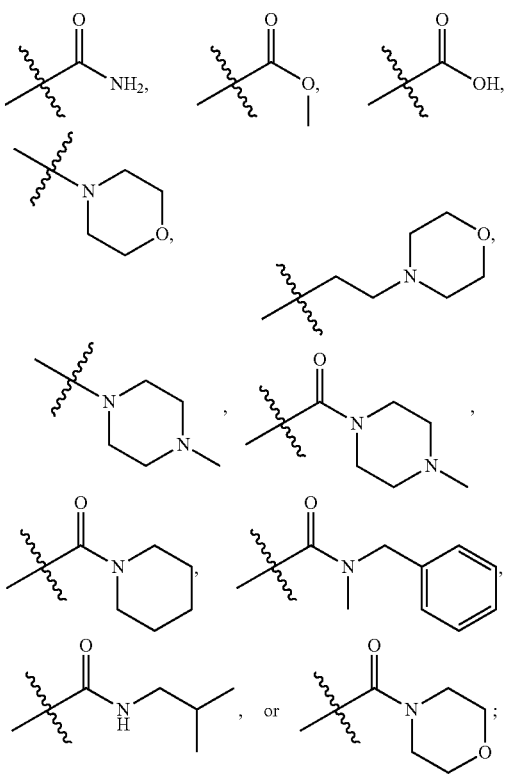

$R^3$ is halogen, —NO$_2$, C$_2$-C$_3$ linear or branched alkyl, C$_2$-C$_3$ linear or branched alkoxy, C$_1$-C$_3$ linear or branched hydroxyl alkyl,

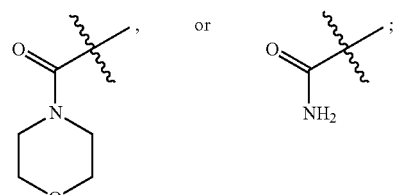

and
$R^4$ is hydrogen,

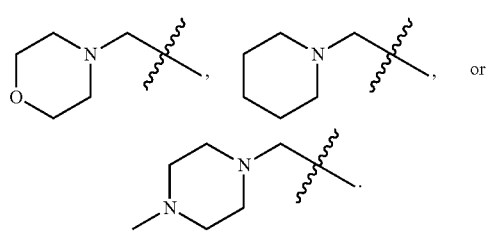

56. The method of claim 55, wherein $R^3$ is C3 alkyl or C3 alkoxy.

* * * * *

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: IRE-1alpha substrate

```
<400> SEQUENCE: 1
caguccgcag cacug                                                  15

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
cctggttgct gaagaggagg                                             20

<210> SEQ ID NO 3
<211> LENGTH: 21
<212> TYPE: DNA
<213> ORGANISM: Artificial Sequence
<220> FEATURE:
<223> OTHER INFORMATION: reverse primer

<400> SEQUENCE: 3
ccatggggag atgttctgga g                                           21
```